(12) United States Patent
Yoshida et al.

(10) Patent No.: US 9,637,483 B2
(45) Date of Patent: May 2, 2017

(54) HETEROCYCLIC COMPOUND

(71) Applicant: TAKEDA PHARMACEUTICAL COMPANY LIMITED, Osaka (JP)

(72) Inventors: Masato Yoshida, Kanagawa (JP); Hiroyuki Nagamiya, Kanagawa (JP); Yusuke Ohba, Osaka (JP); Masaki Seto, Kanagawa (JP); Takatoshi Yogo, Kanagawa (JP); Satoshi Sasaki, Kanagawa (JP); Norihito Tokunaga, Kanagawa (JP); Kazuyoshi Aso, New York, NY (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/779,347

(22) PCT Filed: Mar. 27, 2014

(86) PCT No.: PCT/JP2014/058999
§ 371 (c)(1),
(2) Date: Sep. 23, 2015

(87) PCT Pub. No.: WO2014/157569
PCT Pub. Date: Oct. 2, 2014

(65) Prior Publication Data
US 2016/0039811 A1    Feb. 11, 2016

(30) Foreign Application Priority Data

Mar. 28, 2013    (JP) .................. 2013-070477

(51) Int. Cl.
*A61K 31/437*  (2006.01)
*C07D 401/14*  (2006.01)
*C07D 471/04*  (2006.01)
*C07D 519/00*  (2006.01)

(52) U.S. Cl.
CPC ......... *C07D 471/04* (2013.01); *C07D 519/00* (2013.01)

(58) Field of Classification Search
CPC ........................... C07D 401/14; A61K 31/437
USPC .......................................... 546/119; 514/303
See application file for complete search history.

(56) References Cited

U.S. PATENT DOCUMENTS

| | | |
|---|---|---|
| 9,085,578 B2 * | 7/2015 | Nagamiya |
| 2013/0131039 A1 | 5/2013 | Burgess et al. |
| 2013/0252941 A1 | 9/2013 | Blench et al. |
| 2015/0045349 A1 | 2/2015 | Nagamiya et al. |
| 2015/0141406 A1 | 5/2015 | Nara et al. |

FOREIGN PATENT DOCUMENTS

| | | |
|---|---|---|
| WO | 2010/051549 | 5/2010 |
| WO | 2011/130146 | 10/2011 |
| WO | 2012/066061 | 5/2012 |
| WO | 2013/125543 | 8/2013 |
| WO | 2013/180265 | 12/2013 |

OTHER PUBLICATIONS

International Search Report issued May 20, 2014 in International Application No. PCT/JP2014/058999.
Galal H. Elgemeie et al., "Synthesis of some novel α-cyanoketene S, S-acetals and their use in a heterocyclic synthesis", Journal of Chemical Society, Perkin Transactions 1: Organic and Bio-Organic Chemistry (1997), (21), pp. 3285-3290.
Yoshinori Tominaga et al., "Synthesis and Reactions of 6-Aryl- and 6-Styryl-3-cyano-4-methylthio-2H-pyran-2-ones", Chemical & Pharmaceutical Bulletin (1984), 32(9), pp. 3384-3395.
Arvind Kumar et al., "Keten Dithioacetals. Part 11[1]. Reaction of 3-Cyano-4-methylthio-2(1H)-pyridones with Hydrazine and Guanidine: Synthesis of Novel Substituted and Fused Pyrazolo[4,3-c]pyridone and Pyrido[4,3-d]pyrimidine derivatives", Journal of the Chemical Society, Perkin Transactions 1: Organic and Bio-Organic Chemistry (1972-1999) (1978), (8), pp. 857-862.
Galah H. Elegemeie et al., "A New General Method for Substituted 4-Alkylthio-N-Arylsulphonyl-Amino-2-Pyridones: Reaction of Ketene-SS-Acetals With Arylsulphonylhydrazides", Phosphorous, Sulfur and Silicon and the Related Elements (2001), 170, pp. 171-179.
STN Search Results including CAS Registry Nos. (RN): 1018564-99-2, 1018564-95-8, 1018564-87-8, 1018497-28-3, 1018497-20-5, 1018497-18-1, 1018497-16-9, 1018497-14-7, 1018497-12-5, 1018497-10-3, 1018274-50-4, 1018249-54-1, 1018249-46-1, 908069-44-3, 908068-91-7, 908069-29-4, 907970-80-3.
Extended European Search Report issued Aug. 5, 2016 in corresponding European Application No. 14773826.4.
Brian W. Dymock et al., "Inhibitors of JAK2 and JAK3: an update on the patent literature 2010-2012", Expert Opinion on Therapeutic Patents, vol. 23, No. 4, (2013), pp. 449-501.

\* cited by examiner

*Primary Examiner* — Niloofar Rahmani
(74) *Attorney, Agent, or Firm* — Wenderoth, Lind & Ponack, L.L.P.

(57) ABSTRACT

Provided is a compound or a salt thereof, which has an excellent JAK inhibitory action, and is useful as a prophylactic or therapeutic agent for autoimmune diseases (rheumatoid arthritis, psoriasis, inflammatory bowel disease, Sjogren's syndrome, Behcet's syndrome, multiple sclerosis, systemic lupus erythematosus, etc.), cancer (leukemia, uterine leiomyosarcoma, prostate cancer, multiple myeloma, cachexia, myelofibrosis, etc.) and the like. The present invention relates to a compound represented by the formula (I)

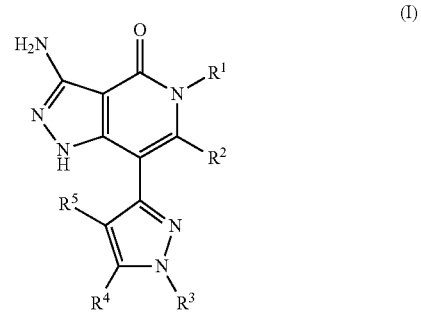

wherein each symbol is as defined in the present specification, or a salt thereof.

6 Claims, No Drawings

HETEROCYCLIC COMPOUND

TECHNICAL FIELD

The present invention relates to a heterocyclic compound having a Janus kinase (In the present specification, sometimes to be abbreviated as "JAK") inhibitory action, which is useful as an agent for the treatment of autoimmune diseases (rheumatoid arthritis, psoriasis, inflammatory bowel disease, Sjogren's syndrome, Behcet's syndrome, multiple sclerosis, systemic lupus erythematosus, etc.), cancer (leukemia, uterine leiomyosarcoma, prostate cancer, multiple myeloma, cachexia, myelofibrosis, etc.) and the like, a pharmaceutical composition containing thereof, and the like.

BACKGROUND OF THE INVENTION

Cytokines are proteins secreted by a cell of the immune system and transduce a signal to a specific cell. Cytokines have various kinds, and many of them are especially associated with immunity and inflammation and also associated with cell proliferation, cell differentiation, cell death, wound healing and the like (Curr Opin Cell Biol. 1991 April; 3(2):171-5.).

The Janus kinase (JAK) family plays a role in cytokine-dependent regulation of the function of cells associated with growth and immune response. JAK family consists of four kinds of Janus kinases (JAK1 (Janus kinase 1), JAK2 (Janus kinase 2), JAK3 (Janus kinase 3) and TYK2 (tyrosine kinase 2)). Among them, JAK1 is known to be involved in signal transduction of cytokines such as IL(interleukin)-2, IL-4, IL-7, IL-15, IL-21, IL-6, OSM (oncostatin M), IL-10 family, IFN(interferon)-α, IFN-β, IFN-γ and the like (Nature Immunology 10, 356-360 (2009)). TYK2 is known to be involved in signal transduction of cytokines such as IFN-α, IFN-β, IL-6, IL-10 family (IL-10, IL-19, IL-20, IL-22, IL-28, IL-29), IL-12, IL-23 and the like (Nature Immunology 10, 356-360 (2009), New York Academy of Science 1246, 34-40 (2011)). In addition, these cytokines play an important role in immune response when exist in an appropriate amount. However, excessive production of them is involved in many autoimmune diseases such as rheumatoid arthritis, psoriasis, inflammatory bowel disease, Sjogren's syndrome, Behcet's syndrome, multiple sclerosis, systemic lupus erythematosus and the like (Journal of Allergy and Clinical Immunology 127, 3, 701-721.e70 (2011), Cytokine & Growth Factor Reviews 19, 41-52 (2008), Invest Ophthalmol Vis Sci. 2008 July; 49(7):3058-3064, Ann Rheum Dis. 2010 July; 69(7): 1325-1328).

Tocilizumab, which is an anti-IL-6 receptor monoclonal antibody, has been approved as a therapeutic drug for rheumatoid arthritis in Japan, Europe and the United States, and furthermore, clinical trials for various diseases in which the IL-6 signaling pathway is suggested to be involved are performed. From the foregoing, a JAK1 inhibitor can be a therapeutic drug for various autoimmune diseases such as rheumatoid arthritis, psoriasis, inflammatory bowel disease, Sjogren's syndrome, Behcet's syndrome, multiple sclerosis, systemic lupus erythematosus and the like (Clinical Science 122, 143-159 (2012)).

Moreover, JAK signal is also associated with differentiation and growth of various carcinoma cells (Trends Biochem. Sci. 33, 122-131 (2008)). Particularly, JAK1 is associated with leukemia and uterine leiomyosarcoma due to the constant activation therein (J Exp Med 205, 751-758 (2008), Oncogene 25, 4016-4026, (2006)). In addition, clinical trials of antibody and low molecule compound which target at IL-6 are performed for cancer diseases such as prostate cancer, multiple myeloma, cachexia, myelofibrosis and the like (Clinical Science 122, 143-159 (2012), The New England Journal of Medicine 363, 1117-1127 (2010)). From the foregoing, a JAK1 inhibitor can be a therapeutic drug for cancer diseases such as leukemia, uterine leiomyosarcoma, prostate cancer, multiple myeloma, cachexia, myelofibrosis and the like.

Ustekinumab, which is an anti-IL-12/23 monoclonal antibody, has been approved as a therapeutic drug for moderate to severe psoriasis patient in Europe, and furthermore, clinical trials for various diseases in which the IL-12/23 signaling pathway is suggested to be involved are performed (J Immunol. 2010 May 1; 184 (9): 4605-9). In addition, involvement of IL-23 signal pathway in the central nervous system diseases such as Alzheimer's disease (e.g., dementia of Alzheimer type and the like) and the like has also been suggested (Nat Med. 2012 December; 18(12):1812-9). In view of the above, a TYK2 inhibitor can be a therapeutic drug for various autoimmune diseases such as rheumatoid arthritis, psoriasis, inflammatory bowel disease, Sjogren's syndrome, Behcet's syndrome, multiple sclerosis, systemic lupus erythematosus and the like, or a therapeutic drug for central nervous system diseases such as Alzheimer's disease (e.g., dementia of Alzheimer type and the like) and the like (Front Biosci. 2011 Jun. 1; 17:3214-32).

Examples of the compound having a structure similar to the compound described in the present specification include the following compounds.

(1) A compound represented by the following formula:

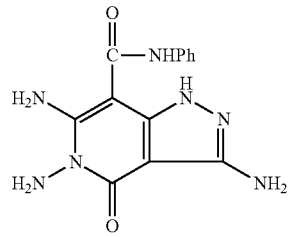

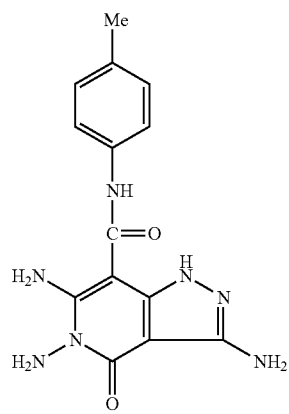

-continued
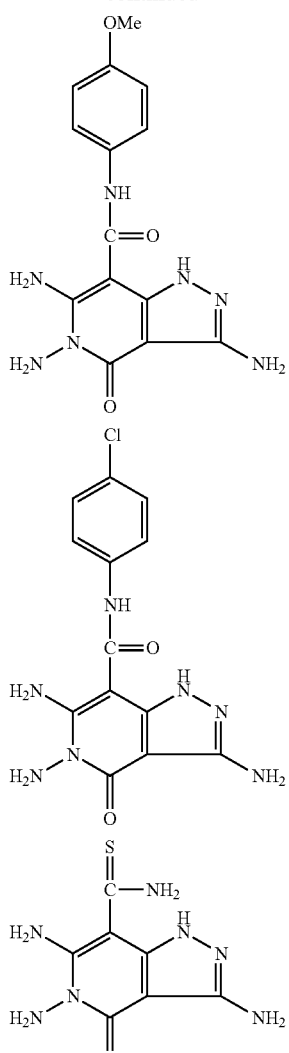
(non-patent document 1).
(2) A compound represented by the following formula:
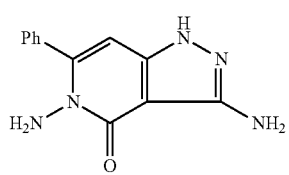 [SMILES: Nc1n[nH]c2cc(-c3ccccc3)n(N)c(=O)c12]
(non-patent document 2).
(3) A compound represented by the following formula:
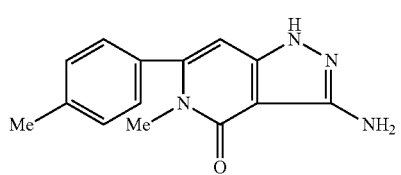
-continued
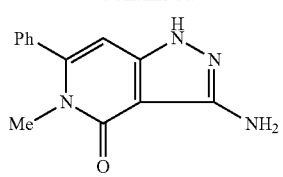
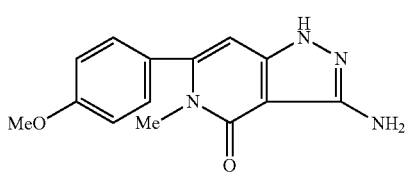
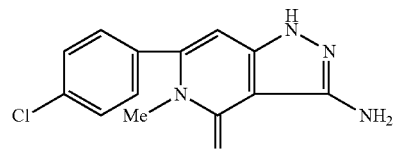
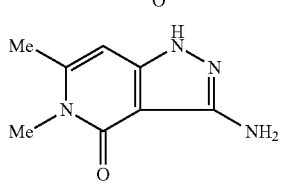
(non-patent document 3).
(4) A compound represented by the following formula:
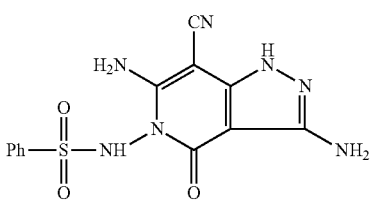
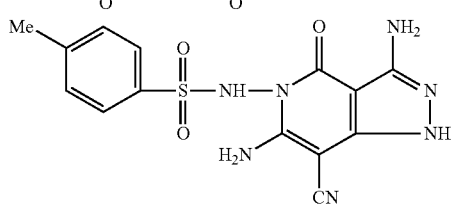
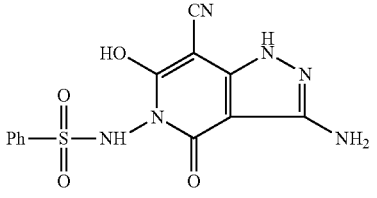
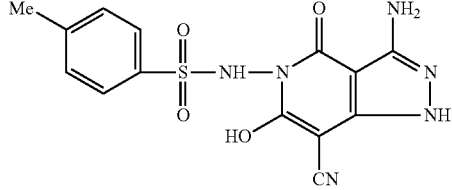

-continued
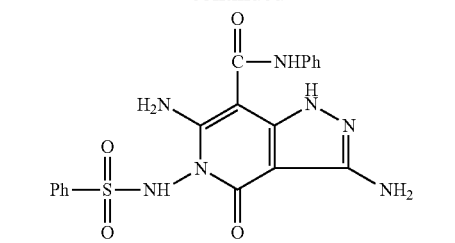
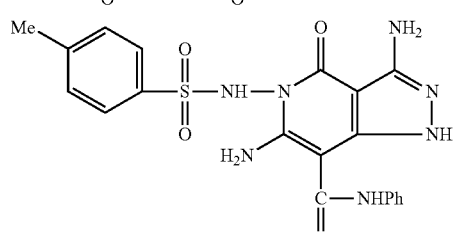
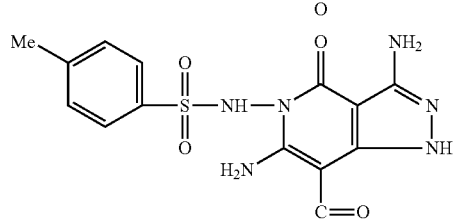
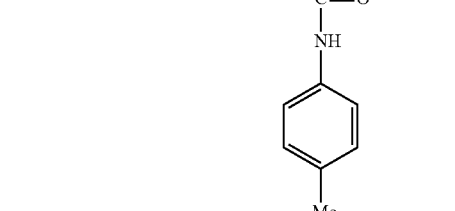
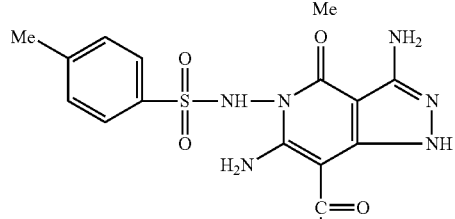
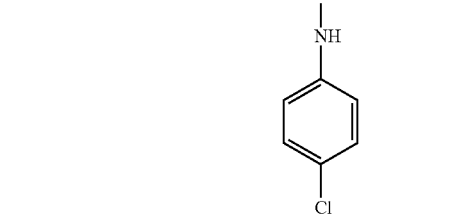
-continued
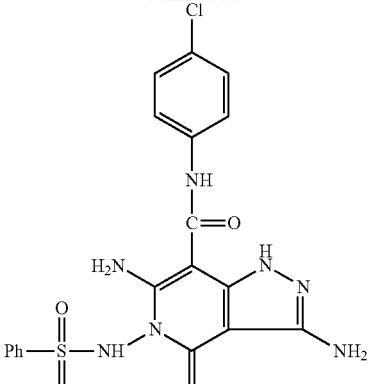
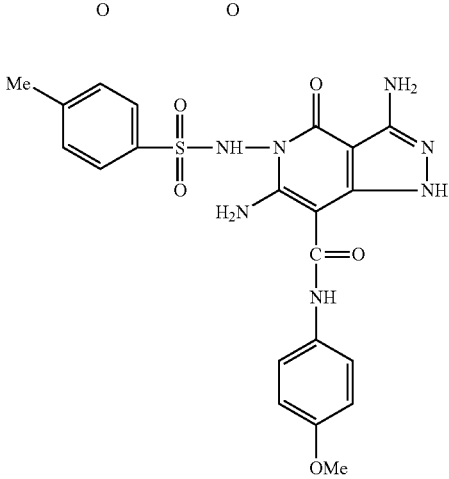
(non-patent document 4).
(5) The following compounds are registered in Chemical Abstract.
1) Registry Number: 1018564-99-2
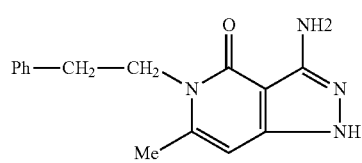 [SMILES: Cc1cc2[nH]nc(N)c2c(=O)n1CCc1ccccc1]
2) Registry Number: 1018564-95-8
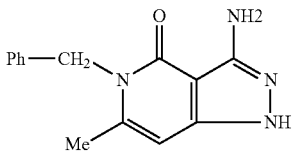 [SMILES: Cc1cc2[nH]nc(N)c2c(=O)n1Cc1ccccc1]
3) Registry Number: 1018564-87-8
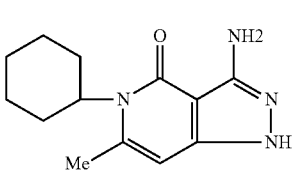 [SMILES: Cc1cc2[nH]nc(N)c2c(=O)n1C1CCCCC1]

4) Registry Number: 1018497-28-3
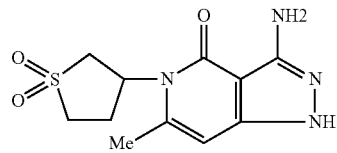 [SMILES: Cc1cc2[nH]nc(N)c2c(=O)n1C1CCS(=O)(=O)C1]
5) Registry Number: 1018497-20-5
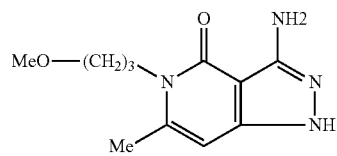
6) Registry Number: 1018497-18-1
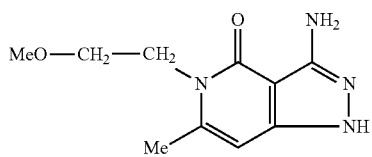 [SMILES: COCCn1c(C)cc2[nH]nc(N)c2c1=O]
7) Registry Number: 1018497-16-9
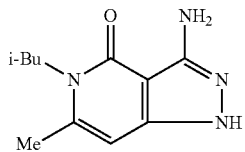
8) Registry Number: 1018497-14-7
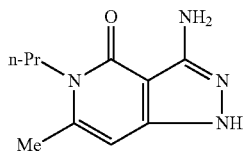
9) Registry Number: 1018497-12-5
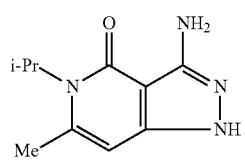
10) Registry Number: 1018497-10-3
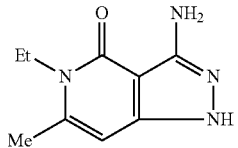
11) Registry Number: 1018274-50-4
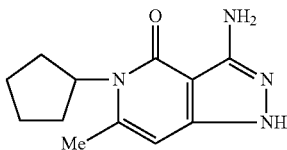 [SMILES: Cc1cc2[nH]nc(N)c2c(=O)n1C1CCCC1]
12) Registry Number: 1018249-54-1
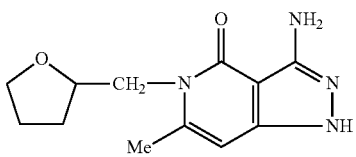 [SMILES: Cc1cc2[nH]nc(N)c2c(=O)n1CC1CCCO1]
13) Registry Number: 1018249-46-1
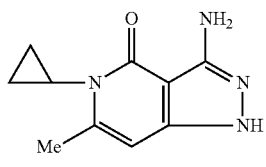 [SMILES: Cc1cc2[nH]nc(N)c2c(=O)n1C1CC1]
14) Registry Number: 1018497-28-3
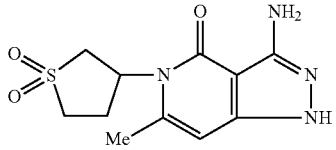
15) Registry Number: 908069-44-3
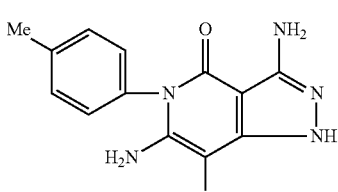

16) Registry Number: 908068-91-7

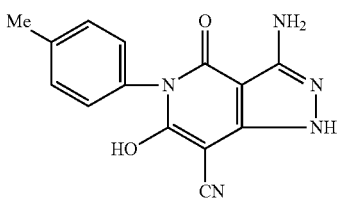 [SMILES: Cc1ccc(-n2c(O)c(C#N)c3[nH]nc(N)c3c2=O)cc1]

17) Registry Number: 908069-29-4

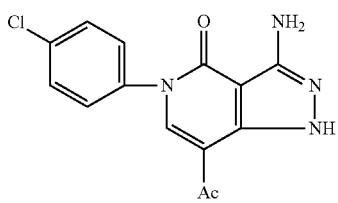 [SMILES: CC(=O)c1cn(-c2ccc(Cl)cc2)c(=O)c2c(N)n[nH]c12]

18) Registry Number: 907970-80-3

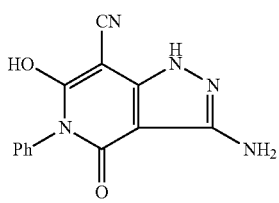 [SMILES: N#Cc1c(O)n(-c2ccccc2)c(=O)c2c(N)n[nH]c12]

DOCUMENT LIST

Non-Patent Documents non-patent document 1: Journal of the Chemical Society, Perkin Transactions 1: Organic and Bio-Organic Chemistry (1997), (21), 3285-3290
non-patent document 2: Chemical & Pharmaceutical Bulletin (1984), 32(9), 3384-95 CODEN: CPBTAL; ISSN: 0009-2363
non-patent document 3: Journal of the Chemical Society, Perkin Transactions 1: Organic and Bio-Organic Chemistry (1972-1999) (1978), (8), 857-62
non-patent document 4: Phosphorus, Sulfur and Silicon and the Related Elements (2001), 170, 171-179

SUMMARY OF THE INVENTION

Problems to be Solved by the Invention

An object of the present invention is to provide a compound having an excellent JAK inhibitory action, which is useful as an agent for the prophylaxis or treatment of autoimmune disease (rheumatoid arthritis, psoriasis, inflammatory bowel disease, Sjogren's syndrome, Behcet's syndrome, multiple sclerosis, systemic lupus erythematosus, etc.), cancer (leukemia, uterine leiomyosarcoma, prostate cancer, multiple myeloma, cachexia, myelofibrosis, etc.) and the like.

Means of Solving the Problems

The present inventors have conducted intensive studies in an attempt to solve the above-mentioned problem and found that a compound represented by the following formula (I) has an excellent JAK inhibitory action, which resulted in the completion of the present invention.

Therefore, the present invention provides the following.
[1] A compound represented by the formula (I):

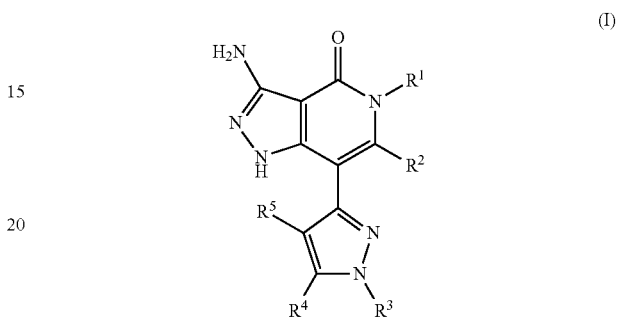

(I)

wherein
$R^1$ is an optionally substituted $C_{1-6}$ alkyl group, or an optionally substituted cyclic group;
$R^2$ is a hydrogen atom or a cyano group;
$R^3$ is an optionally substituted $C_{1-3}$ alkyl group;
$R^4$ is a substituent; and
$R^5$ is a hydrogen atom, a halogen atom, a cyano group, an optionally substituted $C_{1-6}$ alkyl group, an optionally substituted $C_{1-6}$ alkoxy group, or an acyl group, or a salt thereof (hereinafter to be also referred to as compound (I)).
[2] The compound of the above-mentioned [1], wherein $R^1$ is
(1) a $C_{1-6}$ alkyl group optionally substituted by 1 to 5 substituents selected from
  (a) a halogen atom,
  (b) a $C_{3-8}$ cycloalkyl group optionally substituted by 1 to 3 $C_{1-6}$ alkyl groups,
  (c) an oxetanyl group optionally substituted by 1 to 3 $C_{1-6}$ alkyl groups,
  (d) a $C_{1-6}$ alkoxy-carbonyl group,
  (e) a carbamoyl group,
  (f) a hydroxy group, and
  (g) a cyano group,
(2) a $C_{3-10}$ cycloalkyl group optionally substituted by 1 to 3 $C_{1-6}$ alkyl groups, or
(3) a $C_{6-14}$ aryl group optionally substituted by 1 to 3 substituents selected from
  (a) a halogen atom,
  (b) a $C_{1-6}$ alkyl group optionally substituted by 1 to 3 halogen atoms, and
  (c) a cyano group;
$R^2$ is a hydrogen atom or a cyano group;
$R^3$ is a $C_{1-3}$ alkyl group optionally substituted by 1 to 3 substituents selected from a halogen atom and a $C_{1-6}$ alkoxy group;
$R^4$ is
(1) a $C_{1-6}$ alkyl group optionally substituted by 1 to 3 substituents selected from
  (a) a halogen atom,
  (b) a cyano group,
  (c) a hydroxy group, (d) an amino group optionally mono- or di-substituted by $C_{1-6}$ alkyl-carbonyl group(s),
(e) a carbamoyl group optionally mono- or di-substituted by $C_{1-6}$ alkyl group(s), and
(f) a $C_{1-6}$ alkoxy group,
(2) a $C_{3-10}$ cycloalkyl group,
(3) a $C_{6-14}$ aryl group optionally substituted by 1 to 3 substituents selected from
(a) a $C_{1-6}$ alkyl group,
(b) an amino group optionally mono- or di-substituted by $C_{1-6}$ alkyl group(s), and
(c) a carbamoyl group optionally mono- or di-substituted by $C_{1-6}$ alkyl group(s),
(4) a 5- or 6-membered non-aromatic heterocyclic group having one oxygen atom,
(5) a pyrazolyl group, a pyridyl group, a pyrimidinyl group or a pyrazinyl group, each of which is optionally substituted by 1 to 3 $C_{1-6}$ alkyl groups,
(6) a $C_{1-6}$ alkoxy group optionally substituted by 1 to 3 halogen atoms,
(7) a halogen atom,
(8) a cyano group,
(9) a group represented by the formula:

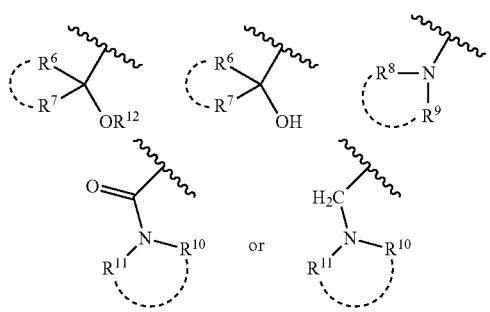

wherein
$R^6$ and $R^7$ are each independently a $C_{1-6}$ alkyl group; or
$R^6$ and $R^7$ form, together with the adjacent carbon atom, cyclobutane, cyclohexane, azetidine, tetrahydropyran or tetrahydrothiopyran, each of which is optionally substituted by 1 to 3 substituents selected from a halogen atom, a carbamoyl group optionally mono- or di-substituted by $C_{1-6}$ alkyl group(s), a $C_{1-6}$ alkyl-carbonyl group, a $C_{1-6}$ alkylsulfonyl group and an oxo group;
$R^{12}$ is a $C_{1-6}$ alkyl group;
$R^8$ and $R^9$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group, or
(xii) a 5- or 6-membered non-aromatic heterocyclic group having one oxygen atom; or
$R^8$ and $R^9$ form, together with the adjacent nitrogen atom,
(i) an aromatic nitrogen-containing heterocycle optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom, or
(ii) a non-aromatic nitrogen-containing heterocycle optionally forming a fused ring, a bridged ring or a spiro ring, which is optionally substituted by 1 to 5 substituents selected from
(a) a $C_{1-6}$ alkyl group optionally substituted by 1 to 3 substituents selected from
(A) a halogen atom,
(B) a hydroxy group,
(C) a cyano group,
(D) a $C_{1-6}$ alkylsulfonyl group,
(E) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group and a $C_{1-6}$ alkylsulfonyl group,
(F) a $C_{1-6}$ alkoxy group,
(G) azetidinyl group, pyrrolidinyl group, piperidyl group or morpholinyl group, each of which is optionally substituted by 1 to 3 substituents selected from a halogen atom and an oxo group, and
(H) a pyrazolyl group,
(b) a hydroxy group,
(c) a $C_{1-6}$ alkoxy group optionally substituted by 1 to 3 halogen atoms,
(d) a halogen atom,
(e) a $C_{1-6}$ alkyl-carbonyl group,
(f) a $C_{1-6}$ alkoxy-$C_{1-6}$ alkyl-carbonyl group,
(g) an oxo group,
(h) a $C_{1-6}$ alkylsulfonyl group,
(i) a $C_{3-10}$ cycloalkylsulfonyl group,
(j) an amino group optionally mono- or di-substituted by $C_{1-6}$ alkyl group(s), and
(k) a cyano group;
$R^{10}$ and $R^{11}$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group optionally substituted by 1 to 3 halogen atoms, (x) a carbamoyl group optionally mono- or di-substituted by $C_{1-6}$ alkyl group(s) optionally substituted by 1 to 3 halogen atoms,
(xi) an aromatic heterocyclic group, or
(xii) a 5- or 6-membered non-aromatic heterocyclic group having one oxygen atom; or $R^{10}$ and $R^{11}$ form, together with the adjacent nitrogen atom,
(i) an aromatic nitrogen-containing heterocycle optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom, or
(ii) a non-aromatic nitrogen-containing heterocycle optionally forming a fused ring or a spiro ring, which is optionally substituted by 1 to 3 substituents selected from
  (a) a $C_{1-6}$ alkyl group optionally substituted by 1 to 3 substituents selected from a halogen atom, a hydroxy group and a $C_{1-6}$ alkoxy group,
  (b) a hydroxy group,
  (c) a $C_{1-6}$ alkoxy group optionally substituted by 1 to 3 halogen atoms,
  (d) a halogen atom,
  (e) a $C_{1-6}$ alkyl-carbonyl group,
  (f) a $C_{1-6}$ alkoxy-$C_{1-6}$ alkyl-carbonyl group, and
  (g) an oxo group, or
(10) a $C_{3-8}$ cycloalkenyl group; and
$R^5$ is a hydrogen atom, or a salt thereof.

[3] 3-Amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one or a salt thereof.

[4] 3-Amino-5-(dicyclopropylmethyl)-7-(1-methyl-5-(morpholin-4-yl)-1H-pyrazol-3-yl)-1,5-dihydro-4H-pyrazolo[4,3-c]pyridin-4-one or a salt thereof.

[5] 3-Amino-5-(dicyclopropylmethyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one or a salt thereof.

[6] A medicament comprising the compound or salt of the above-mentioned [1].

[7] The medicament of the above-mentioned [6], which is a Janus kinase inhibitor.

[8] The medicament of the above-mentioned [6], which is an agent for the prophylaxis or treatment of autoimmune disease.

[9] The medicament of the above-mentioned [8], wherein the autoimmune disease is systemic lupus erythematosus, inflammatory bowel disease, psoriasis, rheumatoid arthritis, Sjogren's syndrome, Behcet's syndrome, or multiple sclerosis.

[10] The compound or salt of the above-mentioned [1] for use in the prophylaxis or treatment of autoimmune disease.

[11] The compound or salt of the above-mentioned [10], wherein the autoimmune disease is systemic lupus erythematosus, inflammatory bowel disease, psoriasis, rheumatoid arthritis, Sjogren's syndrome, Behcet's syndrome, or multiple sclerosis.

[12] A method of inhibiting Janus kinase in a mammal, which comprises administering an effective amount of the compound or salt of the above-mentioned [1] to the mammal.

[13] A method for the prophylaxis or treatment of autoimmune disease, which comprises administering an effective amount of the compound or salt of the above-mentioned [1] to the mammal.

[14] The treatment method of the above-mentioned [13], wherein the autoimmune disease is systemic lupus erythematosus, inflammatory bowel disease, psoriasis, rheumatoid arthritis, Sjogren's syndrome, Behcet's syndrome, or multiple sclerosis.

[15] Use of the compound or salt of the above-mentioned [1] for the production of an agent for the prophylaxis or treatment of autoimmune disease.

[16] Use of the above-mentioned [15], wherein the autoimmune disease is systemic lupus erythematosus, inflammatory bowel disease, psoriasis, rheumatoid arthritis, Sjogren's syndrome, Behcet's syndrome, or multiple sclerosis.

Effect of the Invention

Compound (I) has an excellent JAK inhibitory action, and is useful as a prophylactic or therapeutic agent for autoimmune diseases (systemic lupus erythematosus, inflammatory bowel diseases (Crohn's disease, ulcerative colitis etc.), psoriasis, rheumatoid arthritis, Sjogren's syndrome, Behcet's syndrome, multiple sclerosis etc.), cancer (leukemia, uterine leiomyosarcoma, prostate cancer, multiple myeloma, cachexia, myelofibrosis etc.) and the like.

DETAILED DESCRIPTION OF THE INVENTION

In the present specification, the "halogen atom" means a fluorine atom, a chlorine atom, a bromine atom or an iodine atom.

In the present specification, the "$C_{1-3}$ alkyl (group)" means, for example, methyl, ethyl, propyl or isopropyl.

In the present specification, the "$C_{1-6}$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, 1,2-dimethylpropyl or the like.

In the present specification, the "$C_{1-10}$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl or the like. Of these, a $C_{1-6}$ alkyl group is preferable.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{2-10}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl or the like. Of these, a $C_{2-6}$ alkenyl group is preferable.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "$C_{1-6}$ alkylsulfonyl (group)" means, for example, methylsulfonyl, ethylsulfonyl, propylsulfonyl, isopropylsulfonyl, butylsulfonyl, isobutylsulfonyl, tert-butylsulfonyl or the like.

In the present specification, the "$C_{3-6}$ cycloalkyl (group)" means, for example, cyclopropyl, cyclobutyl, cyclopentyl and cyclohexyl or the like.

In the present specification, the "$C_{3-8}$ cycloalkyl (group)" means, for example, cyclopropyl, cyclobutyl, cyclopentyl, cyclohexyl, cycloheptyl, cyclooctyl or the like. Of these, a $C_{3-6}$ cycloalkyl group is preferable.

In the present specification, the "$C_{3-10}$ cycloalkyl (group)" means, for example, cyclopropyl, cyclobutyl, cyclopentyl, cyclohexyl, cycloheptyl, cyclooctyl, cyclononyl, cyclodecyl or the like. Of these, a $C_{3-6}$ cycloalkyl group is preferable.

In the present specification, the "$C_{3-6}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like. Of these, a $C_{3-6}$ cycloalkenyl group is preferable.

In the present specification, the "$C_{3-10}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl (e.g., 2-cyclohepten-1-yl, 3-cyclohepten-1-yl), cyclooctenyl (e.g., 2-cycloocten-1-yl, 3-cycloocten-1-yl) or the like. Of these, a $C_{3-6}$ cycloalkenyl group is preferable.

In the present specification, the "$C_{4-10}$ cycloalkadienyl (group)" means, for example, 2,4-cyclopentadien-1-yl, 2,4-cyclohexadien-1-yl, 2,5-cyclohexadien-1-yl or the like. Of these, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In addition, the above-mentioned $C_{3-10}$ cycloalkyl group, $C_{3-10}$ cycloalkenyl group and $C_{4-10}$ cycloalkadienyl group may each form a spiro ring group with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{3-10}$ cycloalkylsulfonyl group" means, for example, cyclopropylsulfonyl, cyclobutylsulfonyl, cyclopentylsulfonyl, cyclohexylsulfonyl, cycloheptylsulfonyl, cyclooctylsulfonyl, cyclononylsulfonyl, cyclodecylsulfonyl or the like. Of these, a $C_{3-6}$ cycloalkylsulfonyl group is preferable.

In the present specification, the "$C_{6-14}$ aryl (group)" means, for example, phenyl, 1-naphthyl, 2-naphthyl or the like. Of these, a $C_{6-10}$ aryl group is preferable.

In the present specification, the "$C_{6-14}$ aryloxy (group)" means, for example, phenoxy, 1-naphthyloxy, 2-naphthyloxy or the like.

In the present specification, the "$C_{7-14}$ aralkyl (group)" means, for example, benzyl, phenethyl or the like.

In the present specification, the "$C_{7-14}$ aralkyloxy (group)" means, for example, benzyloxy, phenethyloxy or the like.

In the present specification, the "$C_{8-13}$ arylalkenyl (group)" means, for example, styryl or the like.

In the present specification, the "heterocyclic group" means an aromatic heterocyclic group or a non-aromatic heterocyclic group.

In the present specification, the "aromatic heterocyclic group" means a monocyclic aromatic heterocyclic group or a fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, an (optionally oxidized) sulfur atom and an (optionally oxidized) nitrogen atom, for example, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include 8- to 21-membered fused aromatic heterocyclic groups, specifically, a group derived from a fused ring wherein a ring corresponding to the above-mentioned 5- to 7-membered monocyclic aromatic heterocyclic group is fused with a $C_{6-14}$ aromatic hydrocarbon; and a group derived from a fused ring wherein rings corresponding to the above-mentioned 5- to 7-membered monocyclic aromatic heterocyclic groups are fused, for example, quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group or a fused non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, an (optionally oxidized) sulfur atom and an (optionally oxidized) nitrogen atom, for example, azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), dihydropyranyl (e.g., dihydropyran-3-yl, dihydropyran-4-yl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

In the present specification, examples of the "fused non-aromatic heterocyclic group" include an 8- to 22-membered (preferably 8- to 12-membered) fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated, for example, dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

In the present specification, examples of the "$C_{6-14}$ aromatic hydrocarbon" include benzene and naphthalene.

Each symbol in the formula (I) is explained below.

$R^1$ in the formula (I) is an optionally substituted $C_{1-6}$ alkyl group, or an optionally substituted cyclic group.

The "$C_{1-6}$ alkyl group" of the "optionally substituted $C_{1-6}$ alkyl group" for $R^1$ optionally has 1 to 5 (preferably 1 to 3) substituents at substitutable position(s). Examples of the substituent include substituents selected from the following Substituent Group A. When a plurality of substituents are present, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally substituted by 1 to 3 halogen atoms,
  (d) a $C_{3-8}$ cycloalkenyl group optionally substituted by 1 to 3 halogen atoms,
  (e) a $C_{6-14}$ aryl group optionally substituted by 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally substituted by 1 to 3 halogen atoms;
(9) a $C_{2-6}$ alkynyloxy group (e.g., ethynyloxy, propynyloxy, butynyloxy, pentynyloxy, hexynyloxy) optionally substituted by 1 to 3 halogen atoms;
(10) a $C_{3-8}$ cycloalkyloxy group (e.g., cyclopropyloxy, cyclobutyloxy, cyclopentyloxy, cyclohexyloxy) optionally substituted by 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally substituted by 1 to 3 halogen atoms;
(12) a $C_{6-14}$ aryloxy group optionally substituted by 1 to 3 halogen atoms;
(13) a $C_{7-14}$ aralkyloxy group optionally substituted by 1 to 3 halogen atoms;
(14) a carbamoyl group optionally mono- or di-substituted by substituent(s) selected from
  (a) a $C_{1-6}$ alkyl group,
  (b) a $C_{3-8}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(15) a sulfamoyl group optionally mono- or di-substituted by substituent(s) selected from
  (a) a $C_{1-6}$ alkyl group,
  (b) a $C_{3-8}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(16) formyl;
(17) a $C_{1-6}$ alkyl-carbonyl group optionally substituted by 1 to 3 $C_{1-6}$ alkoxy groups;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, 3-cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) a 8- to 12-membered fused non-aromatic heterocyclylcarbonyl group (e.g., dihydrobenzofuranylcarbonyl);
(30) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{3-8}$ cycloalkyl-carbonyl group,
  (d) a $C_{6-14}$ aryl-carbonyl group optionally substituted by 1 to 3 halogen atoms,
  (e) a 5- or 6-membered monocyclic aromatic heterocyclcarbonyl group,
  (f) a 8- to 12-membered fused aromatic heterocyclylcarbonyl group, (g) a 3- to 8-membered monocyclic non-aromatic heterocyclylcarbonyl group, and
(h) a 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl) optionally substituted by 1 to 3 substituents selected from
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl, morpholinyl) optionally substituted by 1 to 3 substituents selected from
(a) a halogen atom,
(b) a $C_{1-6}$ alkyl group optionally substituted by 1 to 3 halogen atoms or hydroxy groups,
(c) a $C_{1-6}$ alkoxy group optionally substituted by 1 to 3 halogen atoms, and
(d) an oxo group;
(64) a 8- to 12-membered fused non-aromatic heterocyclic group (e.g., dihydrobenzofuranyl) optionally substituted by 1 to 3 substituents selected from
(a) a halogen atom,
(b) a $C_{1-6}$ alkyl group optionally substituted by 1 to 3 halogen atoms,
(c) a $C_{1-6}$ alkoxy group optionally substituted by 1 to 3 halogen atoms, and
(d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, tert-butoxycarbonyl);
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);

(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthiocarbamoyl group (e.g., methylthiocarbamoyl, ethylthiocarbamoyl, propylthiocarbamoyl);
(80) a di-$C_{1-6}$ alkylthiocarbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

Examples of the "cyclic group" of the "optionally substituted cyclic group" for $R^1$ include a $C_{3-10}$ cycloalkyl group, a $C_{3-10}$ cycloalkenyl group, a $C_{4-10}$ cycloalkadienyl group, a $C_{6-14}$ aryl group and a heterocyclic group.

The "cyclic group" of the "optionally substituted cyclic group" for $R^1$ optionally has 1 to 5 (preferably 1 to 3) substituents at substitutable position(s). Examples of such substituent include the substituents selected from the following Substituent Group B. When a plurality of substituents are present, the respective substituents may be the same or different.

Substituent Group B:
(1) the aforementioned Substituent Group A;
(2) a $C_{1-6}$ alkyl group optionally substituted by 1 to 3 substituents selected from
  (a) a halogen atom,
  (b) a cyano group,
  (c) a hydroxy group,
  (d) a $C_{3-10}$ cycloalkyl group optionally substituted by 1 to 3 substituents selected from
    (i) a halogen atom,
    (ii) a cyano group, and
    (iii) a $C_{1-6}$ alkyl group optionally substituted by 1 to 3 halogen atoms;
  (e) a $C_{6-14}$ aryl group optionally substituted by 1 to 3 substituents selected from
    (i) a halogen atom,
    (ii) a cyano group, and
    (iii) a $C_{1-6}$ alkyl group optionally substituted by 1 to 3 halogen atoms,
  (f) a $C_{1-6}$ alkoxy group optionally substituted by 1 to 3 halogen atoms,
  (g) an amino group optionally mono- or di-substituted by $C_{1-6}$ alkyl group(s) or $C_{1-6}$ alkyl-carbonyl group(s),
  (h) a 5- or 6-membered monocyclic aromatic heterocyclic group,
  (i) a 8- to 12-membered fused aromatic heterocyclic group,
  (j) a 3- to 8-membered monocyclic non-aromatic heterocyclic group,
  (k) a 8- to 12-membered fused non-aromatic heterocyclic group,
  (l) a carboxy group
  (m) a $C_{1-6}$ alkoxy-carbonyl group optionally substituted by 1 to 3 halogen atoms, and
  (n) a $C_{1-6}$ alkylsulfonyl group (e.g., methylsulfonyl, ethylsulfonyl, propylsulfonyl, isopropylsulfonyl, butylsulfonyl, isobutylsulfonyl, tert-butylsulfonyl);
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl group(s),
  (e) a carboxy group, and
  (f) a $C_{1-6}$ alkoxy-carbonyl group;
(4) a $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms; and
(5) an oxo group.

$R^1$ is preferably an optionally substituted $C_{1-6}$ alkyl group, an optionally substituted $C_{3-10}$ cycloalkyl group, or an optionally substituted $C_{6-14}$ aryl group.

A more preferable embodiment of $R^1$ is
(1) a $C_{1-6}$ alkyl group (e.g., methyl, ethyl, propyl, isopropyl, isobutyl, 1,2-dimethylpropyl, 1,2,2-trimethylpropyl) optionally substituted by 1 to 5 substituents selected from
  (a) a halogen atom (e.g., fluorine atom),
  (b) a $C_{3-8}$ cycloalkyl group (e.g., cyclopropyl, cyclobutyl) optionally substituted by 1 to 3 $C_{1-6}$ alkyl groups (e.g., methyl),
  (c) an oxetanyl group optionally substituted by 1 to 3 $C_{1-6}$ alkyl groups (e.g., methyl),
  (d) a $C_{1-6}$ alkoxy-carbonyl group (e.g., ethoxycarbonyl),
  (e) a carbamoyl group,
  (f) a hydroxy group, and
  (g) a cyano group,
(2) a $C_{3-10}$ cycloalkyl group (e.g., cyclopentyl, cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
  (a) a halogen atom (e.g., fluorine atom, chlorine atom),
  (b) a $C_{1-6}$ alkyl group (e.g., methyl) optionally substituted by 1 to 3 halogen atoms (e.g., fluorine atom), and
  (c) a cyano group.

A further preferable embodiment of $R^1$ is
(1) a $C_{1-6}$ alkyl group (e.g., methyl, ethyl, propyl, isopropyl, isobutyl, 1,2-dimethylpropyl) optionally substituted by 1 to 5 substituents selected from
  (a) a halogen atom (e.g., fluorine atom),
  (b) a $C_{3-8}$ cycloalkyl group (e.g., cyclopropyl) optionally substituted by 1 to 3 $C_{1-6}$ alkyl groups (e.g., methyl),
  (c) a $C_{1-6}$ alkoxy-carbonyl group (e.g., ethoxycarbonyl),
  (d) a carbamoyl group,
  (e) a hydroxy group, and
  (f) a cyano group,
(2) a $C_{3-10}$ cycloalkyl group (e.g., cyclopentyl, cyclohexyl) optionally substituted by 1 to 3 $C_{1-6}$ alkyl groups (e.g., methyl) or
(3) a $C_{6-14}$ aryl group (e.g., phenyl) optionally substituted by 1 to 3 substituents selected from (a) a halogen atom (e.g., fluorine atom, chlorine atom),
(b) a $C_{1-6}$ alkyl group (e.g., methyl) optionally substituted by 1 to 3 halogen atoms (e.g., fluorine atom), and
(c) a cyano group.

Another more preferable embodiment of $R^1$ is
(1) a $C_{1-6}$ alkyl group (e.g., methyl, ethyl, propyl, isopropyl, isobutyl, 1,2-dimethylpropyl) optionally substituted by 1 to 5 substituents selected from
  (a) a halogen atom (e.g., fluorine atom),
  (b) a $C_{3-8}$ cycloalkyl group (e.g., cyclopropyl) optionally substituted by 1 to 3 $C_{1-6}$ alkyl groups (e.g., methyl),
  (c) a $C_{1-6}$ alkoxy-carbonyl group (e.g., ethoxycarbonyl), and
  (d) a carbamoyl group,
(2) a $C_{3-10}$ cycloalkyl group (e.g., cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
  (a) a halogen atom (e.g., fluorine atom, chlorine atom),
  (b) a $C_{1-6}$ alkyl group (e.g., methyl) optionally substituted by 1 to 3 halogen atoms (e.g., fluorine atom), and
  (c) a cyano group.

Another more preferable embodiment of $R^1$ is
(1) a $C_{1-6}$ alkyl group (e.g., methyl, ethyl, propyl, isopropyl, isobutyl, 1,2-dimethylpropyl) optionally substituted by 1 or 2 $C_{3-8}$ cycloalkyl groups (e.g., cyclopropyl), or
(2) a $C_{3-10}$ cycloalkyl group (e.g., cyclohexyl) optionally substituted by 1 to 3 $C_{1-6}$ alkyl groups (e.g., methyl).

Another more preferable embodiment of $R^1$ is 1,2-dimethylpropyl, 1-cyclopropylethyl, dicyclopropylmethyl or 2-methylcyclohexyl.

$R^2$ in the formula (I) is a hydrogen atom or a cyano group.
$R^2$ is preferably a hydrogen atom.

$R^3$ in the formula (I) is an optionally substituted $C_{1-3}$ alkyl group.

The "$C_{1-3}$ alkyl group" of the "optionally substituted $C_{1-3}$ alkyl group" for $R^3$ optionally has 1 to 5 (preferably 1 to 3) substituents at substitutable position(s). Examples of such substituent include the substituents selected from the aforementioned Substituent Group A. When a plurality of substituents are present, the respective substituents may be the same or different.

$R^3$ is preferably a $C_{1-3}$ alkyl group optionally substituted by 1 to 3 substituents selected from a halogen atom (e.g., fluorine atom) and a $C_{1-6}$ alkoxy group.

A more preferable embodiment of $R^3$ is a $C_{1-3}$ alkyl group (e.g., methyl).

$R^4$ in the formula (I) is a substituent.

$R^4$ is preferably a halogen atom, a cyano group, an optionally substituted hydroxy group, an optionally substituted amino group, an acyl group, an optionally substituted hydrocarbon group (preferably, an optionally substituted $C_{1-6}$ alkyl group, an optionally substituted $C_{3-10}$ cycloalkyl group, an optionally substituted $C_{6-14}$ aryl group, or an optionally substituted $C_{3-10}$ cycloalkenyl group), or an optionally substituted heterocyclic group.

Examples of the "hydrocarbon group" of the "optionally substituted hydrocarbon group" for $R^4$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

The $C_{1-10}$ alkyl group, $C_{2-10}$ alkenyl group and $C_{2-10}$ alkynyl group exemplified as the aforementioned "hydrocarbon group" optionally have 1 to 5 (preferably 1 to 3) substituents at substitutable position(s). Examples of such substituent include the substituents selected from the aforementioned Substituent Group A. When a plurality of substituents are present, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-14}$ aralkyl group and $C_{8-13}$ arylalkenyl group exemplified as the aforementioned "hydrocarbon group" optionally have 1 to 5 (preferably 1 to 3) substituents at substitutable position(s). Examples of such substituent include the substituents selected from the aforementioned Substituent Group B. When a plurality of substituents are present, the respective substituents may be the same or different.

The "$C_{1-6}$ alkyl group" of the "optionally substituted $C_{1-6}$ alkyl group" for $R^4$ optionally has 1 to 5 (preferably 1 to 3) substituents at substitutable position(s). Examples of such substituent include the substituents selected from the aforementioned Substituent Group A. When a plurality of substituents are present, the respective substituents may be the same or different.

The "$C_{3-10}$ cycloalkyl" of the "optionally substituted $C_{3-10}$ cycloalkyl" for $R^4$ optionally has 1 to 5 (preferably 1 to 3) substituents at substitutable position(s). Examples of such substituent include the substituents selected from the aforementioned Substituent Group B. When a plurality of substituents are present, the respective substituents may be the same or different.

The "$C_{6-14}$ aryl group" of the "optionally substituted $C_{6-14}$ aryl group" for $R^4$ optionally has 1 to 5 (preferably 1 to 3) substituents at substitutable position(s). Examples of such substituent include the substituents selected from the aforementioned Substituent Group B. When a plurality of substituents are present, the respective substituents may be the same or different.

The "$C_{3-10}$ cycloalkenyl group" of the "optionally substituted $C_{3-10}$ cycloalkenyl group" for $R^4$ optionally has 1 to 5 (preferably 1 to 3) substituents at substitutable position(s) Examples of such substituent include the substituents selected from the aforementioned Substituent Group B. When a plurality of substituents are present, the respective substituents may be the same or different.

The "heterocyclic group" of the "optionally substituted heterocyclic group" for $R^4$ optionally has 1 to 5 (preferably 1 to 3) substituents at substitutable position(s). Examples of such substituent include the substituents selected from the aforementioned Substituent Group B. When a plurality of substituents are present, the respective substituents may be the same or different.

Examples of the "optionally substituted hydroxy group" for $R^4$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a $C_{1-6}$ alkyl-carbonyl group, a heterocyclic group and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include the substituents selected from the abovementioned Substituent Group A. When a plurality of substituents are present, the respective substituents may be the same or different.

The $C_{3-10}$ cycloalkyl group, $C_{3-10}$ cycloalkenyl group, $C_{6-14}$ aryl group, $C_{7-14}$ aralkyl group, $C_{8-13}$ arylalkenyl group and heterocyclic group optionally have 1 to 5 (preferably 1 to 3) substituents at substitutable position(s). Examples of the substituent include the substituents selected from the above-mentioned Substituent Group B. When a plurality of substituents are present, the respective substituents may be the same or different.

Examples of the "optionally substituted amino group" for $R^4$ include an amino group optionally mono- or di-substituted by substituent(s) selected from $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-14}$ aralkyl group, $C_{8-13}$ arylalkenyl group, heterocyclic group, $C_{1-6}$ alkoxy group and $C_{6-14}$ aryloxy group; acyl group and the like, each of which is optionally substituted.

The $C_{1-10}$ alkyl group, $C_{2-10}$ alkenyl group and $C_{1-6}$ alkoxy group optionally have 1 to 5 (preferably 1 to 3) substituents at substitutable position(s). Examples of such substituent include the substituents selected from the aforementioned Substituent Group A. When a plurality of substituents are present, the respective substituents may be the same or different.

The $C_{3-10}$ cycloalkyl group, $C_{3-10}$ cycloalkenyl group, $C_{6-14}$ aryl group, $C_{7-14}$ aralkyl group, $C_{8-13}$ arylalkenyl group, heterocyclic group and $C_{6-14}$ aryloxy group optionally have 1 to 5 (preferably 1 to 3) substituents at substitutable position(s) Examples of such substituent include the substituents selected from the aforementioned Substituent Group B. When a plurality of substituents are present, the respective substituents may be the same or different.

Examples of the acyl group exemplified as a substituent of the "optionally substituted amino group" include those similar to the "acyl group" for $R^4$ to be mentioned below.

Examples of the "acyl group" for $R^4$ include groups represented by the formula: $-COR^A$, $-CO-OR^A$, $-SO_3R^A$, $-S(O)_2R^A$, $-SOR^A$, $-CO-NR^{A'}R^{B'}$, $-CS-NR^{A'}R^{B'}$ or $-S(O)_2NR^{A'}R^{B'}$ wherein $R^A$ is a hydrogen atom, an optionally substituted hydrocarbon group or an optionally substituted heterocyclic group, and $R^{A'}$ and $R^{B'}$ are the same or different and each is a hydrogen atom, an optionally substituted hydrocarbon group or an optionally substituted heterocyclic group, or $R^{A'}$ and $R^{B'}$ in combination optionally form, together with the adjacent nitrogen atom, an optionally substituted nitrogen-containing heterocycle, and the like.

Examples of the "hydrocarbon group" of the "optionally substituted hydrocarbon group" for $R^4$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

The $C_{1-10}$ alkyl group, $C_{2-10}$ alkenyl group and $C_{2-10}$ alkynyl group, which are exemplified as the above-mentioned "hydrocarbon group", optionally have 1 to 5 (preferably 1 to 3) substituents at substitutable position(s). Examples of the substituent include the substituents selected from the above-mentioned Substituent Group A. When a plurality of substituents are present, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-14}$ aralkyl group and $C_{8-13}$ arylalkenyl group, which are exemplified as the above-mentioned "hydrocarbon group", optionally have 1 to 5 (preferably 1 to 3) substituents at substitutable position(s). Examples of the substituent include the substituents selected from the above-mentioned Substituent Group B. When a plurality of substituents are present, the respective substituents may be the same or different.

The "heterocyclic group" of the "optionally substituted heterocyclic group" for $R^4$, $R^{A'}$ or $R^{B'}$ optionally has 1 to 5 (preferably 1 to 3) substituents at substitutable position(s). Examples of the substituent include the substituents selected from the above-mentioned Substituent Group B. When a plurality of substituents are present, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 to 3) substituents at substitutable position(s). Examples of the substituent include the substituents selected from the above-mentioned Substituent Group B. When a plurality of substituents are present, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
 (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
 (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

$R^4$ is more preferably
(1) a $C_{1-6}$ alkyl group (e.g., methyl, isopropyl, tert-butyl) optionally substituted by 1 to 3 substituents selected from
 (a) a halogen atom (e.g., fluorine atom),
 (b) a cyano group,
 (c) a hydroxy group,
 (d) an amino group optionally mono- or di-substituted by $C_{1-6}$ alkyl-carbonyl group(s) (e.g., acetyl),
 (e) a carbamoyl group optionally mono- or di-substituted by $C_{1-6}$ alkyl group(s) (e.g., methyl), and (f) a 5- or 6-membered monocyclic non-aromatic heterocyclic group (e.g., morpholinyl, pyrrolidinyl, thiomorpholinyl) optionally substituted by 1 to 3 oxo groups, (2) a $C_{3-10}$ cycloalkyl group (e.g., cyclopropyl, cyclobutyl, cyclohexyl) optionally substituted by 1 to 3 substituents selected from (a) a hydroxy group, and (b) a halogen atom (e.g., fluorine atom), (3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methyl), (4) a carbamoyl group optionally mono- or di-substituted by substituent(s) selected from (a) a $C_{1-6}$ alkyl group (e.g., methyl, ethyl) optionally substituted by 1 to 3 $C_{1-6}$ alkoxy groups (e.g., methoxy), (b) a $C_{3-10}$ cycloalkyl group (e.g., cyclopentyl), and (c) a 5- or 6-membered monocyclic non-aromatic heterocyclic group (e.g., tetrahydropyranyl), (5) a 5- to 7-membered monocyclic non-aromatic heterocyclic group (e.g., dihydropyranyl, tetrahydropyranyl, morpholinyl, thiomorpholinyl, piperazinyl, piperidinyl, 1,4-oxazepanyl, pyrrolidinyl, oxazolidinyl) optionally substituted by 1 to 3 substituents selected from (a) a hydroxy group, (b) a $C_{1-6}$ alkyl group (e.g., methyl, isopropyl) optionally substituted by 1 to 3 substituents selected from (i) a hydroxy group, and (ii) a $C_{1-6}$ alkoxy group (e.g., methoxy), (c) an oxo group, (d) a $C_{1-6}$ alkyl-carbonyl group (e.g., acetyl) optionally substituted by 1 to 3 $C_{1-6}$ alkoxy groups (e.g., methoxy), (e) a $C_{1-6}$ alkoxy group (e.g., methoxy), and (f) a halogen atom (e.g., fluorine atom), (6) a 8- to 12-membered fused non-aromatic heterocyclic group (e.g., octahydropyrrolo[1,2-a]pyrazinyl, 2-oxa-7-azaspiro[3.5]nonyl), or (7) a 5- or 6-membered monocyclic non-aromatic heterocyclyl-carbonyl group (e.g., thiomorpholinylcarbonyl, morpholinylcarbonyl) optionally substituted by 1 to 3 oxo groups.

Another preferable example of $R^4$ is (1) a $C_{1-6}$ alkyl group optionally substituted by 1 to 3 substituents selected from (a) a halogen atom (e.g., fluorine atom), (b) a cyano group, (c) a hydroxy group, (d) an amino group optionally mono- or di-substituted by $C_{1-6}$ alkyl-carbonyl group(s) (e.g., acetylamino), and (e) a carbamoyl group optionally mono- or di-substituted by $C_{1-6}$ alkyl group(s) (e.g., dimethylcarbamoyl), (2) a $C_{3-10}$ cycloalkyl group (e.g., cyclopropyl), (3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl), (4) a 5- or 6-membered non-aromatic heterocyclic group having one oxygen atom (e.g., dihydropyranyl, tetrahydropyranyl), or (5) a group represented by the formula

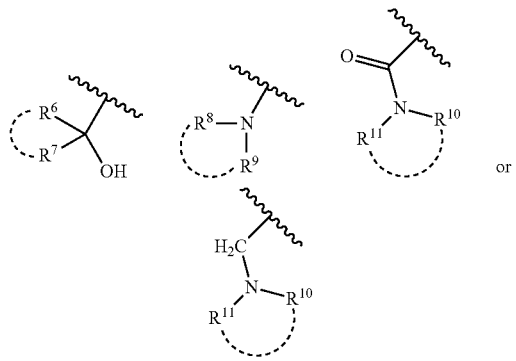

wherein $R^6$ and $R^7$ are each independently an optionally substituted $C_{1-6}$ alkyl group (e.g., methyl, ethyl, propyl, butyl, cyclopropylmethyl); or $R^6$ and $R^7$ form, together with the adjacent carbon atom, an optionally substituted ring (e.g., tetrahydropyran, 1,1-difluorocyclohexane, cyclobutane, tetrahydrothiopyran, tetrahydro-1,1-dioxido-2H-thiopyran);

$R^8$ and $R^9$ are each independently (1)

(i) a hydrogen atom, (ii) a $C_{1-6}$ alkyl group optionally substituted by 1 to 3 substituents selected from a halogen atom, a $C_{3-6}$ cycloalkyl group and a $C_{1-6}$ alkoxy group, (iii) a $C_{3-6}$ cycloalkyl group optionally substituted by 1 to 3 halogen atoms, (iv) a $C_{6-14}$ aryl group optionally substituted by 1 to 3 halogen atoms, (v) a $C_{1-6}$ alkoxy group optionally substituted by 1 to 3 halogen atoms, (vi) a $C_{6-14}$ aryloxy group optionally substituted by 1 to 3 halogen atoms, (vii) a $C_{1-6}$ alkyl-carbonyl group optionally substituted by 1 to 3 halogen atoms, (viii) a $C_{1-6}$ alkoxy-carbonyl group optionally substituted by 1 to 3 halogen atoms, (ix) a $C_{1-6}$ alkylsulfonyl group (e.g., methylsulfonyl) optionally substituted by 1 to 3 halogen atoms, (x) a carbamoyl group optionally mono- or di-substituted by $C_{1-6}$ alkyl group(s) optionally substituted by 1 to 3 halogen atoms, or (xi) an aromatic heterocyclic group (e.g., thienyl, furyl, pyridyl, pyrazolyl, imidazolyl, tetrazolyl, oxazolyl, thiazolyl, oxadiazolyl, thiadiazolyl); or (2) $R^8$ and $R^9$ form, together with the adjacent nitrogen atom, an optionally substituted nitrogen-containing heterocycle;

$R^{10}$ and $R^{11}$ are each independently (1)

(i) a hydrogen atom, (ii) a $C_{1-6}$ alkyl group optionally substituted by 1 to 3 substituents selected from a halogen atom, a $C_{3-6}$ cycloalkyl group and a $C_{1-6}$ alkoxy group, (iii) a $C_{3-6}$ cycloalkyl group optionally substituted by 1 to 3 halogen atoms, (iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a non-aromatic heterocyclic group (e.g., tetrahydropyranyl); or
(2) $R^{10}$ and $R^{11}$ form, together with the adjacent nitrogen atom, an optionally substituted nitrogen-containing heterocycle.

The "$C_{1-6}$ alkyl group" of the "optionally substituted $C_{1-6}$ alkyl group" for $R^6$ optionally has 1 to 5 (preferably 1 to 3) substituents at substitutable position(s). Examples of the substituent include the substituents selected from the above-mentioned Substituent Group A. When a plurality of substituents are present, the respective substituents may be the same or different.

The "$C_{1-6}$ alkyl group" of the "optionally substituted $C_{1-6}$ alkyl group" for $R^7$ optionally has 1 to 5 (preferably 1 to 3) substituents at substitutable position(s). Examples of such substituent include the substituents selected from the aforementioned Substituent Group A. When a plurality of substituents are present, the respective substituents may be the same or different.

Examples of the "optionally substituted nitrogen-containing heterocycle" formed by $R^8$ and $R^9$ together with the adjacent nitrogen atom include
(1) an aromatic nitrogen-containing heterocycle optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(2) a non-aromatic nitrogen-containing heterocycle optionally substituted by 1 to 3 substituents selected from
    (a) a $C_{1-6}$ alkyl group optionally substituted by 1 to 3 halogen atoms,
    (b) a $C_{1-6}$ alkyl group optionally substituted by 1 to 3 hydroxy groups,
    (c) a $C_{1-6}$ alkyl group optionally substituted by 1 to 3 $C_{1-6}$ alkoxy groups,
    (d) a hydroxy group,
    (e) a $C_{1-6}$ alkoxy group optionally substituted by 1 to 3 halogen atoms,
    (f) a halogen atom,
    (g) an acyl group, and
    (h) an oxo group;
and the like. The non-aromatic nitrogen-containing heterocycle optionally further forms a fused ring or a spiro ring.

Preferably, $R^8$ and $R^9$ are each independently a hydrogen atom, methyl, ethyl, propyl, cyclopropyl, cyclopropylmethyl, 2-methoxyethyl, phenyl, methoxy, ethoxy, phenoxy or the like, or $R^8$ and $R^9$ form, together with the adjacent nitrogen atom, morpholine, 2-methylmorpholine, 2,2-dimethylmorpholine, 3-oxomorpholine, piperidine, 4-hydroxy-4-methylpiperidine, 4-methoxypiperidine, 4-(1-hydroxy-1-methylethyl)piperidine, 4,4-difluoropiperidine, 2-oxopiperidine, piperazine, 4-methylpiperazine, 4-acetylpiperazine, 4-(2-methoxyacetyl)piperazine, pyrrolidine, 2-(hydroxymethyl)pyrrolidine, 3-hydroxypyrrolidine, 3-methoxypyrrolidine, 2-(methoxymethyl)pyrrolidine, 3-hydroxy-3-methylpyrrolidine, 2-oxopyrrolidine, hexamethylenimine, oxazolidine, 2-oxooxazolidine, thiomorpholine, 1,1-dioxidothiomorpholine, 1,4-oxazepane, octahydropyrrolo[1,2-a]pyrazine, 2-oxa-7-azaspiro[3.5]nonane and the like.

Examples of the "optionally substituted nitrogen-containing heterocycle" formed by $R^{10}$ and $R^{11}$ together with the adjacent nitrogen atom include
(1) an aromatic nitrogen-containing heterocycle optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(2) a non-aromatic nitrogen-containing heterocycle optionally substituted by 1 to 3 substituents selected from
    (a) a $C_{1-6}$ alkyl group optionally substituted by 1 to 3 halogen atoms,
    (b) a $C_{1-6}$ alkyl group optionally substituted by 1 to 3 hydroxy groups,
    (c) a $C_{1-6}$ alkyl group optionally substituted by 1 to 3 $C_{1-6}$ alkoxy groups,
    (d) a hydroxy group,
    (e) a $C_{1-6}$ alkoxy group optionally substituted by 1 to 3 halogen atoms,
    (f) a halogen atom,
    (g) an acyl group, and
    (h) an oxo group;
and the like. The non-aromatic nitrogen-containing heterocycle is optionally further form a fused ring or a spiro ring.

Preferably, $R^{10}$ and $R^{11}$ are each independently a hydrogen atom, methyl, ethyl, propyl, cyclopropyl, cyclopentyl, cyclopropylmethyl, 2-methoxyethyl, phenyl, methoxy, ethoxy, phenoxy, tetrahydropyranyl or the like, or $R^{10}$ and $R^{11}$ form, together with the adjacent nitrogen atom, morpholine, piperidine, 4-hydroxy-4-methylpiperidine, piperazine, pyrrolidine, hexamethylenimine, 1,1-dioxidothiomorpholine and the like.

Another preferable example of $R^4$ is
(1) a $C_{1-6}$ alkyl group optionally substituted by 1 to 3 substituents selected from
    (a) a halogen atom (e.g., fluorine atom),
    (b) a cyano group,
    (c) a hydroxy group,
    (d) an amino group optionally mono- or di-substituted by $C_{1-6}$ alkyl-carbonyl group(s) (e.g., acetylamino),
    (e) a carbamoyl group optionally mono- or di-substituted by $C_{1-6}$ alkyl group(s) (e.g., dimethylcarbamoyl), and
    (f) a $C_{1-6}$ alkoxy group,
(2) a $C_{3-10}$ cycloalkyl group (e.g., cyclopropyl),
(3) a $C_{6-14}$ aryl group (e.g., phenyl) optionally substituted by 1 to 3 substituents selected from
    (a) a $C_{1-6}$ alkyl group,
    (b) an amino group optionally mono- or di-substituted by $C_{1-6}$ alkyl group(s) (e.g., methylamino, dimethylamino), and (c) a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl),
(5) a pyrazolyl group, a pyridyl group, a pyrimidinyl group or a pyrazinyl group, each of which is optionally substituted by 1 to 3 $C_{1-6}$ alkyl groups,
(6) a $C_{1-6}$ alkoxy group optionally substituted by 1 to 3 halogen atoms,
(7) a halogen atom (e.g., fluorine atom),
(8) a cyano group,
(9) a group represented by the formula

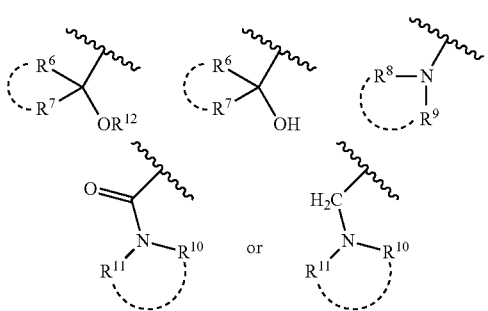

wherein
$R^6$ and $R^7$ are each independently a $C_{1-6}$ alkyl group; or
$R^6$ and $R^7$ form, together with the adjacent carbon atom, cyclobutane, cyclohexane, azetidine, tetrahydropyran or tetrahydrothiopyran, each of which is optionally substituted by 1 to 3 substituents selected from a halogen atom (e.g., fluorine atom), a carbamoyl group optionally mono- or di-substituted by $C_{1-6}$ alkyl group(s), a $C_{1-6}$ alkyl-carbonyl group, a $C_{1-6}$ alkylsulfonyl group and an oxo group;
$R^{12}$ is a $C_{1-6}$ alkyl group;
$R^8$ and $R^9$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or
$R^8$ and $R^9$ form, together with the adjacent nitrogen atom,
(i) an aromatic nitrogen-containing heterocycle optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom, or
(ii) a non-aromatic nitrogen-containing heterocycle optionally forming a fused ring, a bridged ring or a spiro ring (e.g., morpholine, piperidine, piperazine, pyrrolidine, oxazolidine, thiomorpholine, 1,4-oxazepane, 1,4-diazepane, octahydropyrrolo[1,2-a]pyrazine, 3-oxa-8-azabicyclo[3.2.1]octane, 6-oxa-3-azabicyclo[3.3.1]heptane, 3,8-diazabicyclo[3.2.1]octane, 2-oxa-7-azaspiro[3.5]nonane, 2-oxa-6-azaspiro[3.3]heptane, 1,7-diazaspiro[4.4]nonane, 7-oxa-1-azaspiro[4.4]nonane, 1-azaspiro[4.4]nonane, 2,5-diazaspiro[3.4]octane), each of which is optionally substituted by 1 to 5 substituents selected from
(a) a $C_{1-6}$ alkyl group optionally substituted by 1 to 3 substituents selected from
(A) a halogen atom,
(B) a hydroxy group,
(C) a cyano group,
(D) a $C_{1-6}$ alkylsulfonyl group,
(E) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group and a $C_{1-6}$ alkylsulfonyl group,
(F) a $C_{1-6}$ alkoxy group,
(G) an azetidinyl group, a pyrrolidinyl group, a piperidyl group or a morpholinyl group, each of which is optionally substituted by 1 to 3 substituents selected from a halogen atom and an oxo group, and
(H) a pyrazolyl group,
(b) a hydroxy group,
(c) a $C_{1-6}$ alkoxy group optionally substituted by 1 to 3 halogen atoms,
(d) a halogen atom,
(e) a $C_{1-6}$ alkyl-carbonyl group (e.g., acetyl),
(f) a $C_{1-6}$ alkoxy-$C_{1-6}$ alkyl-carbonyl group (e.g., methoxyacetyl),
(g) an oxo group,
(h) a $C_{1-6}$ alkylsulfonyl group (e.g., isopropylsulfonyl, methylsulfonyl),
(i) a $C_{3-10}$ cycloalkylsulfonyl group (e.g., cyclopropylsulfonyl),
(j) an amino group optionally mono- or di-substituted by $C_{1-6}$ alkyl group(s) (e.g., dimethylamino), and
(k) a cyano group;
$R^{10}$ and $R^{11}$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms, (ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or
$R^{10}$ and $R^{11}$ form, together with the adjacent nitrogen atom,
(i) an aromatic nitrogen-containing heterocycle optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom, or
(ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
 (a) a $C_{1-6}$ alkyl group optionally substituted by 1 to 3 substituents selected from a halogen atom, a hydroxy group and a $C_{1-6}$ alkoxy group,
 (b) a hydroxy group,
 (c) a $C_{1-6}$ alkoxy group optionally substituted by 1 to 3 halogen atoms,
 (d) a halogen atom,
 (e) a $C_{1-6}$ alkyl-carbonyl group (e.g., acetyl),
 (f) a $C_{1-6}$ alkoxy-$C_{1-6}$ alkyl-carbonyl group (e.g., methoxyacetyl), and
 (g) an oxo group, or
(10) a $C_{3-8}$ cycloalkenyl group (e.g., cyclohexenyl).
Another preferable example of $R^4$ is
(1) a $C_{1-6}$ alkyl group optionally substituted by 1 to 3 substituents selected from
 (a) a halogen atom (e.g., fluorine atom),
 (b) a cyano group,
 (c) a hydroxy group,
 (d) an amino group optionally mono- or di-substituted by $C_{1-6}$ alkyl-carbonyl group(s) (e.g., acetylamino),
 (e) a carbamoyl group optionally mono- or di-substituted by $C_{1-6}$ alkyl group(s) (e.g., dimethylcarbamoyl), and
 (f) a $C_{1-6}$ alkoxy group,
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

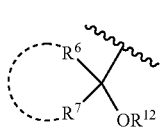 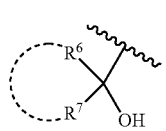 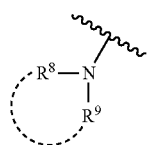 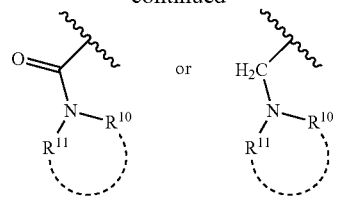

wherein
$R^6$ and $R^7$ are each independently a $C_{1-6}$ alkyl group; or
$R^6$ and $R^7$ form, together with the adjacent carbon atom, cyclobutane, cyclohexane, azetidine, tetrahydropyran or tetrahydrothiopyran, each of which is optionally substituted by 1 to 3 substituents selected from a halogen atom (e.g., fluorine atom), a carbamoyl group optionally mono- or di-substituted by $C_{1-6}$ alkyl group(s), a $C_{1-6}$ alkyl-carbonyl group, a $C_{1-6}$ alkylsulfonyl group and an oxo group;
$R^{12}$ is a $C_{1-6}$ alkyl group;
$R^8$ and $R^9$ are each independently
(i) a $C_{1-6}$ alkyl group optionally substituted by 1 to 3 substituents selected from a halogen atom, a $C_{3-8}$ cycloalkyl group and a $C_{1-6}$ alkoxy group,
(ii) a $C_{3-10}$ cycloalkyl group optionally substituted by 1 to 3 halogen atoms; or
$R^8$ and $R^9$ form, together with the adjacent nitrogen atom, a non-aromatic nitrogen-containing heterocycle optionally forming a fused ring, a bridged ring or a spiro ring (e.g., morpholine, piperidine, piperazine, pyrrolidine, oxazolidine, thiomorpholine, 1,4-oxazepane, 1,4-diazepane, octahydropyrrolo[1,2-a]pyrazine, 3-oxa-8-azabicyclo[3.2.1]octane, 2-oxa-7-azaspiro[3.5]nonane, 2-oxa-6-azaspiro[3.3]heptane), and optionally substituted by 1 to 5 substituents selected from
 (a) a $C_{1-6}$ alkyl group optionally substituted by 1 to 3 substituents selected from
  (A) a hydroxy group,
  (B) a cyano group,
  (C) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group and a $C_{1-6}$ alkylsulfonyl group,
  (D) a $C_{1-6}$ alkoxy group, and
  (E) a pyrrolidinyl group,
 (b) a hydroxy group,
 (c) a $C_{1-6}$ alkoxy group,
 (d) a halogen atom,
 (e) a $C_{1-6}$ alkyl-carbonyl group (e.g., acetyl),
 (f) a $C_{1-6}$ alkoxy-$C_{1-6}$ alkyl-carbonyl group (e.g., methoxyacetyl),
 (g) an oxo group,
 (h) a $C_{1-6}$ alkylsulfonyl group (e.g., isopropylsulfonyl, methylsulfonyl),
 (i) a $C_{3-10}$ cycloalkylsulfonyl group (e.g., cyclopropylsulfonyl),
 (j) an amino group optionally mono- or di-substituted by $C_{1-6}$ alkyl group(s) (e.g., dimethylamino), and
 (k) a cyano group;
$R^{10}$ and $R^{11}$ are each independently
(i) a hydrogen atom,
(ii) a $C_{1-6}$ alkyl group optionally substituted by 1 to 3 $C_{1-6}$ alkoxy groups,
(iii) a $C_{3-10}$ cycloalkyl group, or
(iv) a 5- or 6-membered non-aromatic heterocyclic group having one oxygen atom (e.g., tetrahydropyranyl); or $R^{10}$ and $R^{11}$ form, together with the adjacent nitrogen atom, a non-aromatic nitrogen-containing heterocycle (e.g., morpholine, pyrrolidine, thiomorpholine) optionally substituted by 1 to 3 oxo groups, or (6) a $C_{3-8}$ cycloalkenyl group (e.g., cyclohexenyl).

Another preferable example of $R^4$ is (1) a $C_{1-6}$ alkyl group optionally substituted by 1 to 3 substituents selected from
   (a) a halogen atom (e.g., fluorine atom),
   (b) a cyano group,
   (c) a hydroxy group,
   (d) an amino group optionally mono- or di-substituted by $C_{1-6}$ alkyl-carbonyl group(s) (e.g., acetylamino), and
   (e) a carbamoyl group optionally mono- or di-substituted by $C_{1-6}$ alkyl group(s) (e.g., dimethylcarbamoyl),
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

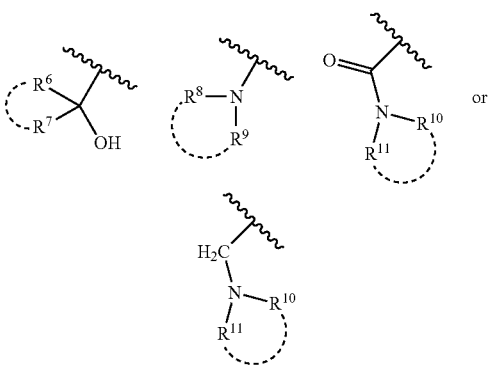

wherein
$R^6$ and $R^7$ are each independently a $C_{1-6}$ alkyl group; or
$R^6$ and $R^7$ form, together with the adjacent carbon atom, cyclobutane, cyclohexane, tetrahydropyran or tetrahydrothiopyran, each of which is optionally substituted by 1 to 3 substituents selected from a halogen atom (e.g., fluorine atom) and an oxo group;
$R^8$ and $R^9$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms, or
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or $R^8$ and $R^9$ form, together with the adjacent nitrogen atom,
(i) an aromatic nitrogen-containing heterocycle optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom, or
(ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
   (a) a $C_{1-6}$ alkyl group optionally substituted by 1 to 3 substituents selected from a halogen atom, a hydroxy group and a $C_{1-6}$ alkoxy group,
   (b) a hydroxy group,
   (c) a $C_{1-6}$ alkoxy group optionally substituted by 1 to 3 halogen atoms,
   (d) a halogen atom,
   (e) a $C_{1-6}$ alkyl-carbonyl group (e.g., acetyl),
   (f) a $C_{1-6}$ alkoxy-$C_{1-6}$ alkyl-carbonyl group (e.g., methoxyacetyl), and
   (g) an oxo group;

$R^{10}$ and $R^{11}$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or $R^{10}$ and $R^{11}$ form, together with the adjacent nitrogen atom,
(i) an aromatic nitrogen-containing heterocycle optionally substituted by 1 to 3 substituents selected from (a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom, or
(ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
(a) a $C_{1-6}$ alkyl group optionally substituted by 1 to 3 substituents selected from a halogen atom, a hydroxy group and a $C_{1-6}$ alkoxy group,
(b) a hydroxy group,
(c) a $C_{1-6}$ alkoxy group optionally substituted by 1 to 3 halogen atoms,
(d) a halogen atom,
(e) a $C_{1-6}$ alkyl-carbonyl group (e.g., acetyl),
(f) a $C_{1-6}$ alkoxy-$C_{1-6}$ alkyl-carbonyl group (e.g., methoxyacetyl), and
(g) an oxo group.
$R^4$ is more preferably
(1) a $C_{1-6}$ alkyl group optionally substituted by 1 to 3 substituents selected from
(a) a halogen atom (e.g., fluorine atom),
(b) a cyano group,
(c) a hydroxy group,
(d) an amino group optionally mono- or di-substituted by $C_{1-6}$ alkyl-carbonyl group(s) (e.g., acetylamino), and
(e) a carbamoyl group optionally mono- or di-substituted by $C_{1-6}$ alkyl group(s) (e.g., dimethylcarbamoyl),
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

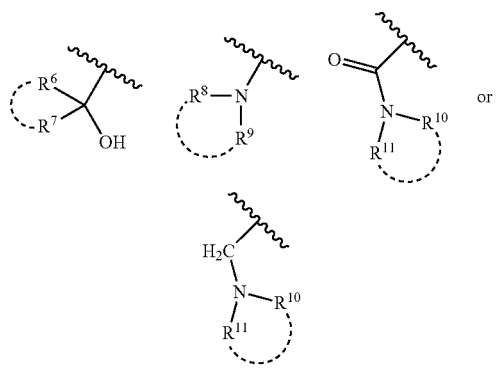

wherein
$R^6$ and $R^7$ are each independently a $C_{1-6}$ alkyl group; or
$R^6$ and $R^7$ form, together with the adjacent carbon atom, cyclobutane, cyclohexane or tetrahydropyran, each of which is optionally substituted by 1 to 3 substituents selected from a halogen atom (e.g., fluorine atom) and an oxo group;

$R^8$ and $R^9$ form, together with the adjacent nitrogen atom, a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
(a) a $C_{1-6}$ alkyl group optionally substituted by 1 to 3 substituents selected from a hydroxy group and a $C_{1-6}$ alkoxy group,
(b) a hydroxy group,
(c) a $C_{1-6}$ alkoxy group,
(d) a halogen atom,
(e) a $C_{1-6}$ alkyl-carbonyl group (e.g., acetyl),
(f) a $C_{1-6}$ alkoxy-$C_{1-6}$ alkyl-carbonyl group (e.g., methoxyacetyl), and
(g) an oxo group;
$R^{10}$ and $R^{11}$ are each independently
(i) a hydrogen atom,
(ii) a $C_{1-6}$ alkyl group optionally substituted by 1 to 3 $C_{1-6}$ alkoxy groups,
(iii) a $C_{3-10}$ cycloalkyl group, or
(iv) a 5- or 6-membered non-aromatic heterocyclic group having one oxygen atom (e.g., tetrahydropyranyl); or
$R^{10}$ and $R^{11}$ form, together with the adjacent nitrogen atom, a non-aromatic nitrogen-containing heterocycle (e.g., morpholine, pyrrolidine, thiomorpholine) optionally substituted by 1 to 3 oxo groups.

$R^5$ in the formula (I) is a hydrogen atom, a halogen atom, a cyano group, an optionally substituted $C_{1-6}$ alkyl group, an optionally substituted $C_{1-6}$ alkoxy group, or an acyl group.

The "$C_{1-6}$ alkyl group" of the "optionally substituted $C_{1-6}$ alkyl group" for $R^5$ optionally has 1 to 5 (preferably 1 to 3) substituents at substitutable position(s). Examples of such substituent include the substituents selected from the aforementioned Substituent Group A. When a plurality of substituents are present, the respective substituents may be the same or different.

The "$C_{1-6}$ alkoxy group" of the "optionally substituted $C_{1-6}$ alkoxy group" for $R^5$ optionally has 1 to 5 (preferably 1 to 3) substituents at substitutable position(s). Examples of such substituent include the substituents selected from the aforementioned Substituent Group A. When a plurality of substituents are present, the respective substituents may be the same or different.

Examples of the "acyl group" for $R^5$ include those similar to the aforementioned "acyl group" for $R^4$.

$R^5$ is preferably a hydrogen atom.

Preferable specific examples of compound (I) include the following.

[Compound A]
Compound (I) wherein
$R^1$ is an optionally substituted $C_{1-6}$ alkyl group, or an optionally substituted cyclic group;
$R^2$ is a hydrogen atom or a cyano group;
$R^3$ is an optionally substituted $C_{1-3}$ alkyl group;
$R^4$ is a substituent;
$R^5$ is a hydrogen atom, a halogen atom, a cyano group, an optionally substituted $C_{1-6}$ alkyl group, an optionally substituted $C_{1-6}$ alkoxy group, or an acyl group.

[Compound B]
Compound (I) wherein
$R^1$ is
(1) a $C_{1-6}$ alkyl group (e.g., methyl, ethyl, propyl, isopropyl, isobutyl, 1,2-dimethylpropyl) optionally substituted by 1 to 5 substituents selected from (a) a halogen atom (e.g., fluorine atom),
(b) a $C_{3-8}$ cycloalkyl group (e.g., cyclopropyl) optionally substituted by 1 to 3 $C_{1-6}$ alkyl groups (e.g., methyl),
(c) a $C_{1-6}$ alkoxy-carbonyl group (e.g., ethoxycarbonyl), and
(d) a carbamoyl group,
(2) a $C_{3-10}$ cycloalkyl group (e.g., cyclopentyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
(a) a halogen atom (e.g., fluorine atom, chlorine atom),
(b) a $C_{1-6}$ alkyl group (e.g., methyl) optionally substituted by 1 to 3 halogen atoms (e.g., fluorine atom), and
(c) a cyano group;

$R^2$ is a hydrogen atom or a cyano group;
$R^3$ is a $C_{1-3}$ alkyl group optionally substituted by 1 to 3 substituents selected from a halogen atom (e.g., fluorine atom) and a $C_{1-6}$ alkoxy group;
$R^4$ is
(1) a $C_{1-6}$ alkyl group (e.g., methyl, isopropyl, tert-butyl) optionally substituted by 1 to 3 substituents selected from
(a) a halogen atom (e.g., fluorine atom),
(b) a cyano group,
(c) a hydroxy group,
(d) an amino group optionally mono- or di-substituted by $C_{1-6}$ alkyl-carbonyl group(s) (e.g., acetyl),
(e) a carbamoyl group optionally mono- or di-substituted by $C_{1-6}$ alkyl group(s) (e.g., methyl), and
(f) a 5- or 6-membered monocyclic non-aromatic heterocyclic group (e.g., morpholinyl, pyrrolidinyl, thiomorpholinyl) optionally substituted by 1 to 3 oxo groups,
(2) a $C_{3-10}$ cycloalkyl group (e.g., cyclopropyl, cyclobutyl, cyclohexyl) optionally substituted by 1 to 3 substituents selected from
(a) a hydroxy group, and
(b) a halogen atom (e.g., fluorine atom),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methyl),
(4) a carbamoyl group optionally mono- or di-substituted by substituent(s) selected from
(a) a $C_{1-6}$ alkyl group (e.g., methyl, ethyl) optionally substituted by 1 to 3 $C_{1-6}$ alkoxy groups (e.g., methoxy),
(b) a $C_{3-10}$ cycloalkyl group (e.g., cyclopentyl), and
(c) a 5- or 6-membered monocyclic non-aromatic heterocyclic group (e.g., tetrahydropyranyl),
(5) a 5- to 7-membered monocyclic non-aromatic heterocyclic group (e.g., dihydropyranyl, tetrahydropyranyl, morpholinyl, thiomorpholinyl, piperazinyl, piperidinyl, 1,4-oxazepanyl, pyrrolidinyl, oxazolidinyl) optionally substituted by 1 to 3 substituents selected from
(a) a hydroxy group,
(b) a $C_{1-6}$ alkyl group (e.g., methyl, isopropyl) optionally substituted by 1 to 3 substituents selected from
(i) a hydroxy group, and
(ii) a $C_{1-6}$ alkoxy group (e.g., methoxy),
(c) an oxo group,
(d) a $C_{1-6}$ alkyl-carbonyl group (e.g., acetyl) optionally substituted by 1 to 3 $C_{1-6}$ alkoxy groups (e.g., methoxy),
(e) a $C_{1-6}$ alkoxy group (e.g., methoxy), and
(f) a halogen atom (e.g., fluorine atom),
(6) a 8- to 12-membered fused non-aromatic heterocyclic group (e.g., octahydropyrrolo[1,2-a]pyrazinyl, 2-oxa-7-azaspiro[3.5]nonyl),
(7) a 5- or 6-membered monocyclic non-aromatic heterocyclyl-carbonyl group (e.g., thiomorpholinylcarbonyl, morpholinylcarbonyl) optionally substituted by 1 to 3 oxo groups; and
$R^5$ is a hydrogen atom.

[Compound C]
Compound (I) wherein
$R^1$ is
(1) a $C_{1-6}$ alkyl group (e.g., methyl, ethyl, propyl, isopropyl, isobutyl, 1,2-dimethylpropyl) optionally substituted by 1 to 5 substituents selected from
(a) a halogen atom (e.g., fluorine atom),
(b) a $C_{3-8}$ cycloalkyl group (e.g., cyclopropyl) optionally substituted by 1 to 3 $C_{1-6}$ alkyl groups (e.g., methyl),
(c) a $C_{1-6}$ alkoxy-carbonyl group (e.g., ethoxycarbonyl), and
(d) a carbamoyl group,
(2) a $C_{3-10}$ cycloalkyl group (e.g., cyclopentyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
(a) a halogen atom (e.g., fluorine atom, chlorine atom),
(b) a $C_{1-6}$ alkyl group (e.g., methyl) optionally substituted by 1 to 3 halogen atoms (e.g., fluorine atom), and
(c) a cyano group;
$R^2$ is a hydrogen atom or a cyano group;
$R^3$ is a $C_{1-3}$ alkyl group optionally substituted by 1 to 3 substituents selected from a halogen atom (e.g., fluorine atom) and a $C_{1-6}$ alkoxy group;
$R^4$ is
(1) a $C_{1-6}$ alkyl group optionally substituted by 1 to 3 substituents selected from
(a) a halogen atom (e.g., fluorine atom),
(b) a cyano group,
(c) a hydroxy group,
(d) an amino group optionally mono- or di-substituted by $C_{1-6}$ alkyl-carbonyl group(s) (e.g., acetylamino), and
(e) a carbamoyl group optionally mono- or di-substituted by $C_{1-6}$ alkyl group(s) (e.g., dimethylcarbamoyl),
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

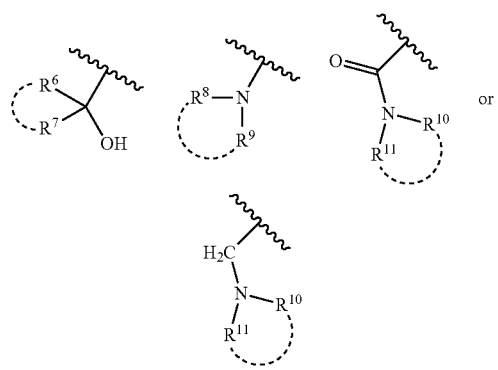

wherein $R^6$ and $R^7$ are each independently a $C_{1-6}$ alkyl group; or $R^6$ and $R^7$ form, together with the adjacent carbon atom, cyclobutane, cyclohexane, tetrahydropyran or tetrahydrothiopyran, each of which is optionally substituted by 1 to 3 substituents selected from a halogen atom (e.g., fluorine atom) and an oxo group;

$R^8$ and $R^9$ are each independently (i) a hydrogen atom, (ii) a $C_{1-6}$ alkyl group optionally substituted by 1 to 3 substituents selected from a halogen atom, a $C_{3-8}$ cycloalkyl group and a $C_{1-6}$ alkoxy group, (iii) a $C_{3-10}$ cycloalkyl group optionally substituted by 1 to 3 halogen atoms, (iv) a $C_{6-14}$ aryl group optionally substituted by 1 to 3 halogen atoms, (v) a $C_{1-6}$ alkoxy group optionally substituted by 1 to 3 halogen atoms, (vi) a $C_{6-14}$ aryloxy group optionally substituted by 1 to 3 halogen atoms, (vii) a $C_{1-6}$ alkyl-carbonyl group optionally substituted by 1 to 3 halogen atoms, (viii) a $C_{1-6}$ alkoxy-carbonyl group optionally substituted by 1 to 3 halogen atoms, (ix) a $C_{1-6}$ alkylsulfonyl group (e.g., methylsulfonyl) optionally substituted by 1 to 3 halogen atoms, (x) a carbamoyl group optionally mono- or di-substituted by $C_{1-6}$ alkyl group(s) optionally substituted by 1 to 3 halogen atoms, or (xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or (xii) a 5- or 6-membered non-aromatic heterocyclic group having one oxygen atom (e.g., tetrahydropyranyl); or $R^8$ and $R^9$ form, together with the adjacent nitrogen atom, (i) an aromatic nitrogen-containing heterocycle optionally substituted by 1 to 3 substituents selected from (a) a $C_{1-6}$ alkyl group optionally substituted by 1 to 3 halogen atoms, (b) a hydroxy group, (c) a $C_{1-6}$ alkoxy group optionally substituted by 1 to 3 halogen atoms, and (d) a halogen atom, or (ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from (a) a $C_{1-6}$ alkyl group optionally substituted by 1 to 3 substituents selected from a halogen atom, a hydroxy group and a $C_{1-6}$ alkoxy group, (b) a hydroxy group, (c) a $C_{1-6}$ alkoxy group optionally substituted by 1 to 3 halogen atoms, (d) a halogen atom, (e) a $C_{1-6}$ alkyl-carbonyl group (e.g., acetyl), (f) a $C_{1-6}$ alkoxy-$C_{1-6}$ alkyl-carbonyl group (e.g., methoxyacetyl), and (g) an oxo group;

$R^{10}$ and $R^{11}$ are each independently (i) a hydrogen atom, (ii) a $C_{1-6}$ alkyl group optionally substituted by 1 to 3 substituents selected from a halogen atom, a $C_{3-8}$ cycloalkyl group and a $C_{1-6}$ alkoxy group, (iii) a $C_{3-10}$ cycloalkyl group optionally substituted by 1 to 3 halogen atoms, (iv) a $C_{6-14}$ aryl group optionally substituted by 1 to 3 halogen atoms, (v) a $C_{1-6}$ alkoxy group optionally substituted by 1 to 3 halogen atoms, (vi) a $C_{6-14}$ aryloxy group optionally substituted by 1 to 3 halogen atoms, (vii) a $C_{1-6}$ alkyl-carbonyl group optionally substituted by 1 to 3 halogen atoms, (viii) a $C_{1-6}$ alkoxy-carbonyl group optionally substituted by 1 to 3 halogen atoms, (ix) a $C_{1-6}$ alkylsulfonyl group (e.g., methylsulfonyl) optionally substituted by 1 to 3 halogen atoms, (x) a carbamoyl group optionally mono- or di-substituted by $C_{1-6}$ alkyl group(s) optionally substituted by 1 to 3 halogen atoms, (xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or (xii) a 5- or 6-membered non-aromatic heterocyclic group having one oxygen atom (e.g., tetrahydropyranyl); or $R^{10}$ and $R^{11}$ form, together with the adjacent nitrogen atom, (i) an aromatic nitrogen-containing heterocycle optionally substituted by 1 to 3 substituents selected from (a) a $C_{1-6}$ alkyl group optionally substituted by 1 to 3 halogen atoms, (b) a hydroxy group, (c) a $C_{1-6}$ alkoxy group optionally substituted by 1 to 3 halogen atoms, and (d) a halogen atom, or (ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from (a) a $C_{1-6}$ alkyl group optionally substituted by 1 to 3 substituents selected from a halogen atom, a hydroxy group and a $C_{1-6}$ alkoxy group, (b) a hydroxy group, (c) a $C_{1-6}$ alkoxy group optionally substituted by 1 to 3 halogen atoms, (d) a halogen atom, (e) a $C_{1-6}$ alkyl-carbonyl group (e.g., acetyl), (f) a $C_{1-6}$ alkoxy-$C_{1-6}$ alkyl-carbonyl group (e.g., methoxyacetyl), and (g) an oxo group; and $R^5$ is a hydrogen atom.

[Compound D]

Compound (I) wherein $R^1$ is (1) a $C_{1-6}$ alkyl group (e.g., methyl, ethyl, propyl, isopropyl, isobutyl, 1,2-dimethylpropyl) optionally substituted by 1 to 5 substituents selected from (a) a halogen atom (e.g., fluorine atom), (b) a $C_{3-8}$ cycloalkyl group (e.g., cyclopropyl) optionally substituted by 1 to 3 $C_{1-6}$ alkyl groups (e.g., methyl), (c) a $C_{1-6}$ alkoxy-carbonyl group (e.g., ethoxycarbonyl), and (d) a carbamoyl group, (2) a $C_{3-10}$ cycloalkyl group (e.g., cyclopentyl) optionally substituted by 1 to 3 $C_{1-6}$ alkyl groups (e.g., methyl), or (3) a $C_{6-14}$ aryl group (e.g., phenyl) optionally substituted by 1 to 3 substituents selected from (a) a halogen atom (e.g., fluorine atom, chlorine atom),
(b) a $C_{1-6}$ alkyl group (e.g., methyl) optionally substituted by 1 to 3 halogen atoms (e.g., fluorine atom), and
(c) a cyano group;

$R^2$ is a hydrogen atom;

$R^3$ is a $C_{1-3}$ alkyl group optionally substituted by 1 to 3 substituents selected from a halogen atom (e.g., fluorine atom) and a $C_{1-6}$ alkoxy group;

$R^4$ is
(1) a $C_{1-6}$ alkyl group optionally substituted by 1 to 3 substituents selected from
  (a) a halogen atom (e.g., fluorine atom),
  (b) a cyano group,
  (c) a hydroxy group,
  (d) an amino group optionally mono- or di-substituted by $C_{1-6}$ alkyl-carbonyl group(s) (e.g., acetylamino), and
  (e) a carbamoyl group optionally mono- or di-substituted by $C_{1-6}$ alkyl group(s) (e.g., dimethylcarbamoyl),
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

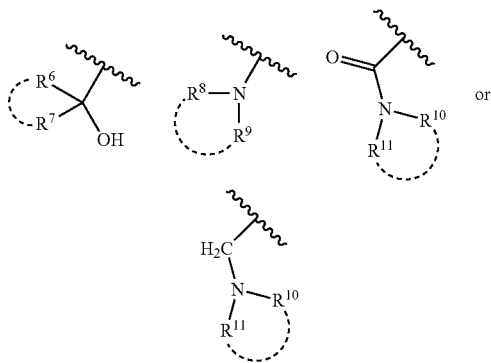

wherein
$R^6$ and $R^7$ are each independently a $C_{1-6}$ alkyl group; or
$R^6$ and $R^7$ form, together with the adjacent carbon atom, cyclobutane, cyclohexane or tetrahydropyran, each of which is optionally substituted by 1 to 3 substituents selected from a halogen atom (e.g., fluorine atom) and an oxo group;
$R^8$ and $R^9$ form, together with the adjacent nitrogen atom, a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
  (a) a $C_{1-6}$ alkyl group optionally substituted by 1 to 3 substituents selected from a hydroxy group and a $C_{1-6}$ alkoxy group,
  (b) a hydroxy group,
  (c) a $C_{1-6}$ alkoxy group,
  (d) a halogen atom,
  (e) a $C_{1-6}$ alkyl-carbonyl group (e.g., acetyl),
  (f) a $C_{1-6}$ alkoxy-$C_{1-6}$ alkyl-carbonyl group (e.g., methoxyacetyl), and
  (g) an oxo group;
$R^{10}$ and $R^{11}$ are each independently
  (i) a hydrogen atom,
  (ii) a $C_{1-6}$ alkyl group optionally substituted by 1 to 3 $C_{1-6}$ alkoxy groups,
  (iii) a $C_{3-10}$ cycloalkyl group, or
  (iv) a 5- or 6-membered non-aromatic heterocyclic group having one oxygen atom (e.g., tetrahydropyranyl); or
$R^{10}$ and $R^{11}$ form, together with the adjacent nitrogen atom, a non-aromatic nitrogen-containing heterocycle (e.g., morpholine, pyrrolidine, thiomorpholine) optionally substituted by 1 to 3 oxo groups; and
$R^5$ is a hydrogen atom.

[Compound C2]
Compound (I) wherein
$R^1$ is
(1) a $C_{1-6}$ alkyl group (e.g., methyl, ethyl, propyl, isopropyl, isobutyl, 1,2-dimethylpropyl, 1,2,2-trimethylpropyl) optionally substituted by 1 to 5 substituents selected from
  (a) a halogen atom (e.g., fluorine atom),
  (b) a $C_{3-8}$ cycloalkyl group (e.g., cyclopropyl, cyclobutyl) optionally substituted by 1 to 3 $C_{1-6}$ alkyl groups (e.g., methyl),
  (c) an oxetanyl group optionally substituted by 1 to 3 $C_{1-6}$ alkyl groups (e.g., methyl),
  (d) a $C_{1-6}$ alkoxy-carbonyl group (e.g., ethoxycarbonyl),
  (e) a carbamoyl group,
  (f) a hydroxy group, and
  (g) a cyano group,
(2) a $C_{3-10}$ cycloalkyl group (e.g., cyclopentyl, cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
  (a) a halogen atom (e.g., fluorine atom, chlorine atom),
  (b) a $C_{1-6}$ alkyl group (e.g., methyl) optionally substituted by 1 to 3 halogen atoms (e.g., fluorine atom), and
  (c) a cyano group;

$R^2$ is a hydrogen atom or a cyano group;

$R^3$ is a $C_{1-3}$ alkyl group optionally substituted by 1 to 3 substituents selected from a halogen atom (e.g., fluorine atom) and a $C_{1-6}$ alkoxy group;

$R^4$ is
(1) a $C_{1-6}$ alkyl group optionally substituted by 1 to 3 substituents selected from
  (a) a halogen atom (e.g., fluorine atom),
  (b) a cyano group,
  (c) a hydroxy group,
  (d) an amino group optionally mono- or di-substituted by $C_{1-6}$ alkyl-carbonyl group(s) (e.g., acetylamino),
  (e) a carbamoyl group optionally mono- or di-substituted by $C_{1-6}$ alkyl group(s) (e.g., dimethylcarbamoyl), and
  (f) a $C_{1-6}$ alkoxy group,
(2) a $C_{3-10}$ cycloalkyl group (e.g., cyclopropyl),
(3) a $C_{6-14}$ aryl group (e.g., phenyl) optionally substituted by 1 to 3 substituents selected from
  (a) a $C_{1-6}$ alkyl group,
  (b) an amino group optionally mono- or di-substituted by $C_{1-6}$ alkyl group(s) (e.g., methylamino, dimethylamino), and
  (c) a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), (5) a pyrazolyl group, a pyridyl group, a pyrimidinyl group or a pyrazinyl group, each of which is optionally substituted by 1 to 3 $C_{1-6}$ alkyl groups,
(6) a $C_{1-6}$ alkoxy group optionally substituted by 1 to 3 halogen atoms,
(7) a halogen atom (e.g., fluorine atom),
(8) a cyano group,
(9) a group represented by the formula

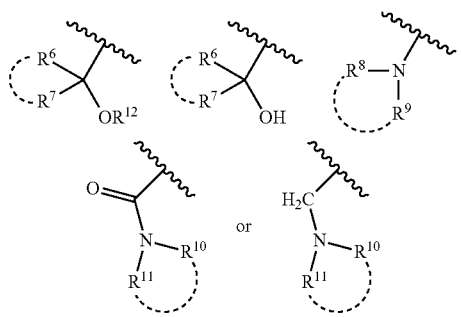

wherein
$R^6$ and $R^7$ are each independently a $C_{1-6}$ alkyl group; or
$R^6$ and $R^7$ form, together with the adjacent carbon atom, cyclobutane, cyclohexane, azetidine, tetrahydropyran or tetrahydrothiopyran, each of which is optionally substituted by 1 to 3 substituents selected from a halogen atom (e.g., fluorine atom), a carbamoyl group optionally mono- or di-substituted by $C_{1-6}$ alkyl group(s), a $C_{1-6}$ alkyl-carbonyl group, a $C_{1-6}$ alkylsulfonyl group and an oxo group;
$R^{12}$ is a $C_{1-6}$ alkyl group;
$R^8$ and $R^9$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms,
(x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or
$R^8$ and $R^9$ form, together with the adjacent nitrogen atom,
(i) an aromatic nitrogen-containing heterocycle optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom, or
(ii) a non-aromatic nitrogen-containing heterocycle optionally forming a fused ring, a bridged ring or a spiro ring (e.g., morpholine, piperidine, piperazine, pyrrolidine, oxazolidine, thiomorpholine, 1,4-oxazepane, 1,4-diazepane, octahydropyrrolo[1,2-a]pyrazine, 3-oxa-8-azabicyclo[3.2.1]octane, 6-oxa-3-azabicyclo[3.3.1]heptane, 3,8-diazabicyclo[3.2.1]octane, 2-oxa-7-azaspiro[3.5]nonane, 2-oxa-6-azaspiro[3.3]heptane, 1,7-diazaspiro[4.4]nonane, 7-oxa-1-azaspiro[4.4]nonane, 1-azaspiro[4.4]nonane, 2,5-diazaspiro[3.4]octane), and optionally substituted by 1 to 5 substituents selected from
(a) a $C_{1-6}$ alkyl group optionally substituted by 1 to 3 substituents selected from
(A) a halogen atom,
(B) a hydroxy group,
(C) a cyano group,
(D) a $C_{1-6}$ alkylsulfonyl group,
(E) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group and a $C_{1-6}$ alkylsulfonyl group,
(F) a $C_{1-6}$ alkoxy group,
(G) an azetidinyl group, a pyrrolidinyl group, a piperidyl group or a morpholinyl group, each of which is optionally substituted by 1 to 3 substituents selected from a halogen atom and an oxo group, and
(H) a pyrazolyl group,
(b) a hydroxy group,
(c) a $C_{1-6}$ alkoxy group optionally substituted by 1 to 3 halogen atoms,
(d) a halogen atom,
(e) a $C_{1-6}$ alkyl-carbonyl group (e.g., acetyl),
(f) a $C_{1-6}$ alkoxy-$C_{1-6}$ alkyl-carbonyl group (e.g., methoxyacetyl),
(g) an oxo group,
(h) a $C_{1-6}$ alkylsulfonyl group (e.g., isopropylsulfonyl, methylsulfonyl),
(i) a $C_{3-10}$ cycloalkylsulfonyl group (e.g., cyclopropylsulfonyl),
(j) an amino group optionally mono- or di-substituted by $C_{1-6}$ alkyl group(s) (e.g., dimethylamino), and
(k) a cyano group;
$R^{10}$ and $R^{11}$ are each independently
(i) a hydrogen atom,
(ii) a $C_{1-6}$ alkyl group optionally substituted by 1 to 3 substituents selected from a halogen atom, a $C_{3-8}$ cycloalkyl group and a $C_{1-6}$ alkoxy group,
(iii) a $C_{3-10}$ cycloalkyl group optionally substituted by 1 to 3 halogen atoms,
(iv) a $C_{6-14}$ aryl group optionally substituted by 1 to 3 halogen atoms,
(v) a $C_{1-6}$ alkoxy group optionally substituted by 1 to 3 halogen atoms,
(vi) a $C_{6-14}$ aryloxy group optionally substituted by 1 to 3 halogen atoms,
(vii) a $C_{1-6}$ alkyl-carbonyl group optionally substituted by 1 to 3 halogen atoms,
(viii) a $C_{1-6}$ alkoxy-carbonyl group optionally substituted by 1 to 3 halogen atoms,
(ix) a $C_{1-6}$ alkylsulfonyl group (e.g., methylsulfonyl) optionally substituted by 1 to 3 halogen atoms, (x) a carbamoyl group optionally mono- or di-substituted by $C_{1-6}$ alkyl group(s) optionally substituted by 1 to 3 halogen atoms,
(xi) an aromatic heterocyclic group (e.g., thienyl, furyl, pyridyl, pyrazolyl, imidazolyl, tetrazolyl, oxazolyl, thiazolyl, oxadiazolyl, thiadiazolyl), or
(xii) a 5- or 6-membered non-aromatic heterocyclic group having one oxygen atom (e.g., tetrahydropyranyl); or $R^{10}$ and $R^{11}$ form, together with the adjacent nitrogen atom,
(i) an aromatic nitrogen-containing heterocycle optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom, or
(ii) a non-aromatic nitrogen-containing heterocycle optionally forming a fused ring or a spiro ring (e.g., morpholine, piperidine, piperazine, pyrrolidine, oxazolidine, thiomorpholine, 1,4-oxazepane, octahydropyrrolo[1,2-a]pyrazine, 2-oxa-7-azaspiro[3.5]nonane), and optionally substituted by 1 to 3 substituents selected from
  (a) a $C_{1-6}$ alkyl group optionally substituted by 1 to 3 substituents selected from a halogen atom, a hydroxy group and a $C_{1-6}$ alkoxy group,
  (b) a hydroxy group,
  (c) a $C_{1-6}$ alkoxy group optionally substituted by 1 to 3 halogen atoms,
  (d) a halogen atom,
  (e) a $C_{1-6}$ alkyl-carbonyl group (e.g., acetyl),
  (f) a $C_{1-6}$ alkoxy-$C_{1-6}$ alkyl-carbonyl group (e.g., methoxyacetyl), and
  (g) an oxo group, or
(10) a $C_{3-8}$ cycloalkenyl group (e.g., cyclohexenyl); and
$R^5$ is a hydrogen atom.

[Compound D2]

Compound (I) wherein
$R^1$ is
(1) a $C_{1-6}$ alkyl group (e.g., methyl, ethyl, propyl, isopropyl, isobutyl, 1,2-dimethylpropyl) optionally substituted by 1 to 5 substituents selected from
  (a) a halogen atom (e.g., fluorine atom),
  (b) a $C_{3-8}$ cycloalkyl group (e.g., cyclopropyl) optionally substituted by 1 to 3 $C_{1-6}$ alkyl groups (e.g., methyl),
  (c) a $C_{1-6}$ alkoxy-carbonyl group (e.g., ethoxycarbonyl),
  (d) a carbamoyl group,
  (e) a hydroxy group, and
  (f) a cyano group,
(2) a $C_{3-10}$ cycloalkyl group (e.g., cyclopentyl, cyclohexyl) optionally substituted by 1 to 3 $C_{1-6}$ alkyl groups (e.g., methyl), or
(3) a $C_{6-14}$ aryl group (e.g., phenyl) optionally substituted by 1 to 3 substituents selected from
  (a) a halogen atom (e.g., fluorine atom, chlorine atom),
  (b) a $C_{1-6}$ alkyl group (e.g., methyl) optionally substituted by 1 to 3 halogen atoms (e.g., fluorine atom), and
  (c) a cyano group;
$R^2$ is a hydrogen atom;
$R^3$ is a $C_{1-3}$ alkyl group optionally substituted by 1 to 3 substituents selected from a halogen atom (e.g., fluorine atom) and a $C_{1-6}$ alkoxy group;
$R^4$ is
(1) a $C_{1-6}$ alkyl group optionally substituted by 1 to 3 substituents selected from
  (a) a halogen atom (e.g., fluorine atom),
  (b) a cyano group,
  (c) a hydroxy group,
  (d) an amino group optionally mono- or di-substituted by $C_{1-6}$ alkyl-carbonyl group(s) (e.g., acetylamino),
  (e) a carbamoyl group optionally mono- or di-substituted by $C_{1-6}$ alkyl group(s) (e.g., dimethylcarbamoyl), and
  (f) a $C_{1-6}$ alkoxy group,
(2) a $C_{3-10}$ cycloalkyl group (e.g., cyclopropyl),
(3) a $C_{6-14}$ aryl group (e.g., phenyl) optionally substituted by 1 to 3 substituents selected from a carbamoyl group optionally mono- or di-substituted by $C_{1-6}$ alkyl group(s) (e.g., methylcarbamoyl),
(4) a 5- or 6-membered non-aromatic heterocyclic group having one oxygen atom (e.g., dihydropyranyl, tetrahydropyranyl), or
(5) a group represented by the formula

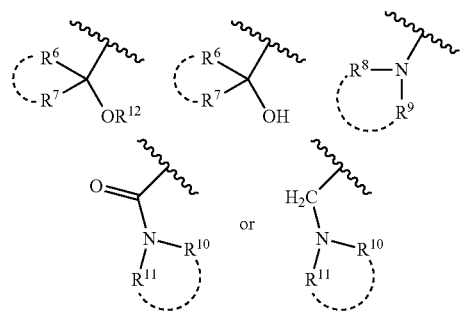

wherein
$R^6$ and $R^7$ are each independently a $C_{1-6}$ alkyl group; or
$R^6$ and $R^7$ form, together with the adjacent carbon atom, cyclobutane, cyclohexane, azetidine, tetrahydropyran or tetrahydrothiopyran, each of which is optionally substituted by 1 to 3 substituents selected from a halogen atom (e.g., fluorine atom), a carbamoyl group optionally mono- or di-substituted by $C_{1-6}$ alkyl group(s), a $C_{1-6}$ alkyl-carbonyl group, a $C_{1-6}$ alkylsulfonyl group and an oxo group;
$R^{12}$ is a $C_{1-6}$ alkyl group;
$R^8$ and $R^9$ are each independently
(i) a $C_{1-6}$ alkyl group optionally substituted by 1 to 3 substituents selected from a halogen atom, a $C_{3-8}$ cycloalkyl group and a $C_{1-6}$ alkoxy group,
(ii) a $C_{3-10}$ cycloalkyl group optionally substituted by 1 to 3 halogen atoms; or
$R^8$ and $R^9$ form, together with the adjacent nitrogen atom, a non-aromatic nitrogen-containing heterocycle optionally forming a fused ring, a bridged ring or a spiro ring (e.g., morpholine, piperidine, piperazine, pyrrolidine, oxazolidine, thiomorpholine, 1,4-oxazepane, 1,4-diazepane, octahydropyrrolo[1,2-a]pyrazine, 3-oxa-8-azabicyclo[3.2.1]octane, 2-oxa-7-azaspiro[3.5]nonane, 2-oxa-6-azaspiro[3.3]heptane) and optionally substituted by 1 to 5 substituents selected from
  (a) a $C_{1-6}$ alkyl group optionally substituted by 1 to 3 substituents selected from
    (A) a hydroxy group,
    (B) a cyano group,
    (C) an amino group optionally mono- or di-substituted by substituent(s) selected from a $C_{1-6}$ alkyl group, a $C_{1-6}$ alkyl-carbonyl group, a $C_{1-6}$ alkoxy-carbonyl group and a $C_{1-6}$ alkylsulfonyl group, (D) a $C_{1-6}$ alkoxy group, and
(E) a pyrrolidinyl group,
(b) a hydroxy group,
(c) a $C_{1-6}$ alkoxy group,
(d) a halogen atom,
(e) a $C_{1-6}$ alkyl-carbonyl group (e.g., acetyl),
(f) a $C_{1-6}$ alkoxy-$C_{1-6}$ alkyl-carbonyl group (e.g., methoxyacetyl),
(g) an oxo group,
(h) a $C_{1-6}$ alkylsulfonyl group (e.g., isopropylsulfonyl, methylsulfonyl),
(i) a $C_{3-10}$ cycloalkylsulfonyl group (e.g., cyclopropylsulfonyl),
(j) an amino group optionally mono- or di-substituted by $C_{1-6}$ alkyl group(s) (e.g., dimethylamino), and
(k) a cyano group;
$R^{10}$ and $R^{11}$ are each independently
(i) a hydrogen atom,
(ii) a $C_{1-6}$ alkyl group optionally substituted by 1 to 3 $C_{1-6}$ alkoxy groups,
(iii) a $C_{3-10}$ cycloalkyl group, or
(iv) a 5- or 6-membered non-aromatic heterocyclic group having one oxygen atom (e.g., tetrahydropyranyl); or
$R^{10}$ and $R^{11}$ form, together with the adjacent nitrogen atom, a non-aromatic nitrogen-containing heterocycle (e.g., morpholine, pyrrolidine, thiomorpholine) optionally substituted by 1 to 3 oxo groups, or
(6) a $C_{3-8}$ cycloalkenyl group (e.g., cyclohexenyl); and
$R^5$ is a hydrogen atom.
[Compound E]
3-amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one or a salt thereof;
3-amino-7-(5-(1-hydroxy-2-methylpropan-2-yl)-1-methyl-1H-pyrazol-3-yl)-5-((2S)-3-methylbutan-2-yl)-1,5-dihydro-4H-pyrazolo[4,3-c]pyridin-4-one or a salt thereof;
3-amino-5-(1-cyclopropylethyl)-7-(1-methyl-5-(morpholin-4-yl)-1H-pyrazol-3-yl)-1,5-dihydro-4H-pyrazolo[4,3-c]pyridin-4-one or a salt thereof;
3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one or a salt thereof;
3-amino-5-((1S)-1-cyclopropylethyl)-7-(5-(4-hydroxy-4-methylpiperidin-1-yl)-1-methyl-1H-pyrazol-3-yl)-1,5-dihydro-4H-pyrazolo[4,3-c]pyridin-4-one or a salt thereof;
3-amino-5-(dicyclopropylmethyl)-7-(1-methyl-5-(morpholin-4-yl)-1H-pyrazol-3-yl)-1,5-dihydro-4H-pyrazolo[4,3-c]pyridin-4-one or a salt thereof; or
3-amino-5-(dicyclopropylmethyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one or a salt thereof.

When compound (I) is in the form of a salt, examples thereof include metal salts, ammonium salt, salts with organic bases, salts with inorganic acids, salts with organic acids, salts with basic or acidic amino acids, and the like. Preferable examples of the metal salt include alkali metal salts such as sodium salt, potassium salt and the like; alkaline earth metal salts such as calcium salt, magnesium salt, barium salt and the like; aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of compound (I) of the present invention is explained below.

Compound (I) and the starting compound thereof can be produced by a means known per se, for example, the method shown in the following scheme and the like. In each step of the following production methods, "room temperature" generally means 10 to 30° C., and each symbol in the chemical structural formulas described in the schemes is as defined above, unless particularly indicated. The compounds in the formulas may also be in the form of salts, and examples of such salt include those similar to the salt of compound (I), and the like.

In each of the following reactions, when the starting compound and intermediate have an amino group, a carboxy group or a hydroxy group as a substituent, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "Protective Groups in Organic Synthesis, 4th Ed." (Theodora W. Greene, Peter G. M. Wuts, Wiley-Interscience, 2006) and the like.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl etc.), a $C_{7-12}$ aralkyloxy-carbonyl group (e.g., benzyloxycarbonyl, 9-fluorenylmethoxycarbonyl etc.), a trityl group, a phthaloyl group, an N,N-dimethylaminomethylene group, a silyl group optionally substituted by a $C_{1-6}$ alkyl group (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-12}$ aralkyl group (e.g., benzyl etc.), a phenyl group, a trityl group, a silyl group optionally substituted by a $C_{1-6}$ alkyl group (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

Examples of the hydroxy-protecting group include a $C_{1-6}$ alkyl group, a phenyl group, a trityl group, a $C_{7-12}$ aralkyl group (e.g., benzyl etc.), a formyl group, a $C_{1-6}$ alkyl-carbonyl group, a benzoyl group, a $C_{7-12}$ aralkyl-carbonyl group (e.g., benzylcarbonyl etc.), a 2-tetrahydropyranyl group, a 2-tetrahydrofuranyl group, a silyl group optionally substituted by a $C_{1-6}$ alkyl group (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

These groups are optionally substituted by 1 to 3 substituents selected from a halogen atom, a $C_{1-6}$ alkyl group, a $C_{1-6}$ alkoxy group and a nitro group.

As a method for removing the above-mentioned protecting groups, a method known per se, for example, the method described in "Protective Groups in Organic Synthesis, 4th Ed.", Wiley-Interscience, Inc. (2006) (Theodora W. Greene, Peter G. M. Wuts) and the like can be mentioned. Specifically, a method using an acid, a base, ultraviolet rays, hydrazine, phenylhydrazine, sodium N-methyldithiocarbamate, tetrabutylammonium fluoride, palladium acetate, trialkylsilyl halides (e.g., trimethylsilyl iodide, trimethylsilyl bromide etc.) and the like, a reduction method and the like are used.

The compound obtained in each step can be used as a reaction mixture or as a crude product in the next reaction. In addition, the compound can be isolated from a reaction mixture according to a conventional method, and can be easily purified by a separation means such as recrystallization, distillation, chromatography and the like.

Compound (I) can be produced using, for example, the following method A, method B, method C, method D, method E, method F, method G, method H, and method I. As the starting compound of each method, a commercially available product may be directly used, or can also be produced by a method known per se or a method analogous thereto.

Of compounds (I), a compound represented by the formula (I-A)

I-A

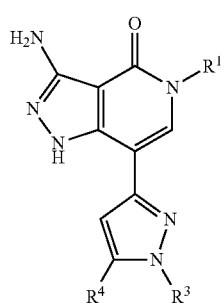

wherein each symbol is as defined above (hereinafter to be abbreviated as compound (I-A)) can be produced by the method shown below or a method analogous thereto. In each step of the following production methods, the starting compound may also be in the form of a salt and, as such salt, those exemplified as the salt of compound (I) are used.

[Method A]

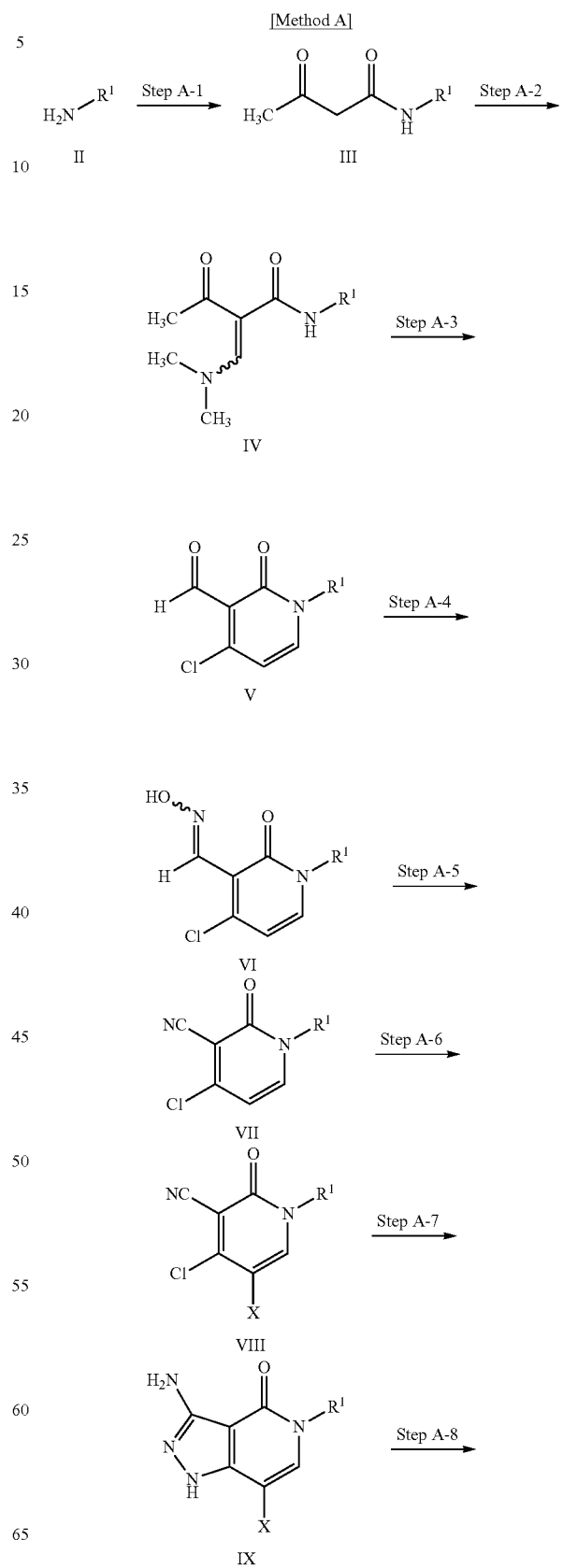

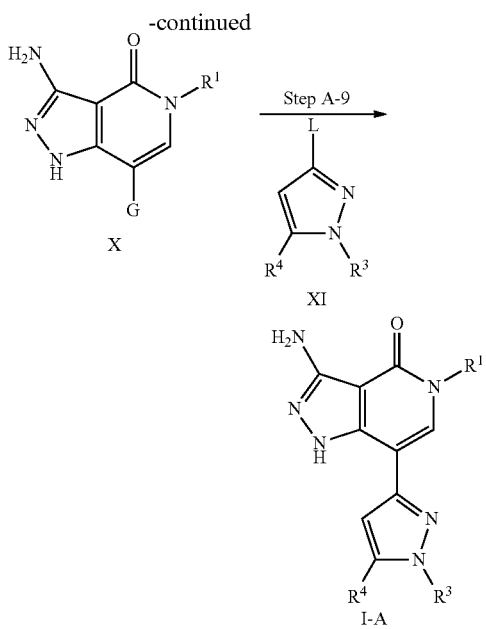

wherein X is a halogen atom, G is —B(OH)₂ or —B(OR)(OR') wherein R and R' are each independently a C$_{1-6}$ alkyl group; or the adjacent R and R' are optionally bonded to form a dioxaborolanyl group (e.g., 4,4,5,5-tetramethyl-1,3,2-dioxaborolan-2-yl group) optionally substituted by 1 to 4 C$_{1-6}$ alkyl groups, L is a leaving group, and other symbols are as defined above.

As compound (II) and compound (XI) to be used as the starting materials in this method, a commercially available product may be directly used, or can also be produced easily by a method known per se or a method analogous thereto.

Examples of the halogen atom for X include a fluorine atom, a chlorine atom, a bromine atom, and an iodine atom. As the leaving group for L include a halogen atom (e.g., chlorine atom, bromine atom, iodine atom and the like), an optionally substituted sulfonyloxy group (e.g., optionally substituted C$_{1-6}$ alkylsulfonyloxy group (e.g., methanesulfonyloxy group, ethanesulfonyloxy group, trifluoromethanesulfonyloxy group and the like); a C$_{6-14}$ arylsulfonyloxy group (e.g., benzenesulfonyloxy group, p-toluenesulfonyloxy group and the like); a C$_{7-16}$ aralkylsulfonyloxy group (e.g., benzylsulfonyloxy group and the like) and the like) and the like are used, and halogen atom is particularly preferable.

The "C$_{1-6}$ alkylsulfonyloxy group" of the "optionally substituted C$_{1-6}$ alkylsulfonyloxy group" for L optionally has 1 to 5 (preferably 1 to 3) substituents at substitutable position(s). Examples of such substituent include the substituents selected from the aforementioned Substituent Group A. When a plurality of substituents are present, the respective substituents may be the same or different. It is preferably a halogen atom (e.g., fluorine atom, chlorine atom, bromine atom, iodine atom and the like).

(Step A-1)

In this step, compound (II) is reacted with an acylating agent to perform an acylation reaction to convert same to compound (III).

Where necessary, this step can be performed in the presence of a base in a solvent that does not adversely influence the reaction.

Examples of the acylating agent to be used in this step include 2,2,6-trimethyl-4H-1,3-dioxin-4-one, diketene, acid chloride, acid anhydride, active ester and the like. Of these, 2,2,6-trimethyl-4H-1,3-dioxin-4-one and diketene are preferable.

The amount of the acylating agent to be used is about 1 mol-about 100 mol, preferably about 1 mol-about 10 mol, per 1 mol of compound (II).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts such as sodium acetate, potassium acetate and the like are preferable.

The amount of the base to be used is about 0.1 mol-about 100 mol, preferably about 1 mol-about 10 mol, per 1 mol of compound (II).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 100° C. The reaction time in this step is generally about 0.1 hr-about 100 hr.

The thus-obtained compound (III) can be isolated and purified by a known separation and purification means, for example, concentration, concentration under reduced pressure, solvent extraction, crystallization, recrystallization, phase transfer, chromatography and the like. Compound (III) may be used for the next reaction without isolation.

(Step A-2)

In this step, compound (III) is reacted with an olefinating agent to convert to compound (IV).

Where necessary, this step can be performed in a solvent that does not adversely influence the reaction.

Examples of the olefinating agent to be used include 1,1-dimethoxy-N,N-dimethylmethanamine, 1,1-diethoxy-N,N-dimethylmethanamine and the like.

The amount of the olefinating agent to be used is about 1 mol-about 100 mol, preferably about 1 mol-about 10 mol, per 1 mol of compound (III).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N- dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 100° C. The reaction time in this step is generally about 0.1 hr-about 100 hr.

The thus-obtained compound (IV) can be isolated and purified by a known separation and purification means, for example, concentration, concentration under reduced pressure, solvent extraction, crystallization, recrystallization, phase transfer, chromatography and the like. Compound (IV) may be used for the next reaction without isolation.
(Step A-3)

In this step, compound (IV) is reacted with a Vilsmeier reagent to convert to compound (V).

Where necessary, this step can be performed in a solvent that does not adversely influence the reaction.

A Vilsmeier reagent is prepared from N,N-dimethylformamide and a chlorinating agent (e.g., phosphorus oxychloride, phosphorus pentachloride, phosgene etc.). Alternatively, a commercially available Vilsmeier reagent can be used.

The amount of the Vilsmeier reagent to be used is about 1 mol-about 100 mol, preferably about 1 mol-about 10 mol, per 1 mol of compound (IV).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (V) can be isolated and purified by a known separation and purification means, for example, concentration, concentration under reduced pressure, solvent extraction, crystallization, recrystallization, phase transfer, chromatography and the like. Compound (V) may be used for the next reaction without isolation.
(Step A-4)

In this step, compound (V) is subjected to an oximation reaction by reacting with hydroxylamine or a salt thereof to convert to compound (VI).

Where necessary, this step can be performed in the presence of an acid or base in a solvent that does not adversely influence the reaction.

The amount of hydroxylamine or a salt thereof to be used is about 1 mol-about 100 mol, preferably about 1 mol-about 10 mol, per 1 mol of compound (V). As the salt of hydroxylamine, those exemplified as the salt of compound (I) can be used.

Examples of the acid to be used include hydrochloric acid, hydrobromic acid, sulfuric acid, trifluoroacetic acid, trifluoromethanesulfonic acid, hydrogen chloride and the like.

The amount of the acid to be used is about 0.1 mol-about 100 mol, per 1 mol of compound (V).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.) and the like. Of these, alkali metal salts such as sodium acetate, potassium acetate and the like are preferable.

The amount of the base to be used is about 0.1 mol-about 100 mol, preferably about 1 mol-about 10 mol, per 1 mol of compound (V).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (VI) can be isolated and purified by a known separation and purification means, for example, concentration, concentration under reduced pressure, solvent extraction, crystallization, recrystallization, phase transfer, chromatography and the like. Compound (VI) may be used for the next reaction without isolation.
(Step A-5)

In this step, compound (VI) is reacted with a dehydrating agent to convert to compound (VII).

Where necessary, this step can be performed in a solvent that does not adversely influence the reaction.

Examples of the dehydrating agent to be used include phosphorus oxychloride, thionyl chloride, oxalyl chloride, acetic anhydride, acetyl chloride, trichloroacetyl chloride and the like.

The amount of the dehydrating agent to be used is about 0.1 mol-about 100 mol per 1 mol of compound (VI).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (VII) can be isolated and purified by a known separation and purification means, for example, concentration, concentration under reduced pressure, solvent extraction, crystallization, recrystallization, phase transfer, chromatography and the like. Compound (VII) may be used for the next reaction without isolation.
(Step A-6)

In this step, compound (VII) is subjected to a substitution reaction by reacting with a halogenating agent to convert to compound (VIII).

Where necessary, this step can be performed in a solvent that does not adversely influence the reaction.

Examples of the halogenating agent to be used include bromine, iodine, N-bromosuccinimide, N-iodosuccinimide and the like. Where necessary, an acid (hydrobromic acid, hydrochloric acid, trifluoroacetic acid etc.) or a base may be added.

The amount of the halogenating agent to be used is about 0.1 mol-about 100 mol per 1 mol of compound (VII). The amount of the acid to be used is about 0.000001 mol-about 100 mol per 1 mol of compound (VII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 1 mol-about 100 mol per 1 mol of compound (VII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (VIII) can be isolated and purified by a known separation and purification means, for example, concentration, concentration under reduced pressure, solvent extraction, crystallization, recrystallization, phase transfer, chromatography and the like. Compound (VIII) may be used for the next reaction without isolation.
(Step A-7)

In this step, compound (VIII) is reacted with hydrazine or a salt thereof or a hydrate thereof to convert to compound (IX).

Where necessary, this step can be performed in a solvent that does not adversely influence the reaction.

The amount of the hydrazine or a salt thereof or a hydrate thereof to be used is about 1 mol-about 100 mol per 1 mol of compound (VIII).

As the salt of hydrazine or hydrate, those exemplified as the salt of compound (I) or hydrate are used.

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (IX) can be isolated and purified by a known separation and purification means, for example, concentration, concentration under reduced pressure, solvent extraction, crystallization, recrystallization, phase transfer, chromatography and the like.
(Step A-8)

In this step, compound (IX) is subjected to a substitution reaction in the presence of a transition metal catalyst to convert to compound (X).

The reaction using a transition metal catalyst can be performed according to a method known per se [e.g., Chemical Reviews, 1995, vol. 95, page 2457 etc.], for example, in the presence of a transition metal catalyst and a base and using, for example, 4,4,4',4',5,5,5',5'-octamethyl-2,2'-bi-1,3,2-dioxaborolane, in a solvent that does not adversely influence the reaction.

The amount of 4,4,4',4',5,5,5',5'-octamethyl-2,2'-bi-1,3,2-dioxaborolane to be used is about 1 mol-about 100 mol, preferably about 1 mol-about 10 mol, per 1 mol of compound (IX).

Examples of the transition metal catalyst to be used include palladium catalysts (e.g., palladium(II) acetate, tris (dibenzylideneacetone)dipalladium(0), palladium(II) chloride, tetrakis(triphenylphosphine)palladium(0), (1,1'-bis(diphenylphosphino)ferrocene)dichloropalladium(II)) etc., nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, or metal oxide (e.g., copper oxide, iron oxide etc.) may be used as a cocatalyst. While the amount of the transition metal catalyst to be used varies depending on the kind of the catalyst, it is generally about 0.0001 mol-about 1 mol, preferably about 0.01 mol-about 0.5 mol, per 1 mol of compound (IX). The amount of the ligand or cocatalyst to be used is generally about 0.0001 mol-about 4 mol, preferably about 0.01 mol-about 2 mol, per 1 mol of compound (IX).

Examples of the base include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts (e.g., sodium carbonate, potassium carbonate, cesium carbonate etc.) are preferable.

The amount of the base to be used is about 0.1 mol-about 100 mol, preferably about 1 mol-about 10 mol, per 1 mol of compound (IX).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (X) can be isolated and purified by a known separation and purification means, for example, concentration, concentration under reduced pressure, solvent extraction, crystallization, recrystallization, phase transfer, chromatography and the like. Compound (X) may be used for the next reaction without isolation.

(Step A-9)

In this step, compound (X) is reacted with compound (XI) by a coupling reaction using a transition metal catalyst to convert to compound (I-A).

The reaction using a transition metal catalyst can be performed by a method known per se [e.g., Chemical Reviews, 1995, vol. 95, page 2457 etc.], for example, in the presence of a transition metal catalyst and a base, in a solvent that does not adversely influence the reaction.

The amount of compound (XI) to be used is about 1 mol-about 100 mol, preferably about 1 mol-about 10 mol, per 1 mol of compound (X).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II)) etc., nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, or metal oxide (e.g., copper oxide, iron oxide etc.) may be used as a cocatalyst. While the amount of the transition metal catalyst to be used varies depending on the kind of the catalyst, it is generally about 0.0001 mol-about 1 mol, preferably about 0.01 mol-about 0.5 mol, per 1 mol of compound (X). The amount of the ligand or cocatalyst to be used is generally about 0.0001 mol-about 4 mol, preferably about 0.01 mol-about 2 mol, per 1 mol of compound (X).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (X).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (I-A) can be isolated and purified by a known separation and purification means, for example, concentration, concentration under reduced pressure, solvent extraction, crystallization, recrystallization, phase transfer, chromatography and the like.

Compound (III), compound (IV), compound (V), compound (VI), compound (VII), compound (VIII), compound (IX), compound (X), and compound (I-A) obtained by the above-mentioned method A can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se.

Compound (IX) can also be produced by method B shown below.

[Method B]

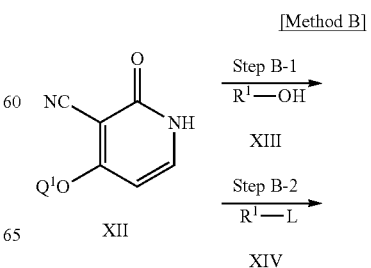

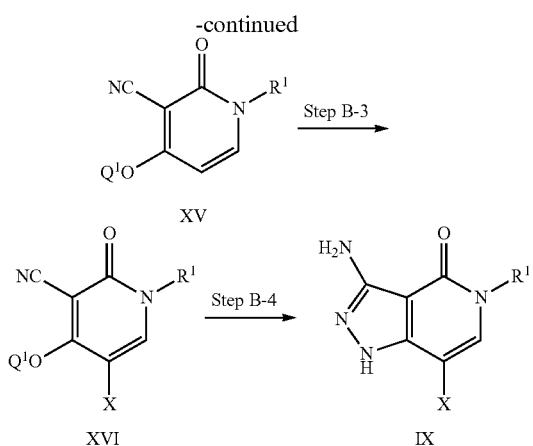

wherein $Q^1$ is a $C_{1-3}$ alkyl group, and other symbols are as defined above.

Examples of the $C_{1-3}$ alkyl group for $Q^1$ include a methyl group, an ethyl group and the like.

As compound (XII), compound (XIII), and compound (XIV) to be used as the starting materials in this method, a commercially available product may be directly used, or can also be produced by a method known per se or a method analogous thereto. In each step of the following production methods, the starting compound may be in the form of a salt and, as such salt, those exemplified as the salt of compound (I) are used.

(Step B-1)

In this step, compound (XII) is reacted with compound (XIII) to convert to compound (XV). This reaction can be performed by a method known per se, for example, the method described in Synthesis 1, 1-28, (1981) and the like, or a method analogous thereto.

The amount of compound (XIII) to be used is about 1 mol-about 100 mol, preferably about 1 mol-about 10 mol, per 1 mol of compound (XII).

That is, this reaction is performed in the presence of an organic phosphorus compound and an electrophile, in a solvent that does not adversely influence the reaction.

Examples of the organic phosphorus compound include triphenylphosphine, tributylphosphine and the like.

Examples of the electrophile include diethyl azodicarboxylate, diisopropyl azodicarboxylate, azodicarbonyldipiperazine, bis(2-methoxyethyl) azodicarboxylate and the like.

The amount of the organic phosphorus compound and electrophile to be used is each about 0.1 mol-about 100 mol, preferably about 1 mol-about 10 mol, relative to compound (XII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XV) can be isolated and purified by a known separation and purification means, for example, concentration, concentration under reduced pressure, solvent extraction, crystallization, recrystallization, phase transfer, chromatography and the like. Compound (XV) may be used for the next reaction without isolation.

Compound (XV) can also be produced by the method shown in the following Step B-2.

(Step B-2)

In this step, compound (XII) is reacted with compound (XIV) to convert to compound (XV).

Where necessary, this step can be performed in the presence of a base and in a solvent that does not adversely influence the reaction. Furthermore, lithium bromide may be added to the solvent.

The amount of compound (XIV) to be used is about 1 mol-about 100 mol, preferably about 1 mol-about 10 mol, per 1 mol of compound (XII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XII).

The amount of lithium bromide to be used is about 0.1 mol-about 100 mol, preferably about 1 mol-about 10 mol, per 1 mol of compound (XII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XV) can be isolated and purified by a known separation and purification means, for example, concentration, concentration under reduced pressure, solvent extraction, crystallization, recrystallization, phase transfer, chromatography and the like. Compound (XV) may be used for the next reaction without isolation.

(Step B-3)

Compound (XVI) is obtained using compound (XV) by a method similar to step A-6 of method A.

(Step B-4)

Compound (IX) is obtained using compound (XVI) by a method similar to step A-7 of method A.

The thus-obtained compound (IX) can be isolated and purified by a known separation and purification means, for example, concentration, concentration under reduced pressure, solvent extraction, crystallization, recrystallization, phase transfer, chromatography and the like.

Compound (XV), compound (XVI), and compound (IX) obtained by the above-mentioned method B can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se. Such reactions can be performed according to a method known per se.

Compound (XV) can also be produced by method C shown below.

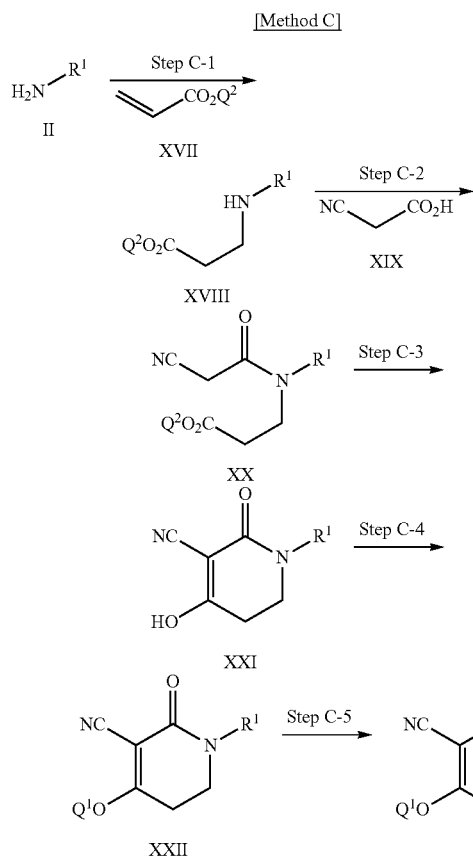

wherein $Q^2$ is a $C_{1-3}$ alkyl group, and other symbols are as defined above.

Examples of the $C_{1-3}$ alkyl group for $Q^2$ include a methyl group, an ethyl group and the like.

As compound (II), compound (XVII), and compound (XIX) to be used as the starting materials in this method, a commercially available product may be directly used, or can also be produced by a method known per se or a method analogous thereto. In each step of the following production methods, the starting compound may be in the form of a salt and, as such salt, those exemplified as the salt of compound (I) are used.

(Step C-1)

In this step, compound (II) is reacted with compound (XVII), where necessary, in the presence of a base to convert to compound (XVIII).

Where necessary, this step can be performed in a solvent that does not adversely influence the reaction.

The amount of compound (XVII) to be used is about 1 mol-about 100 mol, per 1 mol of compound (II).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, organic amines such as triethylamine and the like, alkali metal salts such as sodium acetate, potassium acetate and the like are preferable.

The amount of the base to be used is about 0.1 mol-about 100 mol, preferably about 0.5 mol-about 10 mol, per 1 mol of compound (II).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about $-50°$ C.-about $200°$ C., preferably about $-10°$ C.-about $150°$ C. The reaction time in this step is generally about 0.1 hr-about 200 hr.

The thus-obtained compound (XVIII) can be isolated and purified by a known separation and purification means, for example, concentration, concentration under reduced pressure, solvent extraction, crystallization, recrystallization, phase transfer, chromatography and the like.

(Step C-2)

In this step, compound (XVIII) is subjected to a condensation reaction with compound (XIX) or a reactive derivative thereof to convert to compound (XX). This reaction is performed by a method known per se, for example, 1) a method including direct condensation of compound (XVIII) and compound (XIX), 2) a method including reaction of a reactive derivative of compound (XIX) with compound (XVIII) and the like.

Examples of the reactive derivative of compound (XIX) include acid halides (e.g., acid chloride, acid bromide), imidazolide, mixed acid anhydrides (e.g., anhydride with methyl carbonate, ethyl carbonate, isobutyl carbonate etc.) and the like.

In a method including direct condensation of compound (XVIII) and compound (XIX), this reaction is performed in the presence of a condensing agent, in the presence of an organic amine base, as necessary, in a solvent that does not adversely influence the reaction.

The amount of compound (XIX) to be used is generally about 0.1-10 mol, preferably about 0.3-3 mol, per 1 mol of compound (XVIII).

Examples of the condensing agent include condensing agents known the field, for example, carbodiimide condensation reagents such as dicyclohexylcarbodiimide, diisopropylcarbodiimide, N-[3-(dimethylamino)propyl]-N'-ethylcarbodiimide and hydrochloride thereof and the like; phosphoric acid condensation reagents such as 2,4,6-tripropyl-1,3,5,2,4,6-trioxatriphosphinane 2,4,6-trioxide (synonym, propylphosphonic anhydride (cyclic trimer)), diethyl cyanophosphate, diphenyl azidophosphate and the like; 2-methyl-6-nitrobenzoic anhydride, N,N'-carbonyldiimidazole, 2-chloro-1,3-dimethylimidazolium tetrafluoroborate and the like.

The amount of the condensing agent to be used is generally about 0.1-about 10 mol, preferably about 0.3-about 5 mol, per 1 mol of compound (XIX).

When carbodiimide condensation reagent or 2-methyl-6-nitrobenzoic anhydride is used as a condensing agent as necessary, the reaction efficiency can be improved by using a suitable condensation promoter (e.g., 1-hydroxy-7-azabenzotriazole, 1-hydroxybenzotriazole, N-hydroxysuccinimide, N-hydroxyphthalimide, 4-dimethylaminopyridine etc.).

The amount of the condensation promoter to be used is generally about 0.1-about 10 mol, preferably about 0.3-about 5 mol, per 1 mol of compound (XVIII).

Examples of the organic amine base include trimethylamine, triethylamine, N-ethyldiisopropylamine, N-methylmorpholine, 1,8-diazabicyclo[5.4.0]undec-7-ene, pyridine, N,N-dimethylaniline and the like.

The amount of the organic amine base to be used is generally about 0.1-about 10 mol, preferably about 0.3-about 5 mol, per 1 mol of compound (XIX).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 200 hr.

The thus-obtained compound (XX) can be isolated and purified by a known separation and purification means, for example, concentration, concentration under reduced pressure, solvent extraction, crystallization, recrystallization, phase transfer, chromatography and the like. Compound (XX) may be used for the next reaction without isolation.

(Step C-3)

In this step, compound (XX) is converted to compound (XXI).

This step can be performed in the presence of a base as necessary, in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XX).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XXI) can be isolated and purified by a known separation and purification means, for example, concentration, concentration under reduced pressure, solvent extraction, crystallization, recrystallization, phase transfer, chromatography and the like. Compound (XXI) may be used for the next reaction without isolation.

(Step C-4)

In this step, compound (XXI) is reacted with an alkylating agent to convert to compound (XXII).

This step can be performed in the presence of a base as necessary, in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXI).

Examples of the alkylating agent to be used include dimethyl sulfate, methyl iodide, ethyl iodide and the like The amount of the alkylating agent to be used is about 1 mol-about 100 mol, preferably about 1 mol-about 10 mol, per 1 mol of compound (XXI).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XXII) can be isolated and purified by a known separation and purification means, for example, concentration, concentration under reduced pressure, solvent extraction, crystallization, recrystallization, phase transfer, chromatography and the like. Compound (XXII) may be used for the next reaction without isolation. (Step C-5)

In this step, compound (XXII) is subjected to an oxidation reaction by reacting same with an oxidizing agent to convert to compound (XV).

This step can be performed in a solvent that does not adversely influence the reaction.

Examples of the oxidizing agent to be used include 2,3-dichloro-5,6-dicyano-1,4-benzoquinone, m-chloroperbenzoic acid, hydrogen peroxide water, and Oxone (double salt compound of potassium peroxymonosulfate-potassium hydrogensulfate-potassium sulfate) and the like.

The amount of oxidizing agent to be used is about 1 mol-about 100 mol, preferably about 1 mol-about 10 mol, per 1 mol of compound (XXII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XV) can be isolated and purified by a known separation and purification means, for example, concentration, concentration under reduced pressure, solvent extraction, crystallization, recrystallization, phase transfer, chromatography and the like. Compound (XV) may be used for the next reaction without isolation.

Compound (XVIII), compound (XX), compound (XXI), compound (XXII), and compound (XV) obtained in the above-mentioned method C can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se. Such reactions can be performed according to a method known per se.

Compound (XV) can also be produced by method D shown below.

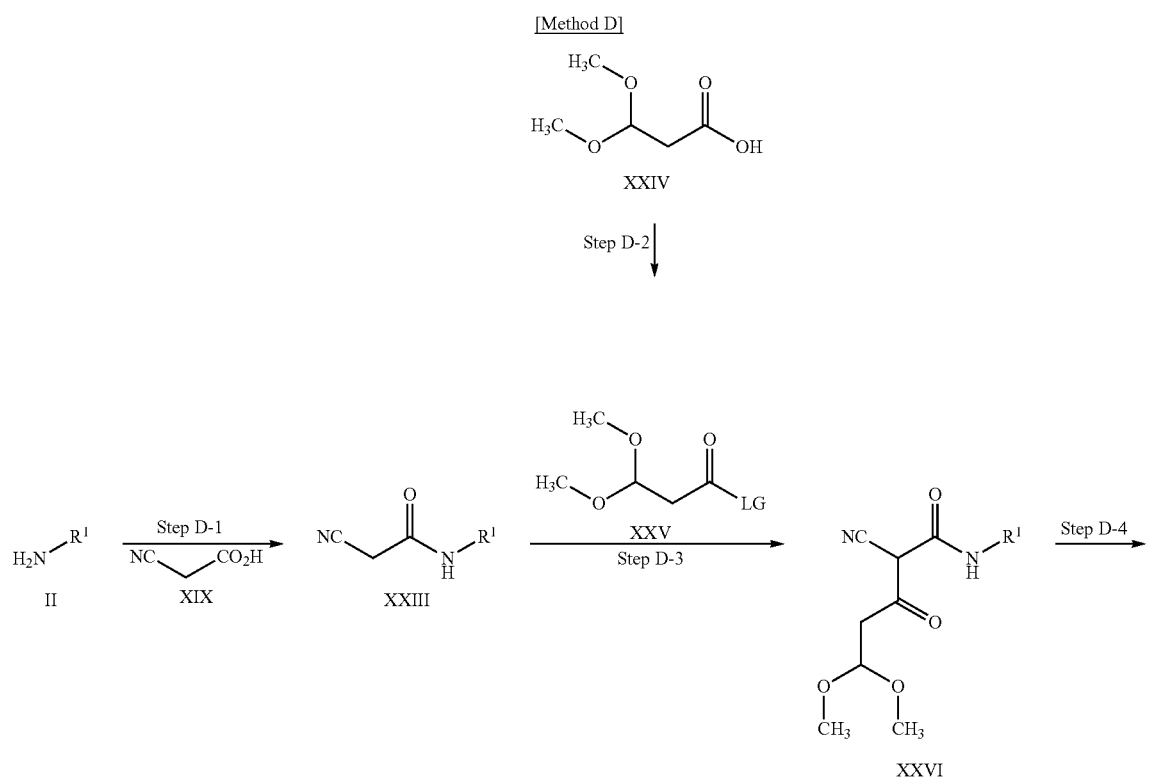

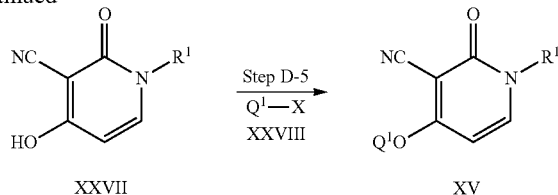

wherein LG is a leaving group, and other symbols are as defined above.

As compound (II), compound (XIX), compound (XXIV), and compound (XXVIII) to be used as the starting materials in this method, a commercially available product may be directly used, or can also be produced by a method known per se or a method analogous thereto. In each step of the following production methods, the starting compound may be in the form of a salt and, as such salt, those exemplified as the salt of compound (I) are used.

Examples of the leaving group for LG include halogen atoms (e.g., chlorine atom, bromine atom, iodine atom and the like), an optionally substituted $C_{1-6}$ alkoxy-carbonyl group, an imidazolyl group, a diethoxyphosphoryloxy group, a succinimidooxy group and the like, and a $C_{1-6}$ alkoxy-carbonyl group is particularly preferable.

The "$C_{1-6}$ alkoxy-carbonyl group" of the "optionally substituted $C_{1-6}$ alkoxy-carbonyl group" for LG optionally has 1 to 5 (preferably 1 to 3) substituent(s) at substitutable position(s). Examples of such substituent include substituents selected from the aforementioned substituent group A can be mentioned. When a plurality of substituents are present, the respective substituents may be the same or different.

(Step D-1)

Compound (XXIII) can be obtained using compound (II) and compound (XIX) and by a method similar to step C-2 of method C.

(Step D-2)

In this step, compound (XXIV) is reacted with a carboxylic acid activating reagent to convert to compound (XXV).

Where necessary, this step can be performed in the presence of a base in a solvent that does not adversely influence the reaction.

Examples of the carboxylic acid activating reagent to be used include methyl chlorocarbonate, ethyl chlorocarbonate, isopropyl chlorocarbonate, N,N'-carbonyldiimidazole, N-hydroxysuccinimide, diethyl cyanophosphate, oxalyl chloride and the like.

The amount of the carboxylic acid activating reagent to be used is about 0.1 mol-about 100 mol, preferably about 1 mol-about 10 mol, per 1 mol of compound (XXIV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXIV).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XXV) can be isolated and purified by a known separation and purification means, for example, concentration, concentration under reduced pressure, solvent extraction, crystallization, recrystallization, phase transfer, chromatography and the like. Compound (XXV) may be used for the next reaction without isolation.

(Step D-3)

In this step, compound (XXIII) and compound (XXV) are converted to compound (XXVI).

Where necessary, this step can be performed in the presence of a base in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXIII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The amount of compound (XXV) to be used is generally about 0.1-10 mol, preferably about 0.3-3 mol, per 1 mol of compound (XXIII).

The reaction temperature in this step is generally about −50° C.-about 200° C., preferably about −10° C.-about 150° C. The reaction time in this step is generally about 0.1 hr-about 100 hr.

The thus-obtained compound (XXVI) can be isolated and purified by a known separation and purification means, for example, concentration, concentration under reduced pressure, solvent extraction, crystallization, recrystallization, phase transfer, chromatography and the like. Compound (XXVI) may be used for the next reaction without isolation.
(Step D-4)

In this step, compound (XXVI) is converted to compound (XXVII) in the presence of an acid.

Where necessary, this step can be performed in the presence of a base in a solvent that does not adversely influence the reaction.

Examples of the acid to be used include mineral acids such as hydrochloric acid, sulfuric acid, hydrobromic acid and the like; organic acids such as acetic acid and the like, and Lewis acids such as trimethylsilyl trifluoromethanesulfonate, triethylsilyl trifluoromethanesulfonate and the like.

The amount of the acid to be used is about 0.1 mol-about 100 mol, preferably about 1 mol-about 10 mol, per 1 mol of compound (XXVI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline, 2,6-dimethylpyridine, 2,4,6-trimethylpyridine etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXVI).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XXVII) can be isolated and purified by a known separation and purification means, for example, concentration, concentration under reduced pressure, solvent extraction, crystallization, recrystallization, phase transfer, chromatography and the like. Compound (XXVII) may be used for the next reaction without isolation.
(Step D-5)

In this step, compound (XXVII) is reacted with compound (XXVIII) to convert to compound (XV).

This step can be performed in the presence of a base, where necessary, in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXVII).

The amount of compound (XXVIII) to be used is about 1 mol about 100 mol, preferably about 1 mol-about 10 mol, per 1 mol of compound (XXVII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XV) can be isolated and purified by a known separation and purification means, for example, concentration, concentration under reduced pressure, solvent extraction, crystallization, recrystallization, phase transfer, chromatography and the like. Compound (XV) may be used for the next reaction without isolation.

Compound (XXIII), compound (XXVI), compound (XXVII), and compound (XV) obtained by the above-mentioned method D can also be further derivatized by subjecting to various known reactions such as condensation reactions such as acylation reaction, alkylation reaction, amidation reaction and the like or oxidation reaction, reduction reaction, hydrolysis, dehydration reaction and the like.

Such reactions can be performed according to a method known per se.

Of compounds (XI), compounds represented by (XI-A), (XI-B), or (XI-C)

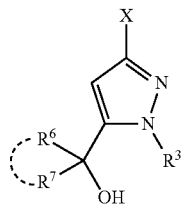

XI-A

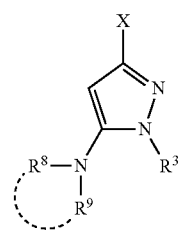

XI-B

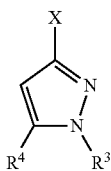

XI-C wherein each symbol is as defined above, can be produced by method E shown below, or a method analogous thereto. In each step of the following production methods, the starting compound may be in the form of a salt and, as such salt, those exemplified as the salt of compound (I) are used.

[Method E]

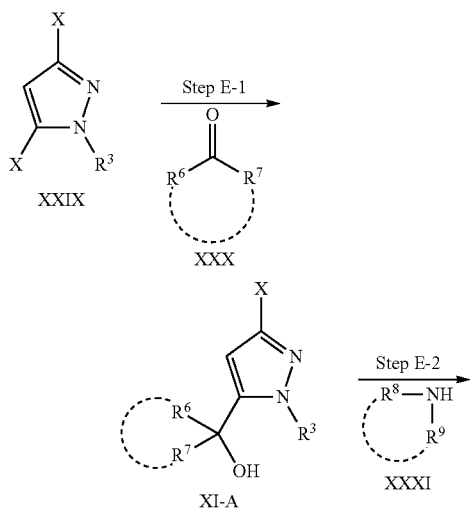

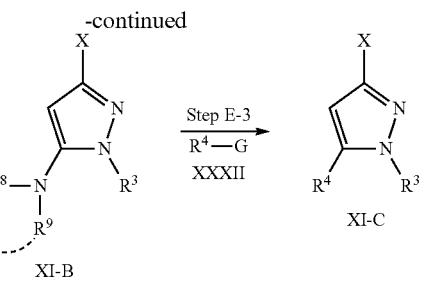

wherein each symbol is as defined above.

As compound (XXIX) to be used as the starting material in this method, a commercially available product may be directly used, or can also be produced by a method known per se [e.g., WO 2012/030922 etc.] or a method analogous thereto. As compound (XXX), compound (XXXI), or compound (XXXII), a commercially available product may be directly used, or can also be produced by a method known per se or a method analogous thereto.

(Step E-1)

In this step, compound (XXIX) is converted to compound (XI-A) by reacting with compound (XXX) in the presence of a base.

Examples of the base to be used include organic lithium reagents (e.g., n-butyllithium, sec-butyllithium, tert-butyllithium etc.) and the like.

The amount of the base to be used is about 0.1 mol-about 100 mol, preferably about 1 mol-about 10 mol, per 1 mol of compound (XXIX).

The amount of compound (XXX) to be used is about 0.1 mol about 100 mol, preferably about 1 mol-about 10 mol, per 1 mol of compound (XXIX).

The solvent in this reaction is not particularly limited as long as the reaction proceeds. Examples of the solvent include hydrocarbons (e.g., benzene, toluene, xylene, hexane, heptane etc.), ethers (e.g., diethyl ether, diisopropyl ether, tert-butyl methyl ether, tetrahydrofuran, 1,4-dioxane, 1,2-dimethoxyethane etc.), and a mixture thereof.

The reaction temperature in this step is generally about −100° C.-about 200° C., preferably about −80° C.-about 50° C. The reaction time in this step is generally about 0.1 hr-about 100 hr.

The thus-obtained compound (XI-A) can be isolated and purified by a known separation and purification means, for example, concentration, concentration under reduced pressure, solvent extraction, crystallization, recrystallization, phase transfer, chromatography and the like. Compound (XI-A) may be used for the next reaction without isolation.

(Step E-2)

In this step, compound (XXIX) is reacted with compound (XXXI) to convert to compound (XI-B). Where necessary, this step can be performed in the presence of a base, with the addition of a transition metal catalyst, in a solvent that does not adversely influence the reaction.

The amount of compound (XXXI) to be used is about 1 mol-about 100 mol, preferably about 1 mol-about 10 mol, relative to compound (XXIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxide (e.g., sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, relative to compound (XXIX).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II)) etc., nickel catalysts (e.g., nickel chloride etc.) and the like. Where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, or metal oxide (e.g., copper oxide, iron oxide etc.) may be used as a cocatalyst.

While the amount of these transition metal catalysts to be used varies depending on the kind of the catalyst, it is generally about 0.0001 mol-about 1 mol, preferably about 0.01 mol-about 0.5 mol, relative to compound (XXIX). The amount of the ligand or cocatalyst to be used is generally about 0.0001 mol-about 4 mol, preferably about 0.01 mol-about 2 mol, relative to compound (XXIX).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XI-B) can be isolated and purified by a known separation and purification means, for example, concentration, concentration under reduced pressure, solvent extraction, crystallization, recrystallization, phase transfer, chromatography and the like. Compound (XI-B) may be used for the next reaction without isolation.
(Step E-3)

In this step, compound (XXIX) is reacted with compound (XXXII) by a coupling reaction using a transition metal catalyst to convert to compound (XI-C).

The reaction using a transition metal catalyst can be performed by a method known per se [e.g., Chemical Reviews, 1995, vol. 95, page 2457 etc.], for example, in the presence of a transition metal catalyst and a base in a solvent that does not adversely influence the reaction.

The amount of compound (XXXII) to be used is about 1 mol about 100 mol, preferably about 1 mol-about 10 mol, per 1 mol of compound (XXIX).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II)) etc., nickel catalysts (e.g., nickel chloride etc.) and the like. Where necessary, a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, or metal oxide (e.g., copper oxide, iron oxide etc.) may be used as a cocatalyst. While the amount of the transition metal catalyst to be used varies depending on the kind of the catalyst, it is generally about 0.0001 mol-about 1 mol, preferably about 0.01 mol-about 0.5 mol, per 1 mol of compound (XXIX). The amount of the ligand or cocatalyst to be used is generally about 0.0001 mol-about 4 mol, preferably about 0.01 mol-about 2 mol, per 1 mol of compound (XXIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXIX).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XI-C) can be isolated and purified by a known separation and purification means, for example, concentration, concentration under reduced pressure, solvent extraction, crystallization, recrystallization, phase transfer, chromatography and the like.

Compound (XI-A), compound (XI-B), and compound (XI-C) obtained by the above-mentioned method E can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se. Such reactions can be performed according to a method known per se.

Compound (XI-B) can also be produced by method F shown below.

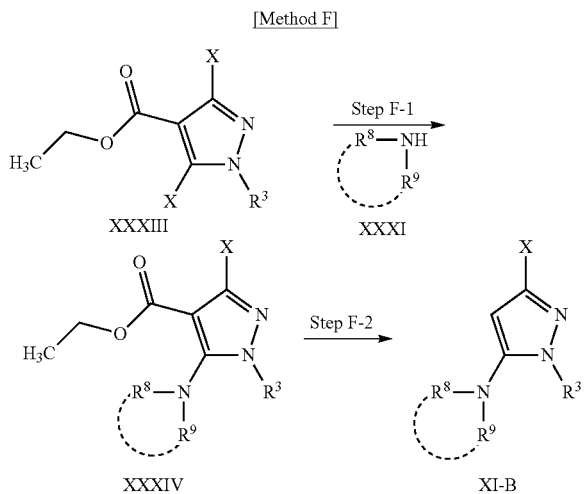

wherein each symbol is as defined above.

As compound (XXXIII) or compound (XXXI) to be used as the starting material in this method, a commercially available product may be directly used, or can also be produced by a method known per se or a method analogous thereto. In each step of the following production methods, the starting compound may be in the form of a salt and, as such salt, those exemplified as the salt of compound (I) are used.

(Step F-1)

In this step, compound (XXXIII) is reacted with compound (XXXI) to convert to compound (XXXIV). Where necessary, this step can be performed in the presence of a base, with the addition of a transition metal catalyst as necessary, in a solvent that does not adversely influence the reaction. A solvent may not be used. As compound (XXXIII) to be used as the starting material in this method, a commercially available product may be directly used, or can also be produced by a method known per se [e.g., Synthetic Communications (2008), 38(5), 674-683 etc.] or a method analogous thereto.

The amount of compound (XXXI) to be used is about 1 mol-about 100 mol, preferably about 1 mol-about 10 mol, relative to compound (XXXIII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxide (e.g., sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, relative to compound (XXXIII).

Examples of the transition metal catalyst to be used include palladium catalysts (e.g., palladium(II) acetate, tris (dibenzylideneacetone)dipalladium(0), palladium(II) chloride, tetrakis(triphenylphosphine)palladium(0), (1,1'-bis(diphenylphosphino)ferrocene)dichloropalladium(II)) etc., nickel catalysts (e.g., nickel chloride etc.) and the like. Where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine etc.) may be added, or metal oxide (e.g., copper oxide, iron oxide etc.) may be used as a cocatalyst.

While the amount of these transition metal catalyst to be used varies depending on the kind of the catalyst, it is generally about 0.0001 mol-about 1 mol, preferably about 0.01 mol-about 0.5 mol, relative to compound (XXXIII). The amount of a ligand or cocatalyst to be used is generally about 0.0001 mol-about 4 mol, preferably about 0.01 mol-about 2 mol, relative to compound (XXXIII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about -50° C.-about 200° C., preferably about -10° C.-about 150° C. The reaction time in this step is generally about 0.1 hr-about 100 hr.

The thus-obtained compound (XXXIV) can be isolated and purified by a known separation and purification means, for example, concentration, concentration under reduced pressure, solvent extraction, crystallization, recrystallization, phase transfer, chromatography and the like. Compound (XXXIV) may be used for the next reaction without isolation.

(Step F-2)

In this step, compound (XXXIV) is converted to compound (XI-B).

This step can be performed in the presence of an acid in a solvent that does not adversely influence the reaction. This step can also be performed by hydrolyzing compound (XXXIV) in the presence of a base in a solvent that does not adversely influence the reaction, and reacting same with an acid.

Examples of the acid include hydrochloric acid, sulfuric acid, hydrobromic acid, acetic acid, trifluoroacetic acid, p-toluenesulfonic acid, trifluoromethanesulfonic acid, a mixture wherein hydrogen chloride gas is dissolved in an organic solvent such as hydrogen chloride-ethyl acetate, hydrogen chloride-methanol and the like, and the like.

The amount of the acid to be used is about 0.1 mol-about 100 mol, preferably about 1 mol-about 10 mol, per 1 mol of compound (XXXIV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline, 2,4,6-trimethylpyridine etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXXIV).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XI-B) can be isolated and purified by a known separation and purification means, for example, concentration, concentration under reduced pressure, solvent extraction, crystallization, recrystallization, phase transfer, chromatography and the like. Compound (XI-B) may be used for the next reaction without isolation.

Compound (XI-D) which is compound (XI) wherein $R^4$ is —$CONR^{10}R^{11}$ can also be produced by, for example, the following method G.

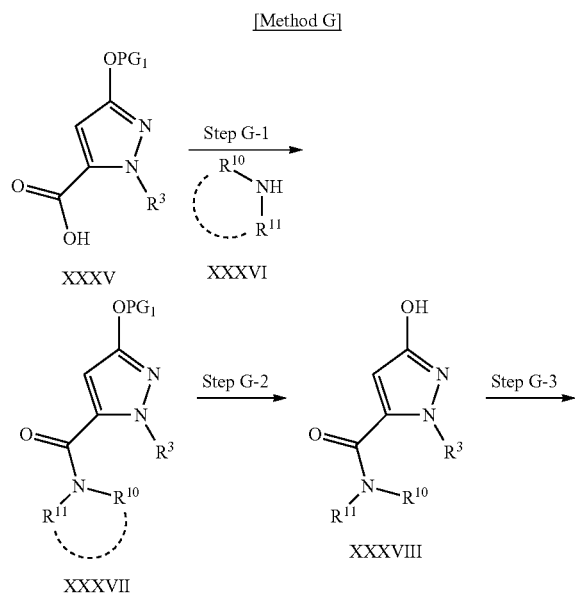

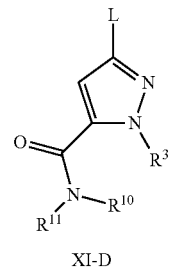

wherein $PG_1$ is a hydroxy-protecting group, and other symbols are as defined above.

Examples of the hydroxy-protecting group for $PG_1$ include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

As compound (XXXV) to be used as the starting material in this method, a commercially available product may be directly used, or can also be produced by a method known per se [e.g., Journal of Medicinal Chemistry (2012), 55(2), 797-811. etc.] or a method analogous thereto. As compound (XXXVI), a commercially available product may be directly used, or can also be produced by a method known per se or a method analogous thereto. In each step of the following production methods, the starting compound may be in the form of a salt and, as such salt, those exemplified as the salt of compound (I) are used.

(Step G-1)

Compound (XXXVII) is obtained by a method similar to method C, step C-2 and using compound (XXXV) and compound (XXXVI).

(Step G-2)

In this step, compound (XXXVII) is deprotected to produce compound (XXXVIII).

When $PG_1$ is methoxymethyl, 2-tetrahydropyranyl or ethoxyethyl, the step is performed in the presence of an acid in a solvent that does not adversely influence the reaction.

Examples of the acid include mineral acids such as hydrochloric acid, sulfuric acid and the like; organic acids such as trifluoroacetic acid, p-toluenesulfonic acid and the like; hydrogen chloride-methanol solution and hydrogen chloride-ethyl acetate solution wherein hydrogen chloride is dissolved in methanol, ethyl acetate and the like, and the like.

The amount of the acid to be used is about 0.1 mol-about 100 mol, preferably about 1 mol-about 10 mol, relative to compound (XXXVII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

When PG$_1$ is benzyl or p-methoxybenzyl, for example, this step can be performed in the presence of a metal catalyst such as palladium-carbon, palladium black, palladium chloride, platinum oxide, platinum black, platinum-palladium, Raney-nickel, Raney cobalt and the like and a hydrogen source, in a solvent that does not adversely influence the reaction.

The amount of the metal catalyst to be used is about 0.001 mol-about 1000 mol, preferably about 0.01 mol-about 100 mol, relative to compound (XXXVII).

Examples of the hydrogen source include hydrogen gas, formic acid, formic acid amine salt, phosphinic acid salt, hydrazine and the like.

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XXXVIII) can be isolated and purified by a known separation and purification means, for example, concentration, concentration under reduced pressure, solvent extraction, crystallization, recrystallization, phase transfer, chromatography and the like. Compound (XXXVIII) may be used for the next reaction without isolation.

(Step G-3)

In this step, compound (XXXVIII) is converted to compound (XI-D).

When L is a trifluoromethanesulfonyloxy group, for example, this step can be performed by reacting with trifluoromethanesulfonic anhydride, N-phenylbis(trifluoromethanesulfonimide) or the like in the presence of a base in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide, lithium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XXXVIII).

The amount of trifluoromethanesulfonic anhydride, N-phenylbis(trifluoromethanesulfonimide) and the like to be used is about 0.1 mol-about 100 mol, preferably about 1 mol-about 10 mol, per 1 mol of compound (XXXVIII).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, N,N-dimethylacetamide, dimethyl sulfoxide, hexamethylphosphoramide, N-methyl-2-pyrrolidone etc.), protic polar solvents (e.g., water, methanol, ethanol, 1-propanol, 2-propanol, 1-butanol, 2-methyl-2-propanol etc.), ethyl acetate, and a mixture thereof.

The reaction temperature in this step is generally about −50° C.-about 200° C., preferably about −10° C.-about 100° C. The reaction time in this step is generally about 0.1 hr-about 100 hr.

The thus-obtained compound (XI-D) can be isolated and purified by a known separation and purification means, for example, concentration, concentration under reduced pressure, solvent extraction, crystallization, recrystallization, phase transfer, chromatography and the like. Compound (XI-D) may be used for the next reaction without isolation.

Compound (XXXVII), compound (XXXVIII), compound (XI-D) obtained by the above-mentioned method G, and starting compound (XXXV) can also be further derivatized by subjecting to various known reactions such as condensation reactions such as acylation reaction, alkylation reaction, amidation reaction and the like or oxidation reaction, reduction reaction, hydrolysis, dehydration reaction, Curtius rearrangement and the like. Such reactions can be performed according to a method known per se.

Of compounds (I), a compound represented by the formula (I-B)

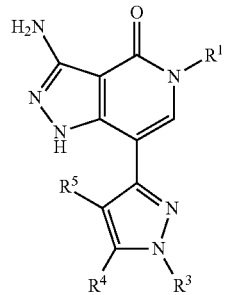

wherein each symbol is as defined above (hereinafter to be abbreviated as compound (I-B)) can be produced by method H shown below, or a method analogous thereto. In each step of the following production methods, the starting compound may be in the form of a salt and, as such salt, those exemplified as the salt of compound (I) are used.

[Method H]

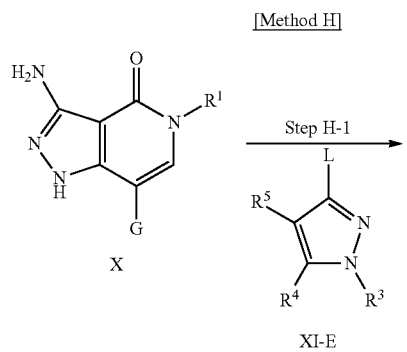

X

XI-E

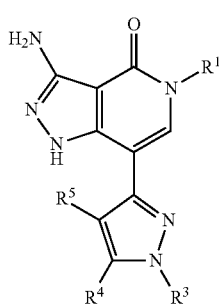

I-B wherein each symbol is as defined above.

As compound (X) to be used as the starting material in this method can also be produce by a method similar to method A, or a method known per se. As compound (XI-E), a commercially available product may be directly used, or can also be produced by a method known per se or a method analogous thereto. In each step of the following production methods, the starting compound may be in the form of a salt and, as such salt, those exemplified as the salt of compound (I) are used.

(Step H-1)

Compound (I-B) is obtained by a method similar to method A, step A-9, and using compound (X) and compound (XI-E).

The thus-obtained compound (I-B) can be isolated and purified by a known separation and purification means, for example, concentration, concentration under reduced pressure, solvent extraction, crystallization, recrystallization, phase transfer, chromatography and the like.

Compound (I-B) obtained by the above-mentioned method H can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se. Such reactions can be performed according to a method known per se.

Of compounds (I), a compound represented by the formula (I-C)

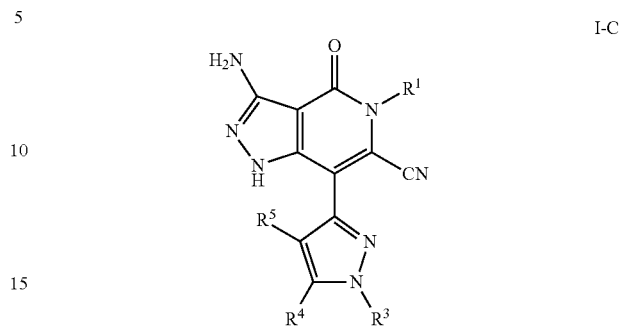

wherein each symbol is as defined above (hereinafter to be abbreviated as compound (I-C)) can be produced by method I shown below, or a method analogous thereto. In each step of the following production methods, the starting compound may be in the form of a salt and, as such salt, those exemplified as the salt of compound (I) are used.

[Method I]

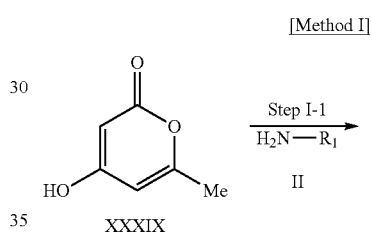

XXXIX

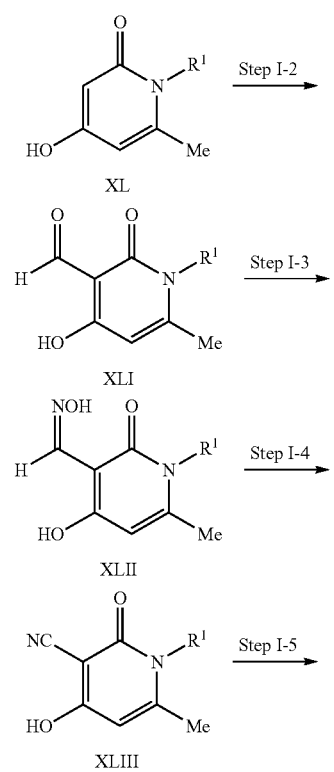

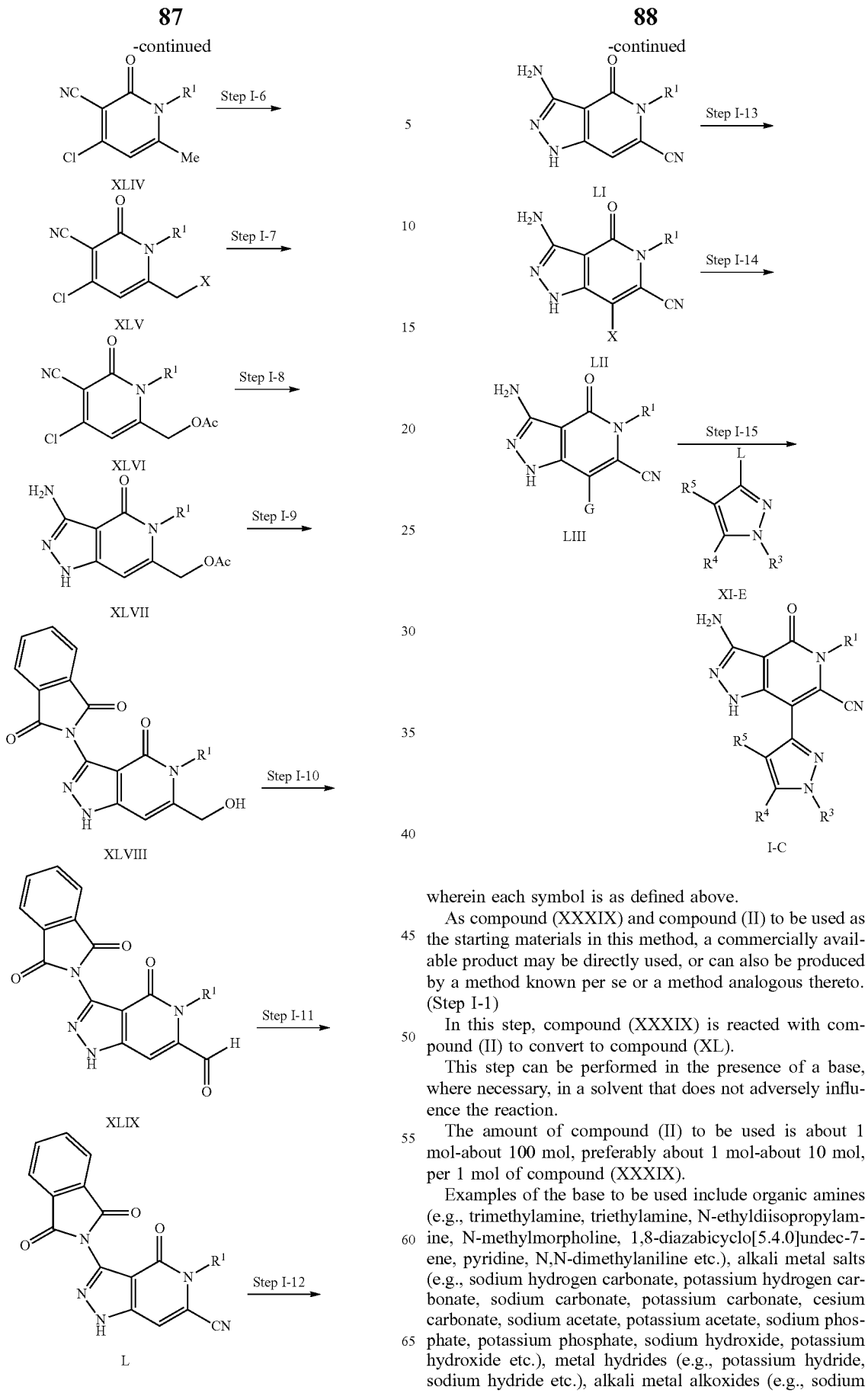

wherein each symbol is as defined above.

As compound (XXXIX) and compound (II) to be used as the starting materials in this method, a commercially available product may be directly used, or can also be produced by a method known per se or a method analogous thereto.
(Step I-1)

In this step, compound (XXXIX) is reacted with compound (II) to convert to compound (XL).

This step can be performed in the presence of a base, where necessary, in a solvent that does not adversely influence the reaction.

The amount of compound (II) to be used is about 1 mol-about 100 mol, preferably about 1 mol-about 10 mol, per 1 mol of compound (XXXIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts (sodium carbonate, potassium carbonate, cesium carbonate etc.) are preferable.

The amount of the base to be used is about 0.1 mol-about 100 mol, preferably about 1 mol-about 10 mol, per 1 mol of compound (XXXIX).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.) and a mixture thereof.

The reaction temperature in this step is generally about −50° C.-about 200° C., preferably about −10° C.-about 200° C. The reaction time in this step is generally about 0.1 hr-about 100 hr.

The thus-obtained compound (XL) can be isolated and purified by a known separation and purification means, for example, concentration, concentration under reduced pressure, solvent extraction, crystallization, recrystallization, phase transfer, chromatography and the like. Compound (XL) may be used for the next reaction without isolation.
(Step I-2)

In this step, compound (XL) is reacted with a formylating agent to convert to compound (XLI).

Where necessary, this step can be performed in the presence of a base in a solvent that does not adversely influence the reaction.

Examples of the formylating agent to be used include chloroform, Vilsmeier reagent and the like.

The Vilsmeier reagent is prepared from N,N-dimethylformamide and a chlorinating agent (e.g., phosphorus oxychloride, phosphorus pentachloride, phosgene etc.). Alternatively, a commercially available Vilsmeier reagent can be used.

The amount of the formylating agent to be used is about 1 mol-about 100 mol, preferably about 1 mol-about 10 mol, per 1 mol of compound (XL).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like. Of these, alkali metal salts (e.g., sodium hydroxide, potassium hydroxide etc.) are preferable.

The amount of the base to be used is about 0.1 mol-about 100 mol, preferably about 1 mol-about 10 mol, per 1 mol of compound (XL).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLI) can be isolated and purified by a known separation and purification means, for example, concentration, concentration under reduced pressure, solvent extraction, crystallization, recrystallization, phase transfer, chromatography and the like. Compound (XLI) may be used for the next reaction without isolation.
(Step I-3)

In this step, compound (XLI) is subjected to an oximation reaction by reacting with hydroxylamine or a salt thereof to convert to compound (XLII).

This step can be performed in the presence of an acid or base as necessary and in a solvent that does not adversely influence the reaction.

The amount of hydroxylamine or a salt thereof to be used is about 1 mol-about 100 mol, preferably about 1 mol-about 10 mol, per 1 mol of compound (XLI).

Examples of the acid to be used include hydrochloric acid, hydrobromic acid, sulfuric acid, trifluoroacetic acid, trifluoromethanesulfonic acid, hydrogen chloride and the like.

The amount of the acid to be used is about 0.1 mol-about 100 mol per 1 mol of compound (XLI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.) and the like. Of these, alkali metal salts such as sodium acetate, potassium acetate and the like are preferable.

The amount of the base to be used is about 0.1-about 100 mol, preferably about 1-about 10 mol, per 1 mol of compound (XLI).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLII) can be isolated and purified by a known separation and purification means, for example, concentration, concentration under reduced pressure, solvent extraction, crystallization, recrystallization, phase transfer, chromatography and the like. Compound (XLII) may be used for the next reaction without isolation.

(Step I-4)

In this step, compound (XLII) is reacted with a dehydrating agent to convert to compound (XLIII).

Where necessary, this step can be performed in a solvent that does not adversely influence the reaction.

Examples of the dehydrating agent to be used include acetic acid, phosphorus oxychloride, thionyl chloride, oxalyl chloride, acetic anhydride, acetyl chloride, trichloroacetyl chloride and the like.

The amount of the dehydrating agent to be used is about 0.1 mol-about 100 mol per 1 mol of compound (XLII).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLIII) can be isolated and purified by a known separation and purification means, for example, concentration, concentration under reduced pressure, solvent extraction, crystallization, recrystallization, phase transfer, chromatography and the like. Compound (XLIII) may be used for the next reaction without isolation.

(Step I-5)

In this step, compound (XLIII) is reacted with a Vilsmeier reagent to convert to compound (XLIV).

Where necessary, this step can be performed in a solvent that does not adversely influence the reaction.

The Vilsmeier reagent is prepared from N,N-dimethylformamide and a chlorinating agent (e.g., phosphorus oxychloride, phosphorus pentachloride, phosgene etc.). Alternatively, a commercially available Vilsmeier reagent can be used.

The amount of Vilsmeier reagent to be used is about 1 mol about 100 mol, preferably about 1 mol-about 10 mol, per 1 mol of compound (XLIII).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLIV) can be isolated and purified by a known separation and purification means, for example, concentration, concentration under reduced pressure, solvent extraction, crystallization, recrystallization, phase transfer, chromatography and the like. Compound (XLIV) may be used for the next reaction without isolation.

(Step I-6)

In this step, compound (XLIV) is subjected to a substitution reaction by reacting with a halogenating agent to convert to compound (XLV).

Where necessary, this step can be performed in the presence of a radical initiator in a solvent that does not adversely influence the reaction.

Examples of the halogenating agent to be used include chlorine, bromine, iodine, N-chlorosuccinimide, N-bromosuccinimide, N-iodosuccinimide and the like.

The amount of the halogenating agent to be used is about 0.1 mol-about 100 mol per 1 mol of compound (XLIV).

Examples of the radical initiator to be used include azobis(isobutyronitrile) and the like.

The amount of the radical initiator to be used is about 0.01 mol-about 10 mol per 1 mol of compound (XLIV).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane, carbon tetrachloride etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLV) can be isolated and purified by a known separation and purification means, for example, concentration, concentration under reduced pressure, solvent extraction, crystallization, recrystallization, phase transfer, chromatography and the like. Compound (XLV) may be used for the next reaction without isolation.

(Step I-7)

In this step, compound (XLV) is reacted with an alkali metal acetate salt to convert to compound (XLVI).

Where necessary, this step can be performed in a solvent that does not adversely influence the reaction.

Examples of the alkali metal acetate salt to be used include sodium acetate, potassium acetate and the like.

The amount of the alkali metal acetate salt to be used is about 1 mol-about 100 mol per 1 mol of compound (XLV).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLVI) can be isolated and purified by a known separation and purification means, for example, concentration, concentration under reduced pressure, solvent extraction, crystallization, recrystallization, phase transfer, chromatography and the like. Compound (XLVI) may be used for the next reaction without isolation.
(Step I-8)

In this step, compound (XLVI) is reacted with hydrazine or a salt thereof to convert to compound (XLVII).

Where necessary, this step can be performed in a solvent that does not adversely influence the reaction.

The amount of hydrazine or a salt thereof to be used is about 1 mol-about 100 mol per 1 mol of compound (XLVI).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLVII) can be isolated and purified by a known separation and purification means, for example, concentration, concentration under reduced pressure, solvent extraction, crystallization, recrystallization, phase transfer, chromatography and the like. Compound (XLVII) may be used for the next reaction without isolation.
(Step I-9)

In this step, compound (XLVII) is reacted with phthalic anhydride to convert to compound (XLVIII).

Where necessary, this step can be performed in a solvent that does not adversely influence the reaction.

The amount of phthalic anhydride to be used is about 1 mol-about 100 mol, preferably about 1 mol-about 10 mol, per 1 mol of compound (XLVII).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (XLVIII) can be isolated and purified by a known separation and purification means, for example, concentration, concentration under reduced pressure, solvent extraction, crystallization, recrystallization, phase transfer, chromatography and the like. Compound (XLVIII) may be used for the next reaction without isolation.
(Step I-10)

In this step, compound (XLVIII) is subjected to an oxidation reaction by reacting with an oxidizing agent to convert to compound (XLIX).

Where necessary, this step can be performed in a solvent that does not adversely influence the reaction.

Examples of the oxidizing agent to be used include hydrogen peroxide, m-chloroperbenzoic acid, Oxone (registered trademark), Dess-Martin periodinane, manganese dioxide, potassium permanganate and the like. Of these, m-chloroperbenzoic acid, Oxone (registered trademark), Dess-Martin periodinane are preferable.

The amount of the oxidizing agent to be used is about 0.5 mol-about 100 mol, preferably about 0.5 mol-about 10 mol, per 1 mol of compound (XLVIII).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 100° C. The reaction time in this step is generally about 0.1 hr-about 100 hr.

The thus-obtained compound (XLIX) can be isolated and purified by a known separation and purification means, for example, concentration, concentration under reduced pressure, solvent extraction, crystallization, recrystallization, phase transfer, chromatography and the like. Compound (XLIX) may be used for the next reaction without isolation.
(Step I-11)

In this step, compound (XLIX) is reacted with a cyanating agent to convert to compound (L).

Where necessary, this step can be performed in the presence of a base in a solvent that does not adversely influence the reaction.

Examples of the cyanating agent to be used include 2,2,2-trifluoro-N-(2,2,2-trifluoroacetoxy)acetamide and the like.

The amount of the cyanating agent to be used is about 1 mol-about 100 mol, preferably about 1 mol-about 10 mol, per 1 mol of compound (XLIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is about 0.1 mol-about 100 mol, preferably about 1 mol-about 10 mol, per 1 mol of compound (XLIX).

In this step, the solvent is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (L) can be isolated and purified by a known separation and purification means, for example, concentration, concentration under reduced pressure, solvent extraction, crystallization, recrystallization, phase transfer, chromatography and the like. Compound (L) may be used for the next reaction without isolation.

(Step I-12)

In this step, compound (L) is reacted with hydrazine or a salt thereof to convert to compound (LI).

Where necessary, this step can be performed in a solvent that does not adversely influence the reaction.

The amount of hydrazine or a salt thereof to be used is about 1 mol-about 100 mol per 1 mol of compound (L).

The solvent in this reaction is not particularly limited as long as the reaction proceeds. Examples of the solvent include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethyl sulfoxide, hexamethylphosphoramide etc.), protic polar solvents (e.g., water, methanol, ethanol, 1-propanol, 2-propanol, 1-butanol, 2-methyl-2-propanol etc.) and a mixture thereof.

The reaction temperature in this step is generally about −50° C.-about 200° C., preferably about −10° C.-about 150° C. The reaction time in this step is generally about 0.1 hr-about 100 hr.

The thus-obtained compound (LI) can be isolated and purified by a known separation and purification means, for example, concentration, concentration under reduced pressure, solvent extraction, crystallization, recrystallization, phase transfer, chromatography and the like.

(Step I-13) Compound (LII) is obtained by a method similar to method A, step A-6, and using compound (LI).

(Step I-14)

Compound (LIII) is obtained by a method similar to method A, step A-8, and using compound (LII).

(Step I-15)

Compound (I-C) is obtained by a method similar to method A, step A-9, and using compound (LIII) and compound (XI-E).

Compound (XL), compound (XLI), compound (XLII), compound (XLIII), compound (XLIV), compound (XLV), compound (XLVI), compound (XLVII), compound (XLVIII), compound (XLIX), compound (L), compound (LI), compound (LII), compound (LIII), compound (I-C) obtained by the above-mentioned method I can also be further derivatized by subjecting to various known reactions such as condensation reactions such as acylation reaction, alkylation reaction, amidation reaction and the like or oxidation reaction, reduction reaction, hydrolysis, dehydration reaction and the like. Such reactions can be performed according to a method known per se. Such reactions can be performed according to a method known per se.

The compounds of the present invention obtained by the above-mentioned production methods can be isolated and purified by a known means such as concentration, concentration under reduced pressure, solvent extraction, crystallization, recrystallization, phase transfer, chromatography and the like. Each starting compound used for the above-mentioned production methods can be isolated and purified by a known means similar to those mentioned above. On the other hand, these starting compounds may be directly used as the starting materials for the next step as a reaction mixture without isolation.

Compound (I) produced by such method can be isolated and purified by a typical separation means such as recrystallization, distillation, chromatography, and the like.

When compound (I) contains an optical isomer, a stereoisomer, a regioisomer or a rotamer, these are also encompassed in compound (I), and can be obtained as a single product according to synthesis and separation methods known per se (e.g., concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow for separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (e.g., MTPA [α-methoxy-α-(trifluoromethyl) phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

Compound (I) may be a crystal.

The crystal of compound (I) can be produced by crystallization of compound (I) by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. To be specific, for example, a concentration method, a cooling method, a reaction method (a diffusion method, an electrolysis method), a hydrothermal growth method, a flux method and the like can be mentioned. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, 1,4-dioxane, etc.), nitriles (e.g., acetonitrile, etc.), ketones (e.g., acetone, etc.), sulfoxides (e.g., dimethyl sulfoxide, etc.), amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two kinds or more at a suitable ratio (e.g., 1:1 to 1:100 (a volume ratio)). Where necessary, a seed crystal can also be used.

The "crystallization from vapor" is, for example, a vaporization method (a sealed tube method, a gas stream method), a gas phase reaction method, a chemical transportation method and the like.

The "crystallization from the melts" is, for example, a normal freezing method (a Czockralski method, a temperature gradient method and a Bridgman method), a zone melting method (a zone leveling method and a floating zone method), a special growth method (a VLS method and a liquid phase epitaxy method) and the like.

Preferable examples of the crystallization method include a method of dissolving compound (I) or a salt thereof in a suitable solvents (e.g., alcohols such as methanol, ethanol, etc., etc.) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

As an analysis method of the obtained crystal is generally a crystal analysis method using powder X-ray diffraction. Examples of the method for determining the crystal orientation include a mechanical method, am optical method and the like.

The crystal of compound (I) obtained by the abovementioned production methods (hereinafter to be abbreviated as "the crystal of the present invention") has high purity, high quality, low hygroscopicity, is not altered even after a long-term preservation under general conditions, and is extremely excellent in the stability. It is also excellent in the biological properties (e.g., in vivo kinetics (absorption, distribution, metabolism, excretion), efficacy expression etc.) and extremely useful as a medicament.

In the present specification, the specific rotation ($[\alpha]_D$) means, for example, a specific rotation measured using a polarimeter (JASCO, measured by P-1030 polarimeter (No. AP-2)) and the like.

In the present specification, the melting point is measured by, for example, a micro melting point apparatus (Yanaco, MP-500D) or DSC (differential scanning calorimetry) apparatus (SEIKO, EXSTAR 6000) and the like.

Compound (I) may be used as a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include (1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation or cyclopropylcarbonylation, and the like);

(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);

(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

Compound (I) may be a hydrate, a non-hydrate, a solvate or a non-solvate.

Compound (I) also encompasses a compound labeled with an isotope (e.g., $^3H$, $^{14}C$, $^{35}S$, $^{125}I$ etc.) and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, heat of fusion, hygroscopicity, solubility and stability etc.). The cocrystal or a salt thereof can be produced according to a cocrystallization a method known per se.

Compound (I) may also be used as a PET tracer.

Since the compound of the present invention has an excellent JAK (JAK1, JAK2, JAK3, TYK2) inhibitory action, it is also useful as safe medicaments based on such action.

Since the compound of the present invention also has IFN-α inhibitory action, IFN-β inhibitory action, IFN-γ inhibitor, IL-2 inhibitor, IL-4 inhibitor, IL-7 inhibitor, IL-15 inhibitor, IL-21 inhibitor, IL-6 inhibitory action, OSM inhibitor, IL-10 inhibitory action, IL-19 inhibitory action, IL-20 inhibitory action, IL-22 inhibitory action, IL-28 inhibitory action, IL-29 inhibitory action, IL-12 inhibitory action, and/or IL-23 inhibitory action (preferably, IL-23 inhibitory action), it is also useful as a safe medicament based on such actions For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for JAK associated diseases, more specifically, the diseases described in (1)-(5) below.

(1) inflammatory diseases (e.g., acute pancreatitis, chronic pancreatitis, asthma, adult respiratory distress syndrome, chronic obstructive pulmonary disease (COPD), inflammatory bone disease, pulmonary sarcoidosis, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis, diabetic nephropathy, uveitis, hidradenitis suppurativa etc.)

(2) autoimmune diseases (e.g., rheumatoid arthritis, psoriasis, inflammatory bowel disease (e.g., Crohn's disease, ulcerative colitis etc.), Sjogren's syndrome, Behcet's syndrome, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis, primary biliary cirrhosis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, multiple myeloma, metastasis melanoma, Kaposi's sacroma, vascular proliferation, cachexia, metastasis of the breast cancer, cancer (e.g., colon cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic schwannoma, retinoblastoma, pharyngeal cancer, laryngeal cancer, cancer of the tongue, thymoma, esophagus cancer, duodenal cancer, colon cancer, rectal cancer, hepatoma, pancreatic endocrine tumor, bile duct cancer, gall bladder cancer, penile cancer, urinary duct cancer, testis tumor, vulvar cancer, cervix cancer, uterine body cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor, fibrous histiocytoma, leiomyosarcoma, rhabdomyosarcoma, cancer of unknown primary), leukemia (e.g., acute leukemia (e.g., acute lymphocytic leukemia, acute myeloid leukemia etc.), chronic leukemia (e.g., chronic lymphocytic leukemia, chronic myeloid leukemia etc.), myelodysplastic syndrome etc.), uterus sarcoma (e.g., mixed mesodermal tumor, uterine leiomyosarcoma, endometrial stromal tumor etc.), myelofibrosis and the like], (5) central nervous system disease (e.g., schizophrenia, Alzheimer's disease (e.g., dementia of Alzheimer type)).

The medicament of the present invention can be preferably used as a prophylactic or therapeutic agent for autoimmune diseases, inflammatory diseases, degenerative joint and bone disease, central nervous system disease or neoplastic disease, more preferably, systemic lupus erythematosus, inflammatory bowel disease (preferably, Crohn's disease or ulcerative colitis), rheumatoid arthritis, psoriasis, Sjogren's syndrome, Behcet's syndrome, multiple sclerosis, Alzheimer's disease (preferably, dementia of Alzheimer type), Castleman's disease, leukemia, uterine leiomyosarcoma, prostate cancer, multiple myeloma, cachexia, or myelofibrosis.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention is excellent in the in vivo kinetics (e.g., plasma drug half-life), shows low toxicity (e.g., HERG inhibition, CYP inhibition, CYP induction), and shows reduction of cytotoxicity, reduction of side effects based on the improvement in JAK selectivity and reduction of drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with rheumatoid arthritis, psoriasis, inflammatory bowel disease, Sjogren's syndrome, Behcet's syndrome, multiple sclerosis, systemic lupus erythematosus, Castleman's disease, leukemia, uterine leiomyosarcoma, prostate cancer, multiple myeloma, cachexia, myelofibrosis or the like, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (free form of compound (I)) can be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, bin ding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidizing agent, colorant, sweetening agent, adsorbing agent, wetting agent and the like can also be used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidizing agent include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, the compound of the present invention is used as a JAK family inhibitor, an IFN-α inhibitor, an IFN-β inhibitor, an IFN-γ inhibitor, an IL-2 inhibitor, an IL-4 inhibitor, an IL-7 inhibitor, an IL-15 inhibitor, an IL-21 inhibitor, an IL-6 inhibitor, an OSM inhibitor, an IL-10 inhibitor, an IL-19 inhibitor, an IL-20 inhibitor, an IL-22 inhibitor, an IL-28 inhibitor, an IL-29 inhibitor, an IL-12 inhibitor, and/or an IL-23 inhibitor, it can be used in combination with the following drugs.
(1) non-steroidal anti-inflammatory drug (NSAIDs)
(i) classical NSAIDs alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor COX-2 selective inhibitor etc.)
salicylic acid derivatives (e.g., celecoxib, aspirin), etoricoxib, valdecoxib, diclofenac, indomethacin, loxoprofen and the like.
(iii) nitric oxide-releasing NSAIDs.
(iv) JAK inhibitor
tofacitinib, ruxolitinib and the like.
(2) disease-modifying anti-rheumatic drugs (DMARDs)
(i) gold preparation
auranofin and the like.
(ii) penicillamine
D-penicillamine.
(iii) aminosalicylic acid preparation
sulfasalazine, mesalamine, olsalazine, balsalazide.
(iv) antimalarial drug
chloroquine and the like.
(v) pyrimidine synthesis inhibitor
leflunomide and the like.
(vi) prograf
(3) anti-cytokine drug
(I) protein drug
(i) TNF inhibitor
etanercept, infliximab, adalimumab, certolizumab pegol, golimumab, PASSTNF-α, soluble TNF-α receptor TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) angiotensin converting enzyme inhibitor
enalapril, captopril, ramipril, lisinopril, cilazapril, perindopril and the like.
(8) angiotensin II receptor antagonist
candesartan, cilexetil (TCV-116), valsartan, irbesartan, olmesartan, eprosartan and the like.
(9) diuretic drug
hydrochlorothiazide, spironolactone, furosemide, indapamide, bendrofluazide, cyclopenthiazide and the like.
(10) cardiotonic drug
digoxin, dobutamine and the like.
(11) β receptor antagonist carvedilol, metoprolol, atenolol and the like.
(12) Ca sensitizer
MCC-135 and the like.
(13) Ca channel antagonist
nifedipine, diltiazem, verapamil and the like.
(14) anti-platelet drug, anticoagulator
heparin, aspirin, warfarin and the like.
(15) HMG-CoA reductase inhibitor
atorvastatin, simvastatin and the like.
(16) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.
(iii) spermatocide
ushercell and the like.
(17) others
(i) T cell inhibitors
(ii) inosine monophosphate dehydrogenase (IMPDH) inhibitor
mycophenolate mofetil and the like.

(iii) adhesion molecule inhibitor
ISIS-2302, selectin inhibitor ELAM-1, VCAM-1, ICAM-1 and the like.
(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) dihydroorotate dehydrogenase (DHODH) inhibitor
(ix) phosphodiesterase IV (PDE IV) inhibitor
roflumilast, CG-1088 and the like.
(x) phospholipase $A_2$ inhibitor
(xi) iNOS inhibitor
VAS-203 and the like.
(xii) microtubule stimulating drug
paclitaxel and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1305 and the like.
(xix) 5-lipoxygenase inhibitor
zileuton and the like.
(xx) cholinesterase inhibitor
galanthamine and the like.
(xxi) tyrosine kinase inhibitor
TYK2 inhibitor (WO 2010/142752) and the like.
(xxii) cathepsin B inhibitor
(xxiii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxix) glucosamine sulfate
(xxx) amiprilose
(xxxi) CD-20 inhibitor
rituximab, ibritumomab, tositumomab, ofatumumab and the like.
(xxxii) BAFF inhibitor
belimumab, tabalumab, atacicept, A-623 and the like.
(xxxiii) CD52 inhibitor
alemtuzumab and the like.
(xxxiv) IL-17 inhibitor
secukinumab (AIN-457), LY-2439821, AMG827 and the like.
(xxxv) PDE4 inhibitor
roflumilast, apremilast and the like.

Other concomitant drugs besides the above-mentioned include for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) antibacterial agent
(i) sulfa drug
sulfamethizole, sulfisoxazole, sulfamonomethoxine, sulfamethizole, salazosulfapyridine, silver sulfadiazine and the like.
(ii) quinolone antibacterial agent
nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
diaphenylsulfone, rifampicin and the like.
(v) antiviral drug
idoxuridine, acyclovir, vidarabine, gancyclovir and the like.
(vi) anti-HIV agent
zidovudine, didanosine, zalcitabine, indinavir sulfate ethanolate, ritonavir and the like.
(vii) antispirochetele
(viii) antibiotic
tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R, 2R)-2-(2,4-difluorophenyl)-2-hydroxy-1-methyl-3-(1H-1,2, 4-triazol-1-yl)propyl]-4-[4-(2,2,3,3-tetrafluoropropoxy) phenyl]-3(2H,4H)-1,2,4-triazolone, fluconazole, itraconazole and the like] and the like.

(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent
metronidazole, tinidazole, diethylcarbamazine citrate, quinine hydrochloride, quinine sulfate and the like.

(4) antitussive and expectorant drug
ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terputaline, oxypetebanol, morphine hydrochloride, dextropethorfan hydrobromide, oxycodone hydrochloride, dimorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic (6-1) local anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) general anesthetic (i) inhalaion anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) antiulcer drug histidine hydrochloride, lansoprazole, metoclopramide, pirenzepine, cimetidine, ranitidine, famotidine, urogastrin, oxethazaine, proglumide, omeprazole, sucralfate, sulpiride, cetraxate, gefarnate, aldioxa, teprenone, prostaglandin and the like.

(8) antiarrhythmic agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) hypotensive diuretic drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant heparin sodium, sodium citrate, activated protein C, tissue factor pathway inhibitor antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zusulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug clofibrate, ethyl 2-chloro-3-[4-(2-methyl-2-phenyl-propoxy)phenyl]propionate [Chem. Pharm. Bull, 38, 2792-2796 (1990)], pravastatin, simvastatin, probucol, bezafibrate, clinofibrate, nicomol, cholestyramine, dextran sulfate sodium and the like.

(15) muscle relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug phenytoin, ethosuximide, acetazolamide, chlordiazepoxide, tripethadione, carbamazepine, phenobarbital, primidone, sulthiame, sodium valproate, clonazepam, diazepam, nitrazepam and the like.

(17) antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) antiallergic drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) cardiac stimulants trans-π-oxocamphor, terephyllol, aminophylline, etilefrine, dopamine, dobutamine, denopamine, vesinarine, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipuzide, phenformin, buformin, metformin and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(28) therapeutic agent for pollakisuria/anischuria flavoxate hydrochloride and the like.

(29) therapeutic agent for atopic dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(31) hypertensor dopamine, dobutamine, denopamine, digitoxin, digoxin, methyldigoxin, lanatoside C, G-strophanthin and the like.

(32) others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with rheumatoid arthritis, psoriasis, inflammatory bowel disease, Sjogren's syndrome, Behcet's syndrome, multiple sclerosis, systemic lupus erythematosus, leukemia, uterine leiomyosarcoma, prostate cancer, multiple myeloma, cachexia, myelofibrosis and the like, about 0.1 mg/kg body weight-about 50 mg/kg body weight, preferably about 1 mg/kg body weight-30 mg/kg body weight, of a free form of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Reference Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, indication of basic silica gel means use of aminopropylsilane-bonded silica gel, and indication of diol silica gel means use of 3-(2,3-dihydroxypropoxy)propylsilane-bonded silica gel. In HPLC (high performance liquid chromatography), indication of C18 means use of octadecyl-bonded silica gel. The ratios of elution solvents are in volume mixing ratios, unless otherwise specified.

In Examples, the following abbreviations are used.
TFA: trifluoroacetic acid
BSA: bovine serum albumin
DMSO: dimethyl sulfoxide
DTT: dithiothreitol
EDTA: ethylenediaminetetraacetic acid
EGTA: glycol etherdiaminetetraacetic acid
HEPES: 4-(2-hydroxyethyl)-1-piperazineethanesulfonic acid
M: molar concentration
$^1$H NMR (proton nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates measured value (found). Generally, a molecular ion peak is observed. In the case of salt, generally, a molecular ion peak or a fragment ion peak of a free form is observed.

Example 1

3-amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one

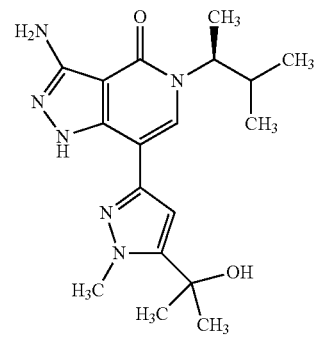 [SMILES: CC(C)[C@H](C)n1cc(-c2cc(C(C)(C)O)n(C)n2)c2[nH]nc(N)c2c1=O]

A) N-((2S)-3-methylbutan-2-yl)-3-oxobutanamide

Under an ice bath, to a solution of (2S)-3-methylbutan-2-amine (30 g, >99% ee, Aldrich) in methanol (180 mL) was added dropwise diketene (29 mL), and the mixture was stirred at room temperature for 20 hr. The solvent was evaporated under reduced pressure, and the residue was purified by silica gel column chromatography (hexane/ethyl acetate) to give the title compound (56.6 g).
MS (ESI+): [M+H]$^+$ 171.8.

B) 2-((dimethylamino)methylene)-N-((2S)-3-methylbutan-2-yl)-3-oxobutanamide

Under an ice bath, to a solution of N-((2S)-3-methylbutan-2-yl)-3-oxobutanamide (56.6 g) obtained in Example 1, Step A, in N,N-dimethylformamide (220 mL) was added dropwise 1,1-dimethoxy-N,N-dimethylmethanamine (88 mL) over 15 min, and the mixture was stirred at room temperature for 20 hr. The solvent was evaporated under reduced pressure to give the title compound (62.7 g).
$^1$H NMR (400 MHz, CDCl$_3$) δ 0.84-0.99 (6H, m), 1.11 (3H, d, J=6.6 Hz), 1.68-1.79 (1H, m), 2.22 (3H, s), 3.11 (6H, brs), 3.85-4.07 (1H, m), 7.51 (1H, brs), 7.62 (1H, brs).

C) 4-chloro-1-((2S)-3-methylbutan-2-yl)-2-oxo-1,2-dihydropyridine-3-carbaldehyde Under an ice bath, to a solution of 2-((dimethylamino)methylene)-N-((2S)-3-methylbutan-2-yl)-3-oxobutanamide (31 g) obtained in Example 1, Step B, in N,N-dimethylformamide (250 mL) was added (chloromethylene)dimethylammonium chloride (75 g). Thereafter, the solution was stirred at 100° C. for 40 min. The reaction mixture was slowly added dropwise to ice water, and extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (17.8 g).
MS (ESI+): [M+H]$^+$ 228.2.

D) 4-chloro-3-((hydroxyimino)methyl)-1-((2S)-3-methylbutan-2-yl)pyridin-2(1H)-one To a solution of 4-chloro-1-((2S)-3-methylbutan-2-yl)-2-oxo-1,2-dihydropyridine-3-carbaldehyde (31.8 g) obtained in Example 1, Step C, in 2-propanol (300 mL) were added hydroxylamine hydrochloride (14.6 g) and concentrated hydrochloric acid (0.43 mL), and the mixture was stirred at 100° C. for 1 hr. The reaction mixture was cooled to room temperature and the solvent was evaporated under reduced pressure. The residue was crystallized (2-propanol/diisopropyl ether) and the resulting solid was collected by filtration, and washed with 2-propanol/diisopropyl ether to give the title compound (23.2 g).

MS (ESI+): [M+H]$^+$ 243.2.

E) 4-chloro-1-((2S)-3-methylbutan-2-yl)-2-oxo-1,2-dihydropyridine-3-carbonitrile To a solution of 4-chloro-3-((hydroxyimino)methyl)-1-((2S)-3-methylbutan-2-yl)pyridin-2(1H)-one (23.2 g) obtained in Example 1, Step D, in acetonitrile (300 mL) was added dropwise thionyl chloride (13.9 mL), and the mixture was stirred at room temperature for 1 hr. The solvent was evaporated under reduced pressure, and diisopropyl ether/ethyl acetate/hexane was added to the residue. Insoluble material was removed by filtration. The filtrate was evaporated under reduced pressure. Ethyl acetate was added to the residue and the mixture was washed successively with saturated aqueous sodium hydrogen carbonate solution and saturated brine, and dried over anhydrous magnesium sulfate. The solvent was evaporated under reduced pressure and the residue was purified by silica gel column chromatography (hexane/ethyl acetate) to give the title compound (14.6 g).

MS (ESI+): [M+H]$^+$ 224.8.

F) 5-bromo-4-chloro-1-((2S)-3-methylbutan-2-yl)-2-oxo-1,2-dihydropyridine-3-carbonitrile To a solution of 4-chloro-1-((2S)-3-methylbutan-2-yl)-2-oxo-1,2-dihydropyridine-3-carbonitrile (14.6 g) obtained in Example 1, Step E, in N,N-dimethylformamide (120 mL) was added N-bromosuccinimide (17.4 g), and the mixture was stirred at 50° C. for 20 hr. Water was added to the reaction mixture, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (19.2 g).

MS (ESI+): [M+H]$^+$ 303.2.

G) 3-amino-7-bromo-5-((2S)-3-methylbutan-2-yl)-1,5-dihydro-4H-pyrazolo[4,3-c]pyridin-4-one To a solution of 5-bromo-4-chloro-1-((2S)-3-methylbutan-2-yl)-2-oxo-1,2-dihydropyridine-3-carbonitrile (19.2 g) obtained in Example 1, Step F, in ethanol (200 mL) was added hydrazine monohydrate (9.5 g), and the mixture was stirred at 90° C. for 1 hr. The reaction mixture was allowed to cool to room temperature and the solvent was evaporated under reduced pressure. The residue was dissolved in a mixed solution of ethyl acetate-tetrahydrofuran-water. The organic layer was separated, washed successively with saturated aqueous sodium hydrogen carbonate solution and saturated brine, and dried over anhydrous magnesium sulfate. The solvent was evaporated under reduced pressure and the residue was purified by silica gel column chromatography (basic silica gel, ethyl acetate/hexane, then ethyl acetate/methanol), and recrystallized (ethyl acetate/diisopropyl ether) to give the title compound (15.5 g).

$^1$H NMR (400 MHz, CDCl$_3$) δ 0.81 (3H, d, J=6.6 Hz), 1.05 (3H, d, J=6.6 Hz), 1.34 (3H, d, J=6.8 Hz), 1.78-1.92 (1H, m), 4.64-5.00 (3H, m), 7.12 (1H, s), 9.27 (1H, brs).

MS (ESI+): [M+H]$^+$ 299.2.

99.4% ee (HPLC (column: CHIRALPAK (registered trademark) AD, 4.6 mmID×250 mmL, manufactured by Daicel Corporation, mobile phase: hexane/ethanol=600/400 (v/v), flow rate: 0.5 mL/min, retention time: 10.00 min))

H) 3-amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (5.40 g) obtained in Example 1, Step G, 4,4,4',4',5,5,5',5'-octamethyl-2,2'-bi-1,3,2-dioxaborolane (9.17 g), tetrakis(triphenylphosphine)palladium(0) (3.13 g), potassium acetate (3.54 g) and N,N-dimethylacetamide (50 mL) was stirred under an argon atmosphere at 110° C. for 4 hr. The reaction mixture was cooled to room temperature, and a solution of 2-(3-bromo-1-methyl-1H-pyrazol-5-yl)propan-2-ol (5.93 g) obtained in Reference Example 4 in N,N-dimethylacetamide (25 mL), aqueous sodium carbonate solution (2 M, 18.05 mL) and tetrakis(triphenylphosphine)palladium(0) (2.09 g) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol), and further fractionated by HPLC (C18, mobile phase: water/acetonitrile (containing 0.1% TFA)). A saturated aqueous sodium hydrogen carbonate solution was added to the obtained fraction, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (2.21 g).

$^1$H NMR (400 MHz, CDCl$_3$) δ 0.74-0.85 (3H, m), 1.04-1.13 (3H, m), 1.23-1.31 (1H, m), 1.37-1.43 (3H, m), 1.70 (6H, s), 1.90-2.00 (1H, m), 4.11 (3H, s), 4.76 (2H, s), 4.84-4.94 (1H, m), 6.26 (1H, s), 7.26 (1H, s), 10.42 (1H, brs).

MS (ESI+): [M+H]$^+$ 359.4.

Example 2

3-amino-7-(5-(2-hydroxypropan-2-yl)-1-methyl-1H-pyrazol-3-yl)-5-(3-methylbutan-2-yl)-1,5-dihydro-4H-pyrazolo[4,3-c]pyridin-4-one

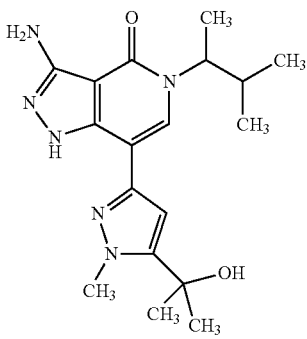 [SMILES: CC(C)C(C)n1cc(-c2cc(C(C)(C)O)n(C)n2)c2[nH]nc(N)c2c1=O]

A) N-(3-methylbutan-2-yl)-3-oxobutanamide

To a mixture of 3-methylbutan-2-amine (30.0 g) and methanol (180 mL) was added diketene (28.9 mL) at 0° C. over 5 min. The reaction mixture was stirred at room temperature for 20 hr. The solvent was evaporated under reduced pressure to give the title compound (58.65 g).

$^1$H NMR (300 MHz, CDCl$_3$) δ 0.90 (6H, dd, J=6.8, 3.1 Hz), 1.09 (3H, d, J=6.8 Hz), 1.61-1.76 (1H, m), 2.27 (3H, s), 3.41 (2H, s), 3.82-3.94 (1H, m), 6.83 (1H, brs).

B) 2-((dimethylamino)methylene)-N-(3-methylbutan-2-yl)-3-oxobutanamide

To a solution of N-(3-methylbutan-2-yl)-3-oxobutanamide (30.0 g) obtained in Example 2, Step A, in N,N-dimethylformamide (110 mL) was added dropwise 1,1-dimethoxy-N,N-dimethylmethanamine (46.5 mL) at 0° C. over 15 min. Thereafter, the reaction mixture was stirred at room temperature for 16 hr. The solvent was evaporated under reduced pressure to give a crude title compound (40.0 g).

$^1$H NMR (300 MHz, CDCl$_3$) δ 0.89-0.97 (6H, m), 1.11 (3H, d, J=6.7 Hz), 1.71-1.80 (1H, m), 2.23 (3H, s), 3.11 (6H, s), 3.83-3.98 (1H, m), 7.46-7.70 (2H, m).

C) 4-chloro-1-(3-methylbutan-2-yl)-2-oxo-1,2-dihydropyridine-3-carbaldehyde

To a solution of crude 2-((dimethylamino)methylene)-N-(3-methylbutan-2-yl)-3-oxobutanamide (40.0 g) obtained in Example 2, Step B, in N,N-dimethylformamide (300 mL) was added (chloromethylene)dimethylammonium chloride (72.4 g) under ice-cooling, and the reaction mixture was heated at 100° C. for 40 min. The reaction mixture was cooled to room temperature, saturated aqueous sodium hydrogen carbonate solution and potassium carbonate were added, and the mixture was extracted with ethyl acetate. The extract was dried over anhydrous magnesium sulfate, and the solvent was evaporated under reduced pressure. The residue was purified by silica gel column chromatography (ethyl acetate/hexane) to give an orange oil. The obtained oil was crystallized from diisopropyl ether/hexane to give the title compound (13.55 g).

$^1$H NMR (300 MHz, CDCl$_3$) δ 0.85 (3H, d, J=6.6 Hz), 1.04 (3H, d, J=6.7 Hz), 1.36 (3H, d, J=6.9 Hz), 1.82-2.00 (1H, m), 4.77-4.93 (1H, m), 6.34 (1H, d, J=7.4 Hz), 7.39 (1H, d, J=7.4 Hz), 10.40 (1H, s).

D) 4-chloro-3-((hydroxyimino)methyl)-1-(3-methylbutan-2-yl)pyridin-2(1H)-one A mixture of 4-chloro-1-(3-methylbutan-2-yl)-2-oxo-1,2-dihydropyridine-3-carbaldehyde (13.55 g) obtained in Example 2, Step C, hydroxylamine hydrochloride (6.20 g), concentrated hydrochloric acid (0.184 mL) and 2-propanol (200 mL) was heated at 100° C. for 1 hr, and cooled to room temperature. The solvent was evaporated under reduced pressure. To the residue was added 2-propanol/diisopropyl ether, and the resulting solid was collected by filtration and washed with 2-propanol/diisopropyl ether to give the title compound (12.48 g).

MS (ESI+): [M+H]$^+$ 243.2.

E) 4-chloro-1-(3-methylbutan-2-yl)-2-oxo-1,2-dihydropyridine-3-carbonitrile

To a solution of 4-chloro-3-((hydroxyimino)methyl)-1-(3-methylbutan-2-yl)pyridin-2(1H)-one (12.48 g) obtained in Example 2, Step D, in acetonitrile (230 mL) was added thionyl chloride (7.47 mL) at room temperature. The reaction mixture was stirred at room temperature for 1 hr. The solvent was evaporated under reduced pressure. To the residue were added diisopropyl ether, ethyl acetate and hexane, and the insoluble material was removed by filtration. The filtrate was evaporated under reduced pressure. Ethyl acetate was added to the residue, and the mixture was washed with saturated aqueous sodium hydrogen carbonate solution and saturated brine, and dried over anhydrous magnesium sulfate. The solvent was evaporated under reduced pressure and the residue was purified by silica gel column chromatography (ethyl acetate/hexane) to give the title compound (8.16 g).

MS (ESI+): [M+H]$^+$ 225.2.

F) 5-bromo-4-chloro-1-(3-methylbutan-2-yl)-2-oxo-1,2-dihydropyridine-3-carbonitrile To a solution of 4-chloro-1-(3-methylbutan-2-yl)-2-oxo-1,2-dihydropyridine-3-carbonitrile (8.10 g) obtained in Example 2, Step E, in N,N-dimethylformamide (80 mL) was added N-bromosuccinimide (9.62 g) at room temperature. The reaction mixture was heated at 50° C. for 20 hr. The reaction mixture was added to water, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (10.92 g).

MS (ESI+): [M+H]$^+$ 303.2.

G) 3-amino-7-bromo-5-(3-methylbutan-2-yl)-1,5-dihydro-4H-pyrazolo[4,3-c]pyridin-4-one To a solution of 5-bromo-4-chloro-1-(3-methylbutan-2-yl)-2-oxo-1,2-dihydropyridine-3-carbonitrile (8.78 g)

obtained in Example 2, Step F, in ethanol (120 mL) was added hydrazine monohydrate (2.17 g) at room temperature. The reaction mixture was heated at 90° C. for 1 hr. To the reaction mixture was added hydrazine monohydrate (1.00 g), and the mixture was heated at 90° C. for 1 hr. The reaction mixture was cooled to room temperature. The solvent was evaporated under reduced pressure. To the residue were added ethyl acetate, tetrahydrofuran and water. The organic layer was separated, washed with saturated aqueous sodium hydrogen carbonate solution and then saturated brine, and dried over anhydrous magnesium sulfate. The solvent was evaporated under reduced pressure and the residue was purified by silica gel column chromatography (ethyl acetate/hexane) to give the title compound (8.38 g).

MS (ESI+): [M+H]$^+$ 299.2.

H) 3-amino-7-(5-(2-hydroxypropan-2-yl)-1-methyl-1H-pyrazol-3-yl)-5-(3-methylbutan-2-yl)-1,5-dihydro-4H-pyrazolo[4,3-c]pyridin-4-one A mixture of 3-amino-7-bromo-5-(3-methylbutan-2-yl)-1,5-dihydro-4H-pyrazolo[4,3-c]pyridin-4-one (200 mg) obtained in Example 2, Step G, 4,4,4',4',5,5,5',5'-octamethyl-2,2'-bi-1,3,2-dioxaborolane (340 mg), tetrakis(triphenylphosphine)palladium(0) (120 mg), potassium acetate (130 mg) and N,N-dimethylacetamide (6.0 mL) was stirred under an argon atmosphere at 110° C. for 4 hr. The reaction mixture was cooled to room temperature, and 2-(3-bromo-1-methyl-1H-pyrazol-5-yl)propan-2-ol (220 mg) obtained in Reference Example 4, aqueous sodium carbonate solution (2 M, 0.67 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol), and fractionated by HPLC (C18, mobile phase: water/acetonitrile (containing 0.1% TFA)). Ethyl acetate was added to the obtained fraction, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (25 mg).

$^1$H NMR (400 MHz, CDCl$_3$) δ 0.81 (3H, d, J=6.6 Hz), 1.07 (3H, d, J=6.6 Hz), 1.39 (3H, d, J=7.1 Hz), 1.70 (3H, s), 1.70 (3H, s), 1.83-2.01 (2H, m), 4.11 (3H, s), 4.63-4.99 (3H, m), 6.24 (1H, s), 7.25 (1H, s), 10.40 (1H, brs).

MS (ESI+): [M+H]$^+$ 359.4.

Example 3

3-amino-7-(5-(1-hydroxy-2-methylpropan-2-yl)-1-methyl-1H-pyrazol-3-yl)-5-((2S)-3-methylbutan-2-yl)-1,5-dihydro-4H-pyrazolo[4,3-c]pyridin-4-one

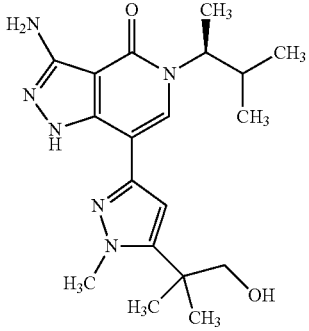 [SMILES: CC(C)[C@H](C)n1cc(-c2cc(C(C)(C)CO)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylacetamide (3 mL) was stirred under an argon atmosphere at 110° C. for 4 hr. The reaction mixture was cooled to room temperature, and a solution of 3-iodo-5-(1-((4-methoxybenzyl)oxy)-2-methylpropan-2-yl)-1-methyl-1H-pyrazole (375 mg) obtained in Reference Example 11 in N,N-dimethylacetamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 4 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a colorless solid (145 mg). Trifluoroacetic acid (2.19 mL) was added to the obtained solid (140 mg) at 0° C. The reaction mixture was stirred under a nitrogen atmosphere at 0° C. for 20 min. To the reaction mixture was added saturated aqueous sodium hydrogen carbonate solution at 0° C., and ethyl acetate was added. The extract was washed with water and saturated brine, dried over anhydrous magnesium sulfate, and concentrated under reduced pressure. The residue was purified by silica gel chromatography (basic silica gel, methanol/ethyl acetate) to give the title compound (81 mg).

$^1$H NMR (300 MHz, CDCl$_3$) δ 0.80 (3H, d, J=6.8 Hz), 1.08 (3H, d, J=6.8 Hz), 1.39 (3H, d, J=6.8 Hz), 1.45 (6H, s), 1.93 (1H, dt, J=9.8, 6.6 Hz), 2.09 (1H, brs), 3.76 (2H, brs), 4.06 (3H, s), 4.76 (2H, s), 4.81-4.95 (1H, m), 6.31 (1H, s), 7.27 (1H, s).

MS (ESI+): [M+H]$^+$ 373.3.

Example 4

3-amino-5-(1-cyclopropylethyl)-7-(1-methyl-5-(morpholin-4-yl)-1H-pyrazol-3-yl)-1,5-dihydro-4H-pyrazolo[4,3-c]pyridin-4-one

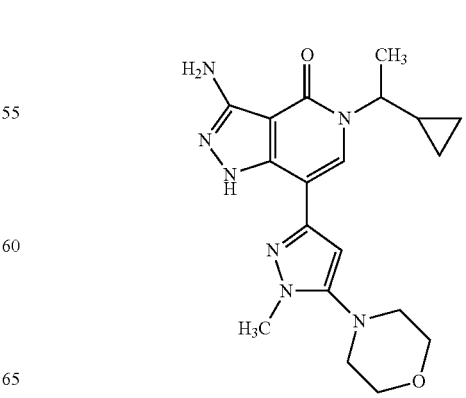

A) 1-(1-cyclopropylethyl)-4-methoxy-2-oxo-1,2-dihydropyridine-3-carbonitrile To a mixture of 4-methoxy-2-oxo-1,2-dihydropyridine-3-carbonitrile (20.0 g), triphenylphosphine (52.4 g), 1-cyclopropylethanol (19.34 mL) and tetrahydrofuran (500 mL) was added bis(2-methoxyethyl) azodicarboxylate (46.8 g) at 0° C. The reaction mixture was stirred at room temperature for 15 hr. The reaction mixture was added to water, and the mixture was extracted with ethyl acetate. The obtained organic layer was washed with water and saturated brine, and dried over anhydrous magnesium sulfate. The solvent was evaporated under reduced pressure and the residue was dissolved in diethyl ether (300 mL), and triphenylphosphine oxide (5 mg) was added. Insoluble materials were collected by filtration. The filtrate was washed with water, and dried over anhydrous magnesium sulfate. The solvent was evaporated under reduced pressure and the residue was purified by silica gel column chromatography (basic silica gel, hexane/ethyl acetate) to give a crude purification product. The crude purification product was purified by silica gel column chromatography (hexane/ethyl acetate) to give the title compound (2.45 g).
MS (ESI+): [M+H]$^+$ 218.9.

B) 5-bromo-1-(1-cyclopropylethyl)-4-methoxy-2-oxo-1,2-dihydropyridine-3-carbonitrile A mixture of 1-(1-cyclopropylethyl)-4-methoxy-2-oxo-1,2-dihydropyridine-3-carbonitrile (2.45 g) obtained in Example 4, Step A, N-bromosuccinimide (3.00 g) and N,N-dimethylformamide (50 mL) was stirred at 60° C. for 16 hr. The reaction mixture was cooled to room temperature and the solvent was evaporated under reduced pressure. The residue was purified by silica gel column chromatography (hexane/ethyl acetate) to give the title compound (2.73 g).
MS (ESI+): [M+H]$^+$ 296.8.

C) 3-amino-7-bromo-5-(1-cyclopropylethyl)-1,5-dihydro-4H-pyrazolo[4,3-c]pyridin-4-one A mixture of 5-bromo-1-(1-cyclopropylethyl)-4-methoxy-2-oxo-1,2-dihydropyridine-3-carbonitrile (1.2 g) obtained in Example 4, Step B, hydrazine monohydrate (1.01 g) and ethanol (20 mL) was stirred at 90° C. for 2 hr. The reaction mixture was cooled to room temperature and the solvent was evaporated under reduced pressure. The residue was purified by silica gel column chromatography (basic silica gel, hexane/ethyl acetate) to give a crude purification product. The crude purification product was dissolved in ethyl acetate, washed with saturated brine, and dried over anhydrous magnesium sulfate. The solvent was evaporated under reduced pressure to give the title compound (1.20 g).
MS (ESI+): [M+H]296.8.

D) 3-amino-5-(1-cyclopropylethyl)-7-(1-methyl-5-(morpholin-4-yl)-1H-pyrazol-3-yl)-1,5-dihydro-4H-pyrazolo[4,3-c]pyridin-4-one A mixture of 3-amino-7-bromo-5-(1-cyclopropylethyl)-1,5-dihydro-4H-pyrazolo[4,3-c]pyridin-4-one (300 mg) obtained in Example 4, Step C, 4,4,4',4',5,5,5',5'-octamethyl-2,2'-bi-1,3,2-dioxaborolane (513 mg), (1,1'-bis(diphenylphosphino)ferrocene)dichloropalladium(II) (111 mg), potassium acetate (198 mg) and N,N-dimethylformamide (4 mL) was stirred under an argon atmosphere at 110° C. for 4 hr. The reaction mixture was cooled to room temperature and a solution of 1-methyl-5-(morpholin-4-yl)-1H-pyrazol-3-yl trifluoromethanesulfonate (430 mg) obtained in Reference Example 47 in N,N-dimethylformamide (1 mL), aqueous sodium carbonate solution (2 M, 1.01 mL) and tetrakis (triphenylphosphine)palladium(0) (117 mg) were added. Under an argon atmosphere, the reaction mixture was stirred at 120° C. for 2 hr. The reaction mixture was cooled to room temperature, water was added, and the mixture was extracted with ethyl acetate/tetrahydrofuran. The extract was washed with saturated brine, and dried over anhydrous magnesium sulfate. The solvent was evaporated under reduced pressure and the residue was purified by silica gel chromatography (basic silica gel, hexane/ethyl acetate) and fractionated by HPLC (C18, mobile phase: water/acetonitrile (containing 10 mM NH$_4$HCO$_3$)), and the obtained fraction was concentrated under reduced pressure. The residue was solidified from diethyl ether to give the title compound (78 mg).
$^1$H NMR (400 MHz, CDCl$_3$) δ 0.33-0.40 (1H, m), 0.46-0.53 (2H, m), 0.69-0.77 (1H, m), 1.10-1.18 (1H, m), 1.45 (3H, d, J=6.8 Hz), 2.94-3.00 (4H, m), 3.78 (3H, s), 3.83-3.90 (4H, m), 4.40-4.51 (1H, m), 4.74 (2H, s), 6.03 (1H, s), 7.52 (1H, s), 10.46 (1H, brs).
MS (ESI+): [M+H]384.1.

Example 5

3-amino-5-((1S)-1-cyclopropylethyl)-7-(1-methyl-5-(morpholin-4-yl)-1H-pyrazol-3-yl)-1,5-dihydro-4H-pyrazolo[4,3-c]pyridin-4-one

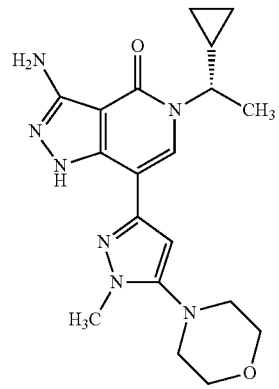 [SMILES: C[C@@H](C1CC1)n1cc(-c2cc(N3CCOCC3)n(C)n2)c2[nH]nc(N)c2c1=O]

The racemate of 3-amino-5-(1-cyclopropylethyl)-7-(1-methyl-5-(morpholin-4-yl)-1H-pyrazol-3-yl)-1,5-dihydro-4H-pyrazolo[4,3-c]pyridin-4-one (193 mg) obtained in Example 4, Step D, was fractionated by SFC (column: CHIRALPAK AS-H, 20 mmID×250 mmL, manufactured by Daicel Corporation, mobile phase: carbon dioxide/methanol/diethylamine=860/140/3 (v/v/v)) to give the title compound (81 mg) having a shorter retention time. Diethyl ether was added to the obtained solid (81 mg), and insoluble material was collected by filtration to give the title compound (76 mg).
99% ee (SFC (column: CHIRALPAK AS-H, 4.6 mmID×250 mmL, manufactured by Daicel Corporation, mobile phase: carbon dioxide/methanol/diethylamine=800/200/3 (v/v/v), flow rate: 3 mL/min, retention time: 4.64 min))
$^1$H NMR (400 MHz, CDCl$_3$) δ 0.32-0.40 (1H, m), 0.45-0.53 (2H, m), 0.67-0.78 (1H, m), 1.09-1.21 (1H, m), 1.45

(3H, d, J=6.8 Hz), 2.92-3.00 (4H, m), 3.78 (3H, s), 3.84-3.90 (4H, m), 4.39-4.50 (1H, m), 4.74 (2H, s), 6.03 (1H, s), 7.52 (1H, s), 10.46 (1H, brs).
MS (ESI+): [M+H]+ 384.1.

Example 6

3-amino-5-((1R)-1-cyclopropylethyl)-7-(1-methyl-5-(morpholin-4-yl)-1H-pyrazol-3-yl)-1,5-dihydro-4H-pyrazolo[4,3-c]pyridin-4-one

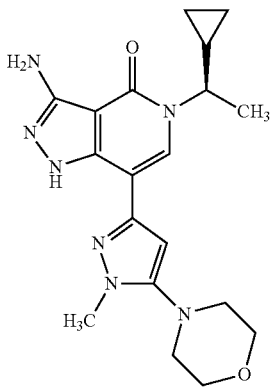 [SMILES: C[C@H](C1CC1)n1cc(-c2cc(N3CCOCC3)n(C)n2)c2[nH]nc(N)c2c1=O]

The racemate of 3-amino-5-(1-cyclopropylethyl)-7-(1-methyl-5-(morpholin-4-yl)-1H-pyrazol-3-yl)-1,5-dihydro-4H-pyrazolo[4,3-c]pyridin-4-one (193 mg) obtained in Example 4, Step D, was fractionated by SFC (column: CHIRALPAK AS-H, 20 mmID×250 mmL, manufactured by Daicel Corporation, mobile phase: carbon dioxide/methanol/diethylamine=860/140/3 (v/v/v)) to give the title compound (88 mg) having a longer retention time. Diethyl ether was added to the obtained solid (88 mg), and insoluble material was collected by filtration to give the title compound (73 mg).
99% ee (SFC (column: CHIRALPAK AS-H, 4.6 mmID× 250 mmL, manufactured by Daicel Corporation, mobile phase: carbon dioxide/methanol/diethylamine=800/200/3 (v/v/v), flow rate: 3 mL/min, retention time: 5.69 min))
1H NMR (400 MHz, CDCl3) δ 0.34-0.41 (1H, m), 0.46-0.55 (2H, m), 0.69-0.78 (1H, m), 1.10-1.19 (1H, m), 1.45 (3H, d, J=6.8 Hz), 2.94-3.00 (4H, m), 3.78 (3H, s), 3.85-3.90 (4H, m), 4.39-4.50 (1H, m), 4.74 (2H, s), 6.03 (1H, s), 7.52 (1H, s), 10.46 (1H, brs).
MS (ESI+): [M+H]+ 384.1.

Example 7

3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one

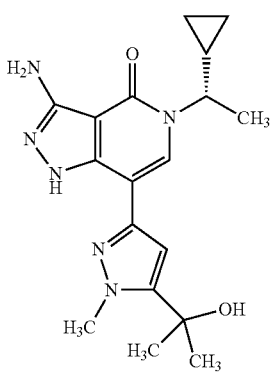 [SMILES: C[C@@H](C1CC1)n1cc(-c2cc(C(C)(C)O)n(C)n2)c2[nH]nc(N)c2c1=O]

A) 3-amino-7-bromo-5-((1S)-1-cyclopropylethyl)-1,5-dihydro-4H-pyrazolo[4,3-c]pyridin-4-one The racemate (1.1 g) of 3-amino-7-bromo-5-(1-cyclopropylethyl)-1,5-dihydro-4H-pyrazolo[4,3-c]pyridin-4-one obtained in Example 4, Step C, was fractionated by HPLC (column: CHIRALPAK AD, 50 mmID×500 mmL, manufactured by Daicel Corporation, mobile phase: hexane/ethanol=800/200 (v/v)) to give the title compound (533 mg) having a shorter retention time.
MS (ESI+): [M+H]+ 297.1.
>99.9% ee (HPLC (column: CHIRALPAK AD, 4.6 mmID×250 mmL, manufactured by Daicel Corporation, mobile phase: hexane/ethanol=800/200 (v/v), flow rate: 1.0 mL/min, retention time: 8.86 min))

B) 3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (800 mg) obtained in Example 7, Step A, 4,4,4',4',5,5,5',5'-octamethyl-2,2'-bi-1,3,2-dioxaborolane (1367 mg), tetrakis(triphenylphosphine)palladium(0) (467 mg), potassium acetate (528 mg) and N,N-dimethylacetamide (12 mL) was stirred under an argon atmosphere at 110° C. for 4 hr. The reaction mixture was cooled to room temperature, and a solution of 2-(3-bromo-1-methyl-1H-pyrazol-5-yl)propan-2-ol (885 mg) obtained in Reference Example 4 in N,N-dimethylacetamide (5 mL), aqueous sodium carbonate solution (2 M, 2.69 mL) and tetrakis(triphenylphosphine)palladium(0) (311 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid (780 mg). The obtained yellow solid (660 mg) was fractionated by HPLC (C18, mobile phase: water/acetonitrile (containing 10 mM NH4HCO3)), and the obtained fraction was concentrated under reduced pressure. The residue was solidified from diethyl ether to give the title compound (278 mg).
MS (ESI+): [M+H]+ 357.0.
1H NMR (400 MHz, CDCl3) δ 0.33-0.40 (1H, m), 0.45-0.54 (2H, m), 0.68-0.77 (1H, m), 1.10-1.18 (1H, m), 1.45 (3H, d, J=6.8 Hz), 1.65-1.71 (6H, m), 2.59 (1H, s), 4.10 (3H, s), 4.38-4.48 (1H, m), 4.72 (2H, s), 6.19 (1H, s), 7.45 (1H, s), 10.39 (1H, s).

Example 8

3-amino-5-((1S)-1-cyclopropylethyl)-7-(5-(4-hydroxy-4-methylpiperidin-1-yl)-1-methyl-1H-pyrazol-3-yl)-1,5-dihydro-4H-pyrazolo[4,3-c]pyridin-4-one

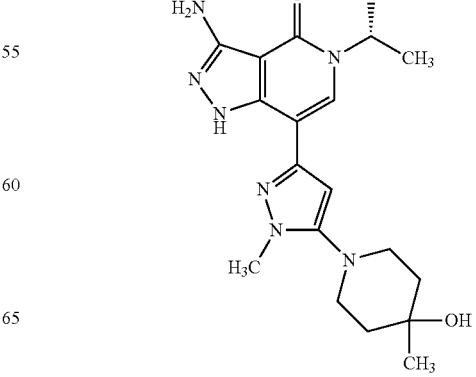

To a mixture of 3-amino-7-bromo-5-((1S)-1-cyclopropylethyl)-1,5-dihydro-4H-pyrazolo[4,3-c]pyridin-4-one (160 mg) obtained in Example 7, Step A, 4,4,4',4',5,5,5',5'-octamethyl-2,2'-bi-1,3,2-dioxaborolane (273 mg), potassium acetate (106 mg) and N,N-dimethylformamide (2 mL) was added tetrakis(triphenylphosphine)palladium(0) (93 mg), and the mixture was stirred under an argon atmosphere at 110° C. for 3 hr. The reaction mixture was cooled to room temperature, and a solution of 1-(3-bromo-1-methyl-1H-pyrazol-5-yl)-4-methylpiperidin-4-ol (221 mg) obtained in Reference Example 13 in N,N-dimethylformamide (2 mL), aqueous sodium carbonate solution (2 M, 0.538 mL) and tetrakis(triphenylphosphine)palladium(0) (62.2 mg) were added. Under an argon atmosphere, the reaction mixture was stirred at 120° C. for 3 hr. The reaction mixture was cooled to room temperature, water was added, and the mixture was extracted twice with ethyl acetate. The extracts were combined, washed with saturated brine, and dried over anhydrous magnesium sulfate. The solvent was evaporated under reduced pressure and the residue was purified by silica gel chromatography (basic silica gel, ethyl acetate) to give a yellow oil (170 mg). The obtained a yellow oil was crystallized from ethyl acetate/hexane to give the title compound (107 mg).

MS (ESI+): [M+H]$^+$ 412.1.

$^1$H NMR (300 MHz, CDCl$_3$) δ 0.30-0.42 (1H, m), 0.43-0.57 (2H, m), 0.65-0.80 (1H, m), 1.06-1.22 (1H, m), 1.35 (3H, s), 1.44 (3H, d, J=6.8 Hz), 1.53-1.92 (5H, m), 2.88-3.00 (2H, m), 3.01-3.13 (2H, m), 3.75 (3H, s), 4.38-4.54 (1H, m), 4.74 (2H, s), 6.03 (1H, s), 7.51 (1H, s), 9.79-11.29 (1H, br).

Example 9

3-amino-5-(1-cyclopropylethyl)-7-(5-(((1,1-dioxidothiomorpholin-4-yl)methyl)-1-methyl-1H-pyrazol-3-yl)-1,5-dihydro-4H-pyrazolo[4,3-c]pyridin-4-one

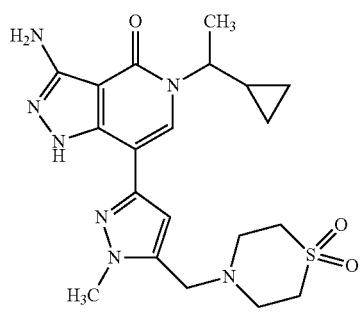 [SMILES: CC(C1CC1)n1cc(-c2cc(CN3CCS(=O)(=O)CC3)n(C)n2)c2[nH]nc(N)c2c1=O]

In the same manner as in Example 1, Step H, the title compound was obtained from 3-amino-7-bromo-5-(1-cyclopropylethyl)-1,5-dihydro-4H-pyrazolo[4,3-c]pyridin-4-one obtained in Example 4, Step C, and 5-((1,1-dioxidothiomorpholin-4-yl)methyl)-1-methyl-1H-pyrazol-3-yl trifluoromethanesulfonate obtained in Reference Example 60.

Example 10

3-amino-5-((2S)-3-methylbutan-2-yl)-7-(1-methyl-5-(4-methylpiperazin-1-yl)-1H-pyrazol-3-yl)-1,5-dihydro-4H-pyrazolo[4,3-c]pyridin-4-one

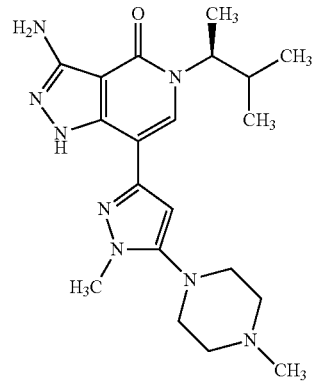 [SMILES: CC(C)[C@H](C)n1cc(-c2cc(N3CCN(C)CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylformamide (3 mL) was stirred under an argon atmosphere at 110° C. for 4 hr. The reaction mixture was cooled to room temperature, and a solution of 1-(3-bromo-1-methyl-1H-pyrazol-5-yl)-4-methylpiperazine (260 mg) obtained in Reference Example 14 in N,N-dimethylformamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a crude purification product. The crude purification product was purified by silica gel chromatography (basic silica gel, methanol/ethyl acetate) to give a crude purification product as a yellow oil. The obtained yellow oil was solidified from ethyl acetate/diisopropyl ether to give the title compound (58 mg).

MS (ESI+): [M+H]$^+$ 399.1.

Example 11

7-(5-(4-acetylpiperazin-1-yl)-1-methyl-1H-pyrazol-3-yl)-3-amino-5-((2S)-3-methylbutan-2-yl)-1,5-dihydro-4H-pyrazolo[4,3-c]pyridin-4-one

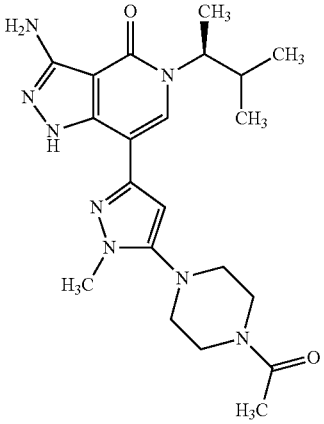 [SMILES: CC(=O)N1CCN(c2cc(-c3cn([C@@H](C)C(C)C)c(=O)c4c(N)n[nH]c34)nn2C)CC1]

A mixture of 3-amino-7-bromo-5-((2S)-3-methylbutan-2-yl)-1,5-dihydro-4H-pyrazolo[4,3-c]pyridin-4-one (180 mg) obtained in Example 1, Step G, 4,4,4',4',5,5,5',5'-octamethyl-2,2'-bi-1,3,2-dioxaborolane (306 mg), (1,1'-bis(diphenylphosphino)ferrocene)dichloropalladium(II) (66 mg), potassium acetate (118 mg) and N,N-dimethylformamide (3 mL) was stirred under an argon atmosphere at 110° C. for 4 hr. The reaction mixture was cooled to room temperature, and a solution of 1-(4-(3-bromo-1-methyl-1H-pyrazol-5-yl)piperazin-1-yl)ethanone (180 mg) obtained in Reference Example 15 in N,N-dimethylformamide (0.5 mL), aqueous sodium carbonate solution (2 M, 0.602 mL) and tetrakis(triphenylphosphine)palladium(0) (70 mg) were added. Under an argon atmosphere, the reaction mixture was stirred at 120° C. overnight. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a crude purification product. The crude purification product was purified by silica gel chromatography (basic silica gel, methanol/ethyl acetate) to give the title compound (15 mg).
MS (ESI+): [M+H]$^+$ 427.2.

Example 12

3-amino-7-(5-(1,1-dioxidothiomorpholin-4-yl)-1-methyl-1H-pyrazol-3-yl)-5-((2S)-3-methylbutan-2-yl)-1,5-dihydro-4H-pyrazolo[4,3-c]pyridin-4-one

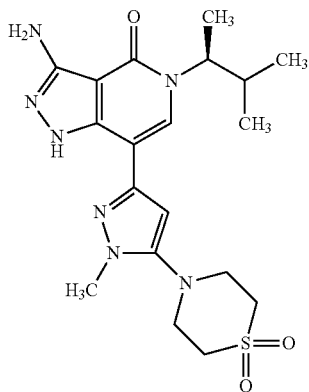 [SMILES: CC(C)[C@H](C)n1cc(-c2cc(N3CCS(=O)(=O)CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), (1,1'-bis(diphenylphosphino)ferrocene)dichloropalladium(II) (92 mg), potassium acetate (164 mg) and N,N-dimethylacetamide (3 mL) was stirred under an argon atmosphere at 110° C. for 4 hr. The reaction mixture was cooled to room temperature, and a solution of 4-(3-bromo-1-methyl-1H-pyrazol-5-yl)thiomorpholine 1,1-dioxide (369 mg) obtained in Reference Example 16 in N,N-dimethylacetamide (0.5 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a crude purification product. The crude purification product was purified by silica gel chromatography (basic silica gel, methanol/ethyl acetate) to give a crude purification product as a yellow solid. The obtained solid was crystallized from ethyl acetate/diisopropyl ether to give the title compound (114 mg).
MS (ESI+): [M+H]$^+$ 434.1.

Example 13

3-amino-5-((2S)-3-methylbutan-2-yl)-7-(1-methyl-5-(1,4-oxazepan-4-yl)-1H-pyrazol-3-yl)-1,5-dihydro-4H-pyrazolo[4,3-c]pyridin-4-one

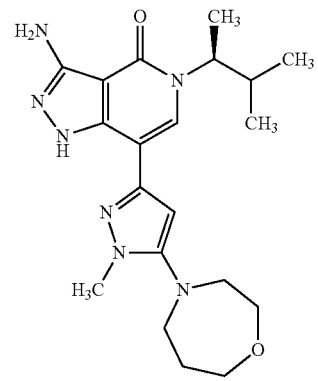 [SMILES: CC(C)[C@H](C)n1cc(-c2cc(N3CCCOCC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), tetrakis(triphenylphosphine)palladium(0) (145 mg), potassium acetate (164 mg) and N,N-dimethylacetamide (3 mL) was stirred under an argon atmosphere at 110° C. for 4 hr. The reaction mixture was cooled to room temperature, and a solution of 4-(3-bromo-1-methyl-1H-pyrazol-5-yl)-1,4-oxazepane (326 mg) obtained in Reference Example 17 in N,N-dimethylacetamide (0.5 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give a yellow solid. The obtained yellow solid was crystallized from ethyl acetate/diisopropyl ether to give the title compound (123 mg).
MS (ESI+): [M+H]$^+$ 400.1.

Example 14

3-amino-7-(5-(4-methoxypiperidin-1-yl)-1-methyl-1H-pyrazol-3-yl)-5-((2S)-3-methylbutan-2-yl)-1,5-dihydro-4H-pyrazolo[4,3-c]pyridin-4-one

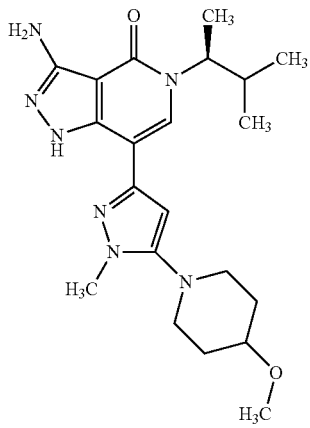 [SMILES: COC1CCN(c2cc(-c3cn([C@@H](C)C(C)C)c(=O)c4c(N)n[nH]c34)nn2C)CC1]

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), (1,1'-bis(diphenylphosphino)ferrocene)dichloropalladium(II) (92 mg), potassium acetate (164 mg) and N,N-dimethylacetamide (3 mL) was stirred under an argon atmosphere at 110° C. for 4 hr. The reaction mixture was cooled to room temperature, and a solution of 1-(3-bromo-1-methyl-1H-pyrazol-5-yl)-4-methoxypiperidine (344 mg) obtained in Reference Example 18 in N,N-dimethylacetamide (0.5 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a crude purification product. The crude purification product was purified by silica gel chromatography (basic silica gel, methanol/ethyl acetate) to give a crude purification product as a yellow amorphous solid. The obtained solid was crystallized from ethyl acetate/diisopropyl ether to give the title compound (58 mg).

MS (ESI+): [M+H]$^+$ 414.1.

Example 15

3-amino-7-(5-(4-(2-hydroxypropan-2-yl)piperidin-1-yl)-1-methyl-1H-pyrazol-3-yl)-5-((2S)-3-methylbutan-2-yl)-1,5-dihydro-4H-pyrazolo[4,3-c]pyridin-4-one

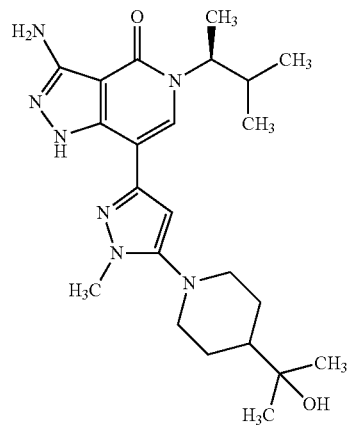 [SMILES: CC(C)[C@H](C)n1cc(-c2cc(N3CCC(C(C)(C)O)CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (3 mL) was stirred under an argon atmosphere at 110° C. for 4 hr. The reaction mixture was cooled to room temperature, and a solution of 2-(1-(3-bromo-1-methyl-1H-pyrazol-5-yl)piperidin-4-yl)propan-2-ol (303 mg) obtained in Reference Example 19 in N,N-dimethylacetamide (1.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give a crude purification product as a yellow solid. The obtained yellow solid was triturated with methanol/ethyl acetate to give a colorless solid. The obtained solid was crystallized from tetrahydrofuran/methanol to give the title compound (70 mg).

MS (ESI+): [M+H]$^+$ 442.2.

Example 16

3-amino-7-(5-(4,4-difluoropiperidin-1-yl)-1-methyl-1H-pyrazol-3-yl)-5-((2S)-3-methylbutan-2-yl)-1,5-dihydro-4H-pyrazolo[4,3-c]pyridin-4-one

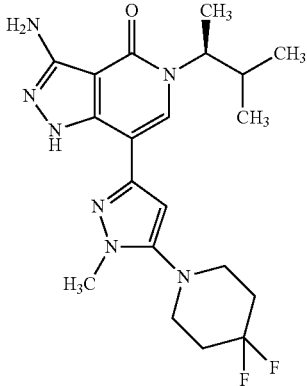 [SMILES: CC(C)[C@H](C)n1cc(-c2cc(N3CCC(F)(F)CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (3 mL) was stirred under an argon atmosphere at 110° C. for 4 hr. The reaction mixture was cooled to room temperature, and 1-(3-bromo-1-methyl-1H-pyrazol-5-yl)-4,4-difluoropiperidine (281 mg) obtained in Reference Example 20, aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water and ethyl acetate were added, and the mixture was filtered through celite, and the aqueous layer was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane and methanol/ethyl acetate) to give the title compound (119 mg).
MS (ESI+): [M+H]$^+$ 420.1.

Example 17

3-amino-7-(5-(4-(methoxyacetyl)piperazin-1-yl)-1-methyl-1H-pyrazol-3-yl)-5-((2S)-3-methylbutan-2-yl)-1,5-dihydro-4H-pyrazolo[4,3-c]pyridin-4-one

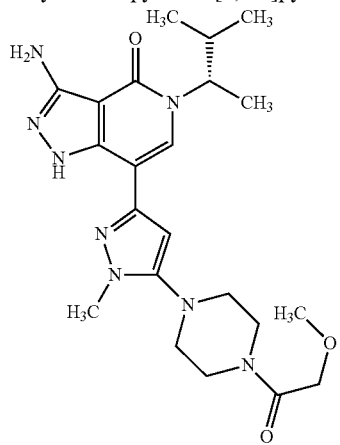

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (77 mg), potassium acetate (131 mg) and N,N-dimethylacetamide (3 mL) was stirred under an argon atmosphere at 110° C. for 4 hr. The reaction mixture was cooled to room temperature, and a solution of 1-(4-(3-bromo-1-methyl-1H-pyrazol-5-yl)piperazin-1-yl)-2-methoxyethanone (318 mg) obtained in Reference Example 21 in N,N-dimethylacetamide (1.5 mL), aqueous sodium carbonate solution (2 M, 0.669 mL) and tetrakis(triphenylphosphine)palladium(0) (116 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane and methanol/ethyl acetate) to give a crude purification product as a yellow solid, which was further fractionated by HPLC (C18, mobile phase: water/acetonitrile (containing 10 mM NH$_4$HCO$_3$)) and the obtained fraction was concentrated under reduced pressure to give a white solid. The obtained solid was crystallized from ethyl acetate/diisopropyl ether to give the title compound (125 mg).
MS (ESI+): [M+H]$^+$ 457.4.

Example 18

3-amino-7-(5-(4-hydroxy-4-methylpiperidin-1-yl)-1-methyl-1H-pyrazol-3-yl)-5-((2S)-3-methylbutan-2-yl)-1,5-dihydro-4H-pyrazolo[4,3-c]pyridin-4-one

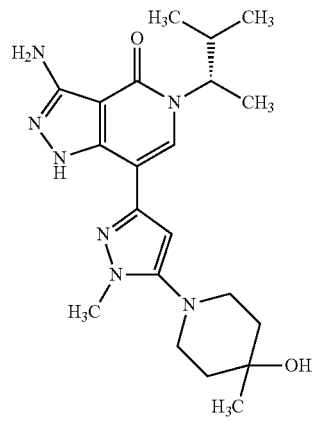 [SMILES: CC(C)[C@H](C)n1cc(-c2cc(N3CCC(C)(O)CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (450 mg) obtained in Example 1, Step G, 4,4,4',4',5,5,5',5'-octamethyl-2,2'-bi-1,3,2-dioxaborolane (764 mg), tetrakis(triphenylphosphine)palladium(0) (261 mg), potassium acetate (295 mg) and N,N-dimethylformamide (6 mL) was stirred under an argon atmosphere at 110° C. for 2 hr. The reaction mixture was cooled to room temperature, and a solution of 1-(3-bromo-1-methyl-1H-pyrazol-5-yl)-4-methylpiperidin-4-ol (619 mg) obtained in Reference Example 13 in N,N-dimethylformamide (4 mL), aqueous sodium carbonate solution (2 M, 1.504 mL) and tetrakis(triphenylphosphine)palladium(0) (174 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give an orange solid. The obtained solid was crystallized from methanol/diisopropyl ether to give the title compound (263 mg).

MS (ESI+): [M+H]⁺ 414.1.

Example 19

3-amino-5-((2S)-3-methylbutan-2-yl)-7-(1-methyl-5-(piperidin-1-yl)-1H-pyrazol-3-yl)-1,5-dihydro-4H-pyrazolo[4,3-c]pyridin-4-one

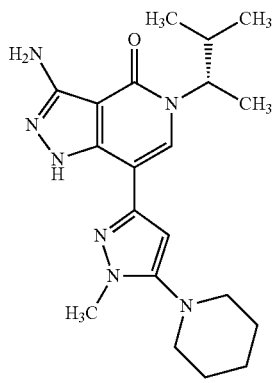 [SMILES: CC(C)[C@H](C)n1cc(-c2cc(N3CCCCC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (190 mg) obtained in Example 1, Step G, 4,4,4',4',5,5,5',5'-octamethyl-2,2'-bi-1,3,2-dioxaborolane (323 mg), tetrakis(triphenylphosphine)palladium(0) (110 mg), potassium acetate (125 mg) and N,N-dimethylformamide (3 mL) was stirred under an argon atmosphere at 110° C. for 2 hr. The reaction mixture was cooled to room temperature, and a solution of 1-(3-bromo-1-methyl-1H-pyrazol-5-yl)piperidine (230 mg) obtained in Reference Example 61 in N,N-dimethylformamide (1 mL), aqueous sodium carbonate solution (2 M, 0.635 mL) and tetrakis(triphenylphosphine)palladium(0) (73 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow amorphous solid. The obtained solid was crystallized from ethyl acetate/diisopropyl ether to give the title compound (37 mg).

MS (ESI+): [M+H]384.1.

Example 20

3-amino-7-(5-((2S)-2-(hydroxymethyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one

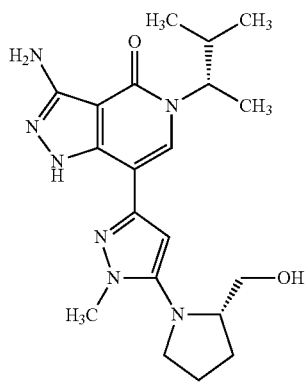 [SMILES: CC(C)[C@H](C)n1cc(-c2cc(N3CCC[C@H]3CO)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (58 mg), potassium acetate (98 mg) and N,N-dimethylacetamide (3 mL) was stirred under an argon atmosphere at 110° C. for 4 hr. The reaction mixture was cooled to room temperature, and ((2S)-1-(3-bromo-1-methyl-1H-pyrazol-5-yl)pyrrolidin-2-yl)methanol (196 mg) obtained in Reference Example 22, aqueous sodium carbonate solution (2 M, 0.501 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give a yellow solid. The obtained solid was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (68 mg).

MS (ESI+): [M+H]⁺ 400.2.

Example 21

3-amino-7-(5-((3R)-3-hydroxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one

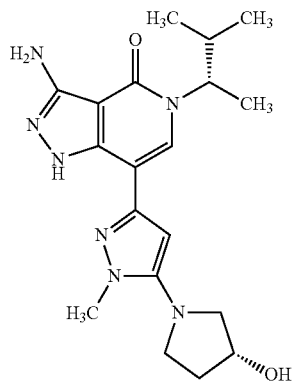

A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (58 mg), potassium acetate (98 mg) and N,N-dimethylacetamide (3 mL) was stirred under an argon atmosphere at 110° C. for 4 hr. The reaction mixture was cooled to room temperature, and a solution of (3R)-1-(3-bromo-1-methyl-1H-pyrazol-5-yl)pyrrolidin-3-ol (123 mg) obtained in Reference Example 23 in N,N-dimethylacetamide (1 mL), aqueous sodium carbonate solution (2 M, 0.501 mL) and tetrakis(triphenylphosphine)palladium (0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give a yellow solid. The obtained solid was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (32 mg).

MS (ESI+): [M+H]$^+$ 386.1.

Example 22

3-amino-7-(5-((2R)-2-(hydroxymethyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one

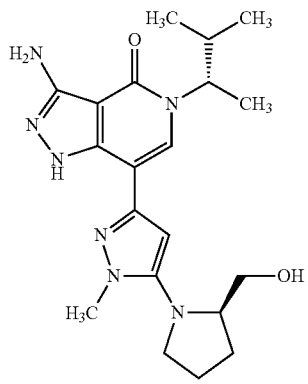 [SMILES: CC(C)[C@H](C)n1cc(-c2cc(N3CCC[C@@H]3CO)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (6 mL) was stirred under an argon atmosphere at 110° C. for 4 hr. The reaction mixture was cooled to room temperature, ((2R)-1-(3-bromo-1-methyl-1H-pyrazol-5-yl)pyrrolidin-2-yl)methanol (226 mg) obtained in Reference Example 24, aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane and methanol/ethyl acetate) to give a yellow solid. The obtained solid was further fractionated by HPLC (C18, mobile phase: water/acetonitrile (containing 0.1% TFA)), and the fraction was washed with saturated aqueous sodium hydrogen carbonate solution and saturated brine, dried over anhydrous magnesium sulfate, and concentrated under reduced pressure. The residue was solidified from ethyl acetate/hexane to give the title compound (102 mg).

MS (ESI+): [M+H]$^+$ 400.4.

Example 23

3-amino-7-(5-((3S)-3-hydroxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one

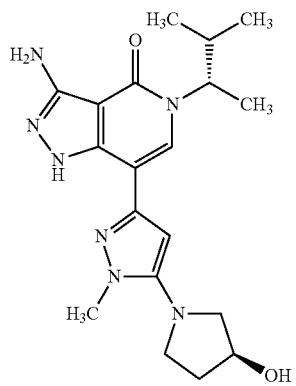

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (6 mL) was stirred under an argon atmosphere at 110° C. for 4 hr. The reaction mixture was cooled to room temperature, (3S)-1-(3-bromo-1-methyl-1H-pyrazol-5-yl)pyrrolidin-3-ol (197 mg) obtained in Reference Example 25, aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane and methanol/ethyl acetate) to give a yellow solid. The obtained solid was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (83 mg).

MS (ESI+): [M+H]$^+$ 386.4.

Example 24

3-amino-7-(5-((3R)-3-methoxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one

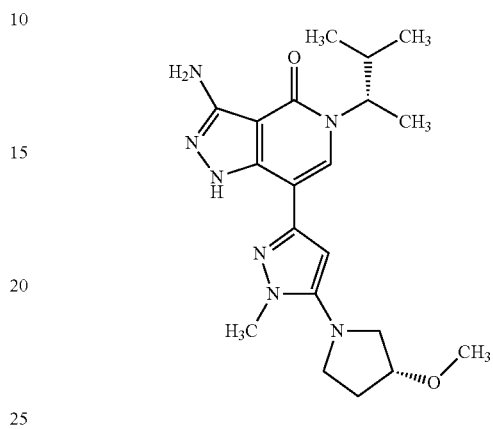

A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (58 mg), potassium acetate (98 mg) and N,N-dimethylacetamide (3 mL) was stirred under an argon atmosphere at 110° C. for 4 hr. The reaction mixture was cooled to room temperature, a solution of 3-bromo-5-((3R)-3-methoxypyrrolidin-1-yl)-1-methyl-1H-pyrazole (196 mg) obtained in Reference Example 26 in N,N-dimethylacetamide (1 mL), aqueous sodium carbonate solution (2 M, 0.501 mL) and tetrakis(triphenylphosphine)palladium(0) (58 mg) were added. Under an argon atmosphere, the reaction mixture was stirred at 120° C. for 16 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a crude purification product. The obtained crude purification product was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (68 mg).

MS (ESI+): [M+H]$^+$ 400.2.

Example 25

3-amino-7-(5-((3S)-3-methoxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one

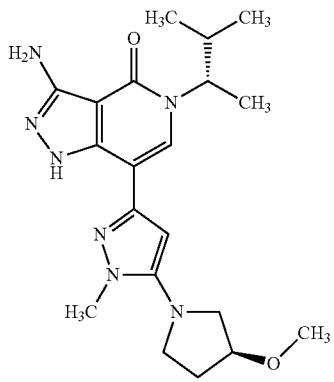 [SMILES: CO[C@H]1CCN(c2cc(-c3cn([C@@H](C)C(C)C)c(=O)c4c(N)n[nH]c34)nn2C)C1]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (6 mL) was stirred under an argon atmosphere at 110° C. for 4 hr. The reaction mixture was cooled to room temperature, 3-bromo-5-((3S)-3-methoxypyrrolidin-1-yl)-1-methyl-1H-pyrazole (226 mg) obtained in Reference Example 27, aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow solid. The obtained solid was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (57 mg).

MS (ESI+): [M+H]$^+$ 400.4.

Example 27

3-amino-5-((2S)-3-methylbutan-2-yl)-7-(1-methyl-5-(pyrrolidin-1-yl)-1H-pyrazol-3-yl)-1,5-dihydro-4H-pyrazolo[4,3-c]pyridin-4-one

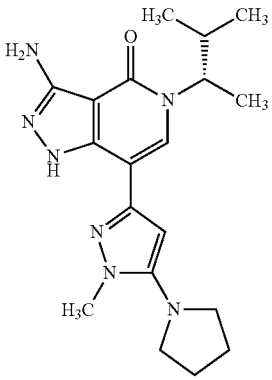

A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (87 mg), potassium acetate (98 mg) and N,N-dimethylformamide (2 mL) was stirred under an argon atmosphere at 110° C. for 3 hr. The reaction mixture was cooled to room temperature, and a solution of 3-bromo-1-methyl-5-(pyrrolidin-1-yl)-1H-pyrazole (173 mg) obtained in Reference Example 29 in N,N-dimethylformamide (1 mL), aqueous sodium carbonate solution (2 M, 0.501 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow solid. The obtained yellow solid was crystallized from ethyl acetate/diisopropyl ether to give the title compound (95 mg).

MS (ESI+): [M+H]$^+$ 370.1.

Example 31

3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one

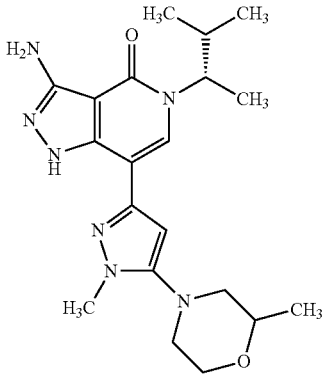 [SMILES: CC1CN(c2cc(-c3cn([C@@H](C)C(C)C)c(=O)c4c(N)n[nH]c34)nn2C)CCO1]

A mixture of 3-amino-7-bromo-5-((2S)-3-methylbutan-2-yl)-1,5-dihydro-4H-pyrazolo[4,3-c]pyridin-4-one (300 mg) obtained in Example 1, Step G, 4,4,4',4',5,5,5',5'-octamethyl-2,2'-bi-1,3,2-dioxaborolane (509 mg), tetrakis(triphenylphosphine)palladium(0) (174 mg), potassium acetate (197 mg) and N,N-dimethylacetamide (4 mL) was stirred under an argon atmosphere at 110° C. for 4 hr. The reaction mixture was cooled to room temperature, and a solution of 4-(3-bromo-1-methyl-1H-pyrazol-5-yl)-2-methylmorpholine (391 mg) obtained in Reference Example 33 in N,N-dimethylacetamide (1.5 mL), aqueous sodium carbonate solution (2 M, 1.003 mL) and tetrakis(triphenylphosphine)palladium(0) (116 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow solid. The obtained yellow solid was solidified from methanol/ethyl acetate to give the title compound (243 mg).

MS (ESI+): [M+H]+ 400.4.

Example 32

3-amino-7-(5-(hexahydropyrrolo[1,2-a]pyrazin-2(H)-yl)-1-methyl-1H-pyrazol-3-yl)-5-((2S)-3-methylbutan-2-yl)-1,5-dihydro-4H-pyrazolo[4,3-c]pyridin-4-one

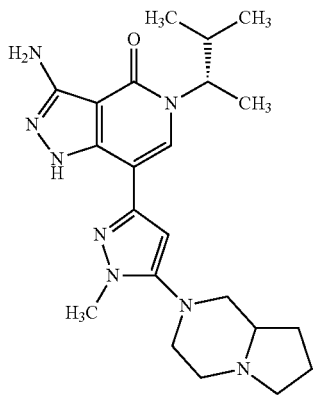 [SMILES: CC(C)[C@H](C)n1cc(-c2cc(N3CCN4CCCC4C3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (300 mg) obtained in Example 1, Step G, 4,4,4',4',5,5,5',5'-octamethyl-2,2'-bi-1,3,2-dioxaborolane (509 mg), tetrakis(triphenylphosphine)palladium(0) (174 mg), potassium acetate (197 mg) and N,N-dimethylacetamide (4 mL) was stirred under an argon atmosphere at 110° C. for 4 hr. The reaction mixture was cooled to room temperature, and a solution of 2-(3-bromo-1-methyl-1H-pyrazol-5-yl)octahydropyrrolo[1,2-a]pyrazine (429 mg) obtained in Reference Example 34 in N,N-dimethylacetamide (1.5 mL), aqueous sodium carbonate solution (2 M, 1.003 mL) and tetrakis(triphenylphosphine)palladium(0) (116 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a crude purification product. The obtained crude purification product was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution, water and saturated brine, dried over anhydrous magnesium sulfate, and concentrated under reduced pressure to give the title compound (199 mg).

MS (ESI+): [M+H]+ 425.2.

Example 33

3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one

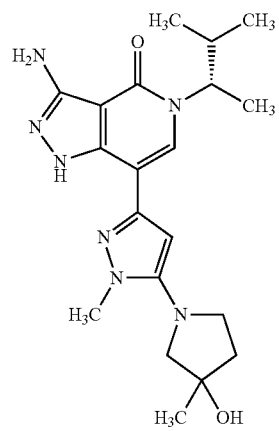

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), tetrakis(triphenylphosphine)palladium(0) (145 mg), potassium acetate (164 mg) and N,N-dimethylformamide (3 mL) was stirred under an argon atmosphere at 110° C. for 2 hr. The reaction mixture was cooled to room temperature, and a solution of 1-(3-bromo-1-methyl-1H-pyrazol-5-yl)-3-methylpyrrolidin-3-ol (326 mg) obtained in Reference Example 35 in N,N-dimethylformamide (2 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, methanol/ethyl acetate) to give a yellow solid. The obtained yellow solid was crystallized from ethyl acetate/diisopropyl ether to give the title compound (179 mg).

MS (ESI+): [M+H]+ 400.1.

Example 34

3-amino-5-((2S)-3-methylbutan-2-yl)-7-(1-methyl-5-(2-oxa-7-azaspiro[3.5]non-7-yl)-1H-pyrazol-3-yl)-1,5-dihydro-4H-pyrazolo[4,3-c]pyridin-4-one

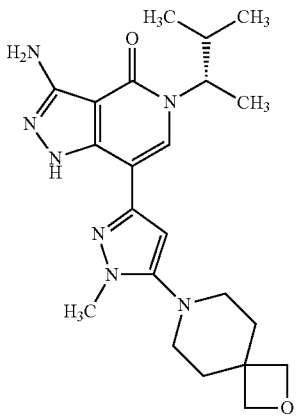 [SMILES: CC(C)[C@H](C)n1cc(-c2cc(N3CCC4(CC3)COC4)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (105 mg) obtained in Example 1, Step G, 4,4,4',4',5,5,5',5'-octamethyl-2,2'-bi-1,3,2-dioxaborolane (177 mg), tetrakis(triphenylphosphine)palladium(0) (61 mg), potassium acetate (69 mg) and N,N-dimethylformamide (2 mL) was stirred under an argon atmosphere at 110° C. for 4 hr. The reaction mixture was cooled to room temperature, and a solution of 7-(3-bromo-1-methyl-1H-pyrazol-5-yl)-2-oxa-7-azaspiro[3.5]nonane (150 mg) obtained in Reference Example 62 in N,N-dimethylformamide (1 mL), aqueous sodium carbonate solution (2 M, 0.349 mL) and tetrakis(triphenylphosphine)palladium(0) (40 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow amorphous solid. The obtained solid was crystallized from ethyl acetate/diisopropyl ether to give the title compound (31 mg).

MS (ESI+): [M+H]$^+$ 426.1.

Example 38

3-amino-7-(5-(1-hydroxycyclobutyl)-1-methyl-1H-pyrazol-3-yl)-5-((2S)-3-methylbutan-2-yl)-1,5-dihydro-4H-pyrazolo[4,3-c]pyridin-4-one

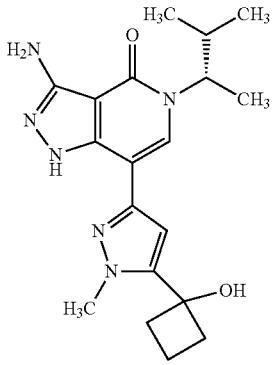

A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (87 mg), potassium acetate (98 mg) and N,N-dimethylacetamide (3 mL) was stirred under an argon atmosphere at 110° C. for 4 hr. The reaction mixture was cooled to room temperature, and a solution of 1-(3-bromo-1-methyl-1H-pyrazol-5-yl)cyclobutanol (174 mg) obtained in Reference Example 66 in N,N-dimethylacetamide (1.5 mL), aqueous sodium carbonate solution (2 M, 0.501 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl-acetate. The extract was washed with saturated brine, and dried over anhydrous magnesium sulfate. The solvent was evaporated under reduced pressure and the residue was purified by silica gel chromatography (basic silica gel, ethyl acetate/hexane and methanol/ethyl acetate) to give a crude purification product as a yellow solid, which was further fractionated by HPLC (C18, mobile phase: water/acetonitrile (containing 0.1% TFA)) and the solvent was concentrated under reduced pressure. Ethyl acetate was added to the obtained residue, and the mixture was washed with saturated aqueous sodium hydrogen carbonate solution and saturated brine, dried over anhydrous magnesium sulfate, concentrated under reduced pressure, and solidified from ethyl acetate/hexane to give the title compound (72 mg).

MS (ESI+): [M+H]$^+$ 371.4.

Example 39

3-amino-7-(5-(3,6-dihydro-2H-pyran-4-yl)-1-methyl-1H-pyrazol-3-yl)-5-((2S)-3-methylbutan-2-yl)-1,5-dihydro-4H-pyrazolo[4,3-c]pyridin-4-one

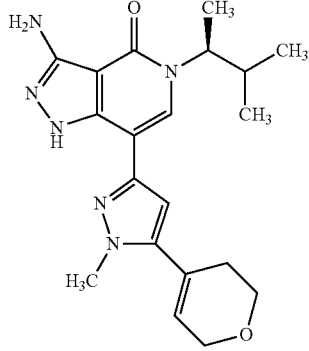 [SMILES: CC(C)[C@H](C)n1cc(-c2cc(C3=CCOCC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), (1,1'-bis(diphenylphosphino)ferrocene)dichloropalladium(II) (92 mg), potassium acetate (164 mg) and N,N-dimethylformamide (3 mL) was stirred under an argon atmosphere at 110° C. for 4 hr. The reaction mixture was cooled to room temperature, and a solution of 3-bromo-5-(3,6-dihydro-2H-pyran-4-yl)-1-methyl-1H-pyrazole (284 mg) obtained in Reference Example 67 in N,N-dimethylformamide (1.0 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane, further, diol silica gel, ethyl acetate/hexane) to give a yellow solid. The obtained yellow solid was crystallized from ethyl acetate to give the title compound (130 mg).

MS (ESI+): [M+H]+ 383.3.

Example 41

3-amino-5-((2S)-3-methylbutan-2-yl)-7-(1-methyl-5-(morpholin-4-yl)-1H-pyrazol-3-yl)-1,5-dihydro-4H-pyrazolo[4,3-c]pyridin-4-one

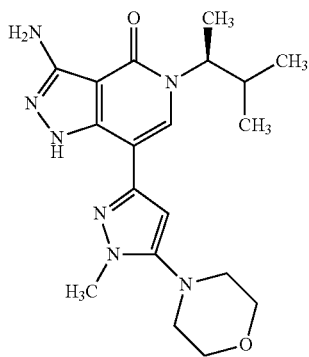 [SMILES: CC(C)[C@H](C)n1cc(-c2cc(N3CCOCC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylacetamide (3 mL) was stirred under an argon atmosphere at 110° C. for 4 hr. The reaction mixture was cooled to room temperature, and a solution of 1-methyl-5-(morpholin-4-yl)-1H-pyrazol-3-yl trifluoromethanesulfonate (295 mg) obtained in Reference Example 47 in N,N-dimethylacetamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 4 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give the title compound (76 mg).

MS (ESI+): [M+H]+ 386.4.

Example 42

3-amino-5-((2S)-3-methylbutan-2-yl)-7-(1-methyl-5-(trifluoromethyl)-1H-pyrazol-3-yl)-1,5-dihydro-4H-pyrazolo[4,3-c]pyridin-4-one

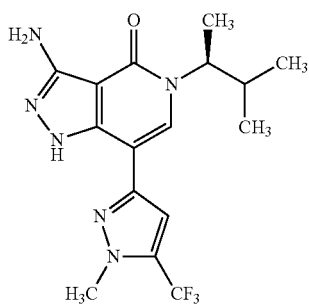 [SMILES: CC(C)[C@H](C)n1cc(-c2cc(C(F)(F)F)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylformamide (3 mL) was stirred under an argon atmosphere at 110° C. for 4 hr. The reaction mixture was cooled to room temperature, and a solution of 1-methyl-5-(trifluoromethyl)-1H-pyrazol-3-yl trifluoromethanesulfonate (279 mg) obtained in Reference Example 69 in N,N-dimethylformamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 4 hr. The reaction mixture was cooled to room temperature, water was added, and the mixture was extracted with ethyl acetate/tetrahydrofuran. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow amorphous solid. The obtained amorphous solid was solidified from ethyl acetate/hexane and washed with diethyl ether to give the title compound (23 mg).

MS (ESI+): [M+H]+ 369.3.

Example 43

3-amino-7-(5-cyclopropyl-1-methyl-1H-pyrazol-3-yl)-5-((2S)-3-methylbutan-2-yl)-1,5-dihydro-4H-pyrazolo[4,3-c]pyridin-4-one

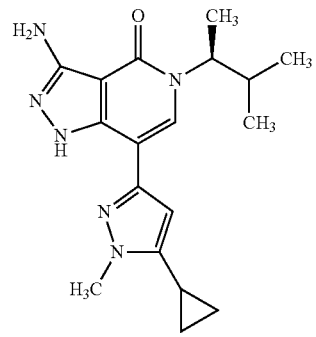 [SMILES: CC(C)[C@H](C)n1cc(-c2cc(C3CC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylacetamide (3 mL) was stirred under an argon atmosphere at 110° C. for 4 hr. The reaction mixture was cooled to room temperature, and a solution of 5-cyclopropyl-1-methyl-1H-pyrazol-3-yl trifluoromethanesulfonate (253 mg) obtained in Reference Example 70 in N,N-dimethylacetamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 4 hr. The reaction mixture was cooled to room temperature, water was added, and the mixture was extracted with ethyl acetate/tetrahydrofuran. The extract was washed with saturated brine, and dried over anhydrous magnesium sulfate. The solvent was evaporated under reduced pressure and the residue was purified by silica gel chromatography (basic silica gel, ethyl acetate/hexane) to give the title compound (77 mg).

MS (ESI+): [M+H]+ 341.2.

Example 48

3-amino-5-((2S)-3-methylbutan-2-yl)-7-(1-methyl-5-(2-oxopiperidin-1-yl)-1H-pyrazol-3-yl)-1,5-dihydro-4H-pyrazolo[4,3-c]pyridin-4-one

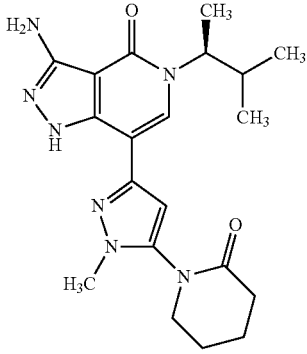 [SMILES: CC(C)[C@H](C)n1cc(-c2cc(N3CCCCC3=O)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylformamide (3 mL) was stirred under an argon atmosphere at 110° C. for 4 hr. The reaction mixture was cooled to room temperature, and a solution of 1-methyl-5-(2-oxopiperidin-1-yl)-1H-pyrazol-3-yl trifluoromethanesulfonate (328 mg) obtained in Reference Example 52 in N,N-dimethylformamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (silica gel, ethyl acetate/hexane) to give a brown solid. The obtained brown solid was further purified by silica gel chromatography (diol silica gel, ethyl acetate/hexane) to give a brown solid. The obtained brown solid was resolidified from ethyl acetate/diisopropyl ether to give the title compound (28 mg).

MS (ESI+): [M+H]$^+$ 398.1.

Example 49

3-amino-5-((2S)-3-methylbutan-2-yl)-7-(1-methyl-5-(3-oxomorpholin-4-yl)-1H-pyrazol-3-yl)-1,5-dihydro-4H-pyrazolo[4,3-c]pyridin-4-one

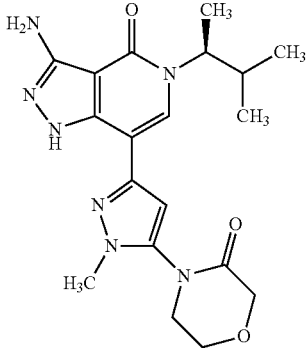

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylformamide (3 mL) was stirred under an argon atmosphere at 110° C. for 4 hr. The reaction mixture was cooled to room temperature, and a solution of 1-methyl-5-(3-oxomorpholino)-1H-pyrazol-3-yl trifluoromethanesulfonate (330 mg) obtained in Reference Example 53 in N,N-dimethylformamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (silica gel, methanol/ethyl acetate) to give a brown solid. The obtained brown solid was further purified by silica gel chromatography (diol silica gel, methanol/ethyl acetate) to give a yellow amorphous solid. The obtained solid was crystallized from ethyl acetate/diisopropyl ether to give the title compound (38 mg).

MS (ESI+): [M+H]$^+$ 400.1.

Example 50

3-(3-amino-5-((2S)-3-methylbutan-2-yl)-4-oxo-4,5-dihydro-1H-pyrazolo[4,3-c]pyridin-7-yl)-N-cyclopentyl-N,1-dimethyl-1H-pyrazole-5-carboxamide

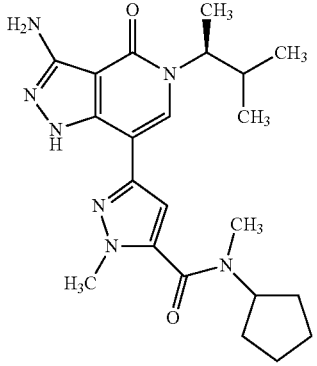 [SMILES: CC(C)[C@H](C)n1cc(-c2cc(C(=O)N(C)C3CCCC3)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), (1,1'-bis(diphenylphosphino)ferrocene)dichloropalladium(II) (73 mg), potassium acetate (131 mg) and N,N-dimethylformamide (3 mL) was stirred under an argon atmosphere at 110° C. for 4 hr. The reaction mixture was cooled to room temperature, and a solution of 5-(cyclopentyl(methyl)carbamoyl)-1-methyl-1H-pyrazol-3-yl trifluoromethanesulfonate (356 mg) obtained in Reference Example 49 in N,N-dimethylformamide (0.5 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (silica gel, methanol/ethyl acetate) to give a brown solid. The obtained brown solid was further purified by silica gel chromatography (diol silica gel, methanol/ethyl acetate) to give a yellow amorphous solid. The solid was further fractionated by HPLC (C18, mobile phase: water/ acetonitrile (containing 10 mM NH₄HCO₃)), and the obtained fraction was concentrated under reduced pressure to give the title compound (59 mg).

MS (ESI+): [M+H]⁺ 426.1.

Example 52

3-amino-5-((2S)-3-methylbutan-2-yl)-7-(1-methyl-5-((2-oxopyrrolidin-1-yl)methyl)-1H-pyrazol-3-yl)-1,5-dihydro-4H-pyrazolo[4,3-c]pyridin-4-one

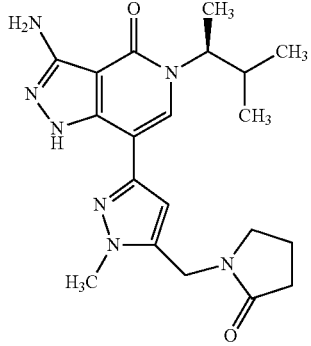 [SMILES: CC(C)[C@H](C)n1cc(-c2cc(CN3CCCC3=O)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (250 mg) obtained in Example 1, Step G, 4,4,4',4',5,5,5',5'-octamethyl-2,2'-bi-1,3,2-dioxaborolane (424 mg), tetrakis(triphenylphosphine)palladium(0) (145 mg), potassium acetate (164 mg) and N,N-dimethylacetamide (3 mL) was stirred under an argon atmosphere at 110° C. for 4 hr. The reaction mixture was cooled to room temperature, and a solution of 1-methyl-5-((2-oxopyrrolidin-1-yl)methyl)-1H-pyrazol-3-yl trifluoromethanesulfonate (410 mg) obtained in Reference Example 58 in N,N-dimethylacetamide (0.5 mL), aqueous sodium carbonate solution (2 M, 0.836 mL) and tetrakis(triphenylphosphine)palladium(0) (97 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a yellow solid. The obtained yellow solid was further purified by silica gel chromatography (basic silica gel, methanol/ethyl acetate) to give a yellow solid. The obtained solid was crystallized from ethyl acetate/diisopropyl ether to give the title compound (25 mg).

MS (ESI+): [M+H]⁺ 398.1.

Example 54

3-amino-5-((2S)-3-methylbutan-2-yl)-7-(1-methyl-5-(2-oxo-1,3-oxazolidin-3-yl)-1H-pyrazol-3-yl)-1,5-dihydro-4H-pyrazolo[4,3-c]pyridin-4-one

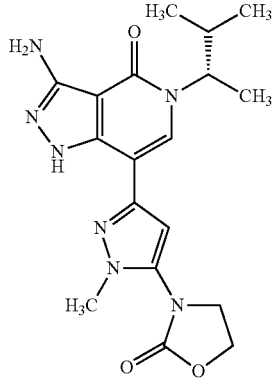 [SMILES: CC(C)[C@H](C)n1cc(-c2cc(N3CCOC3=O)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (146 mg) obtained in Example 1, Step G, 4,4,4',4',5,5,5',5'-octamethyl-2,2'-bi-1,3,2-dioxaborolane (247 mg), tetrakis(triphenylphosphine)palladium(0) (84 mg), potassium acetate (95 mg) and N,N-dimethylformamide (3 mL) was stirred under an argon atmosphere at 110° C. for 2 hr. The reaction mixture was cooled to room temperature, and a solution of 1-methyl-5-(2-oxooxazolidin-3-yl)-1H-pyrazol-3-yl trifluoromethanesulfonate (230 mg) obtained in Reference Example 54 in N,N-dimethylformamide (0.5 mL), aqueous sodium carbonate solution (2 M, 0.486 mL) and tetrakis(triphenylphosphine)palladium(0) (56 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give a brown amorphous solid, which was further fractionated by HPLC (C18, mobile phase: water/acetonitrile (containing 10 mM NH₄HCO₃)), and the obtained fraction was concentrated under reduced pressure, and crystallized from ethyl acetate/diisopropyl ether to give the title compound (19 mg).

MS (ESI+): [M+H]⁺ 386.

Example 55

3-amino-5-((2S)-3-methylbutan-2-yl)-7-(1-methyl-5-(2-oxopyrrolidin-1-yl)-1H-pyrazol-3-yl)-1,5-dihydro-4H-pyrazolo[4,3-c]pyridin-4-one

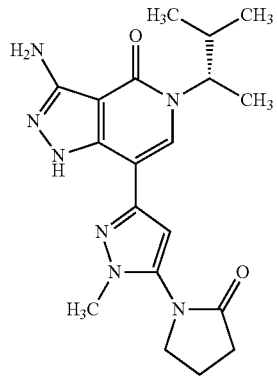

A mixture of 3-amino-7-bromo-5-((2S)-3-methylbutan-2-yl)-1,5-dihydro-4H-pyrazolo[4,3-c]pyridin-4-one (166 mg) obtained in Example 1, Step G, 4,4,4',4',5,5,5',5'-octamethyl-2,2'-bi-1,3,2-dioxaborolane (281 mg), tetrakis(triphenylphosphine)palladium(0) (96 mg), potassium acetate (109 mg) and N,N-dimethylformamide (3 mL) was stirred under an argon atmosphere at 110° C. for 2 hr. The reaction mixture was cooled to room temperature, and a solution of 1-methyl-5-(2-oxopyrrolidin-1-yl)-1H-pyrazol-3-yl trifluoromethanesulfonate (260 mg) obtained in Reference Example 55 in N,N-dimethylformamide (1.0 mL), aqueous sodium carbonate solution (2 M, 0.553 mL) and tetrakis(triphenylphosphine)palladium(0) (64 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (diol silica gel, methanol/ethyl acetate) to give the title compound (21 mg).

MS (ESI+): [M+H]⁺ 384.1.

Example 56

2-(3-(3-amino-5-((2S)-3-methylbutan-2-yl)-4-oxo-4,5-dihydro-1H-pyrazolo[4,3-c]pyridin-7-yl)-1-methyl-1H-pyrazol-5-yl)-N,N,2-trimethylpropanamide

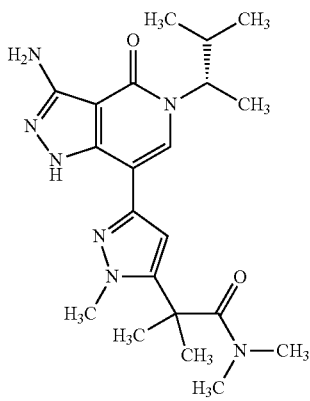 [SMILES: CC(C)[C@H](C)n1cc(-c2cc(C(C)(C)C(=O)N(C)C)n(C)n2)c2[nH]nc(N)c2c1=O]

A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (3 mL) was stirred under an argon atmosphere at 110° C. for 4 hr. The reaction mixture was cooled to room temperature, and a solution of 2-(3-bromo-1-methyl-1H-pyrazol-5-yl)-N,N,2-trimethylpropanamide (275 mg) obtained in Reference Example 72 in N,N-dimethylacetamide (2 mL), aqueous sodium carbonate solution (2 M, 0.669 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/hexane) to give a yellow solid. The obtained yellow solid was further purified by silica gel chromatography (diol silica gel, ethyl acetate/hexane) to give a colorless solid, which was further fractionated by HPLC (C18, mobile phase: water/acetonitrile (containing 10 mM $NH_4HCO_3$)), and the obtained fraction was concentrated under reduced pressure to give a solid. The solid was further solidified from diethyl ether to give the title compound (21 mg).

MS (ESI+): $[M+H]^+$ 414.2.

Examples 26, 28-30, 35-37, 40, 44-47, 51, 53 and 57

The compounds of Examples 26, 28-30, 35-37, 40, 44-47, 51, 53 and 57 were obtained by a method similar to Example 1, Step H, or a method according thereto and using 3-amino-7-bromo-5-((2S)-3-methylbutan-2-yl)-1,5-dihydro-4H-pyrazolo[4,3-c]pyridin-4-one obtained in Example 1, Step G, and halide compounds corresponding to the compounds of Examples 26, 28-30, 35-37, 40, 44-47, 51, 53 and 57, or trifluoromethanesulfonate compounds corresponding to the compounds of Examples 26, 28-30, 35-37, 40, 44-47, 51, 53 and 57. MS in the Tables shows measured values. The halide compounds or trifluoromethanesulfonate compounds used for the synthesis of the compounds of Examples 26, 28-30, 35-37, 40, 44-47, 51, 53 and 57 were commercially available ones or synthesized according to the method described in Reference Examples 14-21, 13, 61, 23-35, or a method analogous thereto, or a method known per se.

TABLE 1

| Ex. No. | IUPAC name | structure | MS |
|---|---|---|---|
| 10 | 3-amino-5-((2S)-3-methylbutan-2-yl)-7-(1-methyl-5-(4-methylpiperazin-1-yl)-1H-pyrazol-3-yl)-1,5-dihydro-4H-pyrazolo[4,3-c]pyridin-4-one | 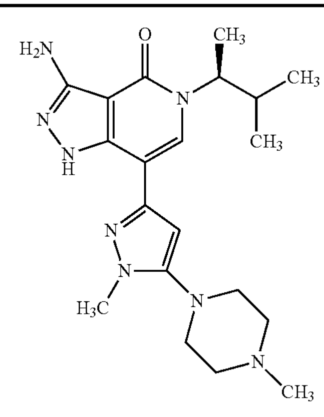 | 399.1 |

| Ex. No. | IUPAC name | structure | MS |
|---|---|---|---|
| 11 | 7-(5-(4-acetylpiperazin-1-yl)-1-methyl-1H-pyrazol-3-yl)-3-amino-5-((2S)-3-methylbutan-2-yl)-1,5-dihydro-4H-pyrazolo[4,3-c]pyridin-4-one | 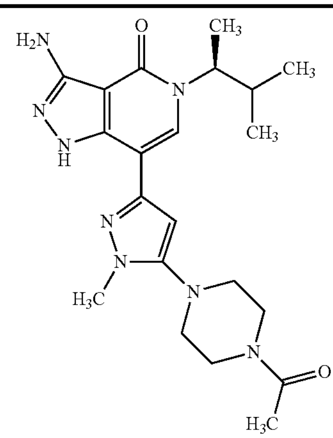 | 427.2 |
| 12 | 3-amino-7-(5-(1,1-dioxidothiomorpholin-4-yl)-1-methyl-1H-pyrazol-3-yl)-5-((2S)-3-methylbutan-2-yl)-1,5-dihydro-4H-pyrazolo[4,3-c]pyridin-4-one | 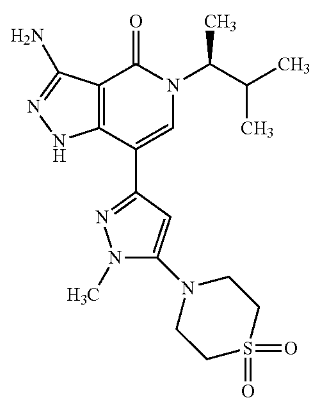 [SMILES: CC(C)[C@H](C)n1cc(-c2cc(N3CCS(=O)(=O)CC3)n(C)n2)c2[nH]nc(N)c2c1=O] | 434.1 |
| 13 | 3-amino-5-((2S)-3-methylbutan-2-yl)-7-(1-methyl-5-(1,4-oxazepan-4-yl)-1H-pyrazol-3-yl)-1,5-dihydro-4H-pyrazolo[4,3-c]pyridin-4-one | 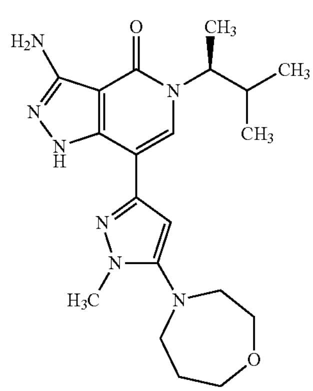 [SMILES: CC(C)[C@H](C)n1cc(-c2cc(N3CCCOCC3)n(C)n2)c2[nH]nc(N)c2c1=O] | 400.1 |

TABLE 1-continued

| Ex. No. | IUPAC name | structure | MS |
|---|---|---|---|
| 14 | 3-amino-7-(5-(4-methoxypiperidin-1-yl)-1-methyl-1H-pyrazol-3-yl)-5-((2S)-3-methylbutan-2-yl)-1,5-dihydro-4H-pyrazolo[4,3-c]pyridin-4-one | 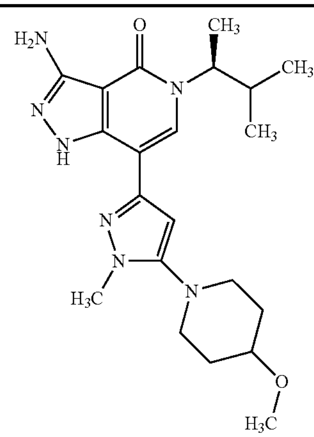 | 414.1 |
| 15 | 3-amino-7-(5-(4-(2-hydroxypropan-2-yl)piperidin-1-yl)-1-methyl-1H-pyrazol-3-yl)-5-((2S)-3-methylbutan-2-yl)-1,5-dihydro-4H-pyrazolo[4,3-c]pyridin-4-one | 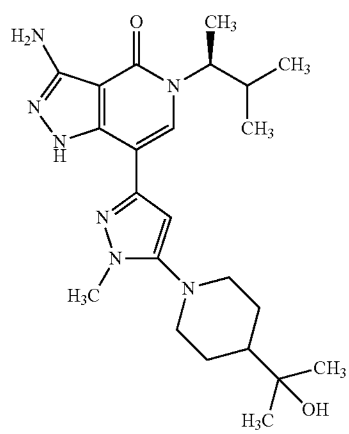 [SMILES: CC(C)[C@H](C)n1cc(-c2cc(N3CCC(C(C)(C)O)CC3)n(C)n2)c2[nH]nc(N)c2c1=O] | 442.2 |
| 16 | 3-amino-7-(5-(4,4-difluoropiperidin-1-yl)-1-methyl-1H-pyrazol-3-yl)-5-((2S)-3-methylbutan-2-yl)-1,5-dihydro-4H-pyrazolo[4,3-c]pyridin-4-one | 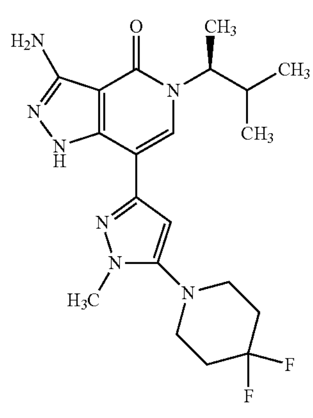 [SMILES: CC(C)[C@H](C)n1cc(-c2cc(N3CCC(F)(F)CC3)n(C)n2)c2[nH]nc(N)c2c1=O] | 420.1 |

TABLE 1-continued

| Ex. No. | IUPAC name | structure | MS |
|---|---|---|---|
| 17 | 3-amino-7-(5-(4-(methoxyacetyl)piperazin-1-yl)-1-methyl-1H-pyrazol-3-yl)-5-((2S)-3-methylbutan-2-yl)-1,5-dihydro-4H-pyrazolo[4,3-c]pyridin-4-one | 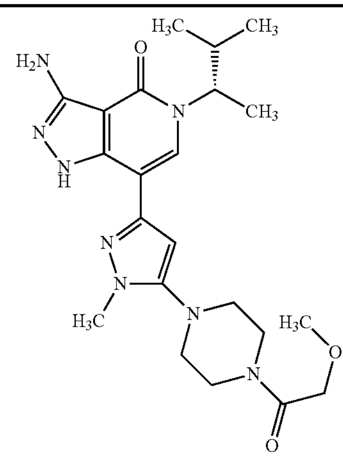 | 457.4 |
| 18 | 3-amino-7-(5-(4-hydroxy-4-methylpiperidin-1-yl)-1-methyl 1H-pyrazol-3-yl)-5-((2S)-3-methylbutan-2-yl)-1,5-dihydro-pyrazolo[4,3-c]pyridin-4-one | 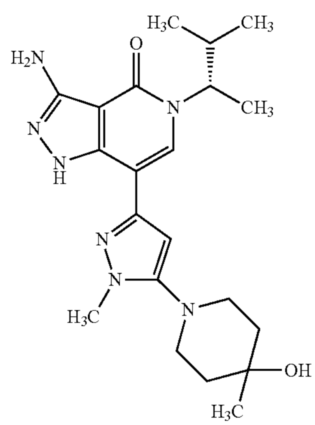 [SMILES: CC(C)[C@H](C)n1cc(-c2cc(N3CCC(C)(O)CC3)n(C)n2)c2[nH]nc(N)c2c1=O] | 414.1 |
| 19 | 3-amino-5-((2S)-3-methylbutan-2-yl)-7-(1-methyl-5-(piperidin-1-yl)-1H-pyrazol-3-yl)-1,5-dihydro-4H-pyrazolo[4, 3-c]pyridin-4-one | 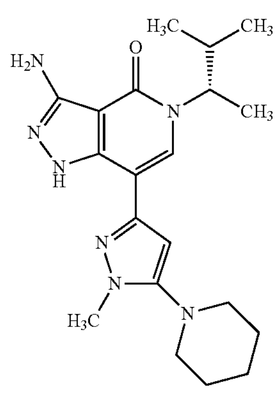 [SMILES: CC(C)[C@H](C)n1cc(-c2cc(N3CCCCC3)n(C)n2)c2[nH]nc(N)c2c1=O] | 384.1 |

TABLE 1-continued

| Ex. No. | IUPAC name | structure | MS |
|---|---|---|---|
| 20 | 3-amino-7-(5-((2S)-2-(hydroxymethyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 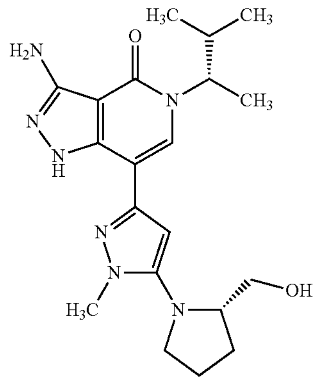 [SMILES: CC(C)[C@H](C)n1cc(-c2cc(N3CCC[C@H]3CO)n(C)n2)c2[nH]nc(N)c2c1=O] | 400.2 |
| 21 | 3-amino-7-(5-((3R)-3-hydroxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 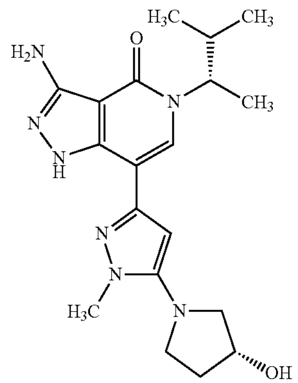 [SMILES: CC(C)[C@H](C)n1cc(-c2cc(N3CC[C@@H](O)C3)n(C)n2)c2[nH]nc(N)c2c1=O] | 386.1 |
| 22 | 3-amino-7-(5-((2R)-2-(hydroxymethyl)pyrrolidin-1-yl)-1-methyl-1H-pyrazol-3-yl)-5-((2S)-3-methylbutan-2-yl]-1,5-dihydro-4H-pyrazolo[4,3-c]pyridin-4-one | 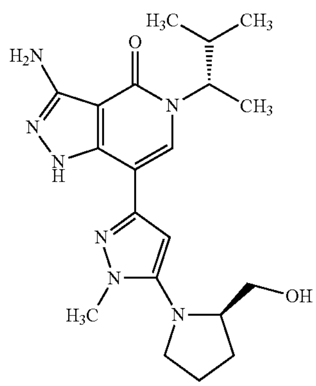 [SMILES: CC(C)[C@H](C)n1cc(-c2cc(N3CCC[C@@H]3CO)n(C)n2)c2[nH]nc(N)c2c1=O] | 400.4 |
| 23 | 3-amino-7-(5-((3S)-3-hydroxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 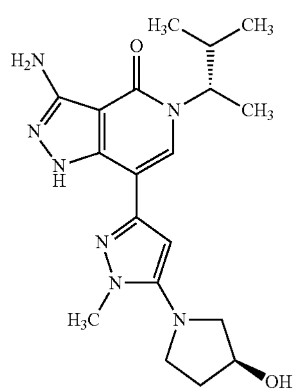 [SMILES: CC(C)[C@H](C)n1cc(-c2cc(N3CC[C@H](O)C3)n(C)n2)c2[nH]nc(N)c2c1=O] | 386.4 |

TABLE 1-continued

| Ex. No. | IUPAC name | structure | MS |
|---|---|---|---|
| 24 | 3-amino-7-(5-((3R)-3-methoxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 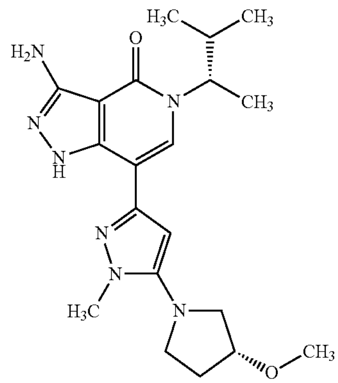 [SMILES: CO[C@@H]1CCN(c2cc(-c3cn([C@@H](C)C(C)C)c(=O)c4c(N)n[nH]c34)nn2C)C1] | 400.2 |
| 25 | 3-amino-7-(5-((3S)-3-methoxypyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 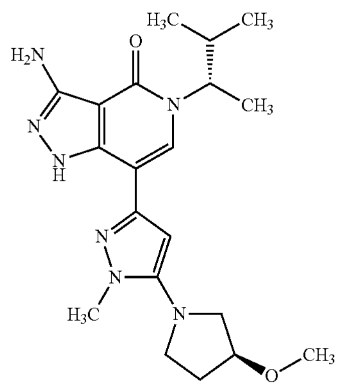 [SMILES: CO[C@H]1CCN(c2cc(-c3cn([C@@H](C)C(C)C)c(=O)c4c(N)n[nH]c34)nn2C)C1] | 400.4 |
| 26 | 3-amino-7-(5-((2S)-2-(methoxymethyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 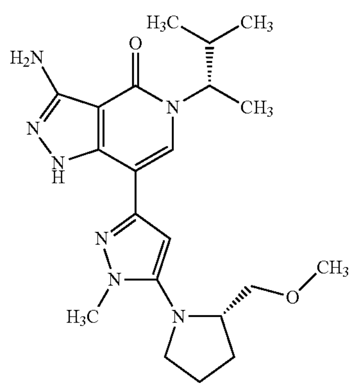 [SMILES: COC[C@@H]1CCCN1c1cc(-c2cn([C@@H](C)C(C)C)c(=O)c3c(N)n[nH]c23)nn1C] | 414.1 |
| 27 | 3-amino-5-((2S)-3-methylbutan-2-yl)-7-(1-methyl-5-(pyrrolidin-1-yl)-1H-pyrazol-3-yl)-1,5-dihydro-4H-pyrazolo[4,3-c]pyridin-4-one | 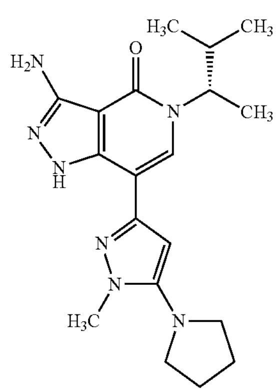 [SMILES: CC(C)[C@H](C)n1cc(-c2cc(N3CCCC3)n(C)n2)c2[nH]nc(N)c2c1=O] | 370.1 |

TABLE 1-continued

| Ex. No. | IUPAC name | structure | MS |
|---|---|---|---|
| 28 | 3-amino-7-(5-(1,1-dioxidothiomorpholin-4-yl)-1-ethyl-1H-pyrazol-3-yl)-5-((2S)-3-methylbutan-2-yl)-1,5-dihydro-4H-pyrazolo[4,3-c]pyridin-4-one | 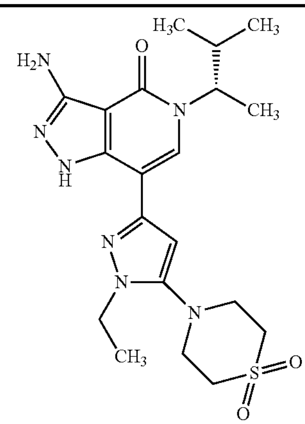 | 448.4 |
| 29 | 3-amino-7-(5-(1,1-dioxidothiomorpholin-4-yl)-1-(2,2,2-trifluoroethyl)-1H-pyrazol-3-yl)-5-((2S)-3-methylbutan-2-yl)-1,5-dihydro-4H-pyrazolo[4,3-c]pyridin-4-one | 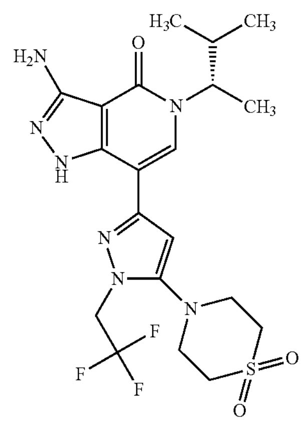 [SMILES: CC(C)[C@H](C)n1cc(-c2cc(N3CCS(=O)(=O)CC3)n(CC(F)(F)F)n2)c2[nH]nc(N)c2c1=O] | 502.3 |
| 30 | 3-amino-7-(5-(2,2-dimethylmorpholin-4-yl)-1-methyl-1H-pyrazol-3-yl)-5-((2S)-3-methylbutan-2-yl)-1,5-dihydro-4H-pyrazolo[4,3-c]pyridin-4-one | 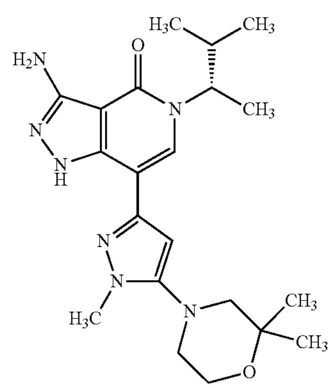 [SMILES: CC(C)[C@H](C)n1cc(-c2cc(N3CCOC(C)(C)C3)n(C)n2)c2[nH]nc(N)c2c1=O] | 414.1 |
| 31 | 3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one | 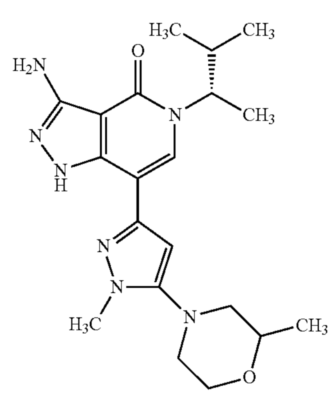 [SMILES: CC1CN(c2cc(-c3cn([C@@H](C)C(C)C)c(=O)c4c(N)n[nH]c34)nn2C)CCO1] | 400.4 |

TABLE 1-continued

| Ex. No. | IUPAC name | structure | MS |
|---|---|---|---|
| 32 | 3-amino-7-(5-(hexahydropyrrolo[1,2-a]pyrazin-2(1H)-yl)-1-methyl-1H-pyrazol-3-yl)-5-((2S)-3-methylbutan-2-yl)-1,5-dihydro-4H-pyrazolo[4,3-c]pyridin-4-one | 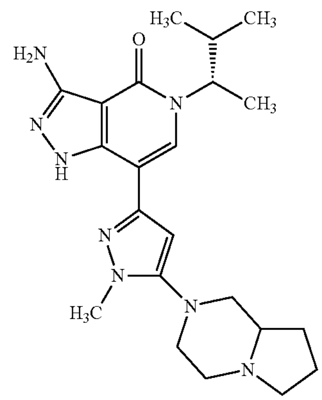 [SMILES: CC(C)[C@H](C)n1cc(-c2cc(N3CCN4CCCC4C3)n(C)n2)c2[nH]nc(N)c2c1=O] | 425.2 |
| 33 | 3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 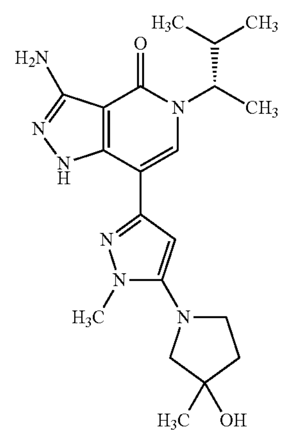 [SMILES: CC(C)[C@H](C)n1cc(-c2cc(N3CCC(C)(O)C3)n(C)n2)c2[nH]nc(N)c2c1=O] | 400.1 |
| 34 | 3-amino-5-((2S)-3-methylbutan-2-yl)-7-(1-methyl-5-(2-oxa-7-azaspiro[3.5]non-7-yl)-1H-pyrazol-3-yl)-1,5-dihydro-4H-pyrazolo[4,3-c]pyridin-4-one | 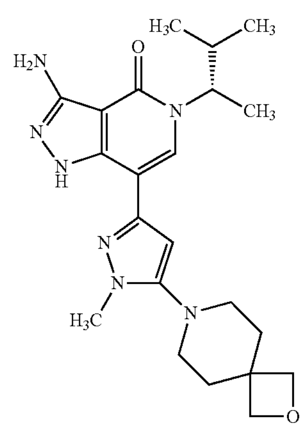 [SMILES: CC(C)[C@H](C)n1cc(-c2cc(N3CCC4(CC3)COC4)n(C)n2)c2[nH]nc(N)c2c1=O] | 426.1 |

TABLE 1-continued

| Ex. No. | IUPAC name | structure | MS |
|---|---|---|---|
| 35 | 3-amino-7-(5-(4-hydroxytetrahydro-2H-pyran-4-yl)-1-methyl-1H-pyrazol-3-yl)-5-((2S)-3-methylbutan-2-yl)-1,5-dihydro-4H-pyrazolo[4,3-c]pyridin-4-one | 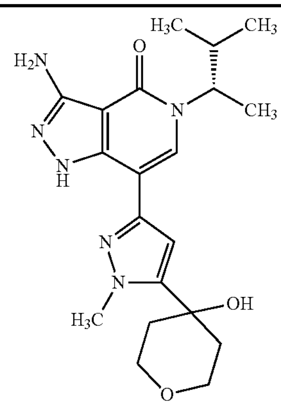 | 401.4 |
| 36 | 3-amino-7-(5-(2-hydroxypropan-2-yl)-1-(2-methoxyethyl)-1H-pyrazol-3-yl)-5-((2S)-3-methylbutan-2-yl)-1,5-dihydro-4H-pyrazolo[4,3-c]pyridin-4-one | 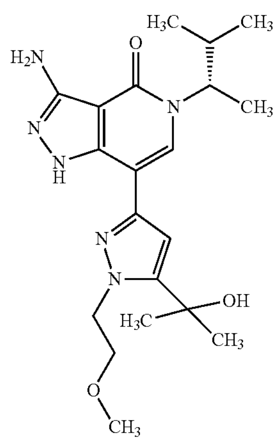 [SMILES: COCCn1nc(-c2cn([C@@H](C)C(C)C)c(=O)c3c(N)n[nH]c23)cc1C(C)(C)O] | 403.4 |
| 37 | 3-amino-7-(5-(4,4-difluoro-1-hydroxycyclohexyl)-1-methyl-1H-pyrazol-3-yl)-5-((2S)-3-methylbutan-2-yl)-1,5-dihydro-4H-pyrazolo[4,3-c]pyridin-4-one | 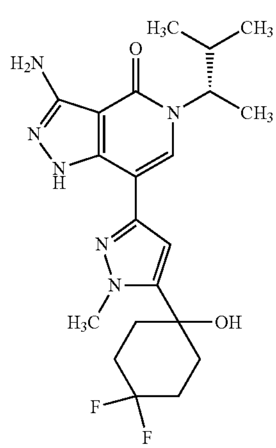 [SMILES: CC(C)[C@H](C)n1cc(-c2cc(C3(O)CCC(F)(F)CC3)n(C)n2)c2[nH]nc(N)c2c1=O] | 435.4 |

TABLE 1-continued

| Ex. No. | IUPAC name | structure | MS |
|---|---|---|---|
| 38 | 3-amino-7-(5-(1-hydroxycyclobutyl)-1-methyl-1H pyrazol-3-yl)-5-((2S)-3-methylbutan-2-yl)-1,5-dihydro-pyrazolo[4,3-c]pyridin-4-one | 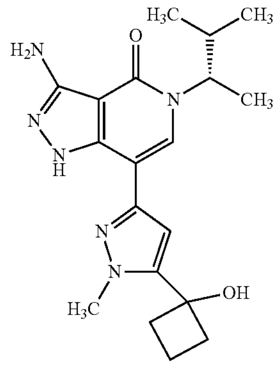 [SMILES: CC(C)[C@H](C)n1cc(-c2cc(C3(O)CCC3)n(C)n2)c2[nH]nc(N)c2c1=O] | 371.4 |
| 39 | 3-amino-7-(5-(3,6-dihydro-2H-pyran-4-yl)-1-methyl-1H-pyrazol-3-yl)-5-((2S)-3-methylbutan-2-yl)-1,5-dihydro-4H-pyrazolo[4,3-c]pyridin-4-one | 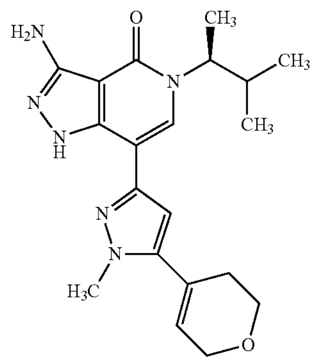 [SMILES: CC(C)[C@H](C)n1cc(-c2cc(C3=CCOCC3)n(C)n2)c2[nH]nc(N)c2c1=O] | 383.3 |
| 40 | 4-(3-(3-amino-5-((2S)-3-methylbutan-2-yl)-4-oxo-4,5-dihydro-1H-pyrazolo[4,3-c]pyridin-7-yl)-1-methyl-1H-pyrazol-5-yl)-N-methylbenzamide | 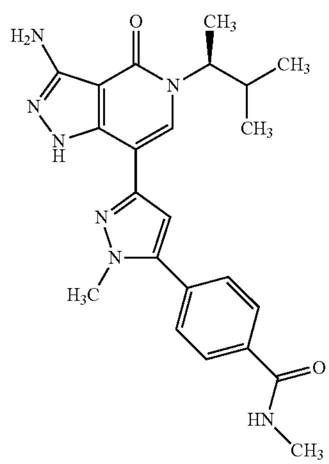 [SMILES: CNC(=O)c1ccc(-c2cc(-c3cn([C@@H](C)C(C)C)c(=O)c4c(N)n[nH]c34)nn2C)cc1] | 434.3 |
| 41 | 3-amino-5-((2S)-3-methylbutan-2-yl)-7-(1-methyl-5-(morpholin-4-yl)-1H-pyrazol-3-yl)-1,5-dihydro-4H-pyrazolo[4,3-c]pyridin-4-one | 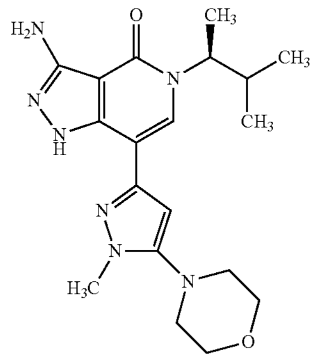 [SMILES: CC(C)[C@H](C)n1cc(-c2cc(N3CCOCC3)n(C)n2)c2[nH]nc(N)c2c1=O] | 386.4 |

TABLE 1-continued

| Ex. No. | IUPAC name | structure | MS |
|---|---|---|---|
| 42 | 3-amino-5-((2S)-3-methylbutan-2-yl)-7-(1-methyl-5-(trifluoromethyl)-1H-pyrazol-3-yl)-1,5-dihydro-4H-pyrazolo[4,3-c]pyridin-4-one | 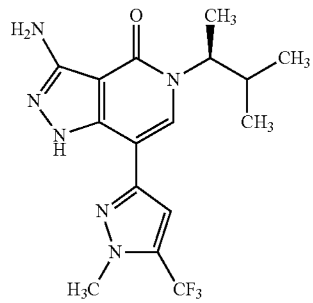 [SMILES: CC(C)[C@H](C)n1cc(-c2cc(C(F)(F)F)n(C)n2)c2[nH]nc(N)c2c1=O] | 369.3 |
| 43 | 3-amino-7-(5-cyclopropyl-1-methyl-1H-pyrazol-3-yl)-5-((2S)-3-methylbutan-2-yl)-1,5-dihydro-4H-pyrazolo[4,3-c]pyridin-4-one | 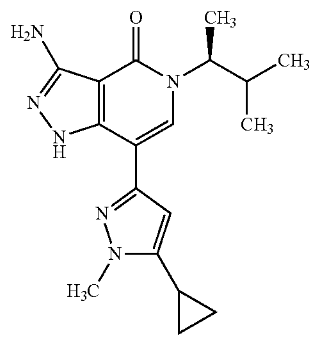 [SMILES: CC(C)[C@H](C)n1cc(-c2cc(C3CC3)n(C)n2)c2[nH]nc(N)c2c1=O] | 341.2 |
| 44 | 3-amino-5-((2S)-3-methylbutan-2-yl)-7-(1-methyl-5-(pyrrolidin-1-ylmethyl)-1H-pyrazol-3-yl)-1,5-dihydro-4H-pyrazolo[4,3-c]pyridin-4-one | 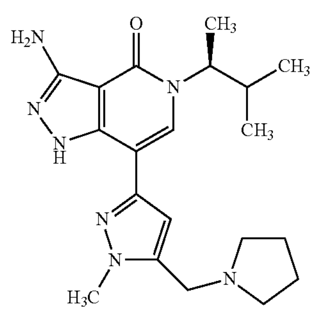 [SMILES: CC(C)[C@H](C)n1cc(-c2cc(CN3CCCC3)n(C)n2)c2[nH]nc(N)c2c1=O] | 384.4 |
| 45 | 3-amino-7-(5-((1,1-dioxidothiomorpholin-4-yl)carbonyl)-1-methyl-1H-pyrazol-3-yl)-5-((2S)-3-methylbutan-2-yl)-1,5-dihydro-4H-pyrazolo[4,3-c]pyridin-4-one | 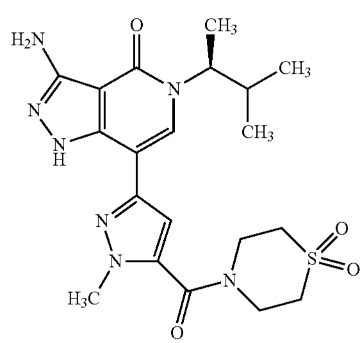 [SMILES: CC(C)[C@H](C)n1cc(-c2cc(C(=O)N3CCS(=O)(=O)CC3)n(C)n2)c2[nH]nc(N)c2c1=O] | 462.1 |

TABLE 1-continued

| Ex. No. | IUPAC name | structure | MS |
|---|---|---|---|
| 46 | 3-(3-amino-5-((2S)-3-methylbutan-2-yl)-4-oxo-4,5-dihydro-1H-pyrazolo[4,3-c]pyridin-7-yl)-N-(2-methoxyethyl)-N,1-dimethyl-1H-pyrazole-5-carboxamide | 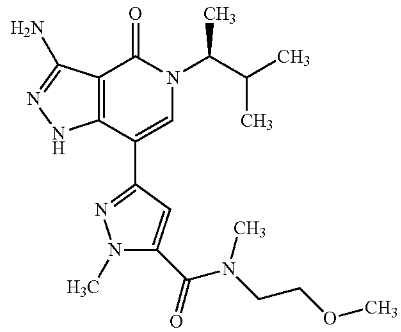 [SMILES: COCCN(C)C(=O)c1cc(-c2cn([C@@H](C)C(C)C)c(=O)c3c(N)n[nH]c23)nn1C] | 416.1 |
| 47 | 3-amino-7-(5-((1,1-dioxidothiomorpholin-4-yl)methyl)-1-methyl-1H-pyrazol-3-yl)-5-((2S)-3-methylbutan-2-yl)-1,5-dihydro-4H-pyrazolo[4,3-c]pyridin-4-one | 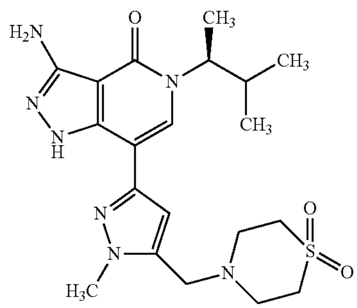 [SMILES: CC(C)[C@H](C)n1cc(-c2cc(CN3CCS(=O)(=O)CC3)n(C)n2)c2[nH]nc(N)c2c1=O] | 448.4 |
| 48 | 3-amino-5-((2S)-3-methylbutan-2-yl)-7-(1-methyl-5-(2-oxopiperidin-1-yl)-1H-pyrazol-3-yl)-1,5-dihydro-4H-pyrazolo[4,3-c]pyridin-4-one | 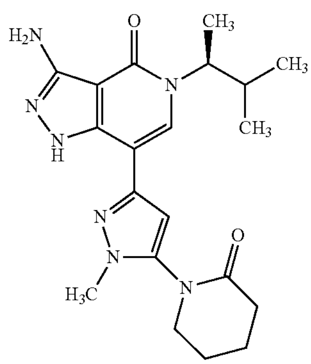 [SMILES: CC(C)[C@H](C)n1cc(-c2cc(N3CCCCC3=O)n(C)n2)c2[nH]nc(N)c2c1=O] | 398.1 |
| 49 | 3-amino-5-((2S)-3-methylbutan-2-yl)-7-(1-methyl-5-(3-oxomorpholin-4-yl)-1H-pyrazol-3-yl)-1,5-dihydro-4H-pyrazolo[4,3-c]pyridin-4-one | 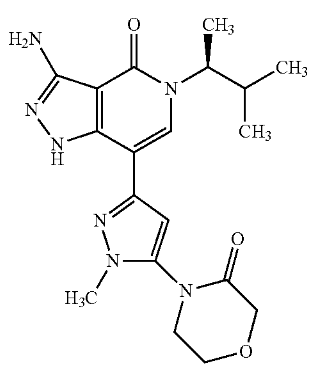 | 400.1 |

TABLE 1-continued

| Ex. No. | IUPAC name | structure | MS |
|---|---|---|---|
| 50 | 3-(3-amino-5-((2S)-3-methylbutan-2-yl)-4-oxo-4,5-dihydro-1H-pyrazolo[4,3-c]pyridin-7-yl)-N-cyclopentyl-N,1-dimethyl-1H-pyrazole-5-carboxamide | 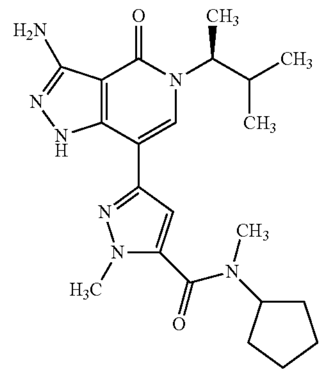 [SMILES: CC(C)[C@H](C)n1cc(-c2cc(C(=O)N(C)C3CCCC3)n(C)n2)c2[nH]nc(N)c2c1=O] | 426.1 |
| 51 | N-(2-(3-(3-amino-5-((2S)-3-methylbutan-2-yl)-4-oxo-4,5-dihydro-1H-pyrazolo[4,3-c]pyridin-7-yl)-1-methyl-1H-pyrazol-5-yl)-2-methylpropyl)acetamide | 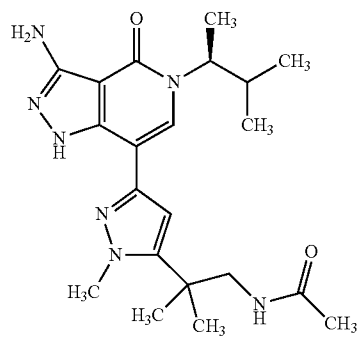 [SMILES: CC(=O)NCC(C)(C)c1cc(-c2cn([C@@H](C)C(C)C)c(=O)c3c(N)n[nH]c23)nn1C] | 414.2 |
| 52 | 3-amino-5-((2S)-3-methylbutan-2-yl)-7-(1-methyl-5-((2-oxopyrrolidin-1-yl)methyl)-1H-pyrazol-3-yl)-1,5-dihydro-4H-pyrazolo[4,3-c]pyridin-4-one | 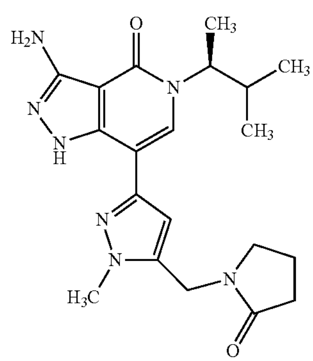 [SMILES: CC(C)[C@H](C)n1cc(-c2cc(CN3CCCC3=O)n(C)n2)c2[nH]nc(N)c2c1=O] | 398.1 |
| 53 | 3-(3-amino-5-((2S)-3-methylbutan-2-yl)-4-oxo-4,5-dihydro-1H-pyrazolo[4,3-c]pyridin-7-yl)-N,1-dimethyl-N-(tetrahydro-2H-pyran-4-yl)-1H-pyrazole-5-carboxamide | 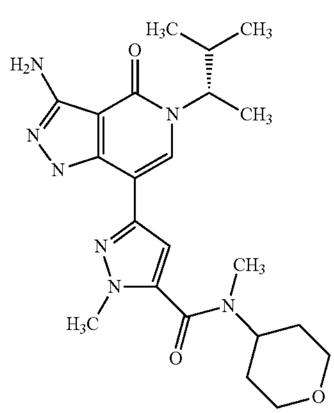 [SMILES: CC(C)[C@H](C)n1cc(-c2cc(C(=O)N(C)C3CCOCC3)n(C)n2)c2[nH]nc(N)c2c1=O] | 442.2 |

TABLE 1-continued

| Ex. No. | IUPAC name | structure | MS |
|---|---|---|---|
| 54 | 3-amino-5-((2S)-3-methylbutan-2-yl)-7-(1-methyl-5-(2-oxo-1,3-oxazolidin-3-yl)-1H-pyrazol-3-yl)-1,5-dihydro-4H-pyrazolo(4,3-c]pyridin-4-one | 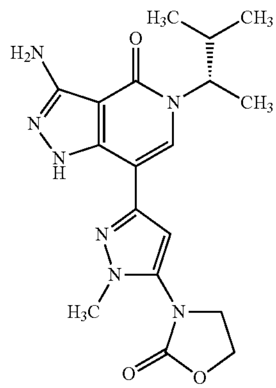 [SMILES: CC(C)[C@H](C)n1cc(-c2cc(N3CCOC3=O)n(C)n2)c2[nH]nc(N)c2c1=O] | 386 |
| 55 | 3-amino-5-((2S)-3-methylbutan-2-yl)-7-(1-methyl-5-(2-oxopyrrolidin-1-yl)-1H-pyrazol-3-yl)-1,5-dihydro-4H-pyrazolo[4,3-c]pyridin-4-one | 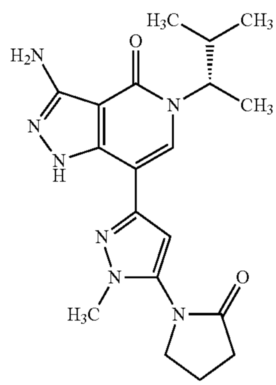 [SMILES: CC(C)[C@H](C)n1cc(-c2cc(N3CCCC3=O)n(C)n2)c2[nH]nc(N)c2c1=O] | 384.1 |
| 56 | 2-(3-(3-amino-5-((2S)-3-methylbutan-2-yl)-4-oxo-4,5-dihydro-1H-pyrazolo[4,3-c]pyridin-7-yl)-1-methyl-1H-pyrazol-5-yl)-N,N,2-trimethylpropanamide | 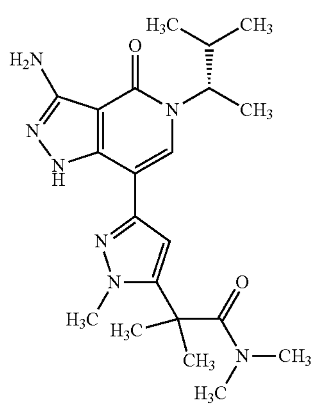 [SMILES: CC(C)[C@H](C)n1cc(-c2cc(C(C)(C)C(=O)N(C)C)n(C)n2)c2[nH]nc(N)c2c1=O] | 414.2 |
| 57 | 2-(3-(3-amino-5-((2S)-3-methylbutan-2-yl)-4-oxo-4,5-dihydro-1H-pyrazolo[4,3-c]pyridin-7-yl)-1-methyl-1H-pyrazol-5-yl)-2-methylpropanenitrile | 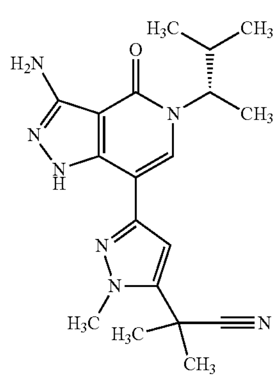 [SMILES: CC(C)[C@H](C)n1cc(-c2cc(C(C)(C)C#N)n(C)n2)c2[nH]nc(N)c2c1=O] | 368.1 |

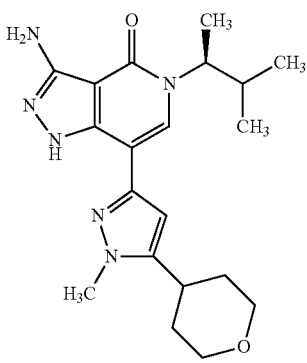

A mixture of 3-amino-7-(5-(3,6-dihydro-2H-pyran-4-yl)-1-methyl-1H-pyrazol-3-yl)-5-((2S)-3-methylbutan-2-yl)-1,5-dihydro-4H-pyrazolo[4,3-c]pyridin-4-one (62 mg) obtained in Example 39, platinum(IV) oxide (8 mg) and methanol (5 mL) was stirred under a hydrogen atmosphere at room temperature for 3 hr. The catalyst was removed by filtration, and the filtrate was concentrated under reduced pressure. The obtained residue was fractionated by HPLC (C18, mobile phase: water/acetonitrile (containing 10 mM $NH_4HCO_3$)), and the obtained fraction was concentrated under reduced pressure. The residue was solidified from diethyl ether to give the title compound (28 mg).

MS (ESI+): [M+H]$^+$ 385.4.

Example 59

3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one

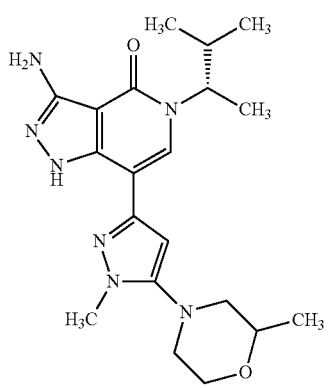

A diastereomeric mixture (110 mg) of 3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one obtained in Example 31 was fractionated by HPLC (column: CHIRALCEL (registered trademark) OD, 50 mmIDx500 mmL, manufactured by Daicel Corporation, mobile phase: hexane/ethanol/diethylamine=900/100/1 (v/v/v)) to give the title compound (53 mg) having a shorter retention time. The obtained solid was dissolved in ethyl acetate, and the mixture was washed with water and saturated brine, and dried over anhydrous magnesium sulfate. The solvent was evaporated under reduced pressure to give the title compound (22 mg).

MS (ESI+): [M+H]$^+$ 400.1.

>99.9% ee (HPLC (column: CHIRALCEL OD, 4.6 mmIDx250 mmL, manufactured by Daicel Corporation, mobile phase: hexane/ethanol/diethylamine=900/100/1 (v/v/v), flow rate: 1.0 mL/min, retention time: 15.46 min))

Example 60

3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one

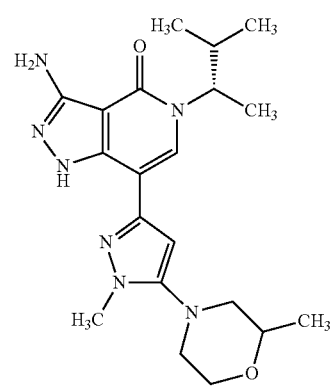 [SMILES: CC1CN(c2cc(-c3cn([C@@H](C)C(C)C)c(=O)c4c(N)n[nH]c34)nn2C)CCO1]

A diastereomeric mixture (110 mg) of 3-amino-5-((2S)-3-methylbutan-2-yl)-7-(1-methyl-5-(2-methylmorpholin-4-yl)-1H-pyrazol-3-yl)-1,5-dihydro-4H-pyrazolo[4,3-c]pyridin-4-one obtained in Example 31 was fractionated by HPLC (column: CHIRALCEL OD, 50 mmIDx500 mmL, manufactured by Daicel Corporation, mobile phase: hexane/ethanol/diethylamine=900/100/1 (v/v/v)) to give the title compound (32 mg) having a longer retention time. The obtained solid (32 mg) was dissolved in ethyl acetate, and the mixture was washed with water and saturated brine, and dried over anhydrous magnesium sulfate. The solvent was evaporated under reduced pressure to give the title compound (15 mg).

MS (ESI+): [M+H]$^+$ 400.1.

>99.9% ee (HPLC (column: CHIRALCEL OD, 4.6 mmIDx250 mmL, manufactured by Daicel Corporation, mobile phase: hexane/ethanol/diethylamine=900/100/1 (v/v/v), flow rate: 1.0 mL/min, retention time: 17.79 min))

Example 61

3-amino-7-(5-(hexahydropyrrolo[1,2-a]pyrazin-2(1H)-yl)-1-methyl-1H-pyrazol-3-yl)-5-((2S)-3-methylbutan-2-yl)-1,5-dihydro-4H-pyrazolo[4,3-c]pyridin-4-one

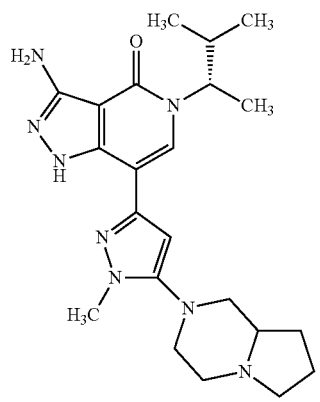 [SMILES: CC(C)[C@H](C)n1cc(-c2cc(N3CCN4CCCC4C3)n(C)n2)c2[nH]nc(N)c2c1=O]

A diastereomeric mixture (179 mg) of 3-amino-7-(5-(hexahydropyrrolo[1,2-a]pyrazin-2(1H)-yl)-1-methyl-1H-pyrazol-3-yl)-5-((2S)-3-methylbutan-2-yl)-1,5-dihydro-4H-pyrazolo[4,3-c]pyridin-4-one obtained in Example 32 was fractionated by SFC (column: CHIRALPAK AD-H, 20 mmID×250 mmL, manufactured by Daicel Corporation, mobile phase: carbon dioxide/2-propanol/diethylamine=700/300/3 (v/v/v)) to give the title compound (81 mg) having a shorter retention time. The obtained solid (81 mg) was dissolved in ethyl acetate, and the mixture was washed with water and saturated brine, and dried over anhydrous magnesium sulfate. The solvent was evaporated under reduced pressure and the residue was solidified from ethyl acetate/hexane to give the title compound (23 mg).

MS (ESI+): [M+H]$^+$ 425.2.

>99% ee (SFC (column: CHIRALPAK AD-H, 4.6 mmID×150 mmL, manufactured by Daicel Corporation, mobile phase: carbon dioxide/2-propanol/diethylamine=700/300/3 (v/v/v), flow rate: 4 mL/min, retention time: 4.11 min))

Example 62

3-amino-7-(5-(hexahydropyrrolo[1,2-a]pyrazin-2(H)-yl)-1-methyl-1H-pyrazol-3-yl)-5-((2S)-3-methylbutan-2-yl)-1,5-dihydro-4H-pyrazolo[4,3-c]pyridin-4-one

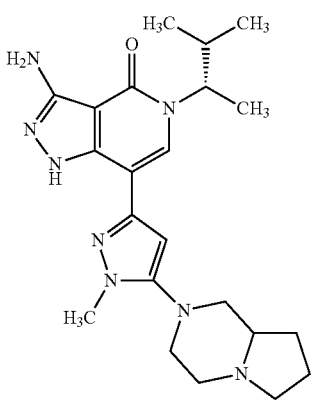 [SMILES: CC(C)[C@H](C)n1cc(-c2cc(N3CCN4CCCC4C3)n(C)n2)c2[nH]nc(N)c2c1=O]

A diastereomeric mixture (179 mg) of 3-amino-7-(5-(hexahydropyrrolo[1,2-a]pyrazin-2(1H)-yl)-1-methyl-1H-pyrazol-3-yl)-5-((2S)-3-methylbutan-2-yl)-1,5-dihydro-4H-pyrazolo[4,3-c]pyridin-4-one obtained in Example 32 was fractionated by SFC (column: CHIRALPAK AD-H, 20 mmID×250 mmL, manufactured by Daicel Corporation, mobile phase: carbon dioxide/2-propanol/diethylamine=700/300/3 (v/v/v)) to give the title compound (70 mg) having a longer retention time. The obtained solid (70 mg) was dissolved in ethyl acetate, and the mixture was washed with water and saturated brine, and dried over anhydrous magnesium sulfate. The solvent was evaporated under reduced pressure and the residue was solidified from ethyl acetate/hexane to give the title compound (35 mg).

MS (ESI+): [M+H]$^+$ 425.2.

>99% ee (SFC (column: CHIRALPAK AD-H, 4.6 mmID×150 mmL, manufactured by Daicel Corporation, mobile phase: carbon dioxide/2-propanol/diethylamine=700/300/3 (v/v/v), flow rate: 4 mL/min, retention time: 5.23 min))

Example 63

3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one

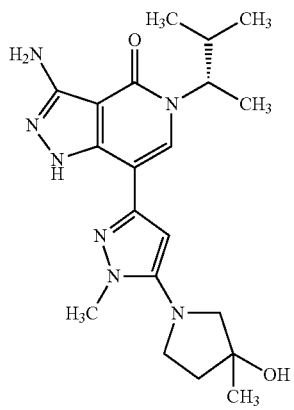 [SMILES: CC(C)[C@H](C)n1cc(-c2cc(N3CCC(C)(O)C3)n(C)n2)c2[nH]nc(N)c2c1=O]

A diastereomeric mixture (100 mg) of 3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one obtained in Example 33 was fractionated by HPLC (column: CHIRALPAK IC, 50 mmID×500 mmL, manufactured by Daicel Corporation, mobile phase: hexane/ethanol/diethylamine=60/40/0.1 (v/v/v)) to give the title compound (47 mg) having a shorter retention time. The obtained solid (47 mg) was solidified from ethyl acetate/hexane to give the title compound (36 mg).

>99.9% ee (HPLC (column: CHIRALPAK IC, 4.6 mmID×250 mmL, manufactured by Daicel Corporation, mobile phase: hexane/ethanol/diethylamine=60/40/0.1 (v/v/v), flow rate: 1.0 mL/min, retention time: 15.39 min))

MS (ESI+): [M+H]$^+$ 400.2.

Example 64

3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one

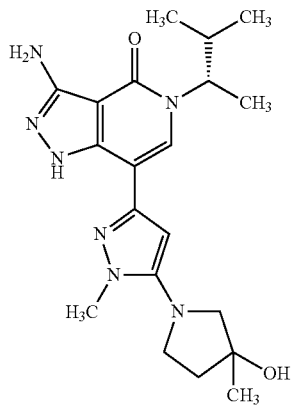

A diastereomeric mixture (100 mg) of 3-amino-7-(5-(3-hydroxy-3-methylpyrrolidin-1-yl)-1-methyl-1H-pyrazol-3-yl)-5-((2S)-3-methylbutan-2-yl)-1,5-dihydro-4H-pyrazolo[4,3-c]pyridin-4-one obtained in Example 33 was fractionated by HPLC (column: CHIRALPAK IC, 50 mmID×500 mmL, manufactured by Daicel Corporation, mobile phase: hexane/ethanol/diethylamine=60/40/0.1 (v/v/v)) to give the title compound (41 mg) having a longer retention time. The obtained solid (41 mg) was solidified from ethyl acetate/hexane to give the title compound (26 mg).

>99.9% ee (HPLC (column: CHIRALPAK IC, 4.6 mmID×250 mmL, manufactured by Daicel Corporation, mobile phase: hexane/ethanol/diethylamine=60/40/0.1 (v/v/v), flow rate: 1.0 mL/min, retention time: 22.65 min))

MS (ESI+): [M+H]$^+$ 400.1.

Example 65

3-(3-amino-5-(2,6-difluorophenyl)-4-oxo-4,5-dihydro-1H-pyrazolo[4,3-c]pyridin-7-yl)-N,1-dimethyl-1H-pyrazole-5-carboxamide

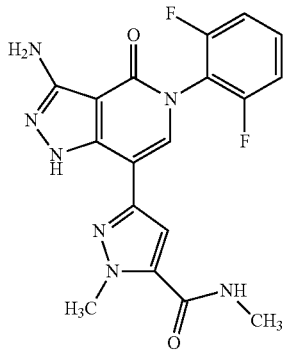 [SMILES: CNC(=O)c1cc(-c2cn(-c3c(F)cccc3F)c(=O)c3c(N)n[nH]c23)nn1C]

A) N-(2,6-difluorophenyl)-3-oxobutanamide

To a mixture of 2,6-difluoroaniline (5.00 g), 2,2,6-trimethyl-4H-1,3-dioxin-4-one (7.16 g) and tetrahydrofuran (13 mL) was added sodium acetate (3.18 g) at room temperature. The reaction mixture was refluxed overnight and cooled to room temperature. The reaction mixture was added to water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (5.04 g).

$^1$H NMR (400 MHz, CDCl$_3$) δ 2.35 (3H, s), 3.67 (2H, s), 6.93-6.99 (2H, m), 7.18-7.24 (1H, m), 8.77 (1H, brs).

B) N-(2,6-difluorophenyl)-2-((dimethylamino)methylene)-3-oxobutanamide

To a mixture of N-(2,6-difluorophenyl)-3-oxobutanamide (5.00 g) obtained in Example 65, Step A and N,N-dimethylformamide (20 mL) was added dropwise 1,1-dimethoxy-N,N-dimethylmethanamine (6.32 mL) at room temperature over 20 min, and the reaction mixture was stirred at room temperature overnight. The solvent was evaporated under reduced pressure, and the residue was purified by silica gel column chromatography (methanol/ethyl acetate) to give the title compound (3.70 g).

$^1$H NMR (400 MHz, CDCl$_3$) δ 2.32 (3H, s), 3.20 (6H, s), 6.89-6.96 (2H, m), 7.09-7.16 (1H, m), 7.71 (1H, s), 10.37 (1H, s).

C) 4-chloro-1-(2,6-difluorophenyl)-2-oxo-1,2-dihydropyridine-3-carbaldehyde

Phosphorus oxychloride (5.14 mL) was slowly added to N,N-dimethylformamide (4.27 mL) under ice-cooling and the mixture was stirred for 15 min. To the reaction mixture was added a solution of N-(2,6-difluorophenyl)-2-((dimethylamino)methylene)-3-oxobutanamide (3.70 g) obtained in Example 65, Step B, in N,N-dimethylformamide (30 mL) under ice-cooling, and the reaction mixture was heated at 125° C. for 30 min. The reaction mixture was cooled to room temperature, poured into ice/saturated brine, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (1.07 g).

$^1$H NMR (400 MHz, CDCl$_3$) δ 6.44 (1H, d, J=7.6 Hz), 7.10-7.16 (2H, m), 7.36 (1H, d, J=7.2 Hz), 7.45-7.53 (1H, m), 10.38 (1H, s).

D) 4-chloro-1-(2,6-difluorophenyl)-3-((hydroxyimino)methyl)pyridin-2(1H)-one

A mixture of 4-chloro-1-(2,6-difluorophenyl)-2-oxo-1,2-dihydropyridine-3-carbaldehyde (1.07 g) obtained in Example 65, Step C, hydroxylamine hydrochloride (414 mg), concentrated hydrochloric acid (0.0120 mL) and 2-propanol (10 mL) was heated at 100° C. for 2 hr, and cooled to room temperature. The resulting solid was collected by filtration and dried under reduced pressure to give the title compound (800 mg).

$^1$H NMR (400 MHz, CDCl$_3$) δ 6.43 (1H, d, J=7.2 Hz), 6.99-7.11 (2H, m), 7.16 (1H, d, J=7.6 Hz), 7.40-7.48 (1H, m), 8.45 (1H, s).

E) 4-chloro-1-(2,6-difluorophenyl)-2-oxo-1,2-dihydropyridine-3-carbonitrile

To a solution (7.0 mL) of 4-chloro-1-(2,6-difluorophenyl)-3-((hydroxyimino)methyl)pyridin-2(1H)-one (800 mg) obtained in Example 65, Step D, in acetonitrile was added phosphorus oxychloride (0.341 mL) at room temperature. The reaction mixture was heated at 100° C. for 1 hr, cooled to room temperature and poured into ice water. The resulting solid was collected by filtration and dried under reduced pressure to give the title compound (600 mg).

$^1$H NMR (400 MHz, CDCl$_3$) δ 6.49 (1H, d, J=7.2 Hz), 7.10-7.15 (2H, m), 7.40 (1H, d, J=7.2 Hz), 7.46-7.54 (1H, m).

F) 5-bromo-4-chloro-1-(2,6-difluorophenyl)-2-oxo-1,2-dihydropyridine-3-carbonitrile To a solution (5.0 mL) of 4-chloro-1-(2,6-difluorophenyl)-2-oxo-1,2-dihydropyridine-3-carbonitrile (670 mg) obtained in Example 65, Step E, in N,N-dimethylformamide was added N-bromosuccinimide (548 mg) at room temperature. The reaction mixture was heated at 50° C. for 4 hr, and cooled to room temperature. Water was added to the reaction mixture, and the mixture was extracted with ethyl acetate.

The extract was washed with water, and dried over anhydrous sodium sulfate, and the solvent was evaporated under reduced pressure. The residue was purified by silica gel column chromatography (ethyl acetate/hexane) to give the title compound (380 mg).

$^1$H NMR (400 MHz, CDCl$_3$) δ 7.11-7.16 (2H, m), 7.48-7.56 (1H, m), 7.73 (1H, s).

G) 3-amino-7-bromo-5-(2,6-difluorophenyl)-1,5-dihydro-4H-pyrazolo[4,3-c]pyridin-4-one To a solution of 5-bromo-4-chloro-1-(2,6-difluorophenyl)-2-oxo-1,2-dihydropyridine-3-carbonitrile (270 mg) obtained in Example 65, Step F in ethanol (10 mL) was added hydrazine monohydrate (0.135 mL) at room temperature. The reaction mixture was heated overnight at 90° C., and cooled to room temperature. The reaction mixture was concentrated under reduced pressure, water was added to the residue, and the mixture was extracted with ethyl acetate. The extract was dried over anhydrous sodium sulfate and the solvent was evaporated under reduced pressure to give the title compound (332 mg).

$^1$H NMR (400 MHz, CDCl$_3$) δ 7.05-7.12 (2H, m), 7.14 (1H, s), 7.39-7.47 (1H, m).

H) 3-(3-amino-5-(2,6-difluorophenyl)-4-oxo-4,5-dihydro-1H-pyrazolo[4,3-c]pyridin-7-yl)-N,1-dimethyl-1H-pyrazole-5-carboxamide In the same manner as in Example 1, Step H, the title compound was obtained from 3-amino-7-bromo-5-(2,6-difluorophenyl)-1,5-dihydro-4H-pyrazolo[4,3-c]pyridin-4-one obtained in Example 65, Step G, and 1-methyl-5-(methylcarbamoyl)-1H-pyrazol-3-yl trifluoromethanesulfonate obtained in Reference Example 41.

MS (ESI+): [M+H]$^+$ 400.1.

Example 66

3-amino-5-(2,6-difluorophenyl)-7-(1-methyl-5-(morpholin-4-ylcarbonyl)-1H-pyrazol-3-yl)-1,5-dihydro-4H-pyrazolo[4,3-c]pyridin-4-one

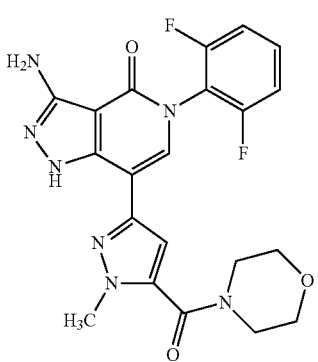 [SMILES: Cn1nc(-c2cn(-c3c(F)cccc3F)c(=O)c3c(N)n[nH]c23)cc1C(=O)N1CCOCC1]

In the same manner as in Example 1, Step H, the title compound was obtained from 3-amino-7-bromo-5-(2,6-difluorophenyl)-1,5-dihydro-4H-pyrazolo[4,3-c]pyridin-4-one obtained in Example 65, Step G, and 1-methyl-5-(morpholin-4-ylcarbonyl)-1H-pyrazol-3-yl trifluoromethanesulfonate obtained in Reference Example 41.

MS (ESI+): [M+H]$^+$ 456.1.

Example 67

2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-fluorobenzonitrile

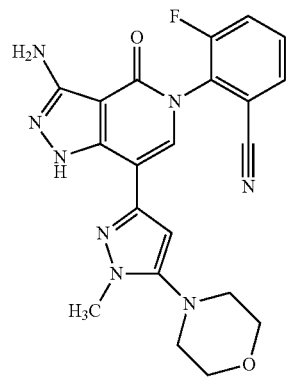

A) N-(2-cyano-6-fluorophenyl)-3-oxobutanamide

To a mixture of 2-amino-3-fluorobenzonitrile (41.9 g), sodium acetate (30.3 g) and toluene (200 mL) was added diketene (28.2 mL) at 0° C. over 10 min. The reaction mixture was stirred at room temperature for 7 hr. To the reaction mixture were sequentially added toluene (150 mL) and diketene (4.7 mL) at room temperature, and the mixture was stirred at room temperature for 16 hr. The reaction mixture was added to water, and the mixture was extracted with ethyl acetate. The extract was washed with water and saturated brine, and dried over anhydrous magnesium sulfate. The solvent was evaporated under reduced pressure and the residue was recrystallized from diisopropyl ether/ethanol to give the title compound (48.64 g).

MS (ESI+): [M+H]$^+$ 221.2.

B) N-(2-cyano-6-fluorophenyl)-2-((dimethylamino)methylene)-3-oxobutanamide

To a mixture of N-(2-cyano-6-fluorophenyl)-3-oxobutanamide (48.60 g) obtained in Example 67, Step A, and N,N-dimethylformamide (200 mL) was added dropwise 1,1-dimethoxy-N,N-dimethylmethanamine (52.6 g) at 0° C. over 10 min, and the reaction mixture was stirred at room temperature for 3 hr. The solvent was evaporated under reduced pressure, water was added to the residue, and the mixture was extracted with ethyl acetate. The extract was dried over anhydrous magnesium sulfate, and the solvent was evaporated under reduced pressure. The residue was recrystallized from ethyl acetate and collected by filtration. The obtained solid was washed with ethyl acetate/diisopropyl ether, and then diisopropyl ether to give the title compound (26.16 g).

MS (ESI+): [M+H]$^+$ 276.1.

C) 2-(4-chloro-3-formyl-2-oxopyridin-1(2H)-yl)-3-fluorobenzonitrile

To a solution of N-(2-cyano-6-fluorophenyl)-2-((dimethylamino)methylene)-3-oxobutanamide (11.00 g) obtained in Example 67, Step B, in N,N-dimethylformamide (150 mL) was added (chloromethylene)dimethylammonium chloride (24.9 g) under ice-cooling, and the reaction mixture was heated at 100° C. for 30 min. The reaction mixture was cooled to room temperature, and added to ice water, and the mixture was extracted with ethyl acetate. The extract was dried over anhydrous magnesium sulfate, and the solvent was evaporated under reduced pressure. The residue was purified by silica gel column chromatography (ethyl acetate/hexane) to give an orange oil. The obtained oil was crystallized from diisopropyl ether/hexane to give the title compound (2.81 g).
MS (ESI+): [M+H]$^+$ 277.1.

D) 2-(4-chloro-3-((hydroxyimino)methyl)-2-oxopyridin-1(2H)-yl)-3-fluorobenzonitrile A mixture of 2-(4-chloro-3-formyl-2-oxopyridin-1(2H)-yl)-3-fluorobenzonitrile (2.70 g) obtained in Example 67, Step C, hydroxylamine hydrochloride (814 mg), sodium acetate (1.60 g) and methanol (60 mL)/water (15 mL) was stirred at room temperature for 1 hr. The reaction mixture was added to ice water. The resulting solid was collected by filtration, and washed with water, 2-propanol and diethyl ether to give the title compound (2.39 g).
MS (ESI+): [M+H]$^+$ 292.0.

E) 4-chloro-1-(2-cyano-6-fluorophenyl)-2-oxo-1,2-dihydropyridine-3-carbonitrile

To a solution of 2-(4-chloro-3-((hydroxyimino)methyl)-2-oxopyridin-1(2H)-yl)-3-fluorobenzonitrile (8.0 g) obtained in Example 67, Step D, in acetonitrile (180 mL) was added thionyl chloride (3.98 mL) at room temperature. The reaction mixture was stirred at room temperature for 1 hr. The solvent was evaporated under reduced pressure, and the residue was crystallized from diisopropyl ether/methanol, and the obtained solid was collected by filtration to give the title compound (7.05 g).
MS (ESI+): [M+H]$^+$ 274.2.

F) 5-bromo-4-chloro-1-(2-cyano-6-fluorophenyl)-2-oxo-1,2-dihydropyridine-3-carbonitrile To a solution of 4-chloro-1-(2-cyano-6-fluorophenyl)-2-oxo-1,2-dihydropyridine-3-carbonitrile (4.0 g) obtained in Example 67, Step E, in N,N-dimethylformamide (40 mL) was added N-bromosuccinimide (3.90 g) at room temperature. The reaction mixture was heated at 50° C. for 16 hr. Water was added to the reaction mixture, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (1.10 g).
MS (ESI+): [M+H]$^+$ 352.1.

G) 2-(3-amino-7-bromo-4-oxo-1,4-dihydro-5H-pyrazolo[4,3-c]pyridin-5-yl)-3-fluorobenzonitrile A solution of 5-bromo-4-chloro-1-(2-cyano-6-fluorophenyl)-2-oxo-1,2-dihydropyridine-3-carbonitrile (4.35 g) obtained in Example 67, Step F, and hydrazine monohydrate (0.658 mL) in ethanol (32 mL)/tetrahydrofuran (64 mL) was heated at 90° C. for 1 hr. To the reaction mixture was added hydrazine monohydrate (0.5 mL), and the mixture was heated at 90° C. for 30 min. The solvent was concentrated under reduced pressure, water was added, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane) to give the title compound (4.12 g).
$^1$H NMR (400 MHz, CDCl$_3$) δ 5.08 (2H, brs), 7.12 (1H, s), 7.45-7.65 (3H, m), 10.46 (1H, brs).

H) 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-fluorobenzonitrile A mixture of 2-(3-amino-7-bromo-4-oxo-1,4-dihydro-5H-pyrazolo[4,3-c]pyridin-5-yl)-3-fluorobenzonitrile (200 mg) obtained in Example 67, Step G, 4,4,4',4',5,5,5',5'-octamethyl-2,2'-bi-1,3,2-dioxaborolane (292 mg), (1,1'-bis(diphenylphosphino)ferrocene)dichloropalladium(II) (22 mg), potassium acetate (113 mg) and N,N-dimethylacetamide (3 mL) was stirred under an argon atmosphere at 110° C. for 4 hr. The reaction mixture was cooled to room temperature, and a solution of 4-(3-bromo-1-methyl-1H-pyrazol-5-yl)morpholine (212 mg) obtained in Reference Example 12 in N,N-dimethylacetamide (0.5 mL), aqueous sodium carbonate solution (2 M, 0.574 mL) and tetrakis(triphenylphosphine)palladium(0) (66 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a crude purification product. The obtained crude purification product was solidified from methanol/ethyl acetate to give the title compound (38 mg).
MS (ESI+): [M+H]$^+$ 435.3.

Example 68

2-(3-amino-7-(5-(3,6-dihydro-2H-pyran-4-yl)-1-methyl-1H-pyrazol-3-yl)-4-oxo-1,4-dihydro-5H-pyrazolo[4,3-c]pyridin-5-yl)-3-fluorobenzonitrile

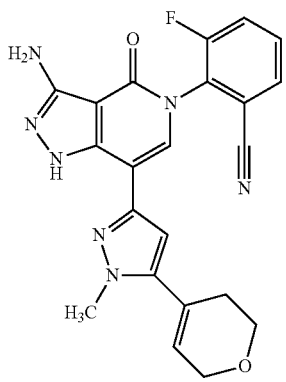

A mixture of 2-(3-amino-7-bromo-4-oxo-1,4-dihydro-5H-pyrazolo[4,3-c]pyridin-5-yl)-3-fluorobenzonitrile (200 mg) obtained in Example 67, Step G, 4,4,4',4',5,5,5',5'- octamethyl-2,2'-bi-1,3,2-dioxaborolane (292 mg), tetrakis(triphenylphosphine)palladium(0) (100 mg), potassium acetate (113 mg) and N,N-dimethylacetamide (3 mL) was stirred under an argon atmosphere at 110° C. for 4 hr. The reaction mixture was cooled to room temperature, and a solution of 3-bromo-5-(3,6-dihydro-2H-pyran-4-yl)-1-methyl-1H-pyrazole (209 mg) obtained in Reference Example 67 in N,N-dimethylacetamide (1.5 mL), aqueous sodium carbonate solution (2 M, 0.574 mL) and tetrakis(triphenylphosphine)palladium(0) (66 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid. The obtained yellow solid was solidified from ethyl acetate to give the title compound (53 mg).

MS (ESI+): [M+H]$^+$ 432.3.

Example 69

2-(3-amino-7-(1-methyl-5-(tetrahydro-2H-pyran-4-yl)-1H-pyrazol-3-yl)-4-oxo-1,4-dihydro-5H-pyrazolo[4,3-c]pyridin-5-yl)-3-fluorobenzonitrile

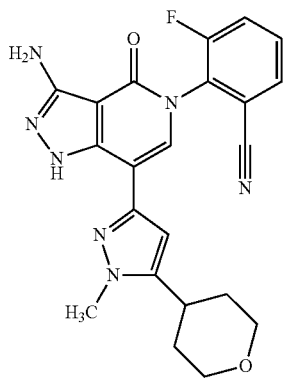 [SMILES: Cn1nc(-c2cn(-c3c(F)cccc3C#N)c(=O)c3c(N)n[nH]c23)cc1C1CCOCC1]

A solution of 2-(3-amino-7-(5-(3,6-dihydro-2H-pyran-4-yl)-1-methyl-1H-pyrazol-3-yl)-4-oxo-1,4-dihydro-5H-pyrazolo[4,3-c]pyridin-5-yl)-3-fluorobenzonitrile (53 mg) obtained in Example 68 and platinum(IV) oxide (10 mg) in methanol (40 mL) was stirred under a hydrogen atmosphere at room temperature for 6 hr. Platinum(IV) oxide (10 mg) was further added and the mixture was stirred under a hydrogen atmosphere at room temperature for 16 hr. Insoluble material was removed through celite, and the solvent was evaporated under reduced pressure. The obtained crude purification product was fractionated by HPLC (C18, mobile phase: water/acetonitrile (containing 5 mM AcONH$_4$)), and the obtained fraction was concentrated under reduced pressure. The obtained residue was dissolved in ethyl acetate, and the mixture was washed with saturated aqueous sodium hydrogen carbonate solution, water and saturated brine, dried over anhydrous magnesium sulfate, and concentrated under reduced pressure to give the title compound (9 mg).

MS (ESI+): [M+H]$^+$ 434.3.

Example 71

2-(3-amino-7-(5-(2-hydroxypropan-2-yl)-1-methyl-1H-pyrazol-3-yl)-4-oxo-1,4-dihydro-5H-pyrazolo[4,3-c]pyridin-5-yl)-3-fluorobenzonitrile

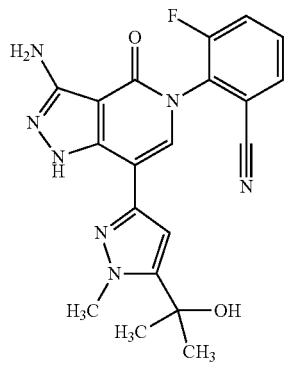 [SMILES: Cn1nc(-c2cn(-c3c(F)cccc3C#N)c(=O)c3c(N)n[nH]c23)cc1C(C)(C)O]

A mixture of 2-(3-amino-7-bromo-4-oxo-1,4-dihydro-5H-pyrazolo[4,3-c]pyridin-5-yl)-3-fluorobenzonitrile (300 mg) obtained in Example 67, Step G, 4,4,4',4',5,5,5',5'-octamethyl-2,2'-bi-1,3,2-dioxaborolane (438 mg), tetrakis(triphenylphosphine)palladium(0) (100 mg), potassium acetate (169 mg) and N,N-dimethylacetamide (3 mL) was stirred under an argon atmosphere at 110° C. for 4 hr. The reaction mixture was cooled to room temperature, and a solution of 2-(3-bromo-1-methyl-1H-pyrazol-5-yl)propan-2-ol (283 mg) obtained in Reference Example 4 in N,N-dimethylacetamide (1.5 mL), aqueous sodium carbonate solution (2 M, 0.862 mL) and tetrakis(triphenylphosphine)palladium(0) (149 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate and methanol/ethyl acetate) to give a yellow solid, which was further fractionated by HPLC (C18, mobile phase: water/acetonitrile (containing 0.1% TFA)). Saturated aqueous sodium hydrogen carbonate solution was added and the solvent was concentrated under reduced pressure. The obtained residue was extracted with ethyl acetate, dried over anhydrous magnesium sulfate, concentrated under reduced pressure, and crystallized from hexane/ethyl acetate to give the title compound (43 mg).

MS (ESI+): [M+H]$^+$ 408.3.

Example 70

The compounds of Example 70 was obtained by a method similar to Example 1, Step H, or Example 58 or a method according thereto and using 2-(3-amino-7-bromo-4-oxo-1,4-dihydro-5H-pyrazolo[4,3-c]pyridin-5-yl)-3-fluorobenzonitrile obtained Example 67, Step G, and a halide compound corresponding to the compound of Example 70. MS in the Table shows measured values. The halide compound used for the synthesis of the compound of Example 70 was synthesized according to the method described in the following Reference Example 14, or a method analogous thereto.

TABLE 2

| Ex. No. | IUPAC name | structure | MS |
|---|---|---|---|
| 68 | 2-(3-amino-7-(5-(3,6-dihydro-2H-pyran-4-yl)-1-methyl-1H-pyrazol-3-yl)-4-oxo-1,4-dihydro-5H-pyrazolo[4,3-c]pyridin-5-yl)-3-fluorobenzonitrile | 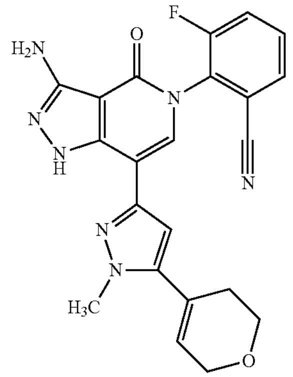 [SMILES: Cn1nc(-c2cn(-c3c(F)cccc3C#N)c(=O)c3c(N)n[nH]c23)cc1C1=CCOCC1] | 432.3 |
| 69 | 2-(3-amino-7-(1-methyl-5-(tetrahydro-2H-pyran-4-yl)-1H-pyrazol-3-yl)-4-oxo-1,4-dihydro-5H-pyrazolo[4,3-c]pyridin-5-yl)-3-fluorobenzonitrile | 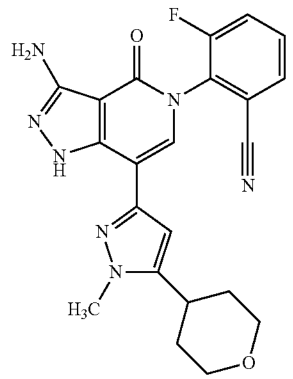 | 434.3 |
| 70 | 2-(3-amino-7-(1-methyl-5-(4-methylpiperazin-1-yl)-1H-pyrazol-3-yl)-4-oxo-1,4-dihydro-5H-pyrazolo[4,3-c]pyridin-5-yl)-3-fluorobenzonitrile | 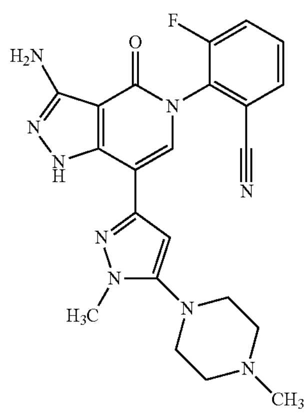 [SMILES: CN1CCN(c2cc(-c3cn(-c4c(F)cccc4C#N)c(=O)c4c(N)n[nH]c34)nn2C)CC1] | 448.1 |

TABLE 2-continued

| Ex. No. | IUPAC name | structure | MS |
|---|---|---|---|
| 71 | 2-(3-amino-7-(5-(2-hydroxypropan-2-yl)-1-methyl-1H-pyrazol-3-yl)-4-oxo-1,4-dihydro-5H-pyrazolo[4,3-c]pyridin-5-yl)-3-fluorobenzonitrile | 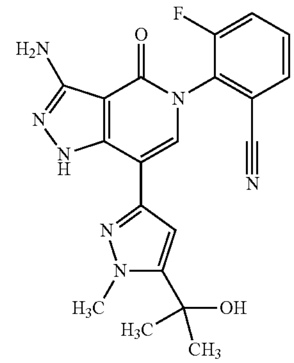 [SMILES: Cn1nc(-c2cn(-c3c(F)cccc3C#N)c(=O)c3c(N)n[nH]c23)cc1C(C)(C)O] | 408.3 |

Examples 72 and 73

The compounds of Examples 72 and 73 were obtained by a method similar to Example 1, or a method according thereto and using 2,2-dimethylcyclopentanamine, and halide compounds corresponding to the compounds of Examples 72 and 73, or trifluoromethanesulfonate compounds corresponding to the compounds of Examples 72 and 73. MS in the Table shows measured values. The halide compounds or trifluoromethanesulfonate compounds used for the synthesis of the compounds of Examples 72 and 73 were synthesized according to the method described in Reference Examples 12 and 60, or a method analogous thereto.

TABLE 3

| Ex. No. | IUPAC name | structure | MS |
|---|---|---|---|
| 72 | 3-amino-5-(2,2-dimethylcyclopentyl)-7-(5-((1,1-dioxidothiomorpholin-4-yl)methyl)-1-methyl-1H-pyrazol-3-yl)-1,5-dihydro-4H-pyrazolo[4,3-c]pyridin-4-one | 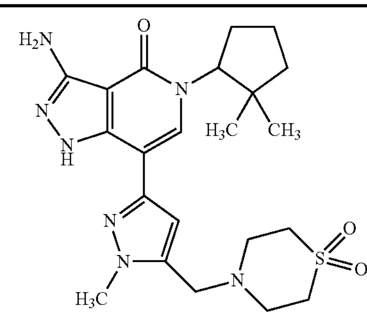 | 474.4 |

TABLE 3-continued

| Ex. No. | IUPAC name | structure | MS |
|---|---|---|---|
| 73 | 3-amino-5-(2,2-dimethylcyclopentyl)-7-(1-methyl-5-(morpholin-4-yl)-1H-pyrazol-3-yl)-1,5-dihydro-4H-pyrazolo[4,3-c]pyridin-4-one | 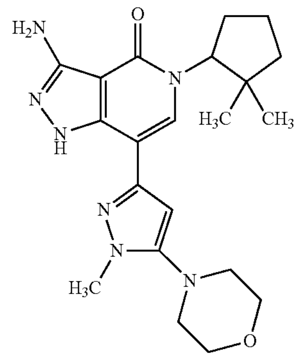 [SMILES: Cn1nc(-c2cn(C3CCCC3(C)C)c(=O)c3c(N)n[nH]c23)cc1N1CCOCC1] | 412.1 |

Example 74

3-amino-5-(2,2-dimethylcyclopentyl)-7-(5-((1,1-dioxidothiomorpholin-4-yl)methyl)-1-methyl-1H-pyrazol-3-yl)-1,5-dihydro-4H-pyrazolo[4,3-c]pyridin-4-one

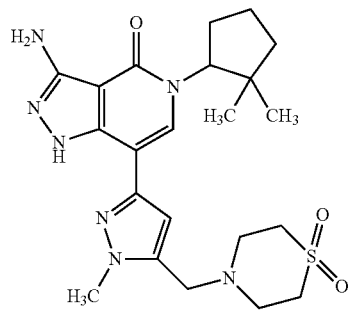 [SMILES: Cn1nc(-c2cn(C3CCCC3(C)C)c(=O)c3c(N)n[nH]c23)cc1CN1CCS(=O)(=O)CC1]

A racemate (105 mg) of 3-amino-5-(2,2-dimethylcyclopentyl)-7-(5-((1,1-dioxidothiomorpholin-4-yl)methyl)-1-methyl-1H-pyrazol-3-yl)-1,5-dihydro-4H-pyrazolo[4,3-c]pyridin-4-one obtained in Example 72 was fractionated by SFC (column: CHIRALCEL OJ-H, 20 mmID×250 mmL, manufactured by Daicel Corporation, mobile phase: carbon dioxide/methanol/diethylamine=800/200/3 (v/v/v)) to give the title compound (44 mg) having a shorter retention time. To the obtained solid (44 mg) was added diethyl ether and insoluble material was filtered off to give the title compound (41 mg).

MS (ESI+): [M+H]$^+$ 474.4.

99% ee (SFC (column: CHIRALCEL OJ-H, 4.6 mmID× 150 mmL, manufactured by Daicel Corporation, mobile phase: carbon dioxide/methanol/diethylamine=800/200/3 (v/v/v), flow rate: 5.0 mL/min, retention time: 3.01 min))

Example 75

3-amino-5-(2,2-dimethylcyclopentyl)-7-(5-((1,1-dioxidothiomorpholin-4-yl)methyl)-1-methyl-1H-pyrazol-3-yl)-1,5-dihydro-4H-pyrazolo[4,3-c]pyridin-4-one

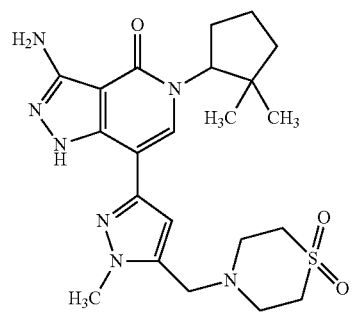 [SMILES: Cn1nc(-c2cn(C3CCCC3(C)C)c(=O)c3c(N)n[nH]c23)cc1CN1CCS(=O)(=O)CC1]

A racemate (105 mg) of 3-amino-5-(2,2-dimethylcyclopentyl)-7-(5-((1,1-dioxidothiomorpholin-4-yl)methyl)-1-methyl-1H-pyrazol-3-yl)-1,5-dihydro-4H-pyrazolo[4,3-c]pyridin-4-one obtained in Example 72 was fractionated by SFC (column: CHIRALCEL OJ-H, 20 mmID×250 mmL, manufactured by Daicel Corporation, mobile phase: carbon dioxide/methanol/diethylamine=800/200/3 (v/v/v)) to give the title compound (48 mg) having a longer retention time. To the obtained solid (48 mg) was added diethyl ether, and insoluble material was filtered off to give the title compound (41 mg).

MS (ESI+): [M+H]$^+$ 474.4.

99% ee (SFC (column: CHIRALCEL OJ-H, 4.6 mmID× 1150 mmL, manufactured by Daicel Corporation, mobile phase: carbon dioxide/methanol/diethylamine=800/200/3 (v/v/v), flow rate: 5.0 mL/min, retention time: 4.80 min))

Example 76

3-amino-5-(2,2-dimethylcyclopentyl)-7-(1-methyl-5-(morpholin-4-yl)-1H-pyrazol-3-yl)-1,5-dihydro-4H-pyrazolo[4,3-c]pyridin-4-one

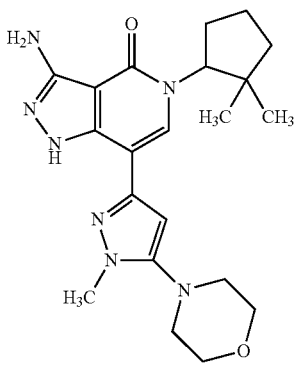 [SMILES: Cn1nc(-c2cn(C3CCCC3(C)C)c(=O)c3c(N)n[nH]c23)cc1N1CCOCC1]

A racemate (210 mg) of 3-amino-5-(2,2-dimethylcyclopentyl)-7-(1-methyl-5-(morpholin-4-yl)-1H-pyrazol-3-yl)-1,5-dihydro-4H-pyrazolo[4,3-c]pyridin-4-one obtained in Example 73 was fractionated by SFC (column: CHIRALPAK AS-H, 20 mmID×250 mmL, manufactured by Daicel Corporation, mobile phase: carbon dioxide/methanol/diethylamine=800/200/3 (v/v/v)) to give the title compound (101 mg) having a shorter retention time. The obtained solid (101 mg) was washed with diisopropyl ether to give the title compound (80 mg).

MS (ESI+): [M+H]$^+$ 412.1.

99% ee (SFC (column: CHIRALPAK AS-H, 4.6 mmID×150 mmL, manufactured by Daicel Corporation, mobile phase: carbon dioxide/methanol/diethylamine=800/200/3 (v/v/v), flow rate: 4 mL/min, retention time: 2.45 min))

Example 77

3-amino-5-(2,2-dimethylcyclopentyl)-7-(1-methyl-5-(morpholin-4-yl)-1H-pyrazol-3-yl)-1,5-dihydro-4H-pyrazolo[4,3-c]pyridin-4-one

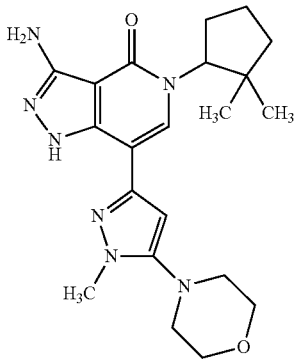 [SMILES: Cn1nc(-c2cn(C3CCCC3(C)C)c(=O)c3c(N)n[nH]c23)cc1N1CCOCC1]

A racemate (210 mg) of 3-amino-5-(2,2-dimethylcyclopentyl)-7-(1-methyl-5-(morpholin-4-yl)-1H-pyrazol-3-yl)-1,5-dihydro-4H-pyrazolo[4,3-c]pyridin-4-one obtained in Example 73 was fractionated by SFC (column: CHIRALPAK AS-H, 20 mmID×250 mmL, manufactured by Daicel Corporation, mobile phase: carbon dioxide/methanol/diethylamine=800/200/3 (v/v/v)) to give the title compound (103 mg) having a longer retention time. The obtained solid (103 mg) was washed with diisopropyl ether to give the title compound (81 mg).

MS (ESI+): [M+H]$^+$ 412.1.

99% ee (SFC (column: CHIRALPAK AS-H, 4.6 mmID×150 mmL, manufactured by Daicel Corporation, mobile phase: carbon dioxide/methanol/diethylamine=800/200/3 (v/v/v), flow rate: 4 mL/min, retention time: 3.43 min))

Example 78

3-amino-5-(dicyclopropylmethyl)-7-(5-(1,1-dioxido-thiomorpholin-4-yl)-1-methyl-1H-pyrazol-3-yl)-1,5-dihydro-4H-pyrazolo[4,3-c]pyridin-4-one

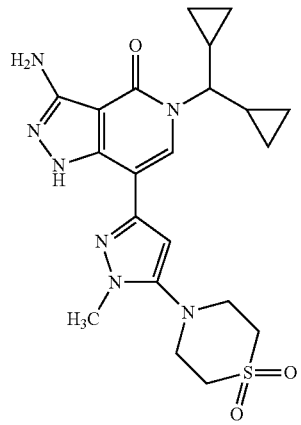 [SMILES: Cn1nc(-c2cn(C(C3CC3)C3CC3)c(=O)c3c(N)n[nH]c23)cc1N1CCS(=O)(=O)CC1]

A) 1-(dicyclopropylmethyl)-4-methoxy-2-oxo-1,2-dihydropyridine-3-carbonitrile

To a mixture of 4-methoxy-2-oxo-1,2-dihydropyridine-3-carbonitrile (5.0 g), triphenylphosphine (13.1 g), dicyclopropylmethanol (7.47 g) and tetrahydrofuran (100 mL) was added bis(2-methoxyethyl) azodicarboxylate (11.7 g) at 0° C. The reaction mixture was stirred at room temperature for 15 hr. The reaction mixture was added to water, and the mixture was extracted with ethyl acetate. The obtained organic layer was washed with water and saturated brine, and dried over anhydrous magnesium sulfate. The solvent was evaporated under reduced pressure and the residue was dissolved in diethyl ether, and triphenylphosphine oxide (5 mg) was added. Insoluble material was filtered off and the filtrate was concentrated under reduced pressure. The residue was purified by silica gel column chromatography (hexane/ethyl acetate) to give a crude purification product, which was purified by silica gel column chromatography (basic silica gel, hexane/ethyl acetate) to give a crude title compound (8.80 g).

MS (ESI+): [M+H]$^+$ 245.3.

B) 5-bromo-1-(dicyclopropylmethyl)-4-methoxy-2-oxo-1,2-dihydropyridine-3-carbonitrile A mixture of 1-(dicyclopropylmethyl)-4-methoxy-2-oxo-1,2-dihydropyridine-3-carbonitrile (1.88 g) obtained in Example 78, Step A, N-bromosuccinimide (1.78 g) and N,N-dimethylformamide (50 mL) was stirred at 60° C. for 2 hr. To the reaction mixture was further added N-bromosuccinimide (1.78 g), and the mixture was stirred at 60° C. for 1 hr. The reaction mixture was cooled to room temperature and the solvent was evaporated under reduced pressure. The residue was purified by silica gel column chromatography (hexane/ethyl acetate) to give the title compound (2.27 g).

$^1$H NMR (400 MHz, CDCl$_3$) δ0.33-0.61 (6H, m), 0.68-0.79 (2H, m), 0.96-1.17 (2H, m), 3.81 (1H, t, J=8.8 Hz), 4.44 (3H, s), 7.82 (1H, s).

C) 3-amino-7-bromo-5-(dicyclopropylmethyl)-1,5-dihydro-4H-pyrazolo[4,3-c]pyridin-4-one A mixture of 5-bromo-1-(dicyclopropylmethyl)-4-methoxy-2-oxo-1,2-dihydropyridine-3-carbonitrile (2.27 g) obtained in Example 78, Step B, hydrazine monohydrate (1.06 g) and ethanol (30 mL) was stirred at 90° C. for 1 hr. The reaction mixture was cooled to room temperature and the solvent was evaporated under reduced pressure. The residue was dissolved in ethyl acetate, tetrahydrofuran, and water, and the organic layer was washed with saturated aqueous sodium hydrogen carbonate solution and saturated brine, and dried over anhydrous magnesium sulfate. The solvent was evaporated under reduced pressure and the residue was purified by silica gel column chromatography (hexane/ethyl acetate) to give the title compound (1.99 g).

MS (ESI+): [M+H]$^+$ 323.3.

D) 3-amino-5-(dicyclopropylmethyl)-7-(5-(1,1-dioxidothiomorpholin-4-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (107 mg), potassium acetate (121 mg) and N,N-dimethylacetamide (6 mL) was stirred under an argon atmosphere at 110° C. for 4 hr. The reaction mixture was cooled to room temperature, 4-(3-bromo-1-methyl-1H-pyrazol-5-yl)thiomorpholine 1,1-dioxide (237 mg) obtained in Reference Example 16, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then methanol/ethyl acetate), and further fractionated by HPLC (C18, mobile phase: water/acetonitrile (containing 10 mM NH$_4$HCO$_3$)). To the obtained fraction was added saturated brine, and the mixture was extracted with ethyl acetate. The obtained organic layer was dried over anhydrous magnesium sulfate, and concentrated under reduced pressure. The residue was solidified from acetonitrile/diisopropyl ether/hexane to give the title compound (62 mg).

MS (ESI+): [M+H]$^+$ 458.4.

Example 79

3-amino-5-(dicyclopropylmethyl)-7-(1-methyl-5-(morpholin-4-yl)-1H-pyrazol-3-yl)-1,5-dihydro-4H-pyrazolo[4,3-c]pyridin-4-one

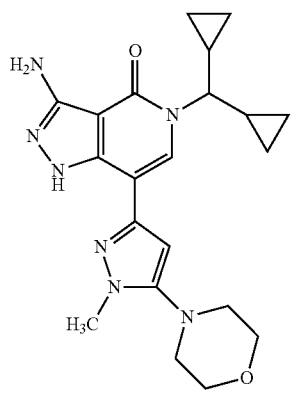

A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (107 mg), potassium acetate (121 mg) and N,N-dimethylacetamide (6 mL) was stirred under an argon atmosphere at 110° C. for 4 hr. The reaction mixture was cooled to room temperature, and 4-(3-bromo-1-methyl-1H-pyrazol-5-yl)morpholine (183 mg) obtained in Reference Example 12, aqueous sodium carbonate solution (2 M, 0.619 mL) and tetrakis(triphenylphosphine)palladium (0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid, which was further fractionated by HPLC (C18, mobile phase: water/acetonitrile (containing 10 mM NH$_4$HCO$_3$)). Ethyl acetate was added to the obtained fraction, and the mixture was washed with saturated aqueous sodium hydrogen carbonate solution and saturated brine, and dried over anhydrous magnesium sulfate. The solvent was evaporated under reduced pressure and the residue was solidified from hexane/ethyl acetate to give the title compound (97 mg).

MS (ESI+): [M+H]$^+$ 410.5.

Example 80

The compound of Example 80 was obtained by a method similar to Example 4, or a method according thereto and using alcohol corresponding to the compound of Example 80, and a halide compound corresponding to the compound of Example 80, and 4-methoxy-2-oxo-1,2-dihydropyridine-3-carbonitrile. MS in the Table shows measured values. The halide compound used for the synthesis of the compound of Example 80 was synthesized by the method described in Reference Example 12 or a method according thereto. Alcohol used for the synthesis of the compound of Example 80 was synthesized by the method described in Reference Example 74 or a method according thereto.

TABLE 4

| Ex. No. | IUPAC name | structure | MS |
|---|---|---|---|
| 78 | 3-amino-5-(dicyclopropylmethyl)-7-(5-(1,1-dioxidothiomorpholin-4-yl)-1-methyl-1H-pyrazol-3-yl)-1,5-dihydro-4H-pyrazolo[4,3-c]pyridin-4-one | 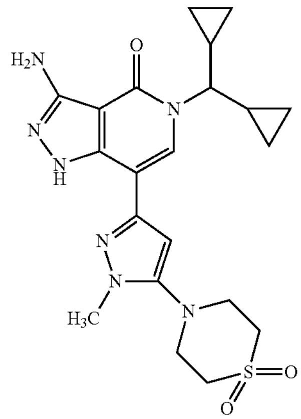 [SMILES: Cn1nc(-c2cn(C(C3CC3)C3CC3)c(=O)c3c(N)n[nH]c23)cc1N1CCS(=O)(=O)CC1] | 458.4 |
| 79 | 3-amino-5-(dicyclopropylmethyl)-7-(1-methyl-5-(morpholin-4-yl)-1H-pyrazol-3-yl)-1,5-dihydro-4H-pyrazolo[4,3-c]pyridin-4-one | 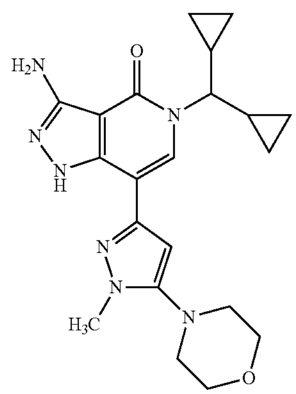 [SMILES: Cn1nc(-c2cn(C(C3CC3)C3CC3)c(=O)c3c(N)n[nH]c23)cc1N1CCOCC1] | 410.5 |
| 80 | 3-amino-5-(1,1-difluoro-3-methylbutan-2-yl)-7-(1-methyl-5-(morpholin-4-yl)-1H-pyrazol-3-yl)-1,5-dihydro-4H-pyrazolo[4,3-c]pyridin-4-one | 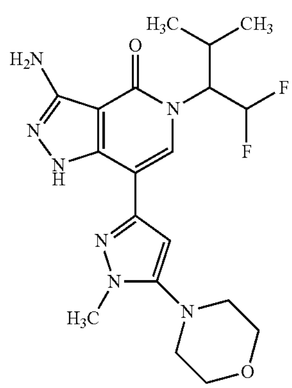 [SMILES: CC(C)C(C(F)F)n1cc(-c2cc(N3CCOCC3)n(C)n2)c2[nH]nc(N)c2c1=O] | 422.3 |

Example 81

3-amino-5-(1-(1-methylcyclopropyl)ethyl)-7-(1-methyl-5-(morpholin-4-yl)-1H-pyrazol-3-yl)-1,5-dihydro-4H-pyrazolo[4,3-c]pyridin-4-one

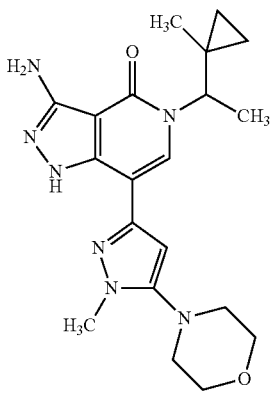 [SMILES: CC(n1cc(-c2cc(N3CCOCC3)n(C)n2)c2[nH]nc(N)c2c1=O)C1(C)CC1]

A) ethyl N-(1-(1-methylcyclopropyl)ethyl)-β-alaninate

A mixture of 1-(1-methylcyclopropyl)ethanamine hydrochloride (500 mg), ethylacrylate (369 mg), triethylamine (373 mg) and ethanol (10 mL) was stirred at room temperature for 5 days. The reaction mixture was concentrated under reduced pressure, and the residue was diluted with saturated aqueous sodium hydrogen carbonate solution, and the mixture was extracted with ethyl acetate. The extract was washed with saturated brine, and dried over anhydrous magnesium sulfate and the solvent was evaporated under reduced pressure to give the title compound (560 mg).

$^1$H NMR (300 MHz, CDCl$_3$) δ 0.12-0.27 (2H, m), 0.33-0.44 (2H, m), 0.98 (3H, s), 1.12 (3H, d, J=6.8 Hz), 1.26 (3H, t, J=7.2 Hz), 1.92 (1H, q, J=6.7 Hz), 2.00-2.50 (1H, br), 2.50-2.60 (2H, m), 2.79-2.91 (1H, m), 2.94-3.09 (1H, m), 4.15 (2H, q, J=7.2 Hz).

B) ethyl N-(cyanoacetyl)-N-(1-(1-methylcyclopropyl)ethyl)-β-alaninate

To a mixture of ethyl N-(1-(1-methylcyclopropyl)ethyl)-β-alaninate (560 mg) obtained in Example 81, Step A, cyanoacetic acid (478 mg), N,N-diisopropylethylamine (726 mg) and dry tetrahydrofuran (10 mL) was added dropwise a 50% solution (2325 mg) of 2,4,6-tripropyl-1,3,5,2,4,6-trioxatriphosphinane 2,4,6-trioxide in ethyl acetate at room temperature, and the mixture was stirred at room temperature overnight. To the reaction mixture was added water (10 mL), and the mixture was stirred for 30 min, and the mixture was extracted with ethyl acetate. The extract was washed with saturated aqueous sodium hydrogen carbonate solution and then saturated brine, and dried over anhydrous magnesium sulfate. The solvent was evaporated under reduced pressure and the residue was purified by silica gel column chromatography (basic silica gel, ethyl acetate) to give the title compound (630 mg).

MS (ESI+): [M+H]$^+$ 266.9.

C) 4-hydroxy-1-(1-(1-methylcyclopropyl)ethyl)-2-oxo-1,2,5,6-tetrahydropyridine-3-carbonitrile To a mixture of ethyl N-(cyanoacetyl)-N-(1-(1-methylcyclopropyl)ethyl)-β-alaninate (620 mg) obtained in Example 81, Step B, and dry tetrahydrofuran (5 mL) was added potassium tert-butoxide (313 mg) at room temperature, and the mixture was stirred at room temperature for 2 hr. The reaction mixture was acidified with 1 M hydrochloric acid, and the mixture was extracted with ethyl acetate. The extract was washed with saturated brine, and dried over anhydrous magnesium sulfate. The solvent was evaporated under reduced pressure. To the residue were added diisopropyl ether and ethyl acetate, and the obtained solid was dried to give the title compound (282 mg).

MS (ESI+): [M+H]$^+$ 220.9.

D) 4-methoxy-1-(1-(1-methylcyclopropyl)ethyl)-2-oxo-1,2,5,6-tetrahydropyridine-3-carbonitrile To a mixture of 4-hydroxy-1-(1-(1-methylcyclopropyl)ethyl)-2-oxo-1,2,5,6-tetrahydropyridine-3-carbonitrile (270 mg) obtained in Example 81, Step C, and dry tetrahydrofuran (10 mL) was added sodium hydride (60% in mineral oil, 51.5 mg), and the mixture was stirred at room temperature for 30 min. Dimethyl sulfate (387 mg) was added at room temperature, and the mixture was stirred under a nitrogen atmosphere at 40° C. overnight. The reaction mixture was added to water, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (ethyl acetate/hexane) to give the title compound (170 mg).

MS (ESI+): [M+H]$^+$ 234.9.

E) 4-methoxy-1-(1-(1-methylcyclopropyl)ethyl)-2-oxo-1,2-dihydropyridine-3-carbonitrile To a mixture of 4-methoxy-1-(1-(1-methylcyclopropyl)ethyl)-2-oxo-1,2,5,6-tetrahydropyridine-3-carbonitrile (160 mg) obtained in Example 81, Step D, and xylene (10 mL) was added 2,3-dichloro-5,6-dicyano-1,4-benzoquinone (171 mg), and the mixture was stirred at 140° C. for 8 hr. Furthermore, 2,3-dichloro-5,6-dicyano-1,4-benzoquinone (155 mg) was added, and the mixture was stirred at 140° C. overnight. The reaction mixture was cooled to room temperature, and concentrated under reduced pressure. The residue was purified by silica gel column chromatography (ethyl acetate) and recrystallized from ethyl acetate/hexane to give the title compound (94 mg).

MS (ESI+): [M+H]$^+$ 233.2.

F) 5-bromo-4-methoxy-1-(1-(1-methylcyclopropyl)ethyl)-2-oxo-1,2-dihydropyridine-3-carbonitrile A mixture of 4-methoxy-1-(1-(1-methylcyclopropyl)ethyl)-2-oxo-1,2-dihydropyridine-3-carbonitrile (90 mg) obtained in Example 81, Step E, N-bromosuccinimide (83 mg) and N,N-dimethylformamide (1.5 mL) was stirred at 60° C. for 4 hr. The mixture was cooled to room temperature, and the reaction mixture was added to water, and the mixture was extracted twice with ethyl acetate. The extracts were combined and washed with water and saturated brine, and

201 dried over anhydrous magnesium sulfate. The solvent was evaporated under reduced pressure and the residue was purified by silica gel column chromatography (ethyl acetate/hexane) to give the title compound (90 mg).

MS (ESI+): [M+H]$^+$ 310.9.

G) 3-amino-7-bromo-5-(1-(1-methylcyclopropyl)ethyl)-1,5-dihydro-4H-pyrazolo[4,3-c]pyridin-4-one A mixture of 5-bromo-4-methoxy-1-(1-(1-methylcyclopropyl)ethyl)-2-oxo-1,2-dihydropyridine-3-carbonitrile (90 mg) obtained in Example 81, Step F, hydrazine monohydrate (72.4 mg) and ethanol (3 mL) was stirred at 90° C. for 2 hr. The mixture was concentrated under reduced pressure, and the residue was purified by silica gel column chromatography (basic silica gel, methanol/ethyl acetate) to give the title compound (80 mg).

MS (ESI+): [M+H]$^+$ 310.9.

H) 3-amino-5-(1-(1-methylcyclopropyl)ethyl)-7-(1-methyl-5-(morpholin-4-yl)-1H-pyrazol-3-yl)-1,5-dihydro-4H-pyrazolo[4,3-c]pyridin-4-one To a mixture of 3-amino-7-bromo-5-(1-(1-methylcyclopropyl)ethyl)-1,5-dihydro-4H-pyrazolo[4,3-c]pyridin-4-one (80 mg) obtained in Example 81, Step G, 4,4,4',4',5,5,5',5'-octamethyl-2,2'-bi-1,3,2-dioxaborolane (131 mg), potassium acetate (50.5 mg) and N,N-dimethylformamide (2 mL) was added tetrakis(triphenylphosphine)palladium(0) (44.6 mg), and the mixture was stirred under an argon atmosphere at 110° C. for 3 hr. The reaction mixture was cooled to room temperature, and a solution of 4-(3-bromo-1-methyl-1H-pyrazol-5-yl)morpholine (95 mg) obtained in Reference Example 12 in N,N-dimethylformamide (1 mL), aqueous sodium carbonate solution (2 M, 0.257 mL) and tetrakis(triphenylphosphine)palladium(0) (29.7 mg) were added. Under an argon atmosphere, the reaction mixture was stirred at 120° C. for 3 hr. The reaction mixture was cooled to room temperature, water was added, and the mixture was extracted twice with ethyl acetate. The extracts were combined, washed with water and saturated brine, and dried over anhydrous magnesium sulfate. The solvent was evaporated under reduced pressure and the residue was purified by silica gel chromatography (basic silica gel, methanol/ethyl acetate), and further fractionated by HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and concentrated under reduced pressure, and the residue was crystallized from ethyl acetate/hexane to give the title compound (4 mg).

MS (ESI+): [M+H]$^+$ 398.2.

202

Example 82

3-amino-7-(1-methyl-5-(morpholin-4-yl)-1H-pyrazol-3-yl)-5-(1,1,1-trifluoro-3-methylbutan-2-yl)-1,5-dihydro-4H-pyrazolo[4,3-c]pyridin-4-one

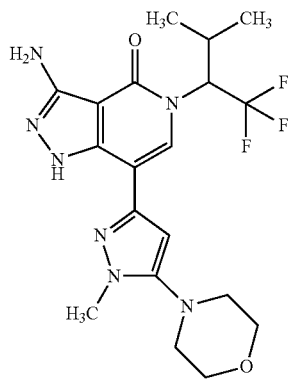 [SMILES: CC(C)C(n1cc(-c2cc(N3CCOCC3)n(C)n2)c2[nH]nc(N)c2c1=O)C(F)(F)F]

A) 2-cyano-N-(1,1,1-trifluoro-3-methylbutan-2-yl)acetamide

To a solution of 1,1,1-trifluoro-3-methylbutan-2-amine hydrochloride (1.8 g) in ethyl acetate (20 mL) were successively added 2-cyanoacetic acid (1.7 g), diisopropylethylamine (5.3 mL), and a 1.7 M solution (8.9 mL) of propylphosphonic anhydride (cyclic trimer) in ethyl acetate, and the mixture was stirred at room temperature overnight. To the reaction mixture was added saturated aqueous sodium hydrogen carbonate solution, and the mixture was extracted with ethyl acetate. The obtained organic layer was washed with saturated brine, and dried over anhydrous magnesium sulfate. The solvent was evaporated under reduced pressure and the residue was purified by silica gel column chromatography (basic silica gel, ethyl acetate) to give the title compound (2.1 g).

$^1$H NMR (400 MHz, CDCl$_3$) δ 0.97-1.09 (6H, m), 2.14-2.39 (1H, m), 3.40-3.59 (2H, m), 4.43-4.59 (1H, m), 6.12 (1H, brs).

B) 2-cyano-5,5-dimethoxy-3-oxo-N-(1,1,1-trifluoro-3-methylbutan-2-yl)pentanamide Under an ice bath, to a solution of 3,3-dimethoxypropanoic acid (2.7 g) in tetrahydrofuran (20 mL) were successively added dropwise triethylamine (4.2 mL) and methyl chlorocarbonate (1.6 mL), and the mixture was stirred at the same temperature for 30 min. The resulting salt was removed by filtration and the solvent was evaporated under reduced pressure to give a mixed acid anhydride.

To a solution of 2-cyano-N-(1,1,1-trifluoro-3-methylbutan-2-yl)acetamide (2.1 g) obtained in Example 82, Step A, in tetrahydrofuran (20 mL) was added sodium hydride (60% in mineral oil, 0.89 g) at 0° C., and the mixture was stirred at the same temperature for 30 min. Under an ice bath, to the reaction mixture was added dropwise a solution of the mixed acid anhydride obtained above in tetrahydrofuran (40 mL), and the mixture was stirred at the same temperature for 30 min. 1 M hydrochloric acid was added to the reaction mixture, and the mixture was extracted with ethyl acetate.

The obtained organic layer was washed with saturated brine, and dried over anhydrous magnesium sulfate. The solvent was evaporated under reduced pressure and the residue was purified by silica gel column chromatography (hexane/ethyl acetate) to give the title compound (4.0 g) as a crude purification product.

MS (ESI−), found: 323.1.

C) 4-hydroxy-2-oxo-1-(1,1,1-trifluoro-3-methylbutan-2-yl)-1,2-dihydropyridine-3-carbonitrile To a solution of 2-cyano-5,5-dimethoxy-3-oxo-N-(1,1,1-trifluoro-3-methylbutan-2-yl)pentanamide (4.0 g) as a crude purification product obtained in Example 82, Step B, in methanol (35 mL) was added dropwise concentrated sulfuric acid (0.65 mL), and the mixture was stirred at 80° C. overnight. Water was added to the reaction mixture, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (450 mg).

MS (ESI−), found: 259.1.

D) 4-methoxy-2-oxo-1-(1,1,1-trifluoro-3-methylbutan-2-yl)-1,2-dihydropyridine-3-carbonitrile To a solution of 4-hydroxy-2-oxo-1-(1,1,1-trifluoro-3-methylbutan-2-yl)-1,2-dihydropyridine-3-carbonitrile (450 mg) obtained in Example 82, Step C, in N,N-dimethylformamide (10 mL) were added potassium carbonate (720 mg) and methyl iodide (0.33 mL), and the mixture was stirred at 50° C. for 3 hr. Water was added to the reaction mixture, and the mixture was extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (210 mg).

MS (ESI+): [M+H]+ 275.2.

E) 5-bromo-4-methoxy-2-oxo-1-(1,1,1-trifluoro-3-methylbutan-2-yl)-1,2-dihydropyridine-3-carbonitrile To a solution of 4-methoxy-2-oxo-1-(1,1,1-trifluoro-3-methylbutan-2-yl)-1,2-dihydropyridine-3-carbonitrile (210 mg) obtained in Example 82, Step D, in N,N-dimethylformamide (7.0 mL) was added N-bromosuccinimide (200 mg), and the mixture was stirred at 50° C. for 2 hr. To the reaction mixture was added saturated aqueous sodium hydrogen carbonate solution, and the mixture was extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (120 mg).

MS (ESI+): [M+H]+ 353.2.

F) 3-amino-7-bromo-5-(1,1,1-trifluoro-3-methylbutan-2-yl)-1,5-dihydro-4H-pyrazolo[4,3-c]pyridin-4-one To a solution of 5-bromo-4-methoxy-2-oxo-1-(1,1,1-trifluoro-3-methylbutan-2-yl)-1,2-dihydropyridine-3-carbonitrile (120 mg) obtained in Example 82, Step E, in ethanol (5.0 mL) was added hydrazine monohydrate (53 mg), and the mixture was stirred at 90° C. for 1 hr. The solvent was evaporated under reduced pressure, and the residue was purified by silica gel column chromatography (hexane/ethyl acetate) to give the title compound (120 mg).

MS (ESI+): [M+H]+ 353.2.

G) 3-amino-7-(1-methyl-5-(morpholin-4-yl)-1H-pyrazol-3-yl)-5-(1,1,1-trifluoro-3-methylbutan-2-yl)-1,5-dihydro-4H-pyrazolo[4,3-c]pyridin-4-one A mixture of 3-amino-7-bromo-5-(1,1,1-trifluoro-3-methylbutan-2-yl)-1,5-dihydro-4H-pyrazolo[4,3-c]pyridin-4-one (123 mg) obtained in Example 82, Step F, 4,4,4',4',5,5,5',5'-octamethyl-2,2'-bi-1,3,2-dioxaborolane (177 mg), tetrakis(triphenylphosphine)palladium(0) (60 mg), potassium acetate (68 mg) and N,N-dimethylacetamide (6 mL) was stirred under an argon atmosphere at 110° C. for 4 hr. The reaction mixture was cooled to room temperature, 4-(3-bromo-1-methyl-1H-pyrazol-5-yl)morpholine (120 mg) obtained in Reference Example 12, aqueous sodium carbonate solution (2 M, 0.348 mL) and tetrakis(triphenylphosphine)palladium(0) (40 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid, which was further fractionated by HPLC (C18, mobile phase: water/acetonitrile (containing 0.1% TFA)). Ethyl acetate was added to the obtained fraction, and the mixture was washed with saturated aqueous sodium hydrogen carbonate solution and saturated brine, and dried over anhydrous magnesium sulfate. The solvent was evaporated under reduced pressure and the residue was solidified from hexane/diisopropyl ether to give the title compound (49 mg).

MS (ESI+): [M+H]+ 440.4.

Example 83

3-amino-5-(1-cyclopropyl-2,2,2-trifluoroethyl)-7-(1-methyl-5-(morpholin-4-yl)-1H-pyrazol-3-yl)-1,5-dihydro-4H-pyrazolo[4,3-c]pyridin-4-one

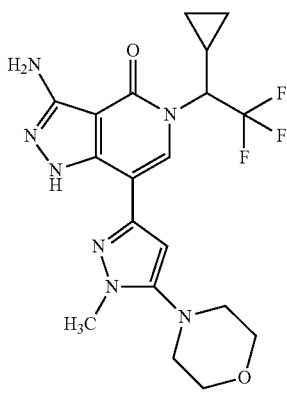 [SMILES: Cn1nc(-c2cn(C(C3CC3)C(F)(F)F)c(=O)c3c(N)n[nH]c23)cc1N1CCOCC1]

A) 2-cyano-N-(1-cyclopropyl-2,2,2-trifluoroethyl) acetamide

To a solution of 1-cyclopropyl-2,2,2-trifluoroethanamine hydrochloride (2.0 g) in tetrahydrofuran (20 mL) were successively added 2-cyanoacetic acid (1.9 g), diisopropylethylamine (6.0 mL) and a 1.7 M solution (14 mL) of propylphosphonic anhydride (cyclic trimer) in ethyl acetate, and the mixture was stirred at room temperature overnight. To the reaction mixture was added saturated aqueous sodium hydrogen carbonate solution, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (basic silica gel, ethyl acetate) to give the title compound (1.7 g).

$^1$H NMR (400 MHz, CDCl$_3$) δ 0.34-0.47 (1H, m), 0.51-0.68 (2H, m), 0.73-0.88 (1H, m), 1.07 (1H, dtt, J=9.6, 8.1, 4.8 Hz), 3.48 (2H, d, J=1.5 Hz), 3.93 (1H, tq, J=9.5, 7.1 Hz), 6.80 (1H, brs).

B) 2-cyano-N-(1-cyclopropyl-2,2,2-trifluoroethyl)-5,5-dimethoxy-3-oxopentanamide Under an ice bath, to a solution of 3,3-dimethoxypropanoic acid (2.2 g) in tetrahydrofuran (20 mL) were successively added dropwise triethylamine (3.5 mL) and methyl chlorocarbonate (0.98 mL), and the mixture was stirred at the same temperature for 30 min. The resulting salt was removed by filtration and the solvent was evaporated under reduced pressure to give a mixed acid anhydride.

To a solution of 2-cyano-N-(1-cyclopropyl-2,2,2-trifluoroethyl)acetamide (1.7 g) obtained in Example 83, Step A, in tetrahydrofuran (20 mL) was added sodium hydride (60% in mineral oil, 0.73 g) at 0° C., and the mixture was stirred at the same temperature for 30 min. Under an ice bath, to the reaction mixture was added dropwise a solution of the mixed acid anhydride obtained above in tetrahydrofuran (40 mL), and the mixture was stirred at the same temperature for 30 min. To the reaction mixture was added 1 M hydrochloric acid, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (hexane/ethyl acetate, then methanol/ethyl acetate) to give the title compound (2.4 g).

MS (ESI−), found: 321.2.

C) 1-(1-cyclopropyl-2,2,2-trifluoroethyl)-4-hydroxy-2-oxo-1,2-dihydropyridine-3-carbonitrile To a solution of 2-cyano-N-(1-cyclopropyl-2,2,2-trifluoroethyl)-5,5-dimethoxy-3-oxopentanamide (2.4 g) obtained in Example 83, Step B, in methanol (30 mL) was added dropwise 2 M hydrochloric acid (37 mL), and the mixture was stirred at 80° C. for 48 hr. Water was added to the reaction mixture, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate, and then methanol/ethyl acetate) to give the title compound (1.0 g) as a crude purification product.

MS (ESI−), found: 257.1.

D) 1-(1-cyclopropyl-2,2,2-trifluoroethyl)-4-methoxy-2-oxo-1,2-dihydropyridine-3-carbonitrile To a solution of the crude purification product of 1-(1-cyclopropyl-2,2,2-trifluoroethyl)-4-hydroxy-2-oxo-1,2-dihydropyridine-3-carbonitrile (1.0 g) obtained in Example 83, Step C, in N,N-dimethylformamide (10 mL) were added potassium carbonate (1.6 g) and methyl iodide (0.73 mL), and the mixture was stirred under a nitrogen atmosphere at 50° C. for 3 hr. Water was added to the reaction mixture, and the mixture was extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (180 mg).

MS (ESI+): [M+H]$^+$ 273.2.

E) 5-bromo-1-(1-cyclopropyl-2,2,2-trifluoroethyl)-4-methoxy-2-oxo-1,2-dihydropyridine-3-carbonitrile To a solution of 1-(1-cyclopropyl-2,2,2-trifluoroethyl)-4-methoxy-2-oxo-1,2-dihydropyridine-3-carbonitrile (180 mg) obtained in Example 83, Step D, in N,N-dimethylformamide (7.0 mL) was added N-bromosuccinimide (180 mg), and the mixture was stirred at 50° C. for 2 hr. To the reaction mixture was added saturated aqueous sodium hydrogen carbonate solution, and the mixture was extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (180 mg).

MS (ESI+): [M+H]$^+$ 351.2.

F) 3-amino-7-bromo-5-(1-cyclopropyl-2,2,2-trifluoroethyl)-1,5-dihydro-4H-pyrazolo[4,3-c]pyridin-4-one To a solution of 5-bromo-1-(1-cyclopropyl-2,2,2-trifluoroethyl)-4-methoxy-2-oxo-1,2-dihydropyridine-3-carbonitrile (180 mg) obtained in Example 83, Step E, in ethanol (30 mL) was added hydrazine monohydrate (78 mg), and the mixture was stirred at 90° C. for 1 hr. The solvent was evaporated under reduced pressure, and ethyl acetate/tetrahydrofuran/water was added to the residue. The organic layer was separated, washed successively with saturated aqueous sodium hydrogen carbonate solution and saturated brine, and dried over anhydrous magnesium sulfate. The solvent was evaporated under reduced pressure and the residue was purified by silica gel column chromatography (hexane/ethyl acetate) to give the title compound (170 mg).

MS (ESI+): [M+H]$^+$ 351.2.

G) 3-amino-5-(1-cyclopropyl-2,2,2-trifluoroethyl)-7-(1-methyl-5-(morpholin-4-yl)-1H-pyrazol-3-yl)-1,5-dihydro-4H-pyrazolo[4,3-c]pyridin-4-one A mixture of 3-amino-7-bromo-5-(1-cyclopropyl-2,2,2-trifluoroethyl)-1,5-dihydro-4H-pyrazolo[4,3-c]pyridin-4-one (165 mg) obtained in Example 83, Step F, 4,4,4',4',5,5, 5',5'-octamethyl-2,2'-bi-1,3,2-dioxaborolane (239 mg), tetrakis(triphenylphosphine)palladium(0) (81 mg), potassium acetate (92 mg) and N,N-dimethylacetamide (6 mL) was stirred under an argon atmosphere at 110° C. for 4 hr. The reaction mixture was cooled to room temperature, 4-(3-bromo-1-methyl-1H-pyrazol-5-yl)morpholine (162 mg) obtained in Reference Example 12, aqueous sodium carbonate solution (2 M, 0.470 mL) and tetrakis(triphenylphosphine)palladium(0) (54 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid, which was further fractionated by HPLC (C18, mobile phase: water/acetonitrile (containing 10 mM $NH_4HCO_3$)). Ethyl acetate was added to the obtained fraction, and the mixture was washed with saturated aqueous sodium hydrogen carbonate solution and saturated brine, and dried over anhydrous magnesium sulfate. The solvent was evaporated under reduced pressure and the residue was solidified from hexane/ethyl acetate to give the title compound (27 mg).

MS (ESI+): $[M+H]^+$ 438.4.

Example 84 ethyl 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanoate

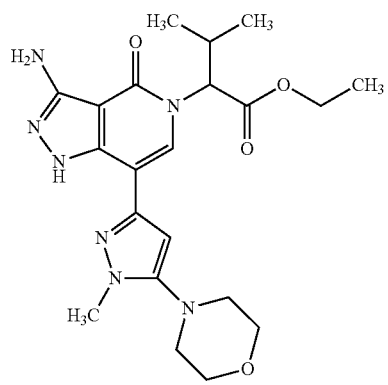 [SMILES: CCOC(=O)C(C(C)C)n1cc(-c2cc(N3CCOCC3)n(C)n2)c2[nH]nc(N)c2c1=O]

A) ethyl 2-(3-cyano-4-methoxy-2-oxopyridin-1(2H)-yl)-3-methylbutanoate

A mixture of 4-methoxy-2-oxo-1,2-dihydropyridine-3-carbonitrile (5.0 g), ethyl 2-bromo-3-methylbutanoate (10.4 g), cesium carbonate (32.6 g) and N,N-dimethylformamide (75 mL) was stirred at 50° C. overnight. The reaction mixture was added to water, and the mixture was extracted twice with ethyl acetate. The extracts were combined, washed with water and then saturated brine, and dried over anhydrous magnesium sulfate. The solvent was evaporated under reduced pressure and the residue was purified by silica gel column chromatography (ethyl acetate/hexane) to give the title compound (6.11 g).

MS (ESI+): $[M+H]^+$ 279.2.

B) ethyl 2-(3-amino-7-bromo-4-oxo-1,4-dihydro-5H-pyrazolo[4,3-c]pyridin-5-yl)-3-methylbutanoate In the same manner as in Example 81, Steps F to G, the title compound was obtained from ethyl 2-(3-cyano-4-methoxy-2-oxopyridin-1(2H)-yl)-3-methylbutanoate obtained in Example 84, Step A.

MS (ESI+): $[M+H]^+$ 357.1.

C) ethyl 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanoate In the same manner as in Example 81, Step H, the title compound was obtained from ethyl 2-(3-amino-7-bromo-4-oxo-1,4-dihydro-5H-pyrazolo[4,3-c]pyridin-5-yl)-3-methylbutanoate obtained in Example 84, Step B, and 4-(3-bromo-1-methyl-1H-pyrazol-5-yl)morpholine obtained in Reference Example 12.

MS (ESI+): $[M+H]^+$ 444.2.

Example 85

2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanamide

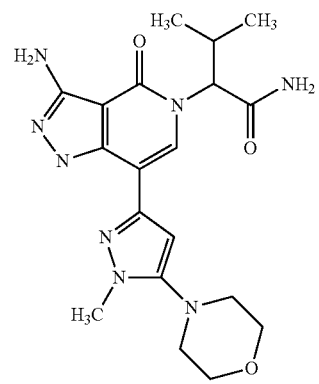 [SMILES: CC(C)C(C(N)=O)n1cc(-c2cc(N3CCOCC3)n(C)n2)c2[nH]nc(N)c2c1=O]

A) 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanoic acid To a mixture of ethyl 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanoate (780 mg) obtained in Example 84 and ethanol (10 mL) was added 2 M aqueous sodium hydroxide solution (3.52 mL), and the mixture was stirred at room temperature for 2 hr. The reaction mixture was added to water, and the aqueous layer was washed with diethyl ether, neutralized with 1 M hydrochloric acid under ice-cooling, and extracted 5 times with ethyl acetate-tetrahydrofuran. The extracts were combined, washed with saturated brine, and dried over anhydrous magnesium sulfate. The solvent was evaporated under reduced pressure to give the title compound (660 mg).

MS (ESI+): $[M+H]^+$ 416.2.

B) 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanamide To a mixture of 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanoic acid (660 mg) obtained in Example 85, Step A, 1H-benzo[d][1,2,3]triazol-1-ol ammonium salt (363 mg), triethylamine (0.443 mL) and N,N-dimethylformamide (10 mL) was added 1-(3-dimethylaminopropyl)-3-ethylcarbodiimide hydrochloride (457 mg), and the mixture was stirred at room temperature overnight. The reaction mixture was diluted with saturated aqueous sodium hydrogen carbonate solution, and extracted 5 times with ethyl acetate-tetrahydrofuran. The extracts were combined, washed with saturated brine, and dried over anhydrous magnesium sulfate. The solvent was evaporated under reduced pressure and the residue was washed with a mixed solvent of N,N-dimethylformamide-ethyl acetate-diisopropyl ether, and dried under reduced pressure to give the title compound (512 mg).

MS (ESI+): [M+H]$^+$ 415.3.

Example 86

3-amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one hydrochloride

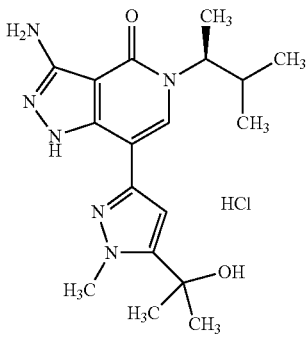 [SMILES: CC(C)[C@H](C)n1cc(-c2cc(C(C)(C)O)n(C)n2)c2[nH]nc(N)c2c1=O ; Cl]

To a solution of 3-amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one (350 mg) obtained in Example 1, Step H, in ethanol (5 mL) was added hydrochloric acid (2.0 M aqueous solution, 0.49 mL) at 0° C., and the mixture was stirred at room temperature for 1 hr. The solvent was evaporated under reduced pressure and the obtained residue was recrystallized (ethanol/ethyl acetate) to give the title compound (284 mg).

$^1$H NMR (400 MHz, DMSO-d$_6$) δ 0.66 (3H, d, J=6.6 Hz), 1.02 (3H, d, J=6.6 Hz), 1.35 (3H, d, J=6.8 Hz), 1.54 (6H, s), 2.02-2.15 (1H, m), 3.18-3.97 (5H, m), 4.04 (3H, s), 4.63-4.71 (1H, m), 6.74 (1H, s), 7.73 (1H, s).

MS (ESI+): [M+H]$^+$ 359.4.

Example 87

3-amino-5-((1S)-1-cyclopropylethyl)-7-(1-methyl-5-(morpholin-4-yl)-1H-pyrazol-3-yl)-1,5-dihydro-4H-pyrazolo[4,3-c]pyridin-4-one

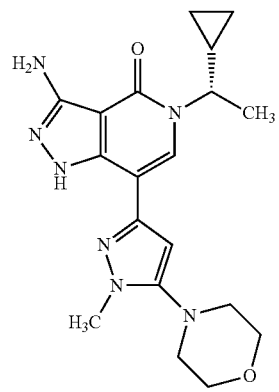 [SMILES: C[C@@H](C1CC1)n1cc(-c2cc(N3CCOCC3)n(C)n2)c2[nH]nc(N)c2c1=O]

A mixture of 3-amino-7-bromo-5-((1S)-1-cyclopropylethyl)-1,5-dihydro-4H-pyrazolo[4,3-c]pyridin-4-one (200 mg) obtained in Example 7, Step A, 4,4,4',4',5,5,5',5'-octamethyl-2,2'-bi-1,3,2-dioxaborolane (342 mg), tetrakis(triphenylphosphine)palladium(0) (117 mg), potassium acetate (132 mg) and N,N-dimethylacetamide (3 mL) was stirred under an argon atmosphere at 110° C. for 5 hr. The reaction mixture was cooled to room temperature, and a solution of 4-(3-bromo-1-methyl-1H-pyrazol-5-yl)morpholine (248 mg) obtained in Reference Example 12 in N,N-dimethylacetamide (0.5 mL), aqueous sodium carbonate solution (2 M, 0.673 mL) and tetrakis(triphenylphosphine)palladium(0) (78 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give a yellow solid. The obtained solid was solidified from ethyl acetate/hexane to give a crude purification product. The crude purification product was recrystallized from ethyl acetate/methanol to give the title compound (52 mg).

MS (ESI+): [M+H]$^+$ 384.4.

$^1$H NMR (400 MHz, CDCl$_3$) δ 0.33-0.41 (1H, m), 0.45-0.54 (2H, m), 0.68-0.77 (1H, m), 1.09-1.20 (1H, m), 1.45 (3H, d, J=6.8 Hz), 2.93-3.01 (4H, m), 3.78 (3H, s), 3.83-3.90 (4H, m), 4.36-4.52 (1H, m), 4.74 (2H, brs), 6.03 (1H, s), 7.52 (1H, s), 10.46 (1H, brs).

>99% ee (SFC (column: CHIRALPAK ASH, 4.6 mmID×250 mmL, manufactured by Daicel Corporation, mobile phase: carbon dioxide/methanol/diethylamine=800/200/3 (v/v/v), flow rate: 3 mL/min, retention time: 4.84 min))

Example 88

3-amino-5-(dicyclopropylmethyl)-7-(5-(2,2-dimethyl-1,1-dioxidothiomorpholin-4-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (110 mg)

obtained in Example 78, Step C, 4,4,4',4',5,5,5',5'-octamethyl-2,2'-bi-1,3,2-dioxaborolane (173 mg), tetrakis(triphenylphosphine)palladium(0) (59 mg), potassium acetate (67 mg) and N,N-dimethylacetamide (3 mL) was stirred under an argon atmosphere at 110° C. for 4 hr. The reaction mixture was cooled to room temperature, and a mixture of 4-(3-bromo-1-methyl-1H-pyrazol-5-yl)-2,2-dimethylthiomorpholine 1,1-dioxide (165 mg) obtained in Reference Example 75 and N,N-dimethylacetamide (1.5 mL), aqueous sodium carbonate solution (2 M, 0.34 mL) and tetrakis (triphenylphosphine)palladium(0) (39 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 5 mM $NH_4HCO_3$)), and the obtained fraction was concentrated under reduced pressure. The residue was solidified from ethyl acetate/diisopropyl ether to give the title compound (8 mg).

Example 89

3-amino-5-(dicyclopropylmethyl)-7-(5-(1-isobutyryl-3-methoxyazetidin-3-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, and a mixture of 1-(3-(3-bromo-1-methyl-1H-pyrazol-5-yl)-3-methoxyazetidin-1-yl)-2-methylpropan-1-one (235 mg) obtained in Reference Example 76 and N,N-dimethylacetamide (0.5 mL), aqueous sodium carbonate solution (2 M, 0.62 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (77 mg).

Example 90

3-amino-5-(dicyclopropylmethyl)-7-(5-(1-(isopropylsulfonyl)-3-methoxyazetidin-3-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, and a mixture of 3-bromo-5-(1-(isopropylsulfonyl)-3-methoxyazetidin-3-yl)-1-methyl-1H-pyrazole (262 mg) obtained in Reference Example 77 and N,N-dimethylacetamide (1.5 mL), aqueous sodium carbonate solution (2 M, 0.62 mL) and tetrakis (triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed successively with water and saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). The obtained fraction was concentrated under reduced pressure. Ethyl acetate was added to the obtained mixture and the mixture was washed successively with saturated aqueous sodium hydrogen carbonate solution, water and saturated brine, dried over anhydrous magnesium sulfate and concentrated under reduced pressure. The residue was solidified from ethyl acetate/hexane. The residue was purified by silica gel chromatography (diol silica gel, hexane/ethyl acetate) and solidified from hexane/ethyl acetate to give the title compound (68 mg).

Example 91

3-amino-5-((1R)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one A) 3-amino-7-bromo-5-((1R)-1-cyclopropylethyl)-1,5-dihydro-4H-pyrazolo[4,3-c]pyridin-4-one A racemate (1.1 g) of 3-amino-7-bromo-5-(1-cyclopropylethyl)-1,5-dihydro-4H-pyrazolo[4,3-c]pyridin-4-one obtained in Example 4, Step C, was fractionated by HPLC (column: CHIRALPAK AD, 50 mmID×500 mmL, manufactured by Daicel Corporation, mobile phase: hexane/ethanol=800/200 (v/v)) to give the title compound (539 mg) having a longer retention time.
MS (ESI+): [M+H]$^+$ 297.1.
>99.9% ee (HPLC (column: CHIRALPAK AD, 4.6 mmID×250 mmL, manufactured by Daicel Corporation, mobile phase: hexane/ethanol=800/200 (v/v), flow rate: 1.0 mL/min, retention time: 10.95 min))

B) 3-amino-5-((1R)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one A mixture of 3-amino-7-bromo-5-((1R)-1-cyclopropylethyl)-1,5-dihydro-4H-pyrazolo[4,3-c]pyridin-4-one (300 mg) obtained in Example 91, Step A, 4,4,4',4',5,5,5',5'-octamethyl-2,2'-bi-1,3,2-dioxaborolane (513 mg), tetrakis (triphenylphosphine)palladium(0) (175 mg), potassium acetate (198 mg) and N,N-dimethylacetamide (6 mL) was stirred under an argon atmosphere at 110° C. for 4 hr. The reaction mixture was cooled to room temperature, and a mixture of 2-(3-bromo-1-methyl-1H-pyrazol-5-yl)propan-2- ol (332 mg) obtained in Reference Example 4 and N,N-dimethylacetamide (3 mL), aqueous sodium carbonate solution (2 M, 1.01 mL) and tetrakis(triphenylphosphine)palladium(0) (117 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the mixture was concentrated under reduced pressure and extracted with ethyl acetate. The extract was dried over anhydrous magnesium sulfate, and concentrated under reduced pressure. The residue was solidified from ethyl acetate/hexane to give the title compound (141 mg).

Example 92

3-amino-5-((1S)-1-cyclopropylethyl)-7-(5-(4-isopropyl-3-oxopiperazin-1-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (200 mg) obtained in Example 7, Step A, 4,4,4',4',5,5,5',5'-octamethyl-2,2'-bi-1,3,2-dioxaborolane (342 mg), tetrakis(triphenylphosphine)palladium(0) (117 mg), potassium acetate (132 mg) and N,N-dimethylacetamide (3 mL) was stirred under an argon atmosphere at 110° C. for 3 hr. The reaction mixture was cooled to room temperature, and a mixture of 4-(3-bromo-1-methyl-1H-pyrazol-5-yl)-1-isopropylpiperazin-2-one (304 mg) obtained in Reference Example 78 and N,N-dimethylacetamide (1.5 mL), aqueous sodium carbonate solution (2 M, 0.67 mL) and tetrakis(triphenylphosphine) palladium(0) (78 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/methanol). The residue was solidified from acetonitrile to give the title compound (57 mg).

Example 93

3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one hydrochloride To a mixture of 3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one (6.0 g) obtained in Example 7, Step B, and ethyl acetate (50 mL) was added 4N hydrochloric acid in ethyl acetate solution (5.05 mL) at 0° C., and the mixture was stirred at 0° C. for 2 hr. Crystals were collected by filtration and the obtained crystals were recrystallized (ethanol/heptane) and dried at 50° C. for 3 hr to give the title compound (2.43 g).

1H NMR (400 MHz, DMSO-d6) δ 0.12-0.22 (1H, m), 0.36-0.47 (2H, m), 0.58-0.70 (1H, m), 1.38-1.48 (4H, m), 1.54 (6H, s), 4.04 (3H, s), 4.16-4.24 (1H, m), 6.71 (1H, s), 7.90 (1H, brs).

Example 94

3-amino-5-((1S)-1-cyclopropylethyl)-7-(5-(4-hydroxy-4-(trifluoromethyl)piperidin-1-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (200 mg) obtained in Example 7, Step A, 4,4,4',4',5,5,5',5'-octamethyl-2,2'-bi-1,3,2-dioxaborolane (342 mg), tetrakis(triphenylphosphine)palladium(0) (117 mg), potassium acetate (132 mg) and N,N-dimethylacetamide (6 mL) was stirred under an argon atmosphere at 110° C. for 4 hr. The reaction mixture was cooled to room temperature, 1-(3-bromo-1-methyl-1H-pyrazol-5-yl)-4-(trifluoromethyl)piperidin-4-ol (265 mg) obtained in Reference Example 79, aqueous sodium carbonate solution (2 M, 0.67 mL) and tetrakis(triphenylphosphine)palladium(0) (78 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 10 mM NH4HCO3)) to the obtained fraction was added saturated aqueous sodium hydrogen carbonate solution, and the mixture was extracted with ethyl acetate. The extract was dried over anhydrous magnesium sulfate, and concentrated under reduced pressure. The residue was solidified from ethyl acetate/hexane to give the title compound (135 mg).

Example 95

3-amino-5-((1S)-1-cyclopropylethyl)-7-(5-(2,2-dimethyl-1,1-dioxidothiomorpholin-4-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (110 mg) obtained in Example 7, Step A, 4,4,4',4',5,5,5',5'-octamethyl-2,2'-bi-1,3,2-dioxaborolane (188 mg), tetrakis(triphenylphosphine)palladium(0) (64 mg), potassium acetate (73 mg) and N,N-dimethylacetamide (3 mL) was stirred under an argon atmosphere at 110° C. for 4 hr. The reaction mixture was cooled to room temperature, and a mixture of 4-(3-bromo-1-methyl-1H-pyrazol-5-yl)-2,2-dimethylthiomorpholine 1,1-dioxide (165 mg) obtained in Reference Example 75 and N,N-dimethylacetamide (1.5 mL), aqueous sodium carbonate solution (2 M, 0.37 mL) and tetrakis (triphenylphosphine)palladium(0) (43 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (69 mg).

Example 96

3-amino-5-((1S)-1-cyclopropylethyl)-7-(5-(1,1-dioxidothiomorpholin-4-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (200 mg) obtained in Example 7, Step A, 4,4,4',4',5,5,5',5'-octamethyl-2,2'-bi-1,3,2-dioxaborolane (342 mg), tetrakis(triphenylphosphine)palladium(0) (78 mg), potassium acetate (132 mg) and N,N-dimethylacetamide (3 mL) was stirred under an argon atmosphere at 110° C. for 4 hr. The reaction mixture was cooled to room temperature, 4-(3-bromo-1-methyl-1H-pyrazol-5-yl)thiomorpholine 1,1-dioxide (297 mg) obtained in Reference Example 16, aqueous sodium carbonate solution (2 M, 0.67 mL) and tetrakis(triphenylphosphine)palladium(0) (78 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 10 mM $NH_4HCO_3$)), and concentrated under reduced pressure. The residue was solidified from ethyl acetate/hexane to give the title compound (143 mg).

Example 97

3-amino-5-((1S)-1-cyclopropylethyl)-7-(5-(1-isobutyryl-3-methoxyazetidin-3-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (150 mg) obtained in Example 7, Step A, 4,4,4',4',5,5,5',5'-octamethyl-2,2'-bi-1,3,2-dioxaborolane (256 mg), tetrakis(triphenylphosphine)palladium(0) (58 mg), potassium acetate (99 mg) and N,N-dimethylacetamide (2 mL) was stirred under an argon atmosphere at 110° C. for 4 hr. The reaction mixture was cooled to room temperature, and a mixture of 1-(3-(3-bromo-1-methyl-1H-pyrazol-5-yl)-3-methoxyazetidin-1-yl)-2-methylpropan-1-one (192 mg) obtained in Reference Example 76 and N,N-dimethylacetamide (2 mL), aqueous sodium carbonate solution (2 M, 0.51 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed successively with water and saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)), and the solvent was concentrated under reduced pressure. Ethyl acetate was added to the residue, and the mixture was washed successively with saturated aqueous sodium hydrogen carbonate solution, water and saturated brine, and dried over anhydrous magnesium sulfate. The solvent was evaporated under reduced pressure and the residue was solidified from ethyl acetate/hexane to give the title compound (53 mg).

Example 98

3-amino-5-((1S)-1-cyclopropylethyl)-7-(5-(1-(isopropylsulfonyl)-3-methoxyazetidin-3-yl)-1-methyl-1H-pyrazol-3-yl)-1,5-dihydro-4H-pyrazolo[4,3-c]pyridin-4-one A mixture of 3-amino-7-bromo-5-((1S)-1-cyclopropylethyl)-1,5-dihydro-4H-pyrazolo[4,3-c]pyridin-4-one (150 mg) obtained in Example 7, Step A, 4,4,4',4',5,5,5',5'-octamethyl-2,2'-bi-1,3,2-dioxaborolane (256 mg), tetrakis(triphenylphosphine)palladium(0) (58 mg), potassium acetate (99 mg) and N,N-dimethylacetamide (2 mL) was stirred under an argon atmosphere at 110° C. for 4 hr. The reaction mixture was cooled to room temperature, and a mixture of 3-bromo-5-(1-(isopropylsulfonyl)-3-methoxyazetidin-3-yl)-1-methyl-1H-pyrazole (213 mg) obtained in Reference Example 77 and N,N-dimethylacetamide (1.5 mL), aqueous sodium carbonate solution (2 M, 0.51 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (91 mg).

Example 99

3-amino-5-(3-hydroxy-3-methylbutan-2-yl)-7-(1-methyl-5-(morpholin-4-yl)-1H-pyrazol-3-yl)-1,5-dihydro-4H-pyrazolo[4,3-c]pyridin-4-one A) ethyl 2-(3-cyano-4-methoxy-2-oxopyridin-1 (2H)-yl)propanoate A mixture of 4-methoxy-2-oxo-1,2-dihydropyridine-3-carbonitrile (5.56 g), ethyl 2-bromopropanoate (10.1 g), cesium carbonate (36.2 g) and N,N-dimethylformamide (75 mL) was stirred at 50° C. overnight. The reaction mixture was added to water, and the mixture was extracted 3 times with ethyl acetate. The extracts were combined, washed with water and then saturated brine, and dried over anhydrous magnesium sulfate. The solvent was evaporated under reduced pressure and the residue was purified by silica gel column chromatography (ethyl acetate/hexane). The obtained solid was washed with ethyl acetate/diisopropyl ether to give the title compound (6.12 g).

MS (ESI+): [M+H]+ 250.8.

B) ethyl 2-(5-bromo-3-cyano-4-methoxy-2-oxopyridin-1(2H)-yl)propanoate

To a solution of ethyl 2-(3-cyano-4-methoxy-2-oxopyridin-1(2H)-yl)propanoate (6.1 g) obtained in Example 99, Step A in N,N-dimethylformamide (60 mL) was added N-bromosuccinimide (5.21 g), and the mixture was stirred at 50° C. for 2 hr. The solvent was concentrated under reduced pressure to about half, saturated aqueous sodium hydrogen carbonate solution was added, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (hexane/ethyl acetate) to give the title compound (6.41 g).

MS (ESI+): [M+H]328.8.

C) ethyl 2-(3-amino-7-bromo-4-oxo-1,4-dihydro-5H-pyrazolo[4,3-c]pyridin-5-yl)propanoate A mixture of ethyl 2-(5-bromo-3-cyano-4-methoxy-2-oxopyridin-1(2H)-yl)propanoate (3.0 g) obtained in Example 99, Step B, hydrazine monohydrate (1.37 g), and ethanol (40 mL) was stirred at 90° C. for 40 min. The reaction mixture was allowed to cool to room temperature, water was added, and the mixture was extracted twice with ethyl acetate. The organic layer was successively washed with water and saturated brine, and dried over anhydrous magnesium sulfate. The solvent was evaporated under reduced pressure and the residue was purified by silica gel column chromatography (ethyl acetate/hexane) to give the title compound (2.36 g).

MS (ESI+): [M+H]+ 328.8.

D) ethyl 2-(3-amino-7-(1-methyl-5-(morpholin-4-yl)-1H-pyrazol-3-yl)-4-oxo-1,4-dihydro-5H-pyrazolo[4,3-c]pyridin-5-yl)propanoate A mixture of ethyl 2-(3-amino-7-bromo-4-oxo-1,4-dihydro-5H-pyrazolo[4,3-c]pyridin-5-yl)propanoate (1.00 g) obtained in Example 99, Step C, 4,4,4',4',5,5,5',5'-octamethyl-2,2'-bi-1,3,2-dioxaborolane (1.54 g), tetrakis(triphenylphosphine)palladium(0) (527 mg), potassium acetate (596 mg) and N,N-dimethylformamide (3 mL) was stirred under an argon atmosphere at 110° C. for 3 hr. The reaction mixture was cooled to room temperature, and a mixture of 4-(3-bromo-1-methyl-1H-pyrazol-5-yl)morpholine (1.12 g) obtained in Reference Example 12 and N,N-dimethylformamide (3 mL), aqueous sodium carbonate solution (2 M, 3.04 mL) and tetrakis(triphenylphosphine)palladium(0) (351 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel column chromatography (basic silica gel, ethyl acetate/methanol). The obtained yellow solid was washed with ethyl acetate/diisopropyl ether to give the title compound (305 mg).

MS (ESI+): [M+H]416.3.

E) 3-amino-5-(3-hydroxy-3-methylbutan-2-yl)-7-(1-methyl-5-(morpholin-4-yl)-1H-pyrazol-3-yl)-1,5-dihydro-4H-pyrazolo[4,3-c]pyridin-4-one To a mixture of ethyl 2-(3-amino-7-(1-methyl-5-(morpholin-4-yl)-1H-pyrazol-3-yl)-4-oxo-1,4-dihydro-5H-pyrazolo[4,3-c]pyridin-5-yl)propanoate obtained in Example 99, Step D and tetrahydrofuran (7 mL) was added methylmagnesium bromide (3 M, diethyl ether solution) (0.64 mL) at −78° C. Under an argon atmosphere, the reaction mixture was stirred at −78° C. for 1 hr and at room temperature overnight. To the reaction mixture was added saturated aqueous ammonium chloride solution at 0° C., and the mixture was extracted twice with ethyl acetate. The obtained organic layer was washed with saturated brine, and dried over anhydrous magnesium sulfate. The solvent was evaporated under reduced pressure and the residue was purified by silica gel column chromatography (basic silica gel, methanol/ethyl acetate) and then by silica gel column chromatography (diol silica gel, ethyl acetate). The obtained solid was crystallized from acetonitrile/ethyl acetate/diisopropyl ether to give the title compound (10 mg).

Example 100

3-amino-7-(5-(2-hydroxypropan-2-yl)-1-methyl-1H-pyrazol-3-yl)-5-((2R)-3-methylbutan-2-yl)-1,5-dihydro-4H-pyrazolo[4,3-c]pyridin-4-one A) 3-amino-7-bromo-5-(3-methylbutan-2-yl)-1,5-dihydro-4H-pyrazolo[4,3-c]pyridin-4-one A racemate (7.89 g) of 3-amino-7-bromo-5-(3-methylbutan-2-yl)-1,5-dihydro-4H-pyrazolo[4,3-c]pyridin-4-one obtained in Example 2, Step G, was fractionated by HPLC (column: CHIRALPAK AD, 50 mmID×500 mmL, manufactured by Daicel Corporation, mobile phase: hexane/ethanol=600/400 (v/v)) to give the title compound (3.48 g) having a longer retention time.

MS (ESI+): [M+H]+ 299.1.

>99.9% ee (HPLC (column: CHIRALPAK AD, 4.6 mmID×250 mmL, manufactured by Daicel Corporation, mobile phase: hexane/ethanol=600/400 (v/v), flow rate: 0.5 mL/min, retention time: 12.14 min))

B) 3-amino-7-(5-(2-hydroxypropan-2-yl)-1-methyl-1H-pyrazol-3-yl)-5-((2R)-3-methylbutan-2-yl)-1,5-dihydro-4H-pyrazolo[4,3-c]pyridin-4-one A mixture of 3-amino-7-bromo-5-(3-methylbutan-2-yl)-1,5-dihydro-4H-pyrazolo[4,3-c]pyridin-4-one (200 mg) obtained in Example 100, Step A, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (6 mL) was stirred under an argon atmosphere at 110° C. for 4 hr. The reaction mixture was cooled to room temperature, 2-(3-bromo-1-methyl-1H-pyrazol-5-yl)propan-2-ol (146 mg) obtained in Reference Example 4, aqueous sodium carbonate solution (2 M, 0.67 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (109 mg).

Example 101

3-amino-7-(5-(isopropyl(methyl)amino)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (87 mg), potassium acetate (98 mg) and N,N-dimethylacetamide (3 mL) was stirred under an argon atmosphere at 110° C. for 4 hr. The reaction mixture was cooled to room temperature, 3-bromo-N-isopropyl-N,1-dimethyl-1H-pyrazol-5-amine (175 mg) obtained in Reference Example 80, aqueous sodium carbonate solution (2 M, 0.50 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (219 mg).

Example 102

3-amino-7-(5-(4-(isopropylsulfonyl)piperazin-1-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (190 mg) obtained in Example 1, Step G, 4,4,4',4',5,5,5',5'-octamethyl-2,2'-bi-1,3,2-dioxaborolane (323 mg), tetrakis(triphenylphosphine)palladium(0) (110 mg), potassium acetate (125 mg) and N,N-dimethylacetamide (3 mL) was stirred under an argon atmosphere at 110° C. for 4 hr. The reaction mixture was cooled to room temperature, and a mixture of 1-(3-bromo-1-methyl-1H-pyrazol-5-yl)-4-(isopropylsulfonyl)piperazine (335 mg) obtained in Reference Example 81 and N,N-dimethylacetamide (1 mL), aqueous sodium carbonate solution (2 M, 0.64 mL) and tetrakis(triphenylphosphine)palladium(0) (73 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate), and the residue was solidified from ethyl acetate/diisopropyl ether to give the title compound (166 mg).

Example 103

3-amino-7-(5-(2-((dimethylamino)methyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (77 mg), potassium acetate (131 mg) and N,N-dimethylacetamide (3 mL) was stirred under an argon atmosphere at 110° C. for 4 hr. The reaction mixture was cooled to room temperature, and a mixture of 1-(1-(3-bromo-1-methyl-1H-pyrazol-5-yl)pyrrolidin-2-yl)-N,N-dimethylmethanamine (288 mg) obtained in Reference Example 82 and N,N-dimethylacetamide (2.0 mL), aqueous sodium carbonate solution (2 M, 0.70 mL) and tetrakis(triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed successively with water and saturated brine, and dried over anhydrous magnesium sulfate. The solvent was evaporated under reduced pressure and the residue was purified by silica gel chromatography (basic silica gel, hexane/ethyl acetate, then ethyl acetate/methanol) to give a crude purification product (169 mg). The crude purification product (169 mg) was fractionated by HPLC (C18, mobile phase: water/acetonitrile (containing 0.1% TFA)) to give a fraction having a shorter retention time. The obtained fraction was concentrated under reduced pressure, ethyl acetate was added, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (7 mg).

Example 104

3-amino-7-(5-(2-((dimethylamino)methyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (77 mg), potassium acetate (131 mg) and N,N-dimethylacetamide (3 mL) was stirred under an argon atmosphere at 110° C. for 4 hr. The reaction mixture was cooled to room temperature, and a mixture of 1-(1-(3-bromo-1-methyl-1H-pyrazol-5-yl)pyrrolidin-2-yl)-N,N-dimethylmethanamine (288 mg) obtained in Reference Example 82 and N,N-dimethylacetamide (2.0 mL), aqueous sodium carbonate solution (2 M, 0.70 mL) and tetrakis (triphenylphosphine)palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed successively with water and saturated brine, and dried over anhydrous magnesium sulfate. The solvent was evaporated under reduced pressure and the residue was purified by silica gel chromatography (basic silica gel, hexane/ethyl acetate, then ethyl acetate/methanol) to give a crude purification product (169 mg). The crude purification product (169 mg) was fractionated by HPLC (C18, mobile phase: water/acetonitrile (containing 0.1% TFA)) to give a fraction having a longer retention time. The obtained fraction was concentrated under reduced pressure, ethyl acetate was added, and the mixture was washed with saturated aqueous sodium hydrogen carbonate solution and saturated brine, dried over anhydrous magnesium sulfate, and concentrated under reduced pressure. The residue was solidified from ethyl acetate/hexane to give the title compound (15 mg).

Example 105

3-amino-5-((2S)-3-methylbutan-2-yl)-7-(1-methyl-5-(2-oxa-6-azaspiro[3.3]hept-6-yl)-1H-pyrazol-3-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (170 mg) obtained in Example 1, Step G, 4,4,4',4',5,5,5',5'-octamethyl-2,2'-bi-1,3,2-dioxaborolane (289 mg), tetrakis(triphenylphosphine)palladium(0) (66 mg), potassium acetate (112 mg) and N,N-dimethylacetamide (3 mL) was stirred under an argon atmosphere at 110° C. for 4 hr. The reaction mixture was cooled to room temperature, and a mixture of 6-(3-bromo-1-methyl-1H-pyrazol-5-yl)-2-oxa-6-azaspiro [3.3]heptane (205 mg) obtained in Reference Example 83 and N,N-dimethylacetamide (2.0 mL), aqueous sodium carbonate solution (2 M, 0.57 mL) and tetrakis(triphenylphosphine)palladium(0) (66 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 10 mM NH$_4$HCO$_3$)), and the solvent was concentrated under reduced pressure. The residue was solidified from ethyl acetate/hexane to give the title compound (56 mg).

Example 106

3-amino-7-(5-(3,3-difluoropyrrolidin-1-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (200 mg) obtained in Example 1, Step G, 4,4,4',4',5,5,5',5'-octamethyl-2,2'-bi-1,3,2-dioxaborolane (340 mg), tetrakis(triphenylphosphine)palladium(0) (116 mg), potassium acetate (131 mg) and N,N-dimethylacetamide (6 mL) was stirred under an argon atmosphere at 110° C. for 4 hr. The reaction mixture was cooled to room temperature, 3-bromo-5-(3,3-difluoropyrrolidin-1-yl)-1-methyl-1H-pyrazole (231 mg) obtained in Reference Example 84, aqueous sodium carbonate solution (2 M, 0.67 mL) and tetrakis(triphenylphosphine) palladium(0) (77 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). To the obtained fraction was added saturated brine, and the mixture was extracted with ethyl acetate. The organic layer was separated, dried over anhydrous magnesium sulfate, and concentrated under reduced pressure. The residue was solidified from ethyl acetate/hexane to give the title compound (115 mg).

Example 107

3-amino-7-(5-(4-(cyclopropylsulfonyl)piperazin-1-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (170 mg) obtained in Example 1, Step G, 4,4,4',4',5,5,5',5'-octamethyl-2,2'-bi-1,3,2-dioxaborolane (289 mg), tetrakis(triphenylphosphine)palladium(0) (98 mg), potassium acetate (112 mg) and N,N-dimethylformamide (3 mL) was stirred under an argon atmosphere at 110° C. for 3 hr. The reaction mixture was cooled to room temperature, and a mixture of 1-(3-bromo-1-methyl-1H-pyrazol-5-yl)-4-(cyclopropylsulfonyl)piperazine (298 mg) obtained in Reference Example 85 and N,N-dimethylformamide (2 mL), aqueous sodium carbonate solution (2 M, 0.57 mL) and tetrakis(triphenylphosphine)palladium(0) (66 mg) were added. Under an argon atmosphere, the reaction mixture was stirred at 120° C. for 3 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/methanol). The residue was solidified from ethyl acetate/diisopropyl ether to give the title compound (138 mg).

Example 108

3-amino-5-((2S)-3-methylbutan-2-yl)-7-(1-methyl-5-(4-(methylsulfonyl)piperazin-1-yl)-1H-pyrazol-3-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (190 mg) obtained in Example 1, Step G, 4,4,4',4',5,5,5',5'-octamethyl-2,2'-bi-1,3,2-dioxaborolane (323 mg), tetrakis(triphenylphosphine)palladium(0) (110 mg), potassium acetate (125 mg) and N,N-dimethylformamide (3 mL) was stirred under an argon atmosphere at 110° C. for 3 hr. The reaction mixture was cooled to room temperature, and a mixture of 1-(3-bromo-1-methyl-1H-pyrazol-5-yl)-4-(methylsulfonyl) piperazine (308 mg) obtained in Reference Example 86 and N,N-dimethylformamide (1 mL), aqueous sodium carbonate solution (2 M, 0.64 mL) and tetrakis(triphenylphosphine) palladium(0) (73 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate/methanol). The residue was solidified from ethyl acetate/diisopropyl ether to give the title compound (34 mg).

Example 109

3-amino-7-(5-(2-methoxypropan-2-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (87 mg), potassium acetate (98 mg) and N,N-dimethylacetamide (3 mL) was stirred under an argon atmosphere at 110° C. for 4 hr. The reaction mixture was cooled to room temperature, and a mixture of 3-bromo-5-(2-methoxypropan-2-yl)-1-methyl-1H-pyrazole (117 mg) obtained in Reference Example 87 and N,N-dimethylacetamide (1.5 mL), aqueous sodium carbonate solution (2 M, 0.50 mL) and tetrakis(triphenylphosphine) palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated brine, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (72 mg).

Example 110

3-amino-7-(5-(4-methoxy-1,1-dioxidotetrahydro-2H-thiopyran-4-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (87 mg), potassium acetate (98 mg) and N,N-dimethylacetamide (3 mL) was stirred under an argon atmosphere at 110° C. for 4 hr. The reaction mixture was cooled to room temperature, and a mixture of 3-bromo-5-(4-methoxy-1,1-dioxidotetrahydro-2H-thiopyran-4-yl)-1-methyl-1H-pyrazole (243 mg) obtained in Reference Example 88 and N,N-dimethylacetamide (1.5 mL), aqueous sodium carbonate solution (2 M, 0.50 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated brine, and the solvent was concentrated under reduced pressure. The obtained mixture was extracted with ethyl acetate, dried over anhydrous magnesium sulfate, and concentrated under reduced pressure. The residue was solidified from ethyl acetate/hexane to give the title compound (53 mg).

Example 111

3-amino-7-(5-(1-isobutyryl-3-methoxyazetidin-3-yl)-1-methyl-1H-pyrazol-3-yl)-5-((2S)-3-methylbutan-2-yl)-1,5-dihydro-4H-pyrazolo[4,3-c]pyridin-4-one A mixture of 3-amino-7-bromo-5-((2S)-3-methylbutan-2-yl)-1,5-dihydro-4H-pyrazolo[4,3-c]pyridin-4-one (150 mg) obtained in Example 1, Step G, 4,4,4',4',5,5,5',5'-octamethyl-2,2'-bi-1,3,2-dioxaborolane (255 mg), tetrakis(triphenylphosphine)palladium(0) (58 mg), potassium acetate (98 mg) and N,N-dimethylacetamide (2 mL) was stirred under an argon atmosphere at 110° C. for 4 hr. The reaction mixture was cooled to room temperature, and a mixture of 1-(3-(3-bromo-1-methyl-1H-pyrazol-5-yl)-3-methoxyazetidin-1-yl)-2-methylpropan-1-one (190 mg) obtained in Reference Example 76 and N,N-dimethylformamide (1.5 mL), aqueous sodium carbonate solution (2 M, 0.50 mL) and tetrakis(triphenylphosphine)palladium(0) (58 mg) were added. Under an argon atmosphere, the reaction mixture was stirred at 120° C. for 2 hr. The reaction mixture was cooled to room temperature, water was added, and the mixture was extracted with ethyl acetate. The extract was washed successively with water and saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). The solvent was concentrated under reduced pressure. Ethyl acetate was added to the obtained mixture, and the mixture was washed successively with saturated aqueous sodium hydrogen carbonate solution, water and saturated brine, dried over anhydrous magnesium sulfate, and concentrated under reduced pressure. The residue was solidified from ethyl acetate/hexane to give the title compound (55 mg).

Example 112

2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile

A) ethyl 2-(5-bromo-3-cyano-4-methoxy-2-oxopyridin-1(2H)-yl)-3-methylbutanoate A mixture of ethyl 2-(3-cyano-4-methoxy-2-oxopyridin-1(2H)-yl)-3-methylbutanoate (7.0 g) obtained in Example 84, Step A, N-bromosuccinimide (5.37 g), and N,N-dimethylformamide (70 mL) was stirred at 50° C. for 2 hr. The solvent was concentrated to about half under reduced pressure, saturated aqueous sodium hydrogen carbonate solution was added, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (hexane/ethyl acetate) to give the title compound (6.54 g).
MS (ESI+): [M+H]$^+$ 357.1.

B) ethyl 2-(3-amino-7-bromo-4-oxo-1,4-dihydro-5H-pyrazolo[4,3-c]pyridin-5-yl)-3-methylbutanoate To a solution of ethyl 2-(5-bromo-3-cyano-4-methoxy-2-oxopyridin-1(2H)-yl)-3-methylbutanoate (6.5 g) obtained in Example 112, Step A in ethanol (80 mL) was added hydrazine monohydrate (2.73 g), and the mixture was stirred at 90° C. for 40 min. The reaction mixture was allowed to cool to room temperature, water was added and the mixture was extracted twice with ethyl acetate. The organic layer was successively washed with water and saturated brine, and dried over anhydrous magnesium sulfate. The solvent was evaporated under reduced pressure and the residue was purified by silica gel column chromatography (ethyl acetate/hexane) to give the title compound (6.12 g).
MS (ESI+): [M+H]357.1.

C) 2-(3-amino-7-bromo-4-oxo-1,4-dihydro-5H-pyrazolo[4,3-c]pyridin-5-yl)-3-methylbutanoic acid A mixture of ethyl 2-(3-amino-7-bromo-4-oxo-1,4-dihydro-5H-pyrazolo[4,3-c]pyridin-5-yl)-3-methylbutanoate (3.5 g) obtained in Example 112, Step B, 2 M aqueous sodium hydroxide solution (19.6 mL) and ethanol (35 mL) was stirred at room temperature for 2 hr. The reaction mixture was added to water, and the mixture was washed with diethyl ether. The aqueous layer was acidified (pH 4) with 1 M hydrochloric acid, and extracted 3 times with ethyl acetate-tetrahydrofuran. The extracts were combined, washed with saturated brine, and dried over anhydrous magnesium sulfate. The solvent was evaporated under reduced pressure to give the title compound (3.41 g).
MS (ESI+): [M+H]$^+$ 328.8.

D) 2-(3-amino-7-bromo-4-oxo-1,4-dihydro-5H-pyrazolo[4,3-c]pyridin-5-yl)-3-methylbutanamide To a mixture of 2-(3-amino-7-bromo-4-oxo-1,4-dihydro-5H-pyrazolo[4,3-c]pyridin-5-yl)-3-methylbutanoic acid (3.4 g) obtained in Example 112, Step C, 1H-benzo[d][1,2,3]triazol-1-ol ammonium salt (2.36 g), triethylamine (2.88 mL) and N,N-dimethylformamide (50 mL) was added 1-(3-dimethylaminopropyl)-3-ethylcarbodiimide hydrochloride (2.97 g), and the mixture was stirred at room temperature under a nitrogen atmosphere overnight. The reaction mixture was diluted with saturated aqueous sodium hydrogen carbonate solution, and extracted twice with ethyl acetate. The extracts were combined, washed with saturated brine, and dried over anhydrous magnesium sulfate. The solvent was evaporated under reduced pressure and the residue was washed with a mixed solvent of ethyl acetate-diisopropyl ether. The obtained solid was washed with diisopropyl ether, and dried under reduced pressure to give the title compound (2.02 g).
MS (ESI+): [M+H]$^+$ 327.8.

E) 2-(3-amino-7-bromo-4-oxo-1,4-dihydro-5H-pyrazolo[4,3-c]pyridin-5-yl)-3-methylbutanenitrile To a mixture of 2-(3-amino-7-bromo-4-oxo-1,4-dihydro-5H-pyrazolo[4,3-c]pyridin-5-yl)-3-methylbutanamide (2.02 g) obtained in Example 112, Step D, and pyridine (60 mL) was added trifluoroacetic anhydride (2.99 mL) at 0° C. The reaction mixture was stirred under a nitrogen atmosphere at 0° C. for 2 hr. To the reaction mixture was added 2 M sodium hydroxide (36.9 mL), and the mixture was stirred at room temperature for 2 hr. The reaction mixture was neutralized with 1 M hydrochloric acid, and extracted twice with ethyl acetate. The obtained organic layer was washed successively with water and saturated brine, and dried over anhydrous magnesium sulfate. The solvent was evaporated under reduced pressure and the residue was purified by silica gel column chromatography (basic silica gel, methanol/ethyl acetate) to give the title compound (1.12 g).
MS (ESI+): [M+H]$^+$ 309.8.

F) 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile A mixture of 2-(3-amino-7-bromo-4-oxo-1,4-dihydro-5H-pyrazolo[4,3-c]pyridin-5-yl)-3-methylbutanenitrile (200 mg) obtained in Example 112, Step E, 4,4,4',4',5,5,5',5'-octamethyl-2,2'-bi-1,3,2-dioxaborolane (328 mg), tetrakis(triphenylphosphine)palladium(0) (112 mg), potassium acetate (127 mg) and N,N-dimethylformamide (3 mL) was stirred under an argon atmosphere at 110° C. for 3 hr. The reaction mixture was cooled to room temperature, and a mixture of 4-(3-bromo-1-methyl-1H-pyrazol-5-yl)morpholine (238 mg) obtained in Reference Example 12 and N,N-dimethylformamide (1 mL), aqueous sodium carbonate solution (2 M, 0.65 mL) and tetrakis(triphenylphosphine)palladium(0) (75 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, ethyl acetate), and the residue was solidified from ethyl acetate/diisopropyl ether to give the title compound (71 mg).

Example 113

2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile A racemate (46 mg) of 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile obtained in Example 112 was fractionated by SFC (column: CHIRALPAK IC, 20 mmID×250 mmL, manufactured by Daicel Corporation, mobile phase: carbon dioxide/methanol/diethylamine=700/300/3 (v/v/v)) to give the title compound having a shorter retention time as a crude purification product (21 mg). The obtained crude purification product was purified by silica gel chromatography (basic silica gel, methanol/ethyl acetate), and the obtained solid was solidified from ethyl acetate/diisopropyl ether to give the title compound (10 mg).

>99% ee (SFC (column: CHIRALPAK IC, 4.6 mmID× 250 mmL, manufactured by Daicel Corporation, mobile phase: carbon dioxide/methanol/diethylamine=700/300/3 (v/v/v), flow rate: 2.5 mL/min, retention time: 12.37 min))

Example 114

2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile A racemate (46 mg) of 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile obtained in Example 112 was fractionated by SFC (column: CHIRALPAK IC, 20 mmID×250 mmL, manufactured by Daicel Corporation, mobile phase: carbon dioxide/methanol/diethylamine=700/300/3 (v/v/v)) to give the title compound having a longer retention time as a crude purification product (21 mg). The obtained crude purification product was purified by silica gel chromatography (basic silica gel, methanol/ethyl acetate), and the obtained solid was solidified from ethyl acetate/diisopropyl ether to give the title compound (11 mg).

>99% ee (SFC (column: CHIRALPAK IC, 4.6 mmID× 250 mmL, manufactured by Daicel Corporation, mobile phase: carbon dioxide/methanol/diethylamine=700/300/3 (v/v/v), flow rate: 2.5 mL/min, retention time: 15.63 min))

Example 115

3-amino-5-(1-cyclopropyl-2-methylpropyl)-7-(1-methyl-5-(morpholin-4-yl)-1H-pyrazol-3-yl)-1,5-dihydro-4H-pyrazolo[4,3-c]pyridin-4-one A) 2-cyano-N-(1-cyclopropyl-2-methylpropyl)acetamide To a mixture of 1-cyclopropyl-2-methylpropan-1-amine hydrochloride (2.3 g), 2-cyanoacetic acid (2.61 g), diisopropylethylamine (8.1 mL), and ethyl acetate (25 mL) was added a 1.7 M solution (18.1 mL) of propylphosphonic anhydride (cyclic trimer) in ethyl acetate at 0° C., and the mixture was stirred under a nitrogen atmosphere at room temperature overnight. To the reaction mixture was added saturated aqueous sodium hydrogen carbonate solution at 0° C., and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (basic silica gel, ethyl acetate) to give the title compound (440 mg).

$^1$H NMR (300 MHz, CDCl$_3$) δ0.23-0.50 (3H, m), 0.58-0.69 (1H, m), 0.75-0.89 (1H, m), 0.99 (6H, dd, J=6.8, 5.7 Hz), 1.85-1.99 (1H, m), 3.10 (1H, m), 3.39 (2H, s), 5.76-6.29 (1H, br).

B) 2-cyano-N-(1-cyclopropyl-2-methylpropyl)-5,5-dimethoxy-3-oxopentanamide

Under an ice bath, to a solution of 3,3-dimethoxypropanoic acid (982 mg) and triethylamine (1.36 mL) in tetrahydrofuran (15 mL) was added dropwise a solution of methyl chlorocarbonate (830 mg) in tetrahydrofuran (15 mL), and the mixture was stirred under a nitrogen atmosphere at the same temperature for 30 min. The solvent was evaporated under reduced pressure to give a mixed acid anhydride.

To a solution of 2-cyano-N-(1-cyclopropyl-2-methylpropyl)acetamide (440 mg) obtained in Example 115, Step A, in tetrahydrofuran (15 mL) was added sodium hydride (60% in mineral oil, 215 mg) at 0° C., and the mixture was stirred at the same temperature for 30 min. Under an ice bath, to the reaction mixture was added dropwise a solution of the mixed acid anhydride obtained above in tetrahydrofuran (40 mL), and the mixture was stirred under a nitrogen atmosphere at the same temperature for 1 hr. To the reaction mixture was added 1 M hydrochloric acid, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (hexane/ethyl acetate) to give the title compound (500 mg) as a crude purification product.

MS (ESI−), found: 295.2

C) 1-(1-cyclopropyl-2-methylpropyl)-4-methoxy-2-oxo-1,2-dihydropyridine-3-carbonitrile To a mixture of 2-cyano-N-(1-cyclopropyl-2-methylpropyl)-5,5-dimethoxy-3-oxopentanamide (500 mg) obtained in Example 115, Step B, 2,4,6-trimethylpyridine (1.23 g), methyl iodide (0.527 mL), and tetrahydrofuran (10 mL) was added trimethylsilyl trifluoromethanesulfonate (1.5 g) at 0° C. The reaction mixture was stirred at 0° C. for 30 min, and at 50° C. for 2 hr. To the reaction mixture was added 1 M hydrochloric acid at 0° C., and the mixture was extracted with ethyl acetate. The obtained organic layer was washed with water and saturated brine, and dried over anhydrous magnesium sulfate. The solvent was evaporated under reduced pressure. To the residue were added potassium carbonate (1.17 g), methyl iodide (0.53 mL), and N,N-dimethylformamide (3 mL), and the reaction mixture was stirred at 50° C. for 2 hr. Water was added to the reaction mixture, and the mixture was extracted with ethyl acetate. The obtained organic layer was successively washed with water and saturated brine, and dried over anhydrous magnesium sulfate. The solvent was evaporated under reduced pressure and the residue was purified by silica gel column chromatography (hexane/ethyl acetate) to give the title compound (100 mg).

MS (ESI+): [M+H]246.9.

D) 5-bromo-1-(1-cyclopropyl-2-methylpropyl)-4-methoxy-2-oxo-1,2-dihydropyridine-3-carbonitrile A mixture of 1-(1-cyclopropyl-2-methylpropyl)-4-methoxy-2-oxo-1,2-dihydropyridine-3-carbonitrile (100 mg) obtained in Example 115, Step C, N-bromosuccinimide (87 mg), and N,N-dimethylformamide (2 mL) was stirred at 60° C. for 2 hr. To the reaction mixture was added saturated aqueous sodium hydrogen carbonate solution, and the mixture was extracted with ethyl acetate. The obtained organic layer was washed with water and saturated brine, and dried over anhydrous magnesium sulfate. The solvent was evaporated under reduced pressure and the residue was purified by silica gel column chromatography (hexane/ethyl acetate) to give the title compound (90 mg).

MS (ESI+): [M+H]$^+$ 324.8.

E) 3-amino-7-bromo-5-(1-cyclopropyl-2-methylpropyl)-1,5-dihydro-4H-pyrazolo[4,3-c]pyridin-4-one A mixture of 5-bromo-1-(1-cyclopropyl-2-methylpropyl)-4-methoxy-2-oxo-1,2-dihydropyridine-3-carbonitrile (90 mg) obtained in Example 115, Step D, hydrazine monohydrate (42 mg), and ethanol (3.0 mL) was stirred at 90° C. for 1 hr. The solvent was evaporated under reduced pressure, and the residue was purified by silica gel column chromatography (basic silica gel, methanol/ethyl acetate) to give the title compound (80 mg).

MS (ESI+): [M+H]$^+$ 324.9.

F) 3-amino-5-(1-cyclopropyl-2-methylpropyl)-7-(1-methyl-5-(morpholin-4-yl)-1H-pyrazol-3-yl)-1,5-dihydro-4H-pyrazolo[4,3-c]pyridin-4-one A mixture of 3-amino-7-bromo-5-(1-cyclopropyl-2-methylpropyl)-1,5-dihydro-4H-pyrazolo[4,3-c]pyridin-4-one (90 mg) obtained in Example 115, Step E, 4,4,4',4',5,5,5',5'-octamethyl-2,2'-bi-1,3,2-dioxaborolane (141 mg), tetrakis(triphenylphosphine)palladium(0) (48 mg), potassium acetate (54 mg) and N,N-dimethylformamide (2 mL) was stirred under an argon atmosphere at 110° C. for 3 hr. The reaction mixture was cooled to room temperature, and a mixture of 4-(3-bromo-1-methyl-1H-pyrazol-5-yl)morpholine (102 mg) obtained in Reference Example 12 and N,N-dimethylformamide (0.5 mL), aqueous sodium carbonate solution (2 M, 0.28 mL) and tetrakis(triphenylphosphine)palladium(0) (32 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate), and the residue was solidified from ethyl acetate/diisopropyl ether to give the title compound (15 mg).

Example 116

3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one A) 5-bromo-4-methoxy-1-(2-methylcyclohexyl)-2-oxo-1,2-dihydropyridine-3-carbonitrile To a mixture of 5-bromo-4-chloro-1-(2-methylcyclohexyl)-2-oxo-1,2-dihydropyridine-3-carbonitrile (WO 2013/125543 A1) (1.76 g) and methanol (15 mL) was added sodium methoxide (28% methanol solution) (1.05 g) at 0° C. The reaction mixture was stirred at room temperature for 1 hr. The reaction mixture was added to water at room temperature, and the mixture was stirred for 10 min. Insoluble material was collected by filtration and washed with water. The obtained solid was dried under reduced pressure at 50° C. to give the title compound (1.55 g).

MS (ESI+): [M+H]$^+$ 324.8.

B) 5-(5-(2-hydroxypropan-2-yl)-1-methyl-1H-pyrazol-3-yl)-4-methoxy-1-(2-methylcyclohexyl)-2-oxo-1,2-dihydropyridine-3-carbonitrile A mixture of 2-(3-bromo-1-methyl-1H-pyrazol-5-yl)propan-2-ol (943 mg) obtained in Reference Example 4, 4,4,4',4',5,5,5',5'-octamethyl-2,2'-bi-1,3,2-dioxaborolane (2.19 g), (1,1'-bis(diphenylphosphino)ferrocene)dichloropalladium(II) (158 mg), potassium acetate (845 mg) and 1,2-dimethoxyethane (5 mL) was stirred under an argon atmosphere at 100° C. for 16 hr. To the reaction mixture was added ethyl acetate, and the insoluble material was removed by filtration. The filtrate was concentrated under reduced pressure. To the residue were added 5-bromo-4-methoxy-1-(2-methylcyclohexyl)-2-oxo-1,2-dihydropyridine-3-carbonitrile (0.7 g) obtained in Example 116, Step A, 1,2-dimethoxyethane (8 mL), aqueous sodium carbonate solution (2 M, 6.46 mL) and tetrakis(triphenylphosphine)palladium(0) (249 mg). Under an argon atmosphere, the reaction mixture was stirred at 100° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate). The obtained solid was washed with diisopropyl ether to give the title compound (223 mg).

MS (ESI+): [M+H]$^+$ 385.1.

C) 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one To a solution of 5-(5-(2-hydroxypropan-2-yl)-1-methyl-1H-pyrazol-3-yl)-4-methoxy-1-(2-methylcyclohexyl)-2-oxo-1,2-dihydropyridine-3-carbonitrile (200 mg) obtained in Example 116, Step B, in ethanol (3 mL) was added hydrazine monohydrate (33 µL), and the mixture was stirred at 80° C. for 2 hr. To the reaction mixture was added hydrazine monohydrate (10 µL), and the mixture was stirred at 80° C. for 2 hr. To the reaction mixture was added water at room temperature and the mixture was extracted with ethyl acetate. The organic layer was separated, successively washed with water and saturated brine, and dried over anhydrous magnesium sulfate. The solvent was evaporated under reduced pressure and the residue was purified by silica gel column chromatography (basic silica gel, ethyl acetate/hexane) to give the title compound (147 mg).

Example 117

3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one A racemate (cis/trans mixture) of 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one (147 mg) obtained in Example 116, Step C, was fractionated by HPLC (column: CHIRALPAK IC, 20 mmID×250 mmL, manufactured by Daicel Corporation, mobile phase: hexane/ ethanol/diethylamine=400/600/1 (v/v/v)) to give a crude purification product (62 mg) of the title compound having the first retention time. The crude purification product (62 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (49 mg). (HPLC (column: CHIRALPAK IC, 4.6 mmID×250 mmL, manufactured by Daicel Corporation, mobile phase: hexane/ethanol/diethylamine=400/600/1 (v/v/v), flow rate: 0.5 mL/min, retention time: 11.47 min))

Example 118

3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one A racemate (cis/trans mixture) of 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one (147 mg) obtained in Example 116, Step C, was fractionated by HPLC (column: CHIRALPAK IC, 20 mmID×250 mmL, manufactured by Daicel Corporation, mobile phase: hexane/ethanol/diethylamine=400/600/1 (v/v/v)) to give a crude purification product (25 mg) of the title compound having the second retention time. The crude purification product (25 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (17 mg). (HPLC (column: CHIRALPAK IC, 4.6 mmID×250 mmL, manufactured by Daicel Corporation, mobile phase: hexane/ethanol/diethylamine=400/600/1 (v/v/v), flow rate: 0.5 mL/min, retention time: 12.84 min))

Example 119

3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one A racemate (cis/trans mixture) of 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one (147 mg) obtained in Example 116, Step C, was fractionated by HPLC (column: CHIRALPAK IC, 20 mmID×250 mmL, manufactured by Daicel Corporation, mobile phase: hexane/ethanol/diethylamine=400/600/1 (v/v/v)) to give a crude purification product (52 mg) of the title compound having the third retention time. The crude purification product (52 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (45 mg). (HPLC (column: CHIRALPAK IC, 4.6 mmID×250 mmL, manufactured by Daicel Corporation, mobile phase: hexane/ethanol/diethylamine=400/600/1 (v/v/v), flow rate: 0.5 mL/min, retention time: 15.40 min))

Example 120

3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one A racemate (cis/trans mixture) of 3-amino-7-(5-(2-hydroxypropan-2-yl)-1-methyl-1H-pyrazol-3-yl)-5-(2-methyl-cyclohexyl)-1,5-dihydro-4H-pyrazolo[4,3-c]pyridin-4-one (147 mg) obtained in Example 116, Step C, was fractionated by HPLC (column: CHIRALPAK IC, 20 mmID×250 mmL, manufactured by Daicel Corporation, mobile phase: hexane/ethanol/diethylamine=400/600/1 (v/v/v)) to give a crude purification product (23 mg) of the title compound having the fourth retention time. The crude purification product (23 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (23 mg). (HPLC (column: CHIRALPAK IC, 4.6 mmID×250 mmL, manufactured by Daicel Corporation, mobile phase: hexane/ethanol/diethylamine=400/600/1 (v/v/v), flow rate: 0.5 mL/min, retention time: 23.84 min))

Example 121

2-(3-amino-7-(5-(2-methoxypropan-2-yl)-1-methyl-1H-pyrazol-3-yl)-4-oxo-1,4-dihydro-5H-pyrazolo[4,3-c]pyridin-5-yl)-3-fluorobenzonitrile A mixture of 2-(3-amino-7-bromo-4-oxo-1,4-dihydro-5H-pyrazolo[4,3-c]pyridin-5-yl)-3-fluorobenzonitrile (150 mg) obtained in Example 67, Step G, 4,4,4',4',5,5,5',5'-octamethyl-2,2'-bi-1,3,2-dioxaborolane (219 mg), tetrakis(triphenylphosphine)palladium(0) (75 mg), potassium acetate (85 mg) and N,N-dimethylacetamide (3 mL) was stirred under an argon atmosphere at 110° C. for 4 hr. The reaction mixture was cooled to room temperature, and a mixture of 3-bromo-5-(2-methoxypropan-2-yl)-1-methyl-1H-pyrazole (151 mg) obtained in Reference Example 87 and N,N-dimethylacetamide (1.5 mL), aqueous sodium carbonate solution (2 M, 0.43 mL) and tetrakis(triphenylphosphine)palladium(0) (50 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/diisopropyl ether to give the title compound (62 mg).

Example 122

2-(3-amino-7-(5-(isopropyl(methyl)amino)-1-methyl-1H-pyrazol-3-yl)-4-oxo-1,4-dihydro-5H-pyrazolo[4,3-c]pyridin-5-yl)-3-fluorobenzonitrile A mixture of 2-(3-amino-7-bromo-4-oxo-1,4-dihydro-5H-pyrazolo[4,3-c]pyridin-5-yl)-3-fluorobenzonitrile (150 mg) obtained in Example 67, Step G, 4,4,4',4',5,5,5',5'-octamethyl-2,2'-bi-1,3,2-dioxaborolane (219 mg), tetrakis(triphenylphosphine)palladium(0) (75 mg), potassium acetate (85 mg) and N,N-dimethylacetamide (3 mL) was stirred under an argon atmosphere at 110° C. for 4 hr. The reaction mixture was cooled to room temperature, and a mixture of 3-bromo-N-isopropyl-N,1-dimethyl-1H-pyrazol-5-amine (150 mg) obtained in Reference Example 80 and N,N-dimethylacetamide (1.5 mL), aqueous sodium carbonate solution (2 M, 0.43 mL) and tetrakis(triphenylphosphine)palladium(0) (50 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/diisopropyl ether to give the title compound (16 mg).

Example 123

2-(3-amino-7-(5-(cyclopentyl(methyl)amino)-1-methyl-1H-pyrazol-3-yl)-4-oxo-1,4-dihydro-5H-pyrazolo[4,3-c]pyridin-5-yl)-3-fluorobenzonitrile A mixture of 2-(3-amino-7-bromo-4-oxo-1,4-dihydro-5H-pyrazolo[4,3-c]pyridin-5-yl)-3-fluorobenzonitrile (150 mg) obtained in Example 67, Step G, 4,4,4',4',5,5,5',5'-octamethyl-2,2'-bi-1,3,2-dioxaborolane (219 mg), tetrakis(triphenylphosphine)palladium(0) (75 mg), potassium acetate (85 mg) and N,N-dimethylacetamide (3 mL) was stirred under an argon atmosphere at 110° C. for 4 hr. The reaction mixture was cooled to room temperature, and a mixture of 3-bromo-N-cyclopentyl-N,1-dimethyl-1H-pyrazol-5-amine (167 mg) obtained in Reference Example 89 and N,N-dimethylacetamide (1.5 mL), aqueous sodium carbonate solution (2 M, 0.43 mL) and tetrakis(triphenylphosphine)palladium(0) (50 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate, then ethyl acetate/methanol) and further fractionated by HPLC (C18, mobile phase: water/acetonitrile (containing 0.1% TFA)). To the obtained fraction was added saturated aqueous sodium hydrogen carbonate solution, and the solvent was concentrated under reduced pressure. The obtained mixture was extracted with ethyl acetate, dried over anhydrous magnesium sulfate, and concentrated under reduced pressure. The residue was solidified from ethyl acetate/diisopropyl ether to give the title compound (56 mg).

Example 124 cis-3-(3-(3-amino-5-(2,6-difluorophenyl)-4-oxo-4,5-dihydro-1H-pyrazolo[4,3-c]pyridin-7-yl)-1-methyl-1H-pyrazol-5-yl)-3-methoxy-N,N-dimethylcyclobutanecarboxamide A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of cis-3-(3-bromo-1-methyl-1H-pyrazol-5-yl)-3-methoxy-N,N-dimethylcyclobutanecarboxamide (222 mg) obtained in Reference Example 90 and N,N-dimethylacetamide (1.5 mL), aqueous sodium carbonate solution (2 M, 0.59 mL) and tetrakis(triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and purified by silica gel chromatography (diol silica gel, hexane/ethyl acetate). The residue was solidified from ethyl acetate/hexane to give the title compound (66 mg).

Example 125

3-amino-5-(2,6-difluorophenyl)-7-(5-((3R)-3-(dimethylamino)pyrrolidin-1-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of (3R)-1-(3-bromo-1-methyl-1H-pyrazol-5-yl)-N,N-dimethylpyrrolidin-3-amine (240 mg) obtained in Reference Example 91 and N,N-dimethylacetamide (1.5 mL), aqueous sodium carbonate solution (2 M, 0.59 mL) and tetrakis(triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and purified by silica gel chromatography (diol silica gel, hexane/ethyl acetate). The residue was solidified from ethyl acetate and recrystallized twice from methanol/ethyl acetate/hexane to give the title compound (41 mg).

Example 126

3-amino-5-(2,6-difluorophenyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (180 mg) obtained in Example 65, Step G, 4,4,4',4',5,5,5',5'-octamethyl-2,2'-bi-1,3,2-dioxaborolane (268 mg), tetrakis(triphenylphosphine)palladium(0) (61 mg), potassium acetate (104 mg) and N,N-dimethylacetamide (3 mL) was stirred under an argon atmosphere at 110° C. for 4 hr. The reaction mixture was cooled to room temperature, and a mixture of 1-((2R)-1-(3-bromo-1-methyl-1H-pyrazol-5-yl)pyrrolidin-2-yl)-N,N-dimethylmethanamine (167 mg) obtained in Reference Example 92 and N,N-dimethylacetamide (1.5 mL), aqueous sodium carbonate solution (2 M, 0.53 mL) and tetrakis(triphenylphosphine)palladium(0) (61 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and purified by silica gel chromatography (diol silica gel, hexane/ethyl acetate). The residue was solidified from ethyl acetate/hexane to give the title compound (20 mg).

Example 127

1-(3-(3-amino-5-(2,6-difluorophenyl)-4-oxo-4,5-dihydro-1H-pyrazolo[4,3-c]pyridin-7-yl)-1-methyl-1H-pyrazol-5-yl)-4-methylpiperidine-4-carbonitrile A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and 1-(3-bromo-1-methyl-1H-pyrazol-5-yl)-4-methylpiperidine-4-carbonitrile (149 mg) obtained in Reference Example 93, aqueous sodium carbonate solution (2 M, 0.59 mL) and tetrakis (triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate). The residue was solidified from methanol/diisopropyl ether to give the title compound (87 mg).

Example 128

3-amino-5-(2,6-difluorophenyl)-7-(5-((2R)-2-(methoxymethyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of 3-bromo-5-((2R)-2-(methoxymethyl)pyrrolidin-1-yl)-1-methyl-1H-pyrazole (241 mg) obtained in Reference Example 94 and N,N-dimethylacetamide (1.5 mL), aqueous sodium carbonate solution (2 M, 0.59 mL) and tetrakis (triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate), and the residue was purified by silica gel chromatography (diol silica gel, hexane/ethyl acetate). The residue was solidified from hexane/ethyl acetate to give the title compound (22 mg).

Example 129

3-amino-5-(2,6-difluorophenyl)-7-(5-(4-methoxy-1,1-dioxidotetrahydro-2H-thiopyran-4-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of 3-bromo-5-(4-methoxy-1,1-dioxidotetrahydro-2H-thiopyran-4-yl)-1-methyl-1H-pyrazole (284 mg) obtained in Reference Example 88 and N,N-dimethylacetamide (1.5 mL), aqueous sodium carbonate solution (2 M, 0.59 mL) and tetrakis(triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate), and solidified from hexane/ethyl acetate. The residue was solidified from ethyl acetate/tetrahydrofuran/methanol to give the title compound (64 mg).

Example 130

3-amino-5-(2,6-difluorophenyl)-7-(5-(1-isobutyryl-3-methoxyazetidin-3-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of 1-(3-(3-bromo-1-methyl-1H-pyrazol-5-yl)-3-methoxyazetidin-1-yl)-2-methylpropan-1-one (222 mg) obtained in Reference Example 76 and N,N-dimethylacetamide (1.5 mL), aqueous sodium carbonate solution (2 M, 0.59 mL) and tetrakis(triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and purified by silica gel chromatography (diol silica gel, hexane/ethyl acetate). The residue was solidified from ethyl acetate/hexane/methanol to give the title compound (69 mg).

Example 131

7-(5-(1-acetyl-3-methoxyazetidin-3-yl)-1-methyl-1H-pyrazol-3-yl)-3-amino-5-(2,6-difluorophenyl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of 1-(3-(3-bromo-1-methyl-1H-pyrazol-5-yl)-3-methoxyazetidin-1-yl)ethanone (253 mg) obtained in Reference Example 95 and N,N-dimethylacetamide (1.5 mL), aqueous sodium carbonate solution (2 M, 0.59 mL) and tetrakis(triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) and purified by silica gel chromatography (diol silica gel, hexane/ethyl acetate). The residue was solidified from methanol/ethyl acetate to give the title compound (44 mg).

Example 132

3-amino-5-(2,6-difluorophenyl)-7-(5-(3-methoxy-1-(methylsulfonyl)azetidin-3-yl)-1-methyl-1H-pyrazol-3-yl)-1,5-dihydro-4H-pyrazolo[4,3-c]pyridin-4-one A mixture of 3-amino-7-bromo-5-(2,6-difluorophenyl)-1,5-dihydro-4H-pyrazolo[4,3-c]pyridin-4-one (200 mg) obtained in Example 65, Step G, 4,4,4',4',5,5,5',5'-octamethyl-2,2'-bi-1,3,2-dioxaborolane (298 mg), tetrakis(triphenylphosphine)palladium(0) (68 mg), potassium acetate (115 mg) and N,N-dimethylacetamide (3 mL) was stirred under an argon atmosphere at 110° C. for 4 hr. The reaction mixture was cooled to room temperature, and a mixture of 3-bromo-5-(3-methoxy-1-(methylsulfonyl)azetidin-3-yl)-1-methyl-1H-pyrazole (285 mg) obtained in Reference Example 96 and N,N-dimethylacetamide (1.5 mL), aqueous sodium carbonate solution (2 M, 0.59 mL) and tetrakis (triphenylphosphine)palladium(0) (68 mg) were added. Under an argon atmosphere, the reaction mixture was stirred at 120° C. for 2 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate). The residue was solidified from methanol/ethyl acetate to give the title compound (29 mg).

Example compounds produced by the above-mentioned production methods or methods shown in the Examples, or a method analogous thereto are shown in the following Tables. MS in the Tables shows measured values.

TABLE 5

| Ex. No. | IUPAC name | structural formula | MS |
|---|---|---|---|
| 88 | 3-amino-5-(dicyclopropylmethyl)-7-(5-(2,2-dimethyl-1,1-dioxidothiomorpholin-4-yl)-1-methyl-1H-pyrazol-3-yl)-1,5-dihydro-4H-pyrazolo[4,3-c]pyridin-4-one | | 486.2 |

TABLE 5-continued
| 89 | 3-amino-5-(dicyclopropylmethyl)-7-(5-(1-isobutyryl)-3-methoxyazetidin-3-yl)-1-methyl-1H-pyrazol-3-yl)-1,5-dihydro-4H-pyrazolo[4,3-c]pyridin-4-one | 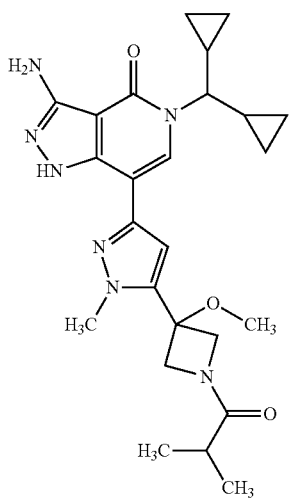 [SMILES: COC1(c2cc(-c3cn(C(C4CC4)C4CC4)c(=O)c4c(N)n[nH]c34)nn2C)CN(C(=O)C(C)C)C1] | 480.2 |
| 90 | 3-amino-5-(dicyclopropylmethyl)-7-(5-(1-(isopropylsulfonyl)-3-methoxyazetidin-3-yl)-1-methyl-1H-pyrazol-3-yl)-1,5-dihydro-4H-pyrazolo[4,3-c]pyridin-4-one | 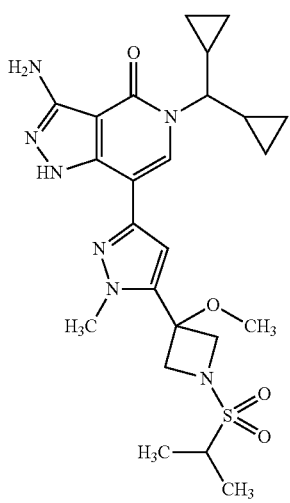 [SMILES: COC1(c2cc(-c3cn(C(C4CC4)C4CC4)c(=O)c4c(N)n[nH]c34)nn2C)CN(S(=O)(=O)C(C)C)C1] | 516.2 |
| 91 | 3-amino-5-((1R)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one | 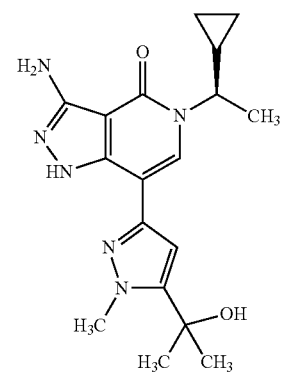 | 357.2 |

TABLE 5-continued

| 92 | 3-amino-5-((1S)-1-cyclopropylethyl)-7-(5-(4-isopropyl-3-oxopiperazin-1-yl)-1-methyl-1H-pyrazol-3-yl)-1,5-dihydro-4H-pyrazolo[4,3-c]pyridin-4-one | 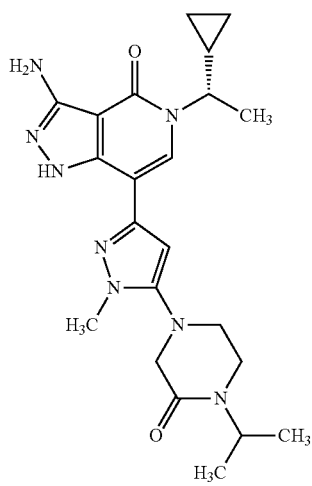 [SMILES: CC(C)N1CCN(c2cc(-c3cn([C@@H](C)C4CC4)c(=O)c4c(N)n[nH]c34)nn2C)CC1=O] | | 439.2 |

| Ex. No. | IUPAC name | structural formula | salt | MS |
|---|---|---|---|---|
| 93 | 3-amino-5-((1S)-1-cyclopropylethyl)-7-(5-(2-hydroxypropan-2-yl)-1-methyl-1H-pyrazol-3-yl)-1,5-dihydro-4H-pyrazolo[4,3-c]pyridin-4-one | 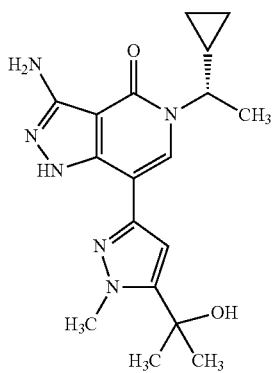 | HCl | 357.2 |
| 94 | 3-amino-5-((1S)-1-cyclopropylethyl)-7-(5-(4-hydroxy-4-(trifluoromethyl)piperidin-1-yl)-1-methyl-1H-pyrazol-3-yl)-1,5-dihydro-4H-pyrazolo[4,3-c]pyridin-4-one | 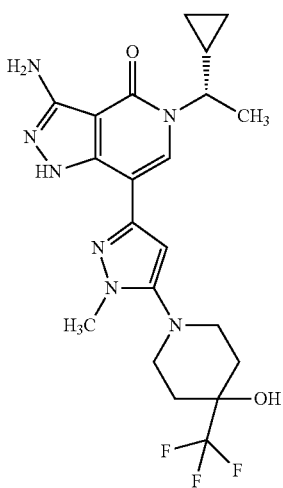 [SMILES: C[C@@H](C1CC1)n1cc(-c2cc(N3CCC(O)(C(F)(F)F)CC3)n(C)n2)c2[nH]nc(N)c2c1=O] | | 466.1 |

TABLE 5-continued

| Ex. No. | IUPAC name | structural formula | MS |
|---|---|---|---|
| 95 | 3-amino-5-((1S)-1-cyclopropylethyl)-7-(5-(2,2-dimethyl-1,1-dioxidothiomorpholin-4-yl)-1-methyl-1H-pyrazol-3-yl)-1,5-dihydro-4H-pyrazolo[4,3-c]pyridin-4-one | 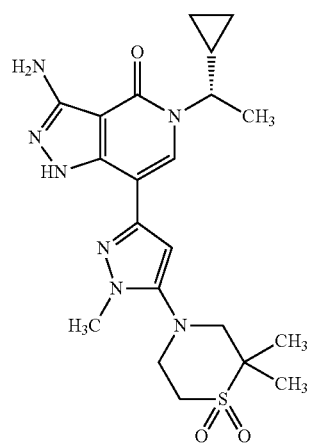 [SMILES: C[C@@H](C1CC1)n1cc(-c2cc(N3CCS(=O)(=O)C(C)(C)C3)n(C)n2)c2[nH]nc(N)c2c1=O] | 460.2 |
| 96 | 3-amino-5-((1S)-1-cyclopropylethyl)-7-(5-(1,1-dioxidothiomorpholin-4-yl)-1-methyl-1H-pyrazol-3-yl)-1,5-dihydro-4H-pyrazolo[4,3-c]pyridin-4-one | 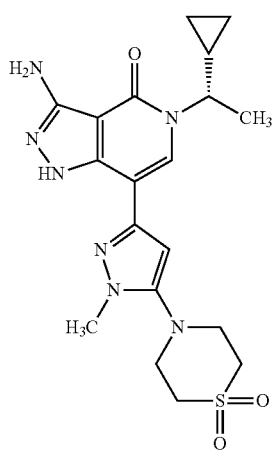 [SMILES: C[C@@H](C1CC1)n1cc(-c2cc(N3CCS(=O)(=O)CC3)n(C)n2)c2[nH]nc(N)c2c1=O] | 432.1 |
| 97 | 3-amino-5-((1S)-1-cyclopropylethyl)-7-(5-(1-isobutyryl-3-methoxyazetidin-3-yl)-1-methyl-1H-pyrazol-3-yl)-1,5-dihydro-4H-pyrazolo[4,3-c]pyridin-4-one | 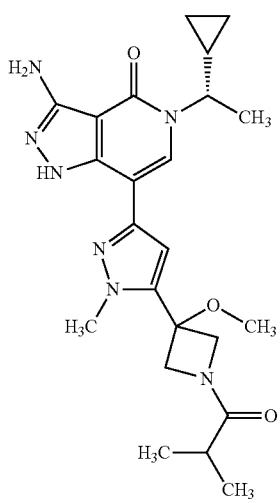 [SMILES: COC1(c2cc(-c3cn([C@@H](C)C4CC4)c(=O)c4c(N)n[nH]c34)nn2C)CN(C(=O)C(C)C)C1] | 454.1 |

TABLE 5-continued

| | | | |
|---|---|---|---|
| 98 | 3-amino-5-((1S)-1-cyclopropylethyl)-7-(5-(1-(isopropylsulfonyl)-3-methoxyazetidin-3-yl)-1-methyl-1H-pyrazol-3-yl)-1,5-dihydro-4H-pyrazolo[4,3-c]pyridin-4-one | 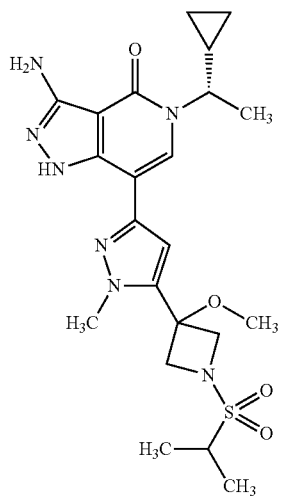 [SMILES: COC1(c2cc(-c3cn([C@@H](C)C4CC4)c(=O)c4c(N)n[nH]c34)nn2C)CN(S(=O)(=O)C(C)C)C1] | 490.2 |
| 99 | 3-amino-5-(3-hydroxy-3-methylbutan-2-yl)-7-(1-methyl-5-(morpholin-4-yl)-1H-pyrazol-3-yl)-1,5-dihydro-4H-pyrazolo[4,3-c]pyridin-4-one | 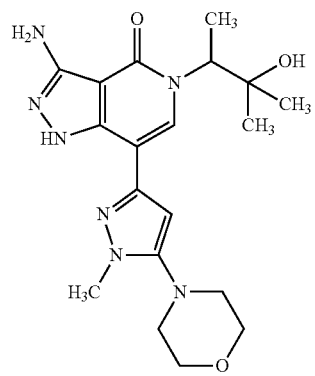 [SMILES: CC(n1cc(-c2cc(N3CCOCC3)n(C)n2)c2[nH]nc(N)c2c1=O)C(C)(C)O] | 402.1 |
| 100 | 3-amino-7-(5-(2-hydroxypropan-2-yl)-1-methyl-1H-pyrazol-3-yl)-5-((2R)-3-methylbutan-2-yl)-1,5-dihydro-4H-pyrazolo[4,3-c]pyridin-4-one | 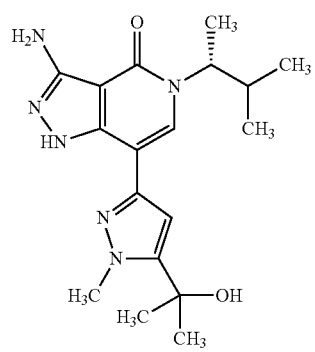 [SMILES: CC(C)[C@@H](C)n1cc(-c2cc(C(C)(C)O)n(C)n2)c2[nH]nc(N)c2c1=O] | 359.2 |
| 101 | 3-amino-7-(5-(isopropyl(methyl)amino)-1-methyl-1H-pyrazol-3-yl)-5-((2S)-3-methylbutan-2-yl)-1,5-dihydro-4H-pyrazolo[4,3-c]pyridin-4-one | 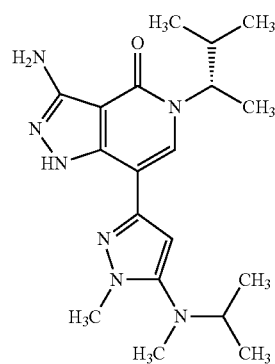 | 372.3 |

| | | | |
|---|---|---|---|
| 102 | 3-amino-7-(5-(4-(isopropylsulfonyl)piperazin-1-yl)-1-methyl-1H-pyrazol-3-yl)-5-((2S)-3-methylbutan-2-yl)-1,5-dihydro-4H-pyrazolo[4,3-c]pyridin-4-one | | 491.2 |
| 103 | 3-amino-7-(5-(2-((dimethylamino)methyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one | | 427.3 |
| 104 | 3-amino-7-(5-(2-((dimethylamino)methyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one | | 427.3 |
| 105 | 3-amino-5-((2S)-3-methylbutan-2-yl)-7-(1-methyl-5-(2-oxa-6-azaspiro[3.3]hept-6-yl)-1H-pyrazol-3-yl)-1,5-dihydro-4H-pyrazolo[4,3-c]pyridin-4-one | | 398.2 |

TABLE 5-continued
| | | | |
|---|---|---|---|
| 106 | 3-amino-7-(5-(3,3-difluoropyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 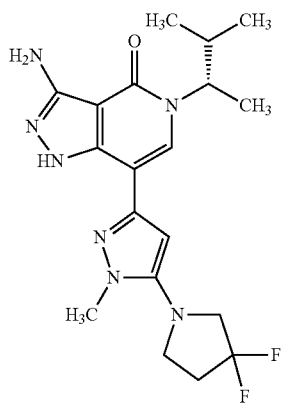 [SMILES: CC(C)[C@H](C)n1cc(-c2cc(N3CCC(F)(F)C3)n(C)n2)c2[nH]nc(N)c2c1=O] | 406.2 |
| 107 | 3-amino-7-(5-(4-(cyclopropylsulfonyl)piperazin-1-yl)-1-methyl-1H-pyrazol-3-yl)-5-((2S)-3-methylbutan-2-yl)-1,5-dihydro-4H-pyrazolo[4,3-c]pyridin-4-one | 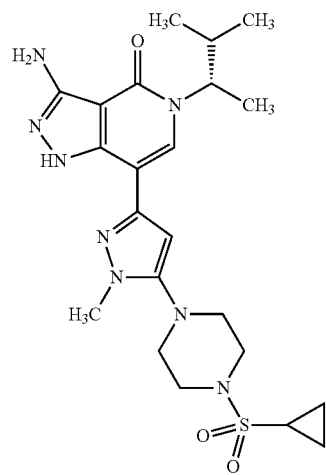 [SMILES: CC(C)[C@H](C)n1cc(-c2cc(N3CCN(S(=O)(=O)C4CC4)CC3)n(C)n2)c2[nH]nc(N)c2c1=O] | 489.3 |
| 108 | 3-amino-5-((2S)-3-methylbutan-2-yl)-7-(1-methyl-5-(4-(methylsulfonyl)piperazin-1-yl)-1H-pyrazol-3-yl)-1,5-dihydro-4H-pyrazolo[4,3-c]pyridin-4-one | 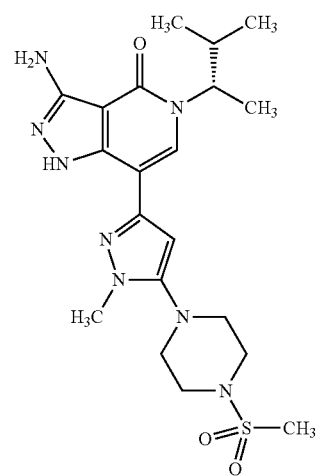 [SMILES: CC(C)[C@H](C)n1cc(-c2cc(N3CCN(S(C)(=O)=O)CC3)n(C)n2)c2[nH]nc(N)c2c1=O] | 463.1 |

TABLE 5-continued
| 109 | 3-amino-7-(5-(2-methoxypropan-2-yl)-1-methyl-1H-pyrazol-3-yl)-5-((2S)-3-methylbutan-2-yl)-1,5-dihydro-4H-pyrazolo[4,3-c]pyridin-4-one | 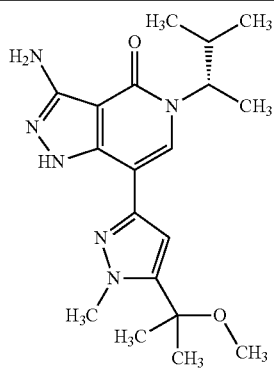 | 373.2 |
| --- | --- | --- | --- |
| 110 | 3-amino-7-(5-(4-methoxy-1,1-dioxidotetrahydro-2H-thiopyran-4-yl)-1-methyl-1H-pyrazol-3-yl)-5-((2S)-3-methylbutan-2-yl)-1,5-dihydro-4H-pyrazolo[4,3-c]pyridin-4-one | 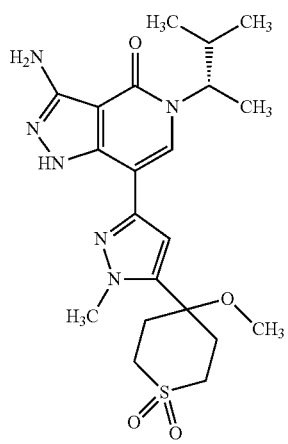 [SMILES: COC1(c2cc(-c3cn([C@@H](C)C(C)C)c(=O)c4c(N)n[nH]c34)nn2C)CCS(=O)(=O)CC1] | 463.1 |
| 111 | 3-amino-7-(5-(1-isobutyryl-3-methoxyazetidin-3-yl)-1-methyl-1H-pyrazol-3-yl)-5-((2S)-3-methylbutan-2-yl)-1,5-dihydro-4H-pyrazolo[4,3-c]pyridin-4-one | 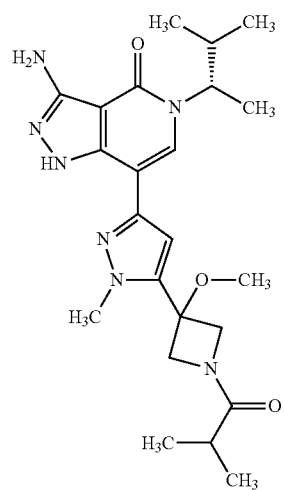 [SMILES: COC1(c2cc(-c3cn([C@@H](C)C(C)C)c(=O)c4c(N)n[nH]c34)nn2C)CN(C(=O)C(C)C)C1] | 456.2 |

TABLE 5-continued

| | | | |
|---|---|---|---|
| 112 | 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile | 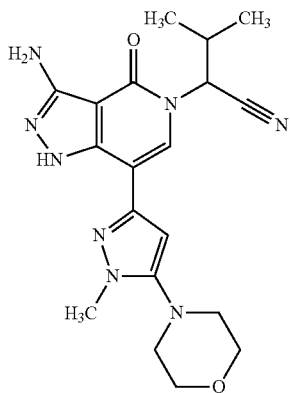 [SMILES: CC(C)C(C#N)n1cc(-c2cc(N3CCOCC3)n(C)n2)c2[nH]nc(N)c2c1=O] | 397.2 |
| 113 | 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile | 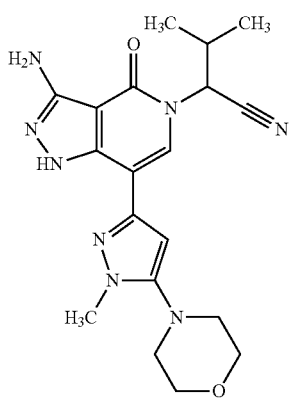 [SMILES: CC(C)C(C#N)n1cc(-c2cc(N3CCOCC3)n(C)n2)c2[nH]nc(N)c2c1=O] | 397.2 |
| 114 | 2-(3-amino-7-(1-methyl-5-(morpholin-4-yl)-1H-pyrazol-3-yl)-4-oxo-1,4-dihydro-5H-pyrazolo[4,3-c]pyridin-5-yl)-3-methylbutanenitrile | 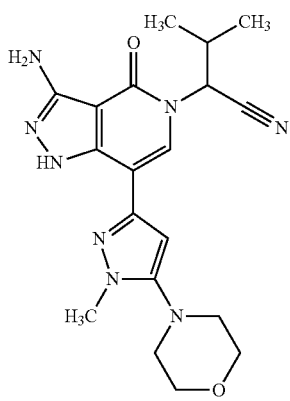 [SMILES: CC(C)C(C#N)n1cc(-c2cc(N3CCOCC3)n(C)n2)c2[nH]nc(N)c2c1=O] | 397.2 |
| 115 | 3-amino-5-(1-cyclopropyl-2-methylpropyl)-7-(1-methyl-5-(morpholin-4-yl)-1H-pyrazol-3-yl)-1,5-dihydro-4H-pyrazolo[4,3-c]pyridin-4-one | 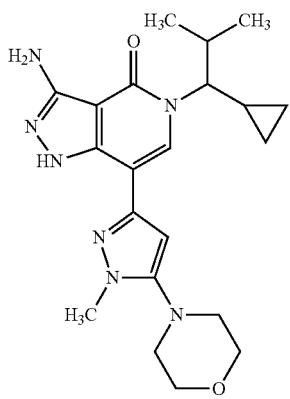 [SMILES: CC(C)C(C1CC1)n1cc(-c2cc(N3CCOCC3)n(C)n2)c2[nH]nc(N)c2c1=O] | 412.2 |

TABLE 5-continued

| | | | | |
|---|---|---|---|---|
| 116 | 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one | 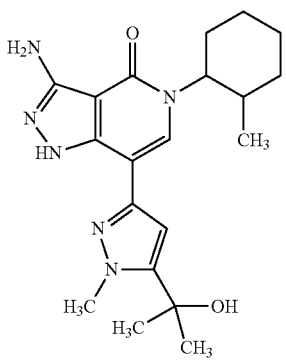 | | 385.0 |
| 117 | 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one | 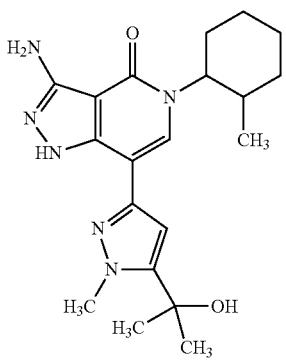 | | 385.2 |
| 118 | 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one | 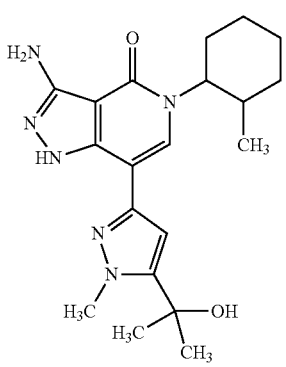 | | 385.2 |
| 119 | 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one | 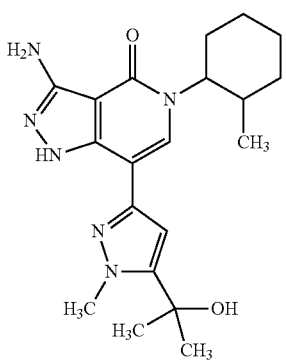 | | 385.2 |

TABLE 5-continued

| 120 | 3-amino-7-(5-(2-hydroxypropan-2-yl)-1-methyl-1H-pyrazol-3-yl)-5-(2-methylcyclohexyl)-1,5-dihydro-4H-pyrazolo[4,3-c]pyridin-4-one | 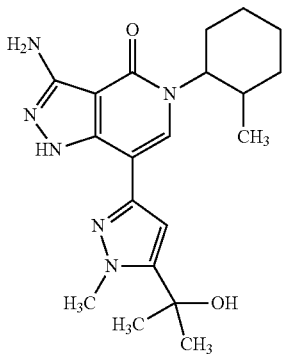 [SMILES: CC1CCCCC1n1cc(-c2cc(C(C)(C)O)n(C)n2)c2[nH]nc(N)c2c1=O] | 385.2 |
| --- | --- | --- | --- |
| 121 | 2-(3-amino-7-(5-(2-methoxypropan-2-yl)-1-methyl-1H-pyrazol-3-yl)-4-oxo-1,4-dihydro-5H-pyrazolo[4,3-c]pyridin-5-yl)-3-fluorobenzonitrile | 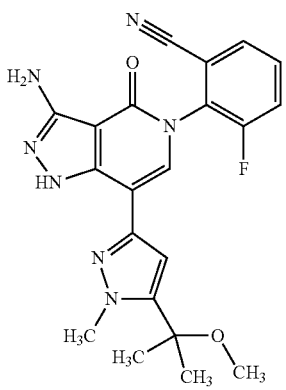 [SMILES: COC(C)(C)c1cc(-c2cn(-c3c(F)cccc3C#N)c(=O)c3c(N)n[nH]c23)nn1C] | 422.1 |
| 122 | 2-(3-amino-7-(5-(isopropyl(methyl)amino)-1-methyl-1H-pyrazol-3-yl)-4-oxo-1,4-dihydro-5H-pyrazolo[4,3-c]pyridin-5-yl)-3-fluorobenzonitrile | 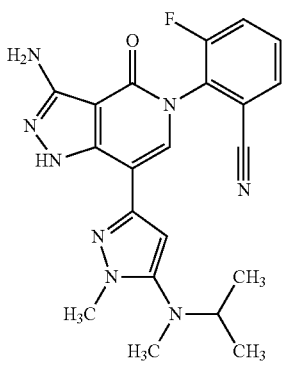 [SMILES: CC(C)N(C)c1cc(-c2cn(-c3c(F)cccc3C#N)c(=O)c3c(N)n[nH]c23)nn1C] | 421.2 |
| 123 | 2-(3-amino-7-(5-(cyclopentyl(methyl)amino)-1-methyl-1H-pyrazol-3-yl)-4-oxo-1,4-dihydro-5H-pyrazolo[4,3-c]pyridin-5-yl)-3-fluorobenzonitrile | 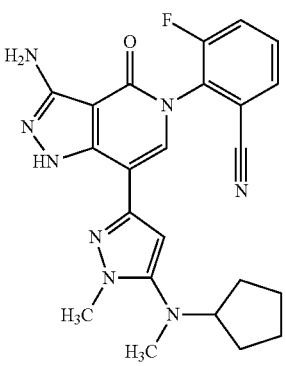 [SMILES: CN(c1cc(-c2cn(-c3c(F)cccc3C#N)c(=O)c3c(N)n[nH]c23)nn1C)C1CCCC1] | 447.1 |

TABLE 5-continued

| 124 | cis-3-(3-(3-amino-5-(2,6-difluorophenyl)-4-oxo-4,5-dihydro-1H-pyrazolo[4,3-c]pyridin-7-yl)-1-methyl-1H-pyrazol-5-yl)-3-methoxy-N,N-dimethylcyclobutanecarboxamide | 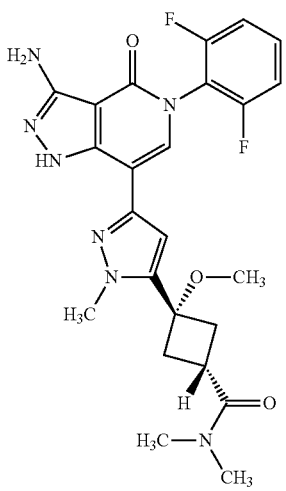 [SMILES: CO[C@]1(c2cc(-c3cn(-c4c(F)cccc4F)c(=O)c4c(N)n[nH]c34)nn2C)C[C@H](C(=O)N(C)C)C1] | 498.1 |
| --- | --- | --- | --- |
| 125 | 3-amino-5-(2,6-difluorophenyl)-7-(5-((3R)-3-(dimethylamino)pyrrolidin-1-yl)-1-methyl-1H-pyrazol-3-yl)-1,5-dihydro-4H-pyrazolo[4,3-c]pyridin-4-one | 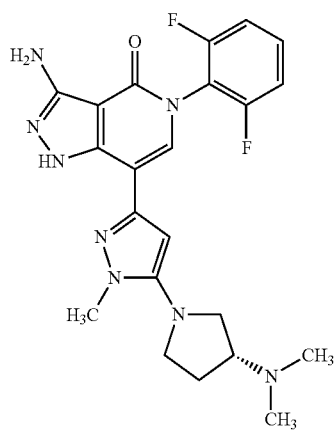 [SMILES: CN(C)[C@@H]1CCN(c2cc(-c3cn(-c4c(F)cccc4F)c(=O)c4c(N)n[nH]c34)nn2C)C1] | 453.0 |
| 126 | 3-amino-5-(2,6-difluorophenyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one | 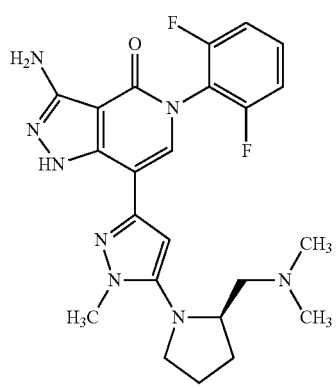 [SMILES: CN(C)C[C@H]1CCCN1c1cc(-c2cn(-c3c(F)cccc3F)c(=O)c3c(N)n[nH]c23)nn1C] | 469.2 |

TABLE 5-continued
| 127 | 1-(3-(3-amino-5-(2,6-difluorophenyl)-4-oxo-4,5-dihydro-1H-pyrazolo[4,3-c]pyridin-7-yl)-1-methyl-1H-pyrazol-5-yl)-4-methylpiperidine-4-carbonitrile | 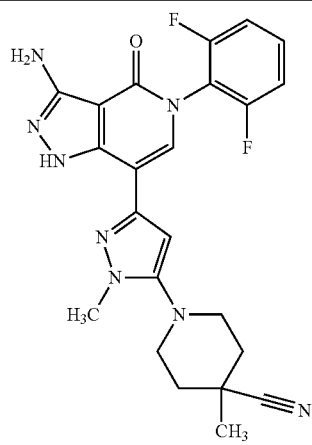 | 463.1 |
| 128 | 3-amino-5-(2,6-difluorophenyl)-7-(5-((2R)-2-(methoxymethyl)pyrrolidin-1-yl)-1-methyl-1H-pyrazol-3-yl)-1,5-dihydro-4H-pyrazolo[4,3-c]pyridin-4-one | 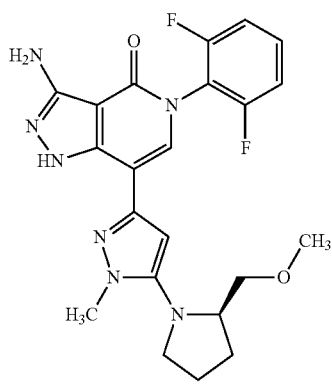 [SMILES: COC[C@H]1CCCN1c1cc(-c2cn(-c3c(F)cccc3F)c(=O)c3c(N)n[nH]c23)nn1C] | 456.1 |
| 129 | 3-amino-5-(2,6-difluorophenyl)-7-(5-(4-methoxy-1,1-dioxidotetrahydro-2H-thiopyran-4-yl)-1-methyl-1H-pyrazol-3-yl)-1,5-dihydro-4H-pyrazolo[4,3-c]pyridin-4-one | 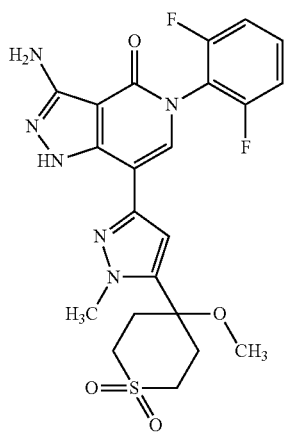 [SMILES: COC1(c2cc(-c3cn(-c4c(F)cccc4F)c(=O)c4c(N)n[nH]c34)nn2C)CCS(=O)(=O)CC1] | 505.1 |

| | | | |
|---|---|---|---|
| 130 | 3-amino-5-(2,6-difluorophenyl)-7-(5-(1-isobutyryl-3-methoxyazetidin-3-yl)-1-methyl-1H-pyrazol-3-yl)-1,5-dihydro-4H-pyrazolo[4,3-c]pyridin-4-one | 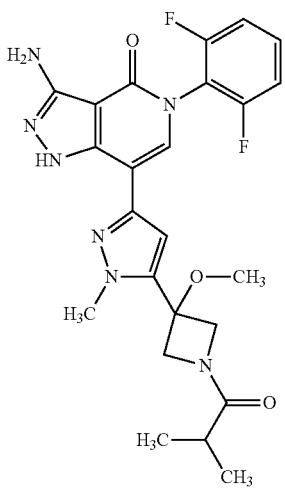 [SMILES: COC1(c2cc(-c3cn(-c4c(F)cccc4F)c(=O)c4c(N)n[nH]c34)nn2C)CN(C(=O)C(C)C)C1] | 498.1 |
| 131 | 7-(5-(1-acetyl-3-methoxyazetidin-3-yl)-1-methyl-1H-pyrazol-3-yl)-3-amino-5-(2,6-difluorophenyl)-1,5-dihydro-4H-pyrazolo[4,3-c]pyridin-4-one | 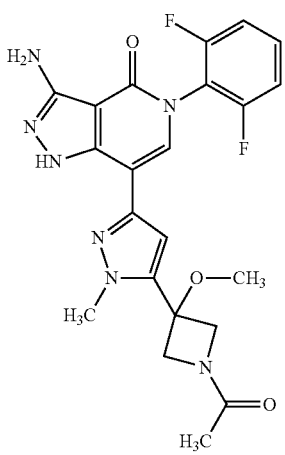 [SMILES: COC1(c2cc(-c3cn(-c4c(F)cccc4F)c(=O)c4c(N)n[nH]c34)nn2C)CN(C(C)=O)C1] | 470.1 |
| 132 | 3-amino-5-(2,6-difluorophenyl)-7-(5-(3-methoxy-1-(methylsulfonyl)azetidin-3-yl)-1-methyl-1H-pyrazol-3-yl)-1,5-dihydro-4H-pyrazolo[4,3-c]pyridin-4-one | 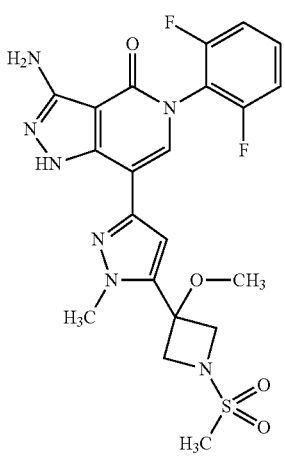 [SMILES: COC1(c2cc(-c3cn(-c4c(F)cccc4F)c(=O)c4c(N)n[nH]c34)nn2C)CN(S(C)(=O)=O)C1] | 506.1 |

TABLE 5-continued

| | | | |
|---|---|---|---|
| 133 | 3-amino-5-((1R)-1-cyclopropylethyl)-7-(5-(4-hydroxy-4-methylpiperidin-1-yl)-1-methyl-1H-pyrazol-3-yl)-1,5-dihydro-4H-pyrazolo[4,3-c]pyridin-4-one | 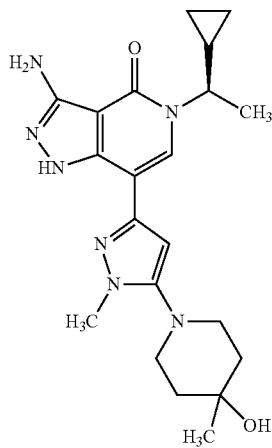 | 412.2 |
| 134 | 3-amino-7-(5-(cyclopentyl(methyl)amino)-1-methyl-1H-pyrazol-3-yl)-5-((2S)-3-methylbutan-2-yl)-1,5-dihydro-4H-pyrazolo[4,3-c]pyridin-4-one | 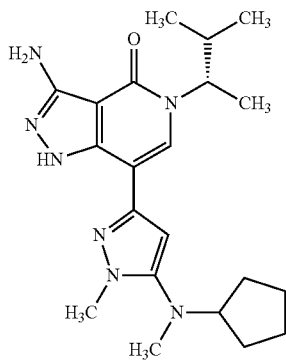 [SMILES: CC(C)[C@H](C)n1cc(-c2cc(N(C)C3CCCC3)n(C)n2)c2[nH]nc(N)c2c1=O] | 398.2 |
| 135 | 3-amino-7-(5-((2R)-2-(methoxymethyl)pyrrolidin-1-yl)-1-methyl-1H-pyrazol-3-yl)-5-((2S)-3-methylbutan-2-yl)-1,5-dihydro-4H-pyrazolo[4,3-c]pyridin-4-one | 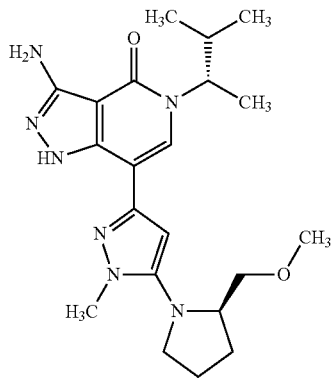 [SMILES: COC[C@H]1CCCN1c1cc(-c2cn([C@@H](C)C(C)C)c(=O)c3c(N)n[nH]c23)nn1C] | 414.2 |
| 136 | 3-amino-7-(5-(1-(isopropylsulfonyl)-3-methoxyazetidin-3-yl)-1-methyl-1H-pyrazol-3-yl)-5-((2S)-3-methylbutan-2-yl)-1,5-dihydro-4H-pyrazolo[4,3-c]pyridin-4-one | 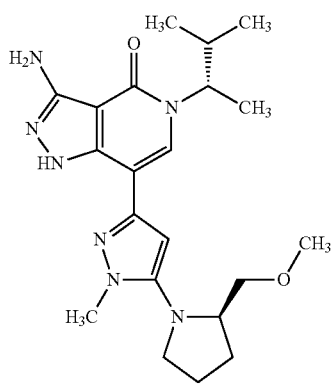 [SMILES: COC[C@H]1CCCN1c1cc(-c2cn([C@@H](C)C(C)C)c(=O)c3c(N)n[nH]c23)nn1C] | 492.3 |

TABLE 5-continued
| | | | | |
|---|---|---|---|---|
| 137 | 2-(3-amino-7-(5-(4,4-difluoro-1-methoxycyclohexyl)-1-methyl-1H-pyrazol-3-yl)-4-oxo-1,4-dihydro-5H-pyrazolo[4,3-c]pyridin-5-yl)-3-methylbutanenitrile | 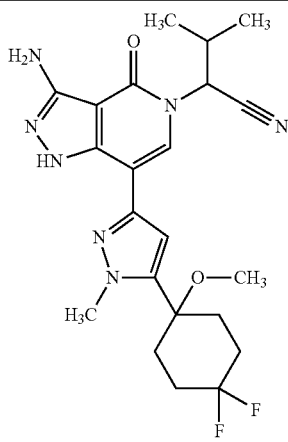 | 458.2 | |
| 138 | 2-(3-amino-7-(5-(4,4-difluoro-1-methoxycyclohexyl)-1-methyl-1H-pyrazol-3-yl)-4-oxo-1,4-dihydro-5H-pyrazolo[4, 3-c]pyridin-5-yl)-3-methylbutanenitrile | 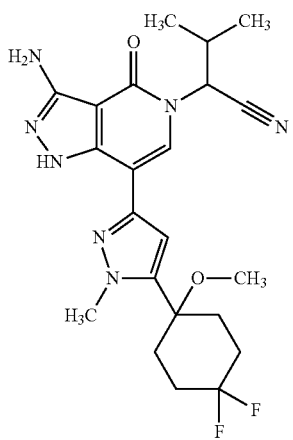 [SMILES: COC1(c2cc(-c3cn(C(C#N)C(C)C)c(=O)c4c(N)n[nH]c34)nn2C)CCC(F)(F)CC1] | 458.1 | |
| 139 | 2-(3-amino-7-(5-(4,4-difluoro-1-methoxycyclohexyl)-1-methyl-1H-pyrazol-3-yl)-4-oxo-1,4-dihydro-5H-pyrazolo[4,3-c]pyridin-5-yl)-3-methylbutanenitrile | 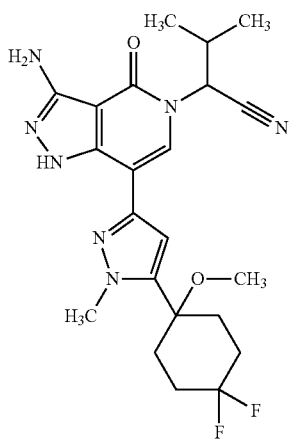 [SMILES: COC1(c2cc(-c3cn(C(C#N)C(C)C)c(=O)c4c(N)n[nH]c34)nn2C)CCC(F)(F)CC1] | 458.1 | |

TABLE 5-continued
| 140 | 3-amino-5-(2,6-difluorophenyl)-7-(5-((3S)-3-(dimethylamino)pyrrolidin-1-yl)-1-methyl-1H-pyrazol-3-yl)-1,5-dihydro-4H-pyrazolo[4,3-c]pyridin-4-one | 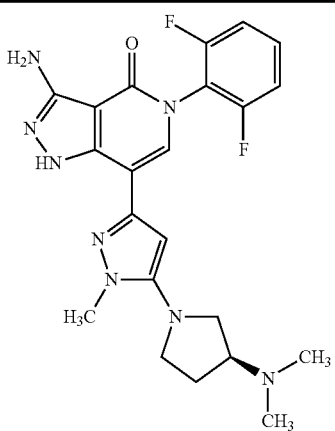 | 455.2 |
|---|---|---|---|
| 141 | 1-(3-(3-amino-5-(2,6-difluorophenyl)-4-oxo-4,5-dihydro-1H-pyrazolo[4,3-c]pyridin-7-yl)-1-methyl-1H-pyrazol-5-yl)piperidine-4-carbonitrile | 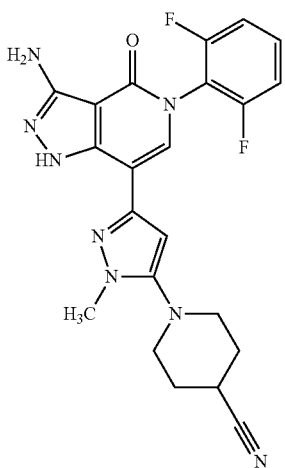 [SMILES: Cn1nc(-c2cn(-c3c(F)cccc3F)c(=O)c3c(N)n[nH]c23)cc1N1CCC(C#N)CC1] | 449.0 |
| 142 | ((2R)-1-(3-(3-amino-5-(2,6-difluorophenyl)-4-oxo-4,5-dihydro-1H-pyrazolo[4,3-c]pyridin-7-yl)-1-methyl-1H-pyrazol-5-yl)pyrrolidin-2-yl)acetonitrile | 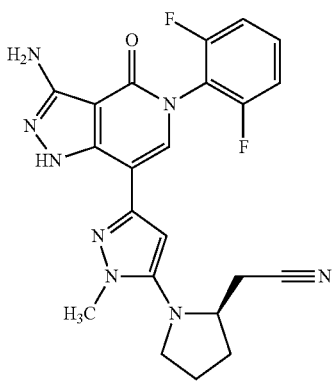 [SMILES: Cn1nc(-c2cn(-c3c(F)cccc3F)c(=O)c3c(N)n[nH]c23)cc1N1CCC[C@@H]1CC#N] | 451.1 |

TABLE 5-continued

| | | | |
|---|---|---|---|
| 143 | 3-amino-5-(2,6-difluorophenyl)-7-(1-methyl-5-(morpholin-4-yl)-1H-pyrazol-3-yl)-1,5-dihydro-4H-pyrazolo[4,3-c]pyridin-4-one | | 428.1 |
| 144 | 3-amino-5-(2,6-difluorophenyl)-7-(5-(1-(isopropylsulfonyl)-3-methoxyazetidin-3-yl)-1-methyl-1H-pyrazol-3-yl)-1,5-dihydro-4H-pyrazolo[4,3-c]pyridin-4-one | | 534.2 |

Example 145

3-amino-5-(dicyclopropylmethyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (236 mg), tetrakis(triphenylphosphine)palladium(0) (54 mg), potassium acetate (91 mg) and N,N-dimethylacetamide (3 mL) was stirred under an argon atmosphere at 110° C. for 4 hr. The reaction mixture was cooled to room temperature, and a solution of 1-((2R)-1-(3-bromo-1-methyl-1H-pyrazol-5-yl)pyrrolidin-2-yl)-N,N-dimethylmethanamine (133 mg) obtained in Reference Example 92 in N,N-dimethylacetamide (2 mL), aqueous sodium carbonate solution (2 M, 0.464 mL) and tetrakis(triphenylphosphine)palladium(0) (54 mg) were added. Under an argon atmosphere, the reaction mixture was stirred at 120° C. for 4 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)). The obtained fraction was concentrated under reduced pressure, and ethyl acetate was added. The organic layer was washed with saturated aqueous sodium hydrogen carbonate solution, water and saturated brine, and dried over anhydrous magnesium sulfate. The solvent was evaporated under reduced pressure and the residue was solidified from ethyl acetate/hexane to give the title compound (20 mg).

Example 146

3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one A) 4-methoxy-5-(1-methyl-5-morpholino-1H-pyrazol-3-yl)-1-(2-methylcyclohexyl)-2-oxo-1,2-dihydropyridine-3-carbonitrile A mixture of 4-(3-bromo-1-methyl-1H-pyrazol-5-yl)morpholine (1.211 g) obtained in Reference Example 12, 4,4,4',4',5,5,5',5'-octamethyl-2,2'-bi-1,3,2-dioxaborolane (2.499 g), (1,1'-bis(diphenylphosphino)ferrocene)dichloropalladium(II) (180 mg), potassium acetate (966 mg) and 1,2-dimethoxyethane (9 mL) was stirred under an argon atmosphere at 100° C. for 20 hr. To the reaction mixture was added ethyl acetate, insoluble material was removed by filtration, and washed with ethyl acetate. The filtrate was concentrated under reduced pressure to give a black solid.

To the obtained solid were added 1,2-dimethoxyethane (15 mL), 5-bromo-4-methoxy-1-(2-methylcyclohexyl)-2-oxo-1,2-dihydropyridine-3-carbonitrile (0.8 g) obtained in Example 116, Step A, aqueous sodium carbonate solution (2 M, 7.38 mL) and tetrakis(triphenylphosphine)palladium(0) (284 mg). Under an argon atmosphere, the reaction mixture was stirred at 100° C. for 4 hr. The reaction mixture was cooled to room temperature, water was added, and the mixture was extracted with ethyl acetate. The extract was washed with saturated brine, and dried over anhydrous magnesium sulfate. The solvent was evaporated under reduced pressure and the residue was purified by silica gel chromatography (basic silica gel, hexane/ethyl acetate) to give the title compound (733 mg).

MS (ESI+): [M+H]$^+$ 412.1.

B) 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one To a solution of 4-methoxy-5-(1-methyl-5-morpholino-1H-pyrazol-3-yl)-1-(2-methylcyclohexyl)-2-oxo-1,2-dihydropyridine-3-carbonitrile (400 mg) obtained in Reference Example 146, Step A, in ethanol (8 mL) was added hydrazine monohydrate (0.189 mL) at room temperature. The reaction mixture was stirred at 80° C. for 2 hr. The solvent was concentrated under reduced pressure, water was added and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate) to give the title compound (202 mg).

Example 147

3-amino-7-(5-(cyclohex-1-en-1-yl)-1-methyl-1H-pyrazol-3-yl)-5-(dicyclopropylmethyl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (400 mg) obtained in Example 78, Step C, 4,4,4',4',5,5,5',5'-octamethyl-2,2'-bi-1,3,2-dioxaborolane (377 mg), tetrakis(triphenylphosphine)palladium(0) (143 mg), potassium acetate (243 mg) and N,N-dimethylacetamide (4 mL) was stirred under an argon atmosphere at 110° C. for 4 hr. The reaction mixture was cooled to room temperature, 3-bromo-5-(cyclohex-1-en-1-yl)-1-methyl-1H-pyrazole (345 mg) obtained in Reference Example 100, aqueous sodium carbonate solution (2 M, 1.238 mL) and tetrakis(triphenylphosphine)palladium(0) (143 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate) to give the title compound (250 mg).

Example 148

3-amino-7-(5-cyclohexyl-1-methyl-1H-pyrazol-3-yl)-5-(dicyclopropylmethyl)-1,5-dihydro-4H-pyrazolo[4,3-c]pyridin-4-one A mixture of 3-amino-7-(5-(cyclohex-1-en-1-yl)-1-methyl-1H-pyrazol-3-yl)-5-(dicyclopropylmethyl)-1,5-dihydro-4H-pyrazolo[4,3-c]pyridin-4-one (200 mg) obtained in Example 147, platinum(IV) oxide (11 mg) and methanol (10 mL) was stirred under a hydrogen atmosphere at room temperature for 48 hr. The catalyst was removed by filtration, and the filtrate was concentrated under reduced pressure. The obtained residue was purified by silica gel chromatography (diol silica gel, hexane/ethyl acetate). The obtained solid was crystallized from ethyl acetate/hexane to give the title compound (148 mg).

Example 149

3-amino-5-(dicyclopropylmethyl)-7-(1-methyl-5-(4-methylpiperazin-1-yl)-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, 1-(3-bromo-1-methyl-1H-pyrazol-5-yl)-4-methylpiperazine (144 mg) obtained in Reference Example 14, aqueous sodium carbonate solution (2 M, 0.464 mL) and tetrakis(triphenylphosphine)palladium(0) (54 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate). The obtained solid was crystallized from ethanol/hexane to give the title compound (61 mg).

Example 150

3-amino-5-(dicyclopropylmethyl)-7-(1-methyl-5-(4-methyl-1,4-diazepan-1-yl)-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, 1-(3-bromo-1-methyl-1H-pyrazol-5-yl)-4-methyl-1,4-diazepane (139 mg) obtained in Reference Example 101, aqueous sodium carbonate solution (2 M, 0.464 mL) and tetrakis(triphenylphosphine)palladium(0) (54 mg) were added. Under an argon atmosphere, the reaction mixture was stirred at 130° C. for 1 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate) and further purified by silica gel chromatography (diol silica gel, methanol/ethyl acetate). The obtained solid was crystallized from ethyl acetate/hexane to give the title compound (54 mg).

Example 151

3-amino-5-(dicyclopropylmethyl)-7-(1-methyl-5-(3-oxa-8-azabicyclo[3.2.1]oct-8-yl)-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (189 mg), tetrakis(triphenylphosphine)palladium(0) (72 mg), potassium acetate (121 mg) and N,N-dimethylacetamide (4 mL) was stirred under an argon atmosphere at 110° C. for 4 hr. The reaction mixture was cooled to room temperature, 8-(3-bromo-1-methyl-1H-pyrazol-5-yl)-3-oxa-8-azabicyclo[3.2.1]octane (220 mg) obtained in Reference Example 102, aqueous sodium carbonate solution (2 M, 0.619 mL) and tetrakis(triphenylphosphine)palladium(0) (72 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, hexane/ethyl acetate). The obtained solid was crystallized from methanol/diisopropyl ether to give the title compound (111 mg).

Example 152

3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one A racemate (cis/trans mixture) of 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one (171 mg) obtained in Example 146, Step B, was fractionated by HPLC (column: CHIRALPAK AD, 50 mmID×500 mmL, manufactured by Daicel Corporation, mobile phase: ethanol/diethylamine=1000/1 (v/v)), and fractions having peaks of the first to third retention times were collected. The collected fractions were concentrated under reduced pressure. The obtained residue was fractionated by HPLC (column: CHIRALPAK AD, 50 mmID×500 mmL, manufactured by Daicel Corporation, mobile phase: hexane/2-propanol/diethylamine=200/800/1 (v/v/v)) to give a crude purification product (24 mg) of the title compound having the first retention time. The crude purification product (24 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (22 mg).

(HPLC (column: CHIRALPAK AD-3, 4.6 mmID×100 mmL, manufactured by Daicel Corporation, mobile phase: hexane/2-propanol/diethylamine=200/800/1 (v/v/v), flow rate: 0.5 mL/min, retention time: 6.80 min))

Example 153

3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one A racemate (cis/trans mixture) of 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one (171 mg) obtained in Example 146, Step B, was fractionated by HPLC (column: CHIRALPAK AD, 50 mmID×500 mmL, manufactured by Daicel Corporation, mobile phase: ethanol/diethylamine=1000/1 (v/v)), and fractions having peaks of the first to third retention times were collected. The collected fractions were concentrated under reduced pressure. The obtained residue was fractionated by HPLC (column: CHIRALPAK AD, 50 mmID×500 mmL, manufactured by Daicel Corporation, mobile phase: hexane/2-propanol/diethylamine=200/800/1 (v/v/v)) to give a crude purification product (63 mg) of the title compound having the second retention time. The crude purification product (63 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (51 mg).

(HPLC (column: CHIRALPAK AD-3, 4.6 mmID×100 mmL, manufactured by Daicel Corporation, mobile phase: hexane/2-propanol/diethylamine=200/800/1 (v/v/v), flow rate: 0.5 mL/min, retention time: 8.88 min))

Example 154

3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one A racemate (cis/trans mixture) of 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one (171 mg) obtained in Example 146, Step B, was fractionated by HPLC (column: CHIRALPAK AD, 50 mmID×500 mmL, manufactured by Daicel Corporation, mobile phase: ethanol/diethylamine=1000/1 (v/v)), and fractions having peaks of the first to third retention times were collected. The collected fractions were concentrated under reduced pressure. The obtained residue was fractionated by HPLC (column: CHIRALPAK AD, 50 mmID×500 mmL, manufactured by Daicel Corporation, mobile phase: hexane/2-propanol/diethylamine=200/800/1 (v/v/v)) to give a crude purification product (33 mg) of the title compound having the third retention time. The crude purification product (33 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (24 mg).

(HPLC (column: CHIRALPAK AD-3, 4.6 mmID×100 mmL, manufactured by Daicel Corporation, mobile phase: hexane/2-propanol/diethylamine=200/800/1 (v/v/v), flow rate: 0.5 mL/min, retention time: 11.23 min))

Example 155

3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one A racemate (cis/trans mixture) of 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one (171 mg) obtained in Example 146, Step B, was fractionated by HPLC (column: CHIRALPAK AD, 50 mmID×500 mmL, manufactured by Daicel Corporation, mobile phase: ethanol/diethylamine=1000/1 (v/v)) to give a crude purification product (74 mg) of the title compound having the fourth retention time. The crude purification product (74 mg) was dissolved in ethyl acetate, washed with saturated aqueous sodium hydrogen carbonate solution, water and saturated brine, and dried over anhydrous magnesium sulfate. The solvent was evaporated under reduced pressure to give the title compound (57 mg). (HPLC (column: CHIRALPAK AD-3, 4.6 mmID×100 mmL, manufactured by Daicel Corporation, mobile phase: hexane/2-propanol/diethylamine=200/800/1 (v/v/v), flow rate: 0.5 mL/min, retention time: 25.96 min))

Example 156

3-amino-5-(dicyclopropylmethyl)-7-(5-((3R)-3-(dimethylamino)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, (3R)-1-(3-bromo-1-methyl-1H-pyrazol-5-yl)-N,N-dimethylpyrrolidin-3-amine (169 mg) obtained in Reference Example 91, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate) and further fractionated by HPLC (C18, mobile phase: water/acetonitrile (containing 0.1% TFA)), and the obtained fraction was concentrated under reduced pressure. Ethyl acetate was added to the residue, and the mixture was washed with saturated aqueous sodium hydrogen carbonate solution, water and saturated brine, dried over anhydrous magnesium sulfate, and concentrated under reduced pressure. The residue was solidified from ethyl acetate/hexane to give the title compound (22 mg).

Example 157

3-amino-5-(dicyclopropylmethyl)-7-(5-((2R)-2-(hydroxymethyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, ((2R)-1-(3-bromo-1-methyl-1H-pyrazol-5-yl)pyrrolidin-2-yl)methanol (161 mg) obtained in Reference Example 24, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate) and further fractionated by HPLC (C18, mobile phase: water/acetonitrile (containing 0.1% TFA)), and the obtained fraction was concentrated under reduced pressure. Ethyl acetate was added to the residue, and the mixture was washed with saturated aqueous sodium hydrogen carbonate solution, water and saturated brine, dried over anhydrous magnesium sulfate, and concentrated under reduced pressure. The residue was solidified from ethyl acetate/hexane to give a crude purification product. The crude purification product was purified by silica gel chromatography (diol silica gel, hexane/ethyl acetate, and then ethyl acetate/methanol), and the obtained solid was solidified from ethyl acetate/hexane to give the title compound (17 mg).

Example 158

3-amino-5-(dicyclopropylmethyl)-7-(1-methyl-5-((2R)-2-(pyrrolidin-1-ylmethyl)pyrrolidin-1-yl)-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (189 mg), tetrakis(triphenylphosphine)palladium(0) (72 mg), potassium acetate (121 mg) and N,N-dimethylacetamide (4 mL) was stirred under an argon atmosphere at 110° C. for 4 hr. The reaction mixture was cooled to room temperature, (R)-3-bromo-1-methyl-5-(2-(pyrrolidin-1-ylmethyl)pyrrolidin-1-yl)-1H-pyrazole (233 mg) obtained in Reference Example 103, aqueous sodium carbonate solution (2 M, 0.619 mL) and tetrakis(triphenylphosphine)palladium(0) (72 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, hexane/ethyl acetate). The obtained solid was crystallized from methanol/diisopropyl ether to give the title compound (65 mg).

Example 159

3-amino-5-(dicyclopropylmethyl)-7-(5-((2R)-2-(methoxymethyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, 3-bromo-5-((2R)-2-(methoxymethyl)pyrrolidin-1-yl)-1-methyl-1H-pyrazole (170 mg) obtained in Reference Example 94, aqueous sodium carbonate solution (2 M, 0.619 mL) and tetrakis (triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate/tetrahydrofuran. The extract was washed with water and saturated brine, and dried over anhydrous magnesium sulfate. The solvent was evaporated under reduced pressure and the residue was purified by silica gel chromatography (basic silica gel, methanol/ethyl acetate) and further fractionated by HPLC (C18, mobile phase: water/acetonitrile (containing 0.1% TFA)). To the obtained fraction was added saturated aqueous sodium hydrogen carbonate solution, and the mixture was concentrated under reduced pressure. Ethyl acetate was added to the residue, and the mixture was washed with saturated aqueous sodium hydrogen carbonate solution, water and saturated brine, dried over anhydrous magnesium sulfate, and concentrated under reduced pressure to give the title compound (76 mg).

Example 160

3-amino-5-(dicyclopropylmethyl)-7-(5-((3S)-3-(dimethylamino)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, (S)-1-(3-bromo-1-methyl-1H-pyrazol-5-yl)-N,N-dimethylpyrrolidin-3-amine (169 mg) obtained in Reference Example 98, aqueous sodium carbonate solution (2 M, 0.619 mL) and tetrakis (triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate) and further fractionated by HPLC (C18, mobile phase: water/acetonitrile (containing 0.1% TFA)). To the obtained fraction was added saturated aqueous sodium hydrogen carbonate solution, and the mixture was concentrated under reduced pressure. Ethyl acetate was added to the residue, and the mixture was washed with saturated aqueous sodium hydrogen carbonate solution, water and saturated brine, dried over anhydrous magnesium sulfate, and concentrated under reduced pressure to give the title compound (72 mg).

Example 161

3-amino-7-(5-cyclopropyl-1-methyl-1H-pyrazol-3-yl)-5-(dicyclopropylmethyl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (180 mg) obtained in Example 78, Step C, 4,4,4',4',5,5,5',5'-octamethyl-2,2'-bi-1,3,2-dioxaborolane (283 mg), tetrakis(triphenylphosphine)palladium(0) (64 mg), potassium acetate (109 mg) and N,N-dimethylacetamide (3 mL) was stirred under an argon atmosphere at 110° C. for 4 hr. The reaction mixture was cooled to room temperature, 5-cyclopropyl-1-methyl-1H-pyrazol-3-yl trifluoromethanesulfonate (151 mg) obtained in Reference Example 70, aqueous sodium carbonate solution (2 M, 0.557 mL) and tetrakis(triphenylphosphine)palladium(0) (64 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, ethyl acetate/hexane, and then methanol/ethyl acetate) and further fractionated by HPLC (C18, mobile phase: water/acetonitrile (containing 10 mM $NH_4HCO_3$)). The obtained fraction was concentrated under reduced pressure to give the title compound (21 mg).

Example 162

3-amino-5-(dicyclopropylmethyl)-7-(5-((8aS)-hexahydropyrrolo[1,2-a]pyrazin-2(1H)-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, (S)-2-(3-bromo-1-methyl-1H-pyrazol-5-yl)octahydropyrrolo[1,2-a]pyrazine (159 mg) obtained in Reference Example 104, aqueous sodium carbonate solution (2 M, 0.464 mL) and tetrakis (triphenylphosphine)palladium(0) (54 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, hexane/ethyl acetate). The obtained solid was crystallized from ethanol/diisopropyl ether to give the title compound (21 mg).

Example 163

3-amino-5-(dicyclopropylmethyl)-7-(5-((8aR)-hexahydropyrrolo[1,2-a]pyrazin-2(1H)-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, (R)-2-(3-bromo-1-methyl-1H-pyrazol-5-yl)octahydropyrrolo[1,2-a]pyrazine (159 mg) obtained in Reference Example 105, aqueous sodium carbonate solution (2 M, 0.464 mL) and tetrakis (triphenylphosphine)palladium(0) (54 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, hexane/ethyl acetate). The obtained solid was crystallized from ethyl acetate/hexane to give the title compound (16 mg).

Example 164

3-amino-5-(dicyclopropylmethyl)-7-(5-((3R)-3-methoxypyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, 3-bromo-5-((3R)-3-methoxypyrrolidin-1-yl)-1-methyl-1H-pyrazole (161 mg) obtained in Reference Example 26, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate) and further purified by silica gel chromatography (diol silica gel, hexane/ethyl acetate). The obtained solid was crystallized from ethyl acetate/hexane to give the title compound (42 mg).

Example 165

3-amino-5-(dicyclopropylmethyl)-7-(1-methyl-5-(trifluoromethyl)-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, 1-methyl-5-(trifluoromethyl)-1H-pyrazol-3-yl trifluoromethanesulfonate (185 mg) obtained in Reference Example 69, aqueous sodium carbonate solution (2 M, 0.619 mL) and tetrakis (triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate) and further fractionated by HPLC (C18, mobile phase: water/acetonitrile (containing 0.1% TFA)), and the obtained fraction was concentrated under reduced pressure. Ethyl acetate was added to the obtained mixture, washed with saturated aqueous sodium hydrogen carbonate solution, water and saturated brine, and dried over anhydrous magnesium sulfate. The solvent was evaporated under reduced pressure and the residue was solidified from ethyl acetate/hexane to give the title compound (16 mg).

Example 166

3-amino-5-(dicyclopropylmethyl)-7-(5-((3S)-3-hydroxypyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium Jo acetate (121 mg) and N,N-dimethylacetamide (3 mL) was stirred under an argon atmosphere at 110° C. for 4 hr. The reaction mixture was cooled to room temperature, (3S)-1-(3-bromo-1-methyl-1H-pyrazol-5-yl)pyrrolidin-3-ol (152 mg) obtained in Reference Example 25, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, hexane/ethyl acetate, and then methanol/ethyl acetate) and further fractionated by HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and the solvent was evaporated under reduced pressure. The residue was solidified from ethyl acetate/hexane to give the title compound (94 mg).

Example 167

3-amino-5-(dicyclopropylmethyl)-7-(5-((3S)-3-methoxypyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg)

obtained in Example 78, Step C, 4,4,4',4',5,5,5',5'-octamethyl-2,2'-bi-1,3,2-dioxaborolane (314 mg), tetrakis(triphenylphosphine)palladium(0) (72 mg), potassium acetate (121 mg) and N,N-dimethylacetamide (3 mL) was stirred under an argon atmosphere at 110° C. for 4 hr. The reaction mixture was cooled to room temperature, 3-bromo-5-((3S)-3-methoxypyrrolidin-1-yl)-1-methyl-1H-pyrazole (161 mg) obtained in Reference Example 27, aqueous sodium carbonate solution (2 M, 0.619 mL) and tetrakis(triphenylphosphine)palladium(0) (72 mg) were added. Under an argon atmosphere, the reaction mixture was stirred at 120° C. for 2 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (basic silica gel, methanol/ethyl acetate) and further fractionated by HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and the solvent was evaporated under reduced pressure. The residue was solidified from ethyl acetate/hexane to give the title compound (70 mg).

Example 168

3-amino-5-(dicyclopropylmethyl)-7-(5-((2S)-2-(hydroxymethyl)pyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (50 mg) obtained in Example 78, Step C, 4,4,4',4',5,5,5',5'-octamethyl-2,2'-bi-1,3,2-dioxaborolane (79 mg), tetrakis(triphenylphosphine)palladium(0) (18 mg), potassium acetate (30 mg) and N,N-dimethylacetamide (1 mL) was stirred under an argon atmosphere at 110° C. for 4 hr. The reaction mixture was cooled to room temperature, ((2S)-1-(3-bromo-1-methyl-1H-pyrazol-5-yl)pyrrolidin-2-yl)methanol (40 mg) obtained in Reference Example 22, aqueous sodium carbonate solution (2 M, 0.155 mL) and tetrakis(triphenylphosphine)palladium(0) (18 mg) were added. Under an argon atmosphere, the reaction mixture was stirred at 120° C. for 2 hr. The reaction mixture was cooled to room temperature, water was added, and the mixture was extracted with ethyl acetate/tetrahydrofuran. The extract was washed with water and saturated brine, and dried over anhydrous magnesium sulfate. The solvent was evaporated under reduced pressure and the residue was purified by silica gel chromatography (basic silica gel, ethyl acetate/hexane, and then methanol/ethyl acetate) and further fractionated by HPLC (C18, mobile phase: water/acetonitrile (containing 10 mM $NH_4HCO_3$)). The obtained fraction was concentrated under reduced pressure to give the title compound (6 mg).

Example 169

3-amino-5-(dicyclopropylmethyl)-7-(5-((3R)-3-hydroxypyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (75 mg) obtained in Example 78, Step C, 4,4,4',4',5,5,5',5'-octamethyl-2,2'-bi-1,3,2-dioxaborolane (71 mg), tetrakis(triphenylphosphine)palladium(0) (27 mg), potassium acetate (46 mg) and N,N-dimethylacetamide (2 mL) was stirred under an argon atmosphere at 110° C. for 4 hr. The reaction mixture was cooled to room temperature, (3R)-1-(3-bromo-1-methyl-1H-pyrazol-5-yl)pyrrolidin-3-ol (63 mg) obtained in Reference Example 23, aqueous sodium carbonate solution (2 M, 0.232 mL) and tetrakis(triphenylphosphine)palladium(0) (27 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further fractionated by HPLC (C18, mobile phase: water/acetonitrile (containing 10 mM $NH_4HCO_3$)). To the obtained fraction was added saturated aqueous sodium hydrogen carbonate solution, and the mixture was extracted with ethyl acetate. The extract was washed with water and saturated brine, and dried over anhydrous magnesium sulfate. The solvent was evaporated under reduced pressure and the residue was crystallized from ethyl acetate/hexane to give the title compound (5 mg).

Example 170

3-amino-5-(dicyclopropylmethyl)-7-(5-(3,3-difluoropyrrolidin-1-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (189 mg), tetrakis(triphenylphosphine)palladium(0) (72 mg), potassium acetate (121 mg) and N,N-dimethylacetamide (4 mL) was stirred under an argon atmosphere at 110° C. for 4 hr. The reaction mixture was cooled to room temperature, 3-bromo-5-(3,3-difluoropyrrolidin-1-yl)-1-methyl-1H-pyrazole (198 mg) obtained in Reference Example 84, aqueous sodium carbonate solution (2 M, 0.619 mL) and tetrakis(triphenylphosphine)palladium(0) (72 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (hexane/ethyl acetate) and further purified by silica gel chromatography (diol silica gel, hexane/ethyl acetate). The obtained solid was crystallized from ethanol/diisopropyl ether to give the title compound (137 mg).

Example 171 tert-butyl(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl) pyrrolidin-2-yl)methyl)methylcarbamate A mixture of 3-amino-7-bromo-5-(dicyclopropylmethyl)-1,5-dihydro-4H-pyrazolo[4,3-c]pyridin-4-one (210 mg) obtained in Example 78, Step C, 4,4,4',4',5,5,5',5'-octamethyl-2,2'-bi-1,3,2-dioxaborolane (198 mg), tetrakis(triphenylphosphine)palladium(0) (75 mg), potassium acetate (128 mg) and N,N-dimethylacetamide (4 mL) was stirred under an argon atmosphere at 110° C. for 4 hr. The reaction mixture was cooled to room temperature, (R)-tert-butyl((1-(3-bromo-1-methyl-1H-pyrazol-5-yl)pyrrolidin-2-yl)methyl)(methyl)carbamate (306 mg) obtained in Reference Example 107, aqueous sodium carbonate solution (2 M, 0.650 mL) and tetrakis(triphenylphosphine)palladium(0) (75 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (hexane/ethyl acetate) and further purified by silica gel chromatography (diol silica gel, hexane/ethyl acetate). The obtained solid was crystallized from ethyl acetate/hexane to give the title compound (245 mg).

Example 172

3-amino-5-(dicyclopropylmethyl)-7-(1-methyl-5-((2R)-2-((methylamino)methyl)pyrrolidin-1-yl)-1H-pyrazol-3-yl)-1,5-dihydro-4H-pyrazolo[4,3-c]pyridin-4-one A mixture of tert-butyl(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)methylcarbamate (237 mg) obtained in Example 171, and a solution (10 mL) of 4N hydrogen chloride in ethyl acetate was stirred at room temperature overnight. The solvent was evaporated under reduced pressure, and the obtained residue was crystallized from ethyl acetate to give the title compound (157 mg).

Example 173

3-amino-5-(dicyclopropylmethyl)-7-(1,5-dimethyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (300 mg) obtained in Example 78, Step C, 4,4,4',4',5,5,5',5'-octamethyl-2,2'-bi-1,3,2-dioxaborolane (283 mg), tetrakis(triphenylphosphine)palladium(0) (107 mg), potassium acetate (182 mg) and N,N-dimethylacetamide (4 mL) was stirred under an argon atmosphere at 110° C. for 4 hr. The reaction mixture was cooled to room temperature, 3-bromo-1,5-dimethyl-1H-pyrazole (195 mg), aqueous sodium carbonate solution (2 M, 0.928 mL) and tetrakis(triphenylphosphine)palladium(0) (107 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (hexane/ethyl acetate) and further purified by silica gel chromatography (diol silica gel, hexane/ethyl acetate). The obtained solid was crystallized from ethyl acetate/diisopropyl ether to give the title compound (104 mg).

Example 174

3-amino-5-(dicyclopropylmethyl)-7-(5-(2-hydroxypropan-2-yl)-1-methyl-1H-pyrazol-3-yl)-1,5-dihydro-4H-pyrazolo[4,3-c]pyridin-4-one A mixture of 3-amino-7-bromo-5-(dicyclopropylmethyl)-1,5-dihydro-4H-pyrazolo[4,3-c]pyridin-4-one (200 mg) obtained in Example 78, Step C, 4,4,4',4',5,5,5',5'-octamethyl-2,2'-bi-1,3,2-dioxaborolane (189 mg), tetrakis(triphenylphosphine)palladium(0) (72 mg), potassium acetate (121 mg) and N,N-dimethylacetamide (4 mL) was stirred under an argon atmosphere at 110° C. for 4 hr. The reaction mixture was cooled to room temperature, 2-(3-bromo-1-methyl-1H-pyrazol-5-yl)propan-2-ol (163 mg) obtained in Reference Example 4, aqueous sodium carbonate solution (2 M, 0.619 mL) and tetrakis(triphenylphosphine)palladium(0) (72 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (hexane/ethyl acetate) and further purified by silica gel chromatography (diol silica gel, hexane/ethyl acetate). The obtained solid was crystallized from ethyl acetate/hexane to give the title compound (84 mg).

Example 175

N-(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylacetamide A mixture of 3-amino-7-bromo-5-(dicyclopropylmethyl)-1,5-dihydro-4H-pyrazolo[4,3-c]pyridin-4-one (150 mg) obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, (R)—N-((1-(3-bromo-1-methyl-1H-pyrazol-5-yl)pyrrolidin-2-yl)methyl)-N-methylacetamide (175 mg) obtained in Reference Example 108, aqueous sodium carbonate solution (2 M, 0.464 mL) and tetrakis(triphenylphosphine)palladium(0) (54 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, methanol/ethyl acetate). The obtained solid was crystallized from ethyl acetate/hexane to give the title compound (60 mg).

Example 176

N-(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylmethanesulfonamide A mixture of 3-amino-7-bromo-5-(dicyclopropylmethyl)-1,5-dihydro-4H-pyrazolo[4,3-c]pyridin-4-one (150 mg)

obtained in Example 78, Step C, 4,4,4',4',5,5,5',5'-octamethyl-2,2'-bi-1,3,2-dioxaborolane (141 mg), tetrakis(triphenylphosphine)palladium(0) (54 mg), potassium acetate (91 mg) and N,N-dimethylacetamide (4 mL) was stirred under an argon atmosphere at 110° C. for 4 hr. The reaction mixture was cooled to room temperature, (R)—N-((1-(3-bromo-1-methyl-1H-pyrazol-5-yl)pyrrolidin-2-yl)methyl)-N-methylmethanesulfonamide (226 mg) obtained in Reference Example 109, aqueous sodium carbonate solution (2 M, 0.464 mL) and tetrakis(triphenylphosphine)palladium(0) (54 mg) were added. Under an argon atmosphere, the reaction mixture was stirred at 130° C. for 5 hr. The reaction mixture was cooled to room temperature, water was added, and the mixture was extracted with ethyl acetate. The extract was washed with water and saturated brine, and dried over anhydrous magnesium sulfate. The solvent was evaporated under reduced pressure and the residue was purified by silica gel chromatography (methanol/ethyl acetate) and further purified by silica gel chromatography (diol silica gel, methanol/ethyl acetate). The obtained solid was crystallized from ethyl acetate/hexane to give the title compound (111 mg).

Example compounds produced by the above-mentioned production methods or methods shown in the Examples, or a method analogous thereto are shown in the following Tables. MS in the Tables shows measured values.

TABLE 6

| Ex. No. | IUPAC name | structural formula | MS |
|---|---|---|---|
| 145 | 3-amino-5-(dicyclopropylmethyl)-7-(5-((2R)-2-((dimethylamino)methyl)pyrrolidin-1-yl)-1-methyl-1H-pyrazol-3-yl)-1,5-dihydro-4H-pyrazolo[4,3-c]pyridin-4-one | | 451.2 |
| 146 | 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one | | 412.2 |
| 147 | 3-amino-7-(5-(cyclohex-1-en-1-yl)-1-methyl-1H-pyrazol-3-yl)-5-(dicyclopropylmethyl)-1,5-dihydro-4H-pyrazolo[4,3-c]pyridin-4-one | | 405.2 |

| | | | |
|---|---|---|---|
| 148 | 3-amino-7-(5-cyclohexyl-1-methyl-1H-pyrazol-3-yl)-5-(dicyclopropylmethyl)-1,5-dihydro-4H-pyrazolo[4,3-c]pyridin-4-one | 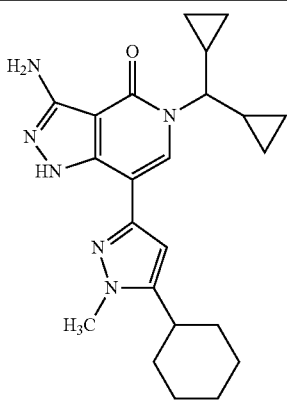 | 407.2 |
| 149 | 3-amino-5-(dicyclopropylmethyl)-7-(1-methyl-5-(4-methylpiperazin-1-yl)-1H-pyrazol-3-yl)-1,5-dihydro-4H-pyrazolo[4,3-c]pyridin-4-one | 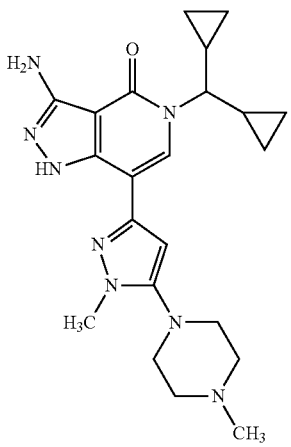 [SMILES: CN1CCN(c2cc(-c3cn(C(C4CC4)C4CC4)c(=O)c4c(N)n[nH]c34)nn2C)CC1] | 423.2 |
| 150 | 3-amino-5-(dicyclopropylmethyl)-7-(1-methyl-5-(4-methyl-1,4-diazepan-1-yl)-1H-pyrazol-3-yl)-1,5-dihydro-4H-pyrazolo[4,3-c]pyridin-4-one | 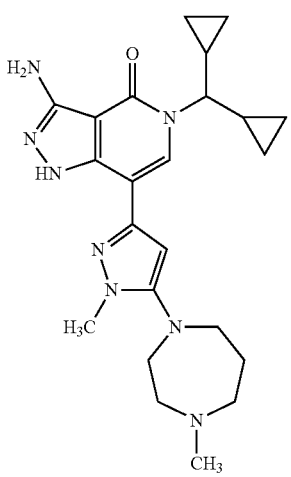 [SMILES: CN1CCCN(c2cc(-c3cn(C(C4CC4)C4CC4)c(=O)c4c(N)n[nH]c34)nn2C)CC1] | 437.2 |

| | | | |
|---|---|---|---|
| 151 | 3-amino-5-(dicyclopropylmethyl)-7-(1-methyl-5-(3-oxa-8-azabicyclo[3.2.1]oct-8-yl)-1H-pyrazol-3-yl)-1,5-dihydro-4H-pyrazolo[4,3-c]pyridin-4-one | 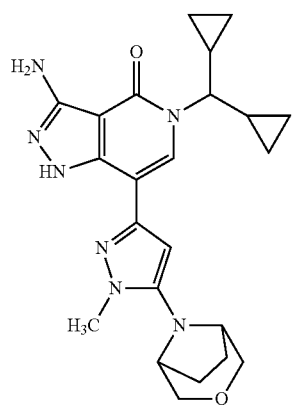 [SMILES: Cn1nc(-c2cn(C(C3CC3)C3CC3)c(=O)c3c(N)n[nH]c23)cc1N1C2CCC1COC2] | 436.2 |
| 152 | 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one | 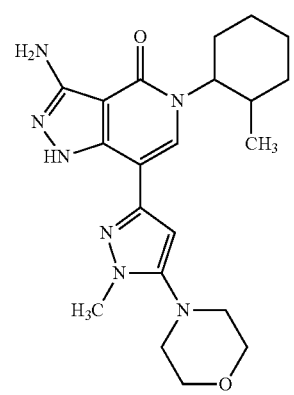 [SMILES: CC1CCCCC1n1cc(-c2cc(N3CCOCC3)n(C)n2)c2[nH]nc(N)c2c1=O] | 412.2 |
| 153 | 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one | 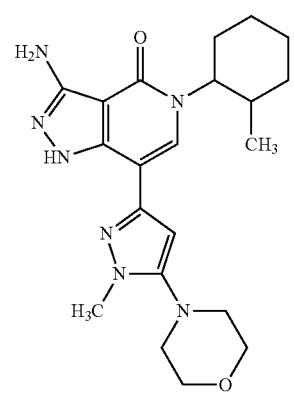 [SMILES: CC1CCCCC1n1cc(-c2cc(N3CCOCC3)n(C)n2)c2[nH]nc(N)c2c1=O] | 412.2 |
| 154 | 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one | 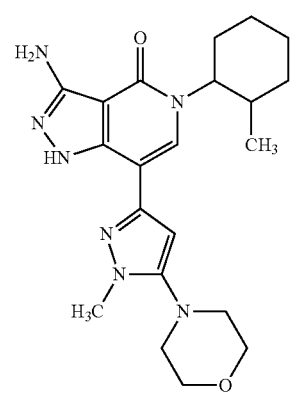 [SMILES: CC1CCCCC1n1cc(-c2cc(N3CCOCC3)n(C)n2)c2[nH]nc(N)c2c1=O] | 412.2 |

TABLE 6-continued

| | | | |
|---|---|---|---|
| 155 | 3-amino-5-(2-methylcyclohexyl)-7-(1-methyl-5-(morpholin-4-yl)-1H-pyrazol-3-yl)-1,5-dihydro-4H-pyrazolo[4,3-c]pyridin-4-one | 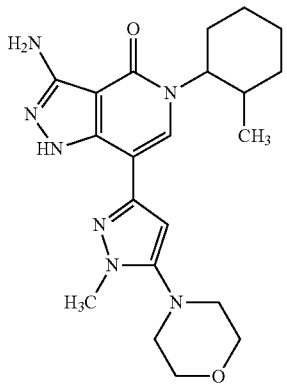 [SMILES: CC1CCCCC1n1cc(-c2cc(N3CCOCC3)n(C)n2)c2[nH]nc(N)c2c1=O] | 412.2 |
| 156 | 3-amino-5-(dicyclopropylmethyl)-7-(5-((3R)-3-(dimethylamino)pyrrolidin-1-yl)-1-methyl-1H-pyrazol-3-yl)-1,5-dihydro-4H-pyrazolo[4,3-c]pyridin-4-one | 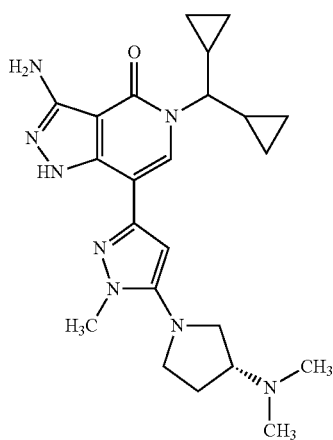 [SMILES: CN(C)[C@@H]1CCN(c2cc(-c3cn(C(C4CC4)C4CC4)c(=O)c4c(N)n[nH]c34)nn2C)C1] | 437.3 |
| 157 | 3-amino-5-(dicyclopropylmethyl)-7-(5-((2R)-2-(hydroxymethyl)pyrrolidin-1-yl)-1-methyl-1H-pyrazol-3-yl)-1,5-dihydro-4H-pyrazolo[4,3-c]pyridin-4-one | 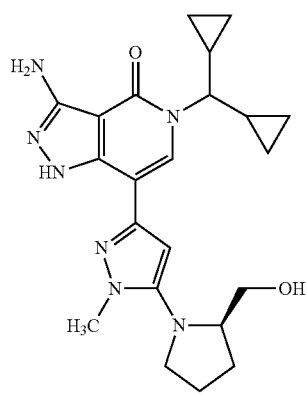 [SMILES: Cn1nc(-c2cn(C(C3CC3)C3CC3)c(=O)c3c(N)n[nH]c23)cc1N1CCC[C@@H]1CO] | 424.2 |
| 158 | 3-amino-5-(dicyclopropylmethyl)-7-(1-methyl-5-((2R)-2-(pyrrolidin-1-ylmethyl)pyrrolidin-1-yl)-1H-pyrazol-3-yl)-1,5-dihydro-4H-pyrazolo[4,3-c]pyridin-4-one | 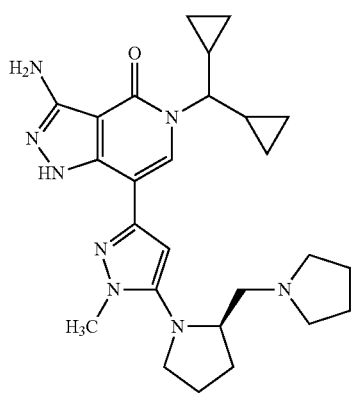 [SMILES: Cn1nc(-c2cn(C(C3CC3)C3CC3)c(=O)c3c(N)n[nH]c23)cc1N1CCC[C@@H]1CN1CCCC1] | 477.3 |

| | | | |
|---|---|---|---|
| 159 | 3-amino-5-(dicyclopropylmethyl)-7-(5-((2R)-2-(methoxymethyl)pyrrolidin-1-yl)-1-methyl-1H-pyrazol-3-yl)-1,5-dihydro-4H-pyrazolo[4,3-c]pyridin-4-one | 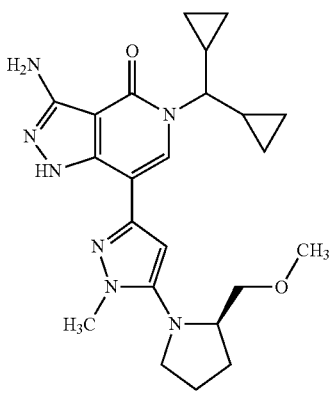 [SMILES: COC[C@H]1CCCN1c1cc(-c2cn(C(C3CC3)C3CC3)c(=O)c3c(N)n[nH]c23)nn1C] | 438.2 |
| 160 | 3-amino-5-(dicyclopropylmethyl)-7-(5-((3S)-3-(dimethylamino)pyrrolidin-1-yl)-1-methyl-1H-pyrazol-3-yl)-1,5-dihydro-4H-pyrazolo[4,3-c]pyridin-4-one | 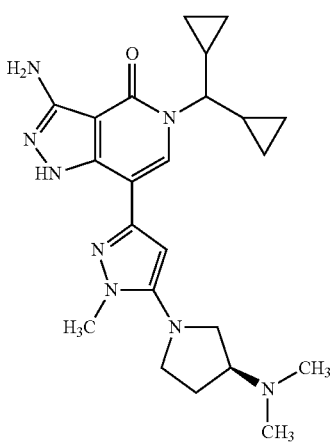 [SMILES: CN(C)[C@H]1CCN(c2cc(-c3cn(C(C4CC4)C4CC4)c(=O)c4c(N)n[nH]c34)nn2C)C1] | 437.2 |
| 161 | 3-amino-7-(5-cyclopropyl-1-methyl-1H-pyrazol-3-yl)-5-(dicyclopropylmethyl)-1,5-dihydro-4H-pyrazolo[4,3-c]pyridin-4-one | 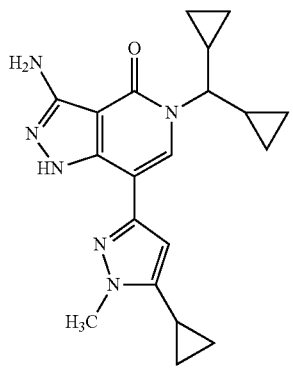 [SMILES: Cn1nc(-c2cn(C(C3CC3)C3CC3)c(=O)c3c(N)n[nH]c23)cc1C1CC1] | 365.2 |
| 162 | 3-amino-5-(dicyclopropylmethyl)-7-(5-((8aS)-hexahydropyrrolo[1,2-a]pyrazin-2(1H)-yl)-1-methyl-1H-pyrazol-3-yl)-1,5-dihydro-4H-pyrazolo[4,3-c]pyridin-4-one | 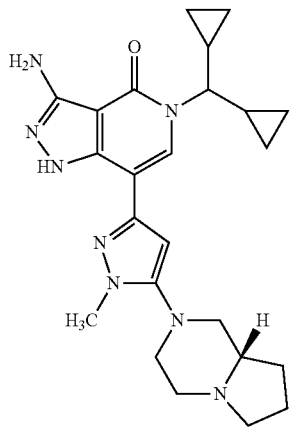 [SMILES: Cn1nc(-c2cn(C(C3CC3)C3CC3)c(=O)c3c(N)n[nH]c23)cc1N1CCN2CCC[C@H]2C1] | 449.3 |

TABLE 6-continued

| 163 | 3-amino-5-(dicyclopropylmethyl)-7-(5-((8aR)-hexahydropyrrolo[1,2-a]pyrazin-2(1H)-yl)-1-methyl-1H-pyrazol-3-yl)-1,5-dihydro-4H-pyrazolo[4,3-c]pyridin-4-one | 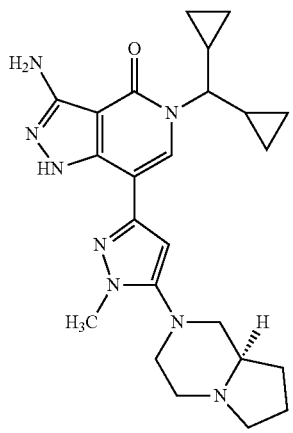 [SMILES: Cn1nc(-c2cn(C(C3CC3)C3CC3)c(=O)c3c(N)n[nH]c23)cc1N1CCN2CCC[C@@H]2C1] | 449.2 |
| --- | --- | --- | --- |
| 164 | 3-amino-5-(dicyclopropylmethyl)-7-(5-((3R)-3-methoxypyrrolidin-1-yl)-1-methyl-1H-pyrazol-3-yl)-1,5-dihydro-4H-pyrazolo[4,3-c]pyridin-4-one | 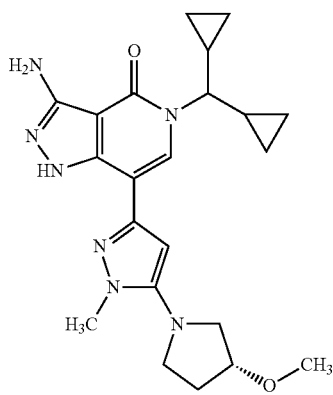 [SMILES: CO[C@@H]1CCN(c2cc(-c3cn(C(C4CC4)C4CC4)c(=O)c4c(N)n[nH]c34)nn2C)C1] | 424.2 |
| 165 | 3-amino-5-(dicyclopropylmethyl)-7-(1-methyl-5-(trifluoromethyl)-1H-pyrazol-3-yl)-1,5-dihydro-4H-pyrazolo[4,3-c]pyridin-4-one | 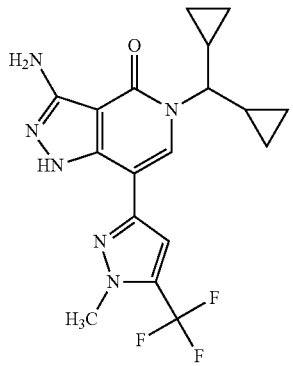 [SMILES: Cn1nc(-c2cn(C(C3CC3)C3CC3)c(=O)c3c(N)n[nH]c23)cc1C(F)(F)F] | 393.2 |
| 166 | 3-amino-5-(dicyclopropylmethyl)-7-(5-((3S)-3-hydroxypyrrolidin-1-yl)-1-methyl-1H-pyrazol-3-yl)-1,5-dihydro-4H-pyrazolo[4,3-c]pyridin-4-one | 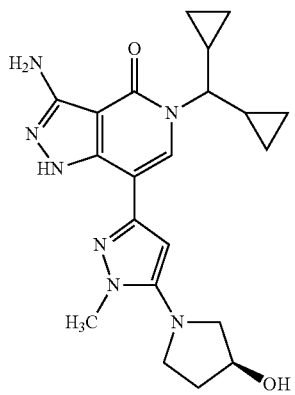 [SMILES: Cn1nc(-c2cn(C(C3CC3)C3CC3)c(=O)c3c(N)n[nH]c23)cc1N1CC[C@H](O)C1] | 410.2 |

TABLE 6-continued

| Ex. No. | IUPAC name | structural formula | salt | MS |
|---|---|---|---|---|
| 167 | 3-amino-5-(dicyclopropylmethyl)-7-(5-((3S)-3-methoxypyrrolidin-1-yl)-1-methyl-1H-pyrazol-3-yl)-1,5-dihydro-4H-pyrazolo[4,3-c]pyridin-4-one | 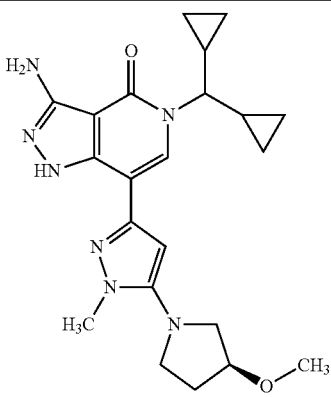 | | 424.2 |
| 168 | 3-amino-5-(dicyclopropylmethyl)-7-(5-((2S)-2-(hydroxymethyl)pyrrolidin-1-yl)-1-methyl-1H-pyrazol-3-yl)-1,5-dihydro-4H-pyrazolo[4,3-c]pyridin-4-one | 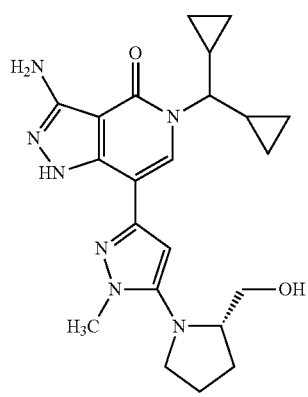 [SMILES: Cn1nc(-c2cn(C(C3CC3)C3CC3)c(=O)c3c(N)n[nH]c23)cc1N1CCC[C@H]1CO] | | 424.2 |
| 169 | 3-amino-5-(dicyclopropylmethyl)-7-(5-((3R)-3-hydroxypyrrolidin-1-yl)-1-methyl-1H-pyrazol-3-yl)-1,5-dihydro-4H-pyrazolo[4,3-c]pyridin-4-one | 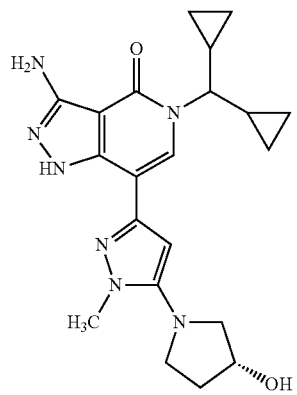 [SMILES: Cn1nc(-c2cn(C(C3CC3)C3CC3)c(=O)c3c(N)n[nH]c23)cc1N1CC[C@@H](O)C1] | | 410.2 |

| Ex. No. | IUPAC name | structural formula | salt | MS |
|---|---|---|---|---|
| 170 | 3-amino-5-(dicyclopropylmethyl)-7-(5-(3,3-difluoropyrrolidin-1-yl)-1-methyl-1H-pyrazol-3-yl)-1,5-dihydro-4H-pyrazolo[4,3-c]pyridin-4-one | 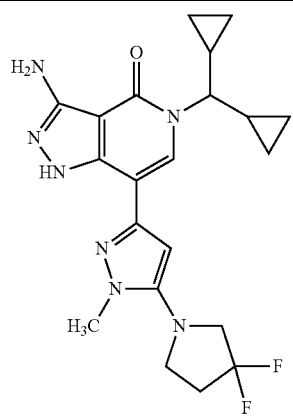 | | 430.1 |

| | | | | |
|---|---|---|---|---|
| 171 | tert-butyl (((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)methylcarbamate | 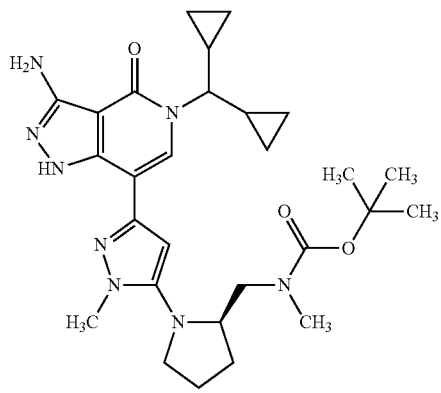 [SMILES: CN(C[C@H]1CCCN1c1cc(-c2cn(C(C3CC3)C3CC3)c(=O)c3c(N)n[nH]c23)nn1C)C(=O)OC(C)(C)C] | | 537.3 |
| 172 | 3-amino-5-(dicyclopropylmethyl)-7-(1-methyl-5-((2R)-2-((methylamino)methyl)pyrrolidin-1-yl)-1H-pyrazol-3-yl)-1,5-dihydro-4H-pyrazolo[4,3-c]pyridin-4-one | 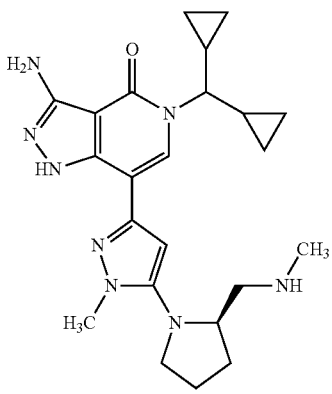 [SMILES: CNC[C@H]1CCCN1c1cc(-c2cn(C(C3CC3)C3CC3)c(=O)c3c(N)n[nH]c23)nn1C] | 2HCl | 437.2 |
| 173 | 3-amino-5-(dicyclopropylmethyl)-7-(1,5-dimethyl-1H-pyrazol-3-yl)-1,5-dihydro-4H-pyrazolo[4,3-c]pyridin-4-one | 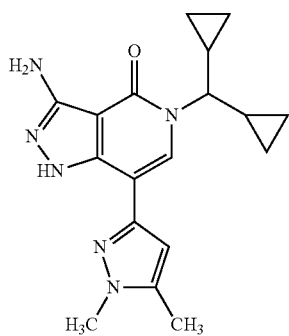 [SMILES: Cc1cc(-c2cn(C(C3CC3)C3CC3)c(=O)c3c(N)n[nH]c23)nn1C] | | 339.1 |

TABLE 6-continued

| Ex. No. | IUPAC name | structural formula | MS |
|---|---|---|---|
| 174 | 3-amino-5-(dicyclopropylmethyl)-7-(5-(2-hydroxypropan-2-yl)-1-methyl-1H-pyrazol-3-yl)-1,5-dihydro-4H-pyrazolo[4,3-c]pyridin-4-one | 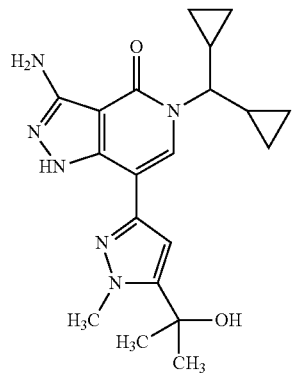 [SMILES: Cn1nc(-c2cn(C(C3CC3)C3CC3)c(=O)c3c(N)n[nH]c23)cc1C(C)(C)O] | 383.1 |
| 175 | N-(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylacetamide | 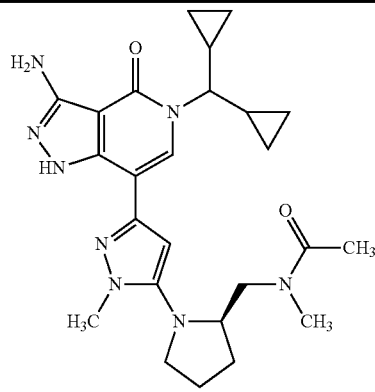 | 479.2 |
| 176 | N-(((2R)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylmethanesulfonamide | 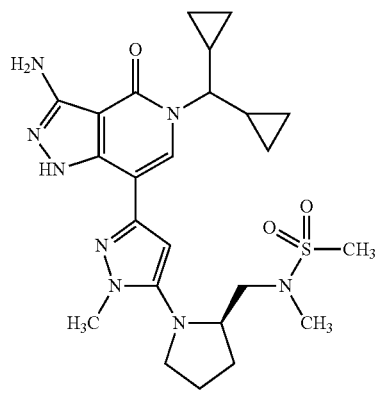 [SMILES: CN(C[C@H]1CCCN1c1cc(-c2cn(C(C3CC3)C3CC3)c(=O)c3c(N)n[nH]c23)nn1C)S(C)(=O)=O] | 515.2 |

The compounds shown in the following Examples can be produced by the above-mentioned production methods or methods shown in Examples and Reference Examples, or a method analogous thereto.

TABLE 7

| Ex. No. | IUPAC name | structural formula |
|---|---|---|
| 177 | 3-amino-5-(dicyclopropylmethyl)-7-(1-methyl-5-((2S)-2-((methylamino)methyl)pyrrolidin-1-yl)-1H-pyrazol-3-yl)-1,5-dihydro-4H-pyrazolo[4,3-c]pyridin-4-one | |
| 178 | 3-amino-5-(dicyclopropylmethyl)-7-(5-((2S)-2-((dimethylamino)methyl)pyrrolidin-1-yl)-1-methyl-1H-pyrazol-3-yl)-1,5-dihydro-4H-pyrazolo[4,3-c]pyridin-4-one | |
| 179 | N-(((2S)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylacetamide | |

TABLE 7-continued

| Ex. No. | IUPAC name | structural formula |
|---|---|---|
| 180 | N-(((2S)-1-(3-(3-amino-5-(dicyclopropylmethyl)-4-oxo-4,5-dihydro-1H-pyrazolo[4,3-c]pyridin-7-yl)-1-methyl-1H-pyrazol-5-yl)pyrrolidin-2-yl)methyl)-N-methylmethanesulfonamide | |
| 181 | 3-amino-5-(dicyclopropylmethyl)-7-(5-((2R)-2-((3,3-difluoropyrrolidin-1-yl)methyl)pyrrolidin-1-yl)-1-methyl-1H-pyrazol-3-yl)-1,5-dihydro-4H-pyrazolo[4,3-c]pyridin-4-one | |
| 182 | 3-amino-5-(dicyclopropylmethyl)-7-(5-((2S)-2-((3,3-difluoropyrrolidin-1-yl)methyl)pyrrolidin-1-yl)-1-methyl-1H-pyrazol-3-yl)-1,5-dihydro-4H-pyrazolo[4,3-c]pyridin-4-one | |
| 183 | 3-amino-5-(dicyclopropylmethyl)-7-(1-methyl-5-((2R)-2-((methylsulfonyl)methyl)pyrrolidin-1-yl)-1H-pyrazol-3-yl)-1,5-dihydro-4H-pyrazolo[4,3-c]pyridin-4-one | |

TABLE 7-continued

| Ex. No. | IUPAC name |
|---|---|
| 184 | 3-amino-5-(dicyclopropylmethyl)-7-(1-methyl-5-((2S)-2-((methylsulfonyl)methyl)pyrrolidin-1-yl)-1H-pyrazol-3-yl)-1,5-dihydro-4H-pyrazolo[4,3-c]pyridin-4-one |
| 185 | 3-amino-5-(dicyclopropylmethyl)-7-(1-methyl-5-((2R)-2-((2-oxopyrrolidin-1-yl)methyl)pyrrolidin-1-yl)-1H-pyrazol-3-yl)-1,5-dihydro-4H-pyrazolo[4,3-c]pyridin-4-one |
| 186 | 3-amino-5-(dicyclopropylmethyl)-7-(1-methyl-5-((2S)-2-((2-oxopyrrolidin-1-yl)methyl)pyrrolidin-1-yl)-1H-pyrazol-3-yl)-1,5-dihydro-4H-pyrazolo[4,3-c]pyridin-4-one |
| 187 | 3-amino-5-(dicyclopropylmethyl)-7-(1-methyl-5-(7-methyl-1,7-diazaspiro[4.4]non-1-yl)-1H-pyrazol-3-yl)-1,5-dihydro-4H-pyrazolo[4,3-c]pyridin-4-one |

TABLE 7-continued

| Ex. No. | IUPAC name | structural formula |
|---|---|---|
| 188 | 3-amino-5-(dicyclopropylmethyl)-7-(1-methyl-5-(7-oxa-1-azaspiro[4.4]non-1-yl)-1H-pyrazol-3-yl)-1,5-dihydro-4H-pyrazolo[4,3-c]pyridin-4-one | |
| 189 | 3-amino-7-(5-(1-azaspiro[4.4]non-1-yl)-1-methyl-1H-pyrazol-3-yl)-5-(dicyclopropylmethyl)-1,5-dihydro-4H-pyrazolo[4,3-c]pyridin-4-one | |
| 190 | 3-amino-5-(dicyclopropylmethyl)-7-(1-methyl-5-(2-methyl-2,5-diazaspiro[3.4]oct-5-yl)-1H-pyrazol-3-yl)-1,5-dihydro-4H-pyrazolo[4,3-c]pyridin-4-one | |
| 191 | 3-amino-5-(dicyclopropylmethyl)-7-(1-methyl-5-(pyridin-3-yl)-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 192 | 3-amino-5-(dicyclopropylmethyl)-7-(1-methyl-5-(4-methylpyridin-3-yl)-1H-pyrazol-3-yl)-1,5-dihydro-4H-pyrazolo[4,3-c]pyridin-4-one | |
| 193 | 3-amino-5-(dicyclopropylmethyl)-7-(1-methyl-5-(pyridin-2-yl)-1H-pyrazol-3-yl)-1,5-dihydro-4H-pyrazolo[4,3-c]pyridin-4-one | |
| 194 | 3-amino-5-(dicyclopropylmethyl)-7-(1-methyl-5-(3-methylpyridin-2-yl)-1H-pyrazol-3-yl)-1,5-dihydro-4H-pyrazolo[4,3-c]pyridin-4-one | |
| 195 | 3-amino-5-(dicyclopropylmethyl)-7-(5-(3-(dimethylamino)phenyl)-1-methyl-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 196 | 3-amino-5-(dicyclopropylmethyl)-7-(1-methyl-5-(3-(methylamino)phenyl)-1H-pyrazol-3-yl)-1,5-dihydro-4H-pyrazolo[4,3-c]pyridin-4-one | |
| 197 | 3-amino-5-(dicyclopropylmethyl)-7-(1-methyl-5-(pyrimidin-5-yl)-1H-pyrazol-3-yl)-1,5-dihydro-4H-pyrazolo[4,3-c]pyridin-4-one | |
| 198 | 3-amino-5-(dicyclopropylmethyl)-7-(1-methyl-5-(pyrazin-2-yl)-1H-pyrazol-3-yl)-1,5-dihydro-4H-pyrazolo[4,3-c]pyridin-4-one | |
| 199 | 3-amino-5-(dicyclopropylmethyl)-7-(1-methyl-5-(pyrimidin-2-yl)-1H-pyrazol-3-yl)-1,5-dihydro-4H-pyrazolo[4,3-c]pyridin-4-one | |

| Ex. No. | IUPAC name | structural formula |
|---|---|---|
| 200 | 3-amino-5-(dicyclopropylmethyl)-7-(5-(5-(dimethylamino)-2-methylphenyl)-1-methyl-1H-pyrazol-3-yl)-1,5-dihydro-4H-pyrazolo[4,3-c]pyridin-4-one | |
| 201 | 3-amino-5-(dicyclopropylmethyl)-7-(1-methyl-5-(2-methyl-5-(methylamino)phenyl)-1H-pyrazol-3-yl)-1,5-dihydro-4H-pyrazolo[4,3-c]pyridin-4-one | |
| 202 | 3-amino-5-(dicyclopropylmethyl)-7-(1,2'-dimethyl-1H,2'H-3,3'-bipyrazol-5'-yl)-1,5-dihydro-4H-pyrazolo[4,3-c]pyridin-4-one | |

TABLE 7-continued

| Ex. No. | IUPAC name | structural formula |
|---|---|---|
| 203 | 3-amino-5-(dicyclopropylmethyl)-7-(2'-methyl-1H,2'H-3,3'-bipyrazol-5'-yl)-1,5-dihydro-4H-pyrazolo[4,3-c]pyridin-4-one | |
| 204 | 3-amino-5-(dicyclopropylmethyl)-7-(1',2-dimethyl-1'H,2H-3,4'-bipyrazol-5-yl)-1,5-dihydro-4H-pyrazolo[4,3-c]pyridin-4-one | |
| 205 | 3-amino-5-(dicyclopropylmethyl)-7-(2-methyl-1'H,2H-3,4'-bipyrazol-5-yl)-1,5-dihydro-4H-pyrazolo[4,3-c]pyridin-4-one | |
| 206 | 3-(3-amino-5-(dicyclopropylmethyl)-4-oxo-4,5-dihydro-1H-pyrazolo[4,3-c]pyridin-7-yl)-1-methyl-1H-pyrazole-5-carbonitrile | |

TABLE 7-continued

| Ex. No. | IUPAC name | structural formula |
|---|---|---|
| 207 | 3-amino-5-(dicyclopropylmethyl)-7-(5-(difluoromethyl)-1-methyl-1H-pyrazol-3-yl)-1,5-dihydro-4H-pyrazolo[4,3-c]pyridin-4-one | |
| 208 | 3-amino-5-(dicyclopropylmethyl)-7-(5-fluoro-1-methyl-1H-pyrazol-3-yl)-1,5-dihydro-4H-pyrazolo[4,3-c]pyridin-4-one | |
| 209 | 3-amino-5-(dicyclopropylmethyl)-7-(5-ethyl-1-methyl-1H-pyrazol-3-yl)-1,5-dihydro-4H-pyrazolo[4,3-c]pyridin-4-one | |
| 210 | 3-amino-5-(dicyclopropylmethyl)-7-(5-isopropyl-1-methyl-1H-pyrazol-3-yl)-1,5-dihydro-4H-pyrazolo[4,3-c]pyridin-4-one | |

TABLE 7-continued

| Ex. No. | IUPAC name |
|---|---|
| 211 | 3-amino-5-(dicyclopropylmethyl)-7-(1-methyl-5-(2,2,2-trifluoroethyl)-1H-pyrazol-3-yl)-1,5-dihydro-4H-pyrazolo[4,3-c]pyridin-4-one |
| 212 | 3-amino-5-(dicyclopropylmethyl)-7-(5-(2,2-difluoroethyl)-1-methyl-1H-pyrazol-3-yl)-1,5-dihydro-4H-pyrazolo[4,3-c]pyridin-4-one |
| 213 | 3-amino-5-(dicyclopropylmethyl)-7-(1-methyl-5-((2R)-2-(morpholin-4-ylmethyl)pyrrolidin-1-yl)-1H-pyrazol-3-yl)-1,5-dihydro-4H-pyrazolo[4,3-c]pyridin-4-one |
| 214 | 3-amino-5-(dicyclopropylmethyl)-7-(1-methyl-5-((2S)-2-(morpholin-4-ylmethyl)pyrrolidin-1-yl)-1H-pyrazol-3-yl)-1,5-dihydro-4H-pyrazolo[4,3-c]pyridin-4-one |

TABLE 7-continued

| Ex. No. | IUPAC name | structural formula |
|---|---|---|
| 215 | 3-amino-5-(dicyclopropylmethyl)-7-(1-methyl-5-((2R)-2-(piperidin-1-ylmethyl)pyrrolidin-1-yl)-1H-pyrazol-3-yl)-1,5-dihydro-4H-pyrazolo[4,3-c]pyridin-4-one | |
| 216 | 3-amino-5-(dicyclopropylmethyl)-7-(1-methyl-5-((2S)-2-(piperidin-1-ylmethyl)pyrrolidin-1-yl)-1H-pyrazol-3-yl)-1,5-dihydro-4H-pyrazolo[4,3-c]pyridin-4-one | |
| 217 | 3-amino-5-(dicyclopropylmethyl)-7-(5-((2R)-2-((4,4-difluoropiperidin-1-yl)methyl)pyrrolidin-1-yl)-1-methyl-1H-pyrazol-3-yl)-1,5-dihydro-4H-pyrazolo[4,3-c]pyridin-4-one | |
| 218 | 3-amino-5-(dicyclopropylmethyl)-7-(5-((2S)-2-((4,4-difluoropiperidin-1-yl)methyl)pyrrolidin-1-yl)-1-methyl-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 219 | 3-amino-5-(dicyclopropylmethyl)-7-(5-methoxy)-1-methyl-1H-pyrazol-3-yl)-1,5-dihydro-4H-pyrazolo[4,3-c]pyridin-4-one | |
| 220 | 3-amino-5-(dicyclopropylmethyl)-7-(5-(difluoromethoxy)-1-methyl-1H-pyrazol-3-yl)-1,5-dihydro-4H-pyrazolo[4,3-c]pyridin-4-one | |
| 221 | 3-amino-5-(dicyclopropylmethyl)-7-(1-methyl-5-(6-oxa-3-azabicyclo[3.1.1]hept-3-yl)-1H-pyrazol-3-yl)-1,5-dihydro-4H-pyrazolo[4,3-c]pyridin-4-one | |
| 222 | 3-amino-5-(dicyclopropylmethyl)-7-(1-methyl-5-((2S)-2-(1H-pyrazol-1-ylmethyl)pyrrolidin-1-yl)-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 223 | 3-amino-5-(dicyclopropylmethyl)-7-(1-methyl-5-((2R)-2-(1H-pyrazol-1-ylmethyl)pyrrolidin-1-yl)-1H-pyrazol-3-yl)-1,5-dihydro-4H-pyrazolo[4,3-c]pyridin-4-one | |
| 224 | 3-amino-7-(5-((2R)-2-(azetidin-1-ylmethyl)pyrrolidin-1-yl)-1-methyl-1H-pyrazol-3-yl)-5-(dicyclopropylmethyl)-1,5-dihydro-4H-pyrazolo[4,3-c]pyridin-4-one | |
| 225 | 3-amino-7-(5-((2S)-2-(azetidin-1-ylmethyl)pyrrolidin-1-yl)-1-methyl-1H-pyrazol-3-yl)-5-(dicyclopropylmethyl)-1,5-dihydro-4H-pyrazolol[4,3-c]pyridin-4-one | |
| 226 | 3-amino-5-(dicyclopropylmethyl)-7-(5-((2R)-2-((3,3-difluoroazetidin-1-yl)methyl)pyrrolidin-1-yl)-1-methyl-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 227 | 3-amino-5-(dicyclopropylmethyl)-7-(5-((2S)-2-((3,3-difluoroazetidin-1-yl)methyl)pyrrolidin-1-yl)-1-methyl-1H-pyrazol-3-yl)-1,5-dihydro-4H-pyrazolo[4,3-c]pyridin-4-one | |
| 228 | 3-amino-5-(dicyclopropylmethyl)-7-(1-methyl-5-(3-methyl-3,8-diazabicyclo[3.2.1]oct-8-yl)-1H-pyrazol-3-yl)-1,5-dihydro-4H-pyrazolo[4,3-c]pyridin-4-one | |
| 229 | 3-amino-5-(dicyclopropylmethyl)-7-(5-(4-hydroxy-4-(trifluoromethyl)piperidin-1-yl)-1-methyl-1H-pyrazol-3-yl)-1,5-dihydro-4H-pyrazolo[4,3-c]pyridin-4-one | |

TABLE 7-continued

| Ex. No. | IUPAC name | structural formula |
|---|---|---|
| 230 | 3-amino-5-(dicyclopropylmethyl)-7-(5-(4-hydroxy-4-methylpiperidin-1-yl)-1-methyl-1H-pyrazol-3-yl)-1,5-dihydro-4H-pyrazolo[4,3-c]pyridin-4-one | |
| 231 | 3-amino-5-(3,3-dimethylbutan-2-yl)-7-(5-(2-hydroxypropan-2-yl)-1-methyl-1H-pyrazol-3-yl)-1,5-dihydro-4H-pyrazolo[4,3-c]pyridin-4-one | |
| 232 | 3-amino-5-(3,3-dimethylbutan-2-yl)-7-(1-methyl-5-(morpholin-4-yl)-1H-pyrazol-3-yl)-1,5-dihydro-4H-pyrazolo[4,3-c]pyridin-4-one | |
| 233 | 3-amino-7-(5-(2-((dimethylamino)methyl)pyrrolidin-1-yl)-1-methyl-1H-pyrazol-3-yl)-5-(3,3-dimethylbutan-2-yl)-1,5-dihydro-4H-pyrazolo[4,3-c]pyridin-4-one | |

TABLE 7-continued

| Ex. No. | IUPAC name | structural formula |
|---|---|---|
| 234 | 3-amino-7-(5-(2-hydroxypropan-2-yl)-1-methyl-1H-pyrazol-3-yl)-5-(1-(1-methylcyclobutyl)ethyl)-1,5-dihydro-4H-pyrazolo[4,3-c]pyridin-4-one | |
| 235 | 3-amino-5-(1-(1-methylcyclobutyl)ethyl)-7-(1-methyl-5-(morpholin-4-yl)-1H-pyrazol-3-yl)-1,5-dihydro-4H-pyrazolo[4,3-c]pyridin-4-one | |
| 236 | 3-amino-7-(5-(2-((dimethylamino)methyl)pyrrolidin-1-yl)-1-methyl-1H-pyrazol-3-yl)-5-(1-(1-methylcyclobutyl)ethyl)-1,5-dihydro-4H-pyrazolo[4,3-c]pyridin-4-one | |
| 237 | 3-amino-7-(5-(2-hydroxypropan-2-yl)-1-methyl-1H-pyrazol-3-yl)-5-(1-(3-methyloxetan-3-yl)ethyl)-1,5-dihydro-4H-pyrazolo[4,3-c]pyridin-4-one | |

TABLE 7-continued

| Ex. No. | IUPAC name | structural formula |
|---|---|---|
| 238 | 3-amino-7-(1-methyl-5-(morpholin-4-yl)-1H-pyrazol-3-yl)-5-(1-(3-methyloxetan-3-yl)ethyl)-1,5-dihydro-4H-pyrazolo[4,3-c]pyridin-4-one | |
| 239 | 3-amino-7-(5-(2-((dimethylamino)methyl)pyrrolidin-1-yl)-1-methyl-1H-pyrazol-3-yl)-5-(1-(3-methyloxetan-3-yl)ethyl)-1,5-dihydro-4H-pyrazolo[4,3-c]pyridin-4-one | |

Reference Example 1 ethyl 3,5-dibromo-1H-pyrazole-4-carboxylate

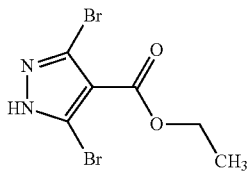

To a mixed solution of ethyl 1H-pyrazole-4-carboxylate (31.0 g), sodium acetate (118 g), ethanol (200 mL) and water (300 mL) was added bromine (141 g), and the mixture was stirred at room temperature for 10 hr. To the reaction mixture was added sodium thiosulfate (175 g), and the solvent was evaporated under reduced pressure. The reaction mixture was poured into water, and the mixture was extracted with ethyl acetate. The extract was washed with saturated brine, and dried over anhydrous magnesium sulfate. The solvent was evaporated under reduced pressure to give the title compound (65.1 g).

MS (ESI+): [M+H]$^+$ 296.7.

Reference Example 2 ethyl 3,5-dibromo-1-methyl-1H-pyrazole-4-carboxylate

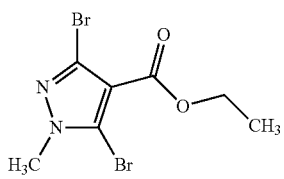

To a solution of ethyl 3,5-dibromo-1H-pyrazole-4-carboxylate (30.0 g) obtained in Reference Example 1 in tetrahydrofuran (400 mL) was added sodium hydride (60% in mineral oil, 4.23 g) at 0° C. Under a nitrogen atmosphere, the mixture was stirred at 0° C. for 1 hr. Iodomethane (41.4 g) was added at 0° C., and the mixture was stirred at room temperature for 10 hr. Water was added to the reaction mixture, and the solvent was evaporated under reduced pressure. The reaction mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (31.1 g).

MS (ESI+): [M+H]$^+$ 310.7.

Reference Example 3

3,5-dibromo-1-methyl-1H-pyrazole

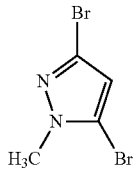

A mixture of ethyl 3,5-dibromo-1-methyl-1H-pyrazole-4-carboxylate (40.0 g) obtained in Reference Example 2 and 50% aqueous sulfuric acid solution (150 mL, v/v) was stirred at 160° C. for 90 min. The reaction mixture was diluted with water (300 mL) at 0° C., and the mixture was extracted with ethyl acetate (500 mL×2, 300 mL×1). The extract was washed with saturated brine (300 mL), and dried over anhydrous magnesium sulfate. The solvent was evaporated under reduced pressure to give the title compound (26.5 g).

MS (ESI+): [M+H]$^+$ 238.6.

Reference Example 4

2-(3-bromo-1-methyl-1H-pyrazol-5-yl)propan-2-ol

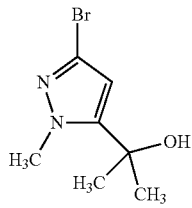

To a solution of 3,5-dibromo-1-methyl-1H-pyrazole (14.1 g) obtained in Reference Example 3 in tetrahydrofuran (200 mL) was added dropwise n-butyllithium (1.6 M hexane solution, 40.4 mL) at −78° C. Under an argon atmosphere, the mixture was stirred at −78° C. for 30 min, propan-2-one (5.61 mL) was added to the reaction mixture and the mixture was stirred at room temperature for 10 hr. To the reaction mixture was added water (400 mL), and the mixture was extracted with ethyl acetate (400 mL, 500 mL). The extract was washed with saturated brine (300 mL), and dried over anhydrous magnesium sulfate. The solvent was evaporated under reduced pressure and the residue was purified by silica gel column chromatography (hexane/ethyl acetate) to give the title compound (9.06 g).

MS (ESI+): [M+H]$^+$ 218.8.

Reference Example 5 methyl 3-((4-methoxybenzyl)oxy)-2,2-dimethylpropanoate

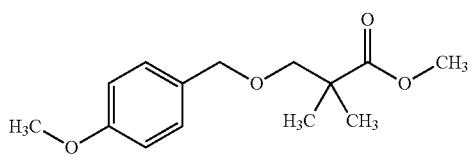

To a solution of methyl 3-hydroxy-2,2-dimethylpropanoate (0.676 mL) in N,N-dimethylformamide (20 mL) was added sodium hydride (60% in mineral oil, 254 mg) at 0° C. Under a nitrogen atmosphere, the reaction mixture was stirred at 0° C. for 30 min, 1-(chloromethyl)-4-methoxybenzene (0.790 mL) and tetrabutylammonium iodide (0.196 g) were added at 0° C. The reaction mixture was allowed to warm to room temperature over 2 hr and stirred overnight under a nitrogen atmosphere. To the reaction mixture was added saturated aqueous ammonium chloride solution, and the mixture was extracted with diethyl ether. The extract was washed with saturated brine, and dried over anhydrous magnesium sulfate. The solvent was evaporated under reduced pressure and the residue was purified by silica gel column chromatography (ethyl acetate/hexane) to give the title compound (1.15 g).

$^1$H NMR (300 MHz, CDCl$_3$) δ 1.14-1.23 (6H, m), 3.41 (2H, s), 3.67 (3H, s), 3.80 (3H, s), 4.40-4.47 (2H, m), 6.84-6.92 (2H, m), 7.21-7.26 (2H, m).

Reference Example 6

5-((4-methoxybenzyl)oxy)-4,4-dimethyl-3-oxopentanenitrile

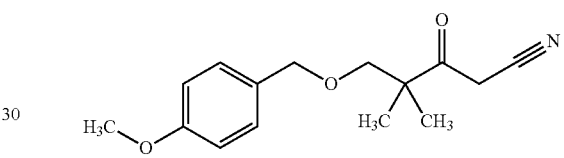

A mixture of sodium hydride (60% in mineral oil, 5.53 g) and tetrahydrofuran (200 mL) was stirred under a nitrogen atmosphere at 70° C. for 30 min. To the reaction mixture was added a solution of methyl 3-((4-methoxybenzyl)oxy)-2,2-dimethylpropanoate (23.26 g) obtained in Reference Example 5 and acetonitrile (7.27 mL) in tetrahydrofuran (100 mL) at 70° C. The reaction mixture was stirred under a nitrogen atmosphere at 70° C. overnight. The solvent was evaporated under reduced pressure. To the reaction mixture was added ethyl acetate, 1 M hydrochloric acid was further added at room temperature, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (17.12 g).

$^1$H NMR (300 MHz, CDCl$_3$) δ 1.17 (6H, s), 3.36 (2H, s), 3.63 (2H, s), 3.82 (3H, s), 4.42 (2H, s), 6.86-6.92 (2H, m), 7.17-7.24 (2H, m).

Reference Example 7

5-(1-((4-methoxybenzyl)oxy)-2-methylpropan-2-yl)-1H-pyrazol-3-amine

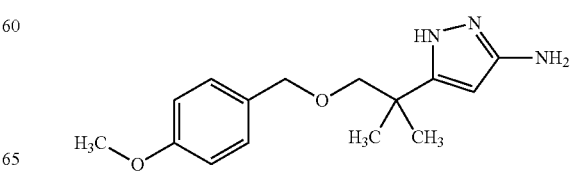

To a solution of 5-((4-methoxybenzyl)oxy)-4,4-dimethyl-3-oxopentanenitrile (17.11 g) obtained in Reference Example 6 in methanol (200 mL) was added hydrazine monohydrate (4.77 mL) at room temperature. The reaction mixture was heated under a nitrogen atmosphere at 70° C. for 6 hr. The reaction mixture was concentrated under reduced pressure, and the residue was purified by silica gel column chromatography (ethyl acetate/methanol) to give the title compound (12.25 g).

MS (ESI+): [M+H]$^+$ 276.3.

Reference Example 8

2-(5-(1-((4-methoxybenzyl)oxy)-2-methylpropan-2-yl)-1H-pyrazol-3-yl)-1H-isoindole-1,3(2H)-dione

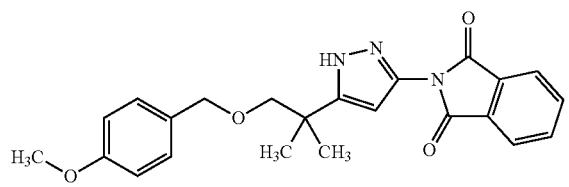 [SMILES: COc1ccc(COCC(C)(C)c2cc(N3C(=O)c4ccccc4C3=O)n[nH]2)cc1]

To a solution of 5-(1-((4-methoxybenzyl)oxy)-2-methylpropan-2-yl)-1H-pyrazol-3-amine (12.25 g) obtained in Reference Example 7 in N,N-dimethylformamide (180 mL) were added phthalic anhydride (6.59 g) and acetic acid (2.55 mL) at room temperature. The reaction mixture was stirred under a nitrogen atmosphere at 90° C. overnight. To the reaction mixture was added a mixed solution of saturated aqueous sodium hydrogen carbonate solution/water (1:1) at room temperature, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (3.61 g).

MS (ESI+): [M+H]$^+$ 406.3.

Reference Example 9

2-(5-(1-((4-methoxybenzyl)oxy)-2-methylpropan-2-yl)-1-methyl-1H-pyrazol-3-yl)-1H-isoindole-1,3(2H)-dione

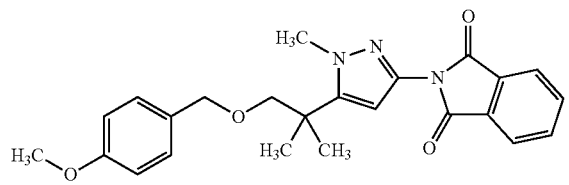 [SMILES: COc1ccc(COCC(C)(C)c2cc(N3C(=O)c4ccccc4C3=O)nn2C)cc1]

To a solution of 2-(5-(1-((4-methoxybenzyl)oxy)-2-methylpropan-2-yl)-1H-pyrazol-3-yl)-1H-isoindole-1,3(2H)-dione (7.32 g) obtained in Reference Example 8 in tetrahydrofuran (120 mL) was added sodium hydride (60% in mineral oil, 1.08 g) at 0° C. The reaction mixture was stirred under a nitrogen atmosphere at 0° C. for 10 min, iodomethane (2.26 mL) was added at room temperature, and the mixture was stirred under a nitrogen atmosphere at room temperature for 1 hr. To the reaction mixture was added saturated aqueous ammonium chloride solution, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (4.97 g).

MS (ESI+): [M+H]$^+$ 420.3.

Reference Example 10

5-(1-((4-methoxybenzyl)oxy)-2-methylpropan-2-yl)-1-methyl-1H-pyrazol-3-amine

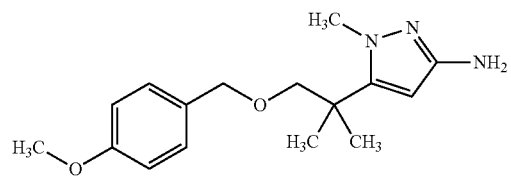 [SMILES: COc1ccc(COCC(C)(C)c2cc(N)nn2C)cc1]

To a solution of 2-(5-(1-((4-methoxybenzyl)oxy)-2-methylpropan-2-yl)-1H-pyrazol-3-yl)-1H-isoindole-, 3 (2H)-dione (750 mg) obtained in Reference Example 9 in methanol (7 mL) was added hydrazine monohydrate (0.095 mL) at room temperature. The reaction mixture was heated under a nitrogen atmosphere at 65° C. for 3 hr. The precipitate was removed by filtration, and washed with ethyl acetate, and the filtrate was concentrated under reduced pressure. To the residue was added toluene, the precipitate was removed by filtration, and the filtrate was purified by silica gel column chromatography (basic silica gel, ethyl acetate/hexane) to give the title compound (450 mg).

MS (ESI+): [M+H]$^+$ 290.3.

Reference Example 11

3-iodo-5-(1-((4-methoxybenzyl)oxy)-2-methylpropan-2-yl)-1-methyl-1H-pyrazole

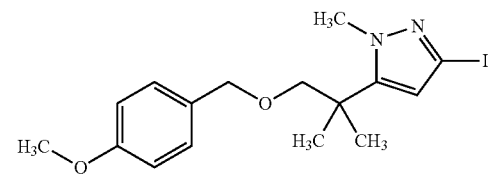 [SMILES: COc1ccc(COCC(C)(C)c2cc(I)nn2C)cc1]

To a mixture of 5-(1-((4-methoxybenzyl)oxy)-2-methylpropan-2-yl)-1-methyl-1H-pyrazol-3-amine (450 mg) obtained in Reference Example 10 and diiodomethane (6.26 mL) was added isoamyl nitrite (0.334 mL) at room temperature. The reaction mixture was stirred under a nitrogen atmosphere at room temperature overnight. To the reaction mixture was added isoamyl nitrite (0.564 mL), and the mixture was stirred under a nitrogen atmosphere at 130° C. for 2 hr, and concentrated under reduced pressure. The residue was purified by silica gel column chromatography (ethyl acetate/hexane) to give the title compound (409 mg).

MS (ESI+): [M+H]$^+$ 401.2.

Reference Example 12

4-(3-bromo-1-methyl-1H-pyrazol-5-yl)morpholine

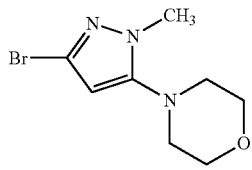

A) ethyl 3-bromo-1-methyl-5-morpholino-1H-pyrazole-4-carboxylate

A mixture of ethyl 3,5-dibromo-1-methyl-1H-pyrazole-4-carboxylate (10.0 g) obtained in Reference Example 2 and morpholine (11.17 g) was stirred at 150° C. for 10 hr. The reaction mixture was added to water while stirring at room temperature, and the obtained crystals were washed successively with water and hexane, and dried under reduced pressure to give the title compound (7.80 g).
MS (ESI+): [M+H]$^+$ 319.8.

B) 4-(3-bromo-1-methyl-1H-pyrazol-5-yl)morpholine

A mixture of ethyl 3-bromo-1-methyl-5-morpholino-1H-pyrazole-4-carboxylate (7.70 g) obtained in Reference Example 12, Step A, 2 M aqueous sodium hydroxide solution (48.4 mL) and ethanol (80 mL) was stirred at 60° C. for 2 hr 30 min. To the reaction mixture was added concentrated sulfuric acid (12.9 mL) at 0° C., and the mixture was stirred at 60° C. for 30 min. The reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure to give the title compound (5.87 g).
MS (ESI+): [M+H]$^+$ 245.7.

Reference Example 13

1-(3-bromo-1-methyl-1H-pyrazol-5-yl)-4-methylpiperidin-4-ol

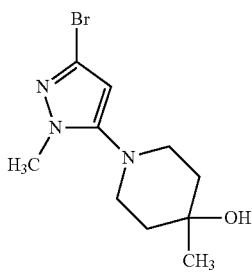

A) ethyl 3-bromo-5-(4-hydroxy-4-methylpiperidin-1-yl)-1-methyl-1H-pyrazole-4-carboxylate A mixture of ethyl 3,5-dibromo-1-methyl-1H-pyrazole-4-carboxylate (2.71 g) obtained in Reference Example 2, 4-methylpiperidin-4-ol (1.0 g) and potassium carbonate (1.2 g) was stirred at 160° C. for 3 hr. After cooling, the reaction mixture was partitioned between water and ethyl acetate. The organic layer was washed with saturated brine, and dried over anhydrous magnesium sulfate. The solvent was evaporated under reduced pressure and the residue was purified by silica gel column chromatography (basic silica gel, ethyl acetate/hexane) to give the title compound (1.0 g).
MS (ESI+): [M+H]$^+$ 345.9.

B) 1-(3-bromo-1-methyl-1H-pyrazol-5-yl)-4-methylpiperidin-4-ol

A mixture of ethyl 3-bromo-5-(4-hydroxy-4-methylpiperidin-1-yl)-1-methyl-1H-pyrazole-4-carboxylate (1.0 g) obtained in Reference Example 13, Step A, 2 M aqueous sodium hydroxide solution (7.22 mL) and ethanol (10 mL) was stirred at 70° C. for 2 hr. To the reaction mixture was added concentrated sulfuric acid (1.848 mL) at 0° C., and the mixture was stirred at 60° C. for 30 min. The reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure to give the title compound (0.68 g).
MS (ESI+): [M+H]$^+$ 273.8.

Reference Example 14

1-(3-bromo-1-methyl-1H-pyrazol-5-yl)-4-methylpiperazine

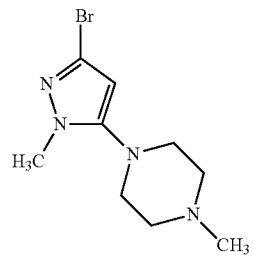

A) ethyl 3-bromo-1-methyl-5-(4-methylpiperazin-1-yl)-1H-pyrazole-4-carboxylate A mixture of ethyl 3,5-dibromo-1-methyl-1H-pyrazole-4-carboxylate (2.00 g) obtained in Reference Example 2, 1-methylpiperazine (963 mg), potassium carbonate (1.06 g), and N-methyl-pyrrolidone (12 mL) was heated under microwave irradiation at 160° C. for 4 hr. After cooling, saturated aqueous sodium hydrogen carbonate solution was added and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (basic silica gel, ethyl acetate/hexane) to give the title compound (1.7 g).
MS (ESI+): [M+H]$^+$ 330.9.

B) 1-(3-bromo-1-methyl-1H-pyrazol-5-yl)-4-methylpiperazine

A mixture of ethyl 3-bromo-1-methyl-5-(4-methylpiperazin-1-yl)-1H-pyrazole-4-carboxylate (1.70 g) obtained in Reference Example 14, Step A, 2 M aqueous sodium hydroxide solution (12.8 mL) and ethanol (15 mL) was stirred at 70° C. for 2 hr. To the reaction mixture was added concentrated sulfuric acid (3.28 mL) at 0° C., and the mixture was stirred at 70° C. for 2 hr. The reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure and the residue was solidified from diethyl ether/hexane to give the title compound (1.13 g).
MS (ESI+): [M+H]$^+$ 258.8.

Reference Example 15

1-(4-(3-bromo-1-methyl-1H-pyrazol-5-yl)piperazin-1-yl)ethanone

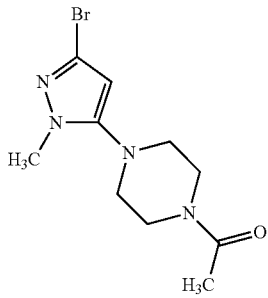

A) ethyl 5-(4-acetylpiperazin-1-yl)-3-bromo-1-methyl-1H-pyrazole-4-carboxylate

A mixture of ethyl 3,5-dibromo-1-methyl-1H-pyrazole-4-carboxylate (2.00 g) obtained in Reference Example 2 and 1-(piperazin-1-yl)ethanone (3.29 g) was heated at 160° C. for 4 hr. After cooling, water was added to the reaction mixture, and the mixture was extracted twice with ethyl acetate. The extracts were combined, washed with saturated brine, and dried over anhydrous magnesium sulfate. The solvent was evaporated under reduced pressure and the residue was purified by silica gel column chromatography (basic silica gel, ethyl acetate/hexane) to give the title compound (1.98 g).
MS (ESI+): [M+H]$^+$ 358.9.

B) 1-(3-bromo-1-methyl-1H-pyrazol-5-yl)piperazine

A mixture of ethyl 5-(4-acetylpiperazin-1-yl)-3-bromo-1-methyl-1H-pyrazole-4-carboxylate (1.95 g) obtained in Reference Example 15, Step A, 2 M aqueous sodium hydroxide solution (13.6 mL) and ethanol (20 mL) was stirred at 80° C. for 4 hr. To the reaction mixture was added concentrated sulfuric acid (3.47 mL) at 0° C., and the mixture was stirred at 60° C. for 3 hr. The reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure to give the title compound (1.31 g).
MS (ESI+): [M+H]$^+$ 244.8.

C) 1-(4-(3-bromo-1-methyl-1H-pyrazol-5-yl)piperazin-1-yl)ethanone

To a solution of 1-(3-bromo-1-methyl-1H-pyrazol-5-yl)piperazine (300 mg) obtained in Reference Example 15, Step B, and triethylamine (0.21 mL) in tetrahydrofuran (10 mL) was added acetyl chloride (0.096 mL) at 0° C. The reaction mixture was stirred at room temperature for 2 hr. Water was added to the reaction mixture, and the mixture was extracted twice with ethyl acetate. The extracts were combined, washed with saturated brine, and dried over anhydrous magnesium sulfate. The solvent was evaporated under reduced pressure to give the title compound (350 mg).
MS (ESI+): [M+H]$^+$ 286.8.

Reference Example 16

4-(3-bromo-1-methyl-1H-pyrazol-5-yl)thiomorpholine 1,1-dioxide

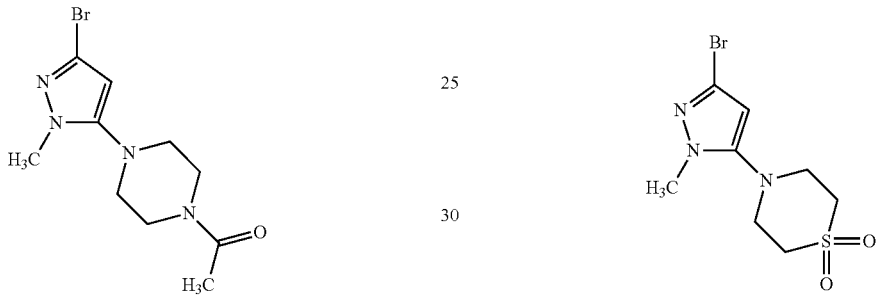

A) ethyl 3-bromo-5-(1,1-dioxidothiomorpholino)-1-methyl-1H-pyrazole-4-carboxylate A mixture of ethyl 3,5-dibromo-1-methyl-1H-pyrazole-4-carboxylate (3.27 g) obtained in Reference Example 2, thiomorpholine 1,1-dioxide (5.12 g) and N-methyl-pyrrolidone (12 mL) was heated under microwave irradiation at 200° C. for 5 hr. After cooling, water was added to the reaction mixture, and the mixture was extracted 3 times with ethyl acetate. The extracts were combined, washed with saturated brine, and dried over anhydrous magnesium sulfate. The solvent was evaporated under reduced pressure and the residue was purified by silica gel column chromatography (ethyl acetate/hexane) to give the title compound (1.2 g) as a crude purification product.
$^1$H NMR (400 MHz, CDCl$_3$) δ1.43 (3H, t, J=7.1 Hz), 3.20 (4H, t, J=5.5 Hz), 3.42-3.51 (4H, m), 3.76-3.79 (3H, m), 4.37 (2H, q, J=7.2 Hz).

B) 4-(3-bromo-1-methyl-1H-pyrazol-5-yl)thiomorpholine 1,1-dioxide

A mixture of ethyl 3-bromo-5-(1,1-dioxidothiomorpholino)-1-methyl-1H-pyrazole-4-carboxylate (1.2 g) obtained in Reference Example 16, Step A, 2 M aqueous sodium hydroxide solution (8.19 mL) and ethanol (10 mL) was stirred at 70° C. for 2 hr. To the reaction mixture was added concentrated sulfuric acid (1.75 mL), and the mixture was stirred at 60° C. for 30 min. The reaction mixture was alkalified by adding 8 M aqueous sodium hydroxide solution, and the resulting solid was collected by filtration, and washed with water to give the title compound (0.44 g).

¹H NMR (400 MHz, CDCl₃) δ3.14-3.27 (4H, m), 3.39-3.54 (4H, m), 3.72 (3H, s), 5.97 (1H, s).

Reference Example 17

4-(3-bromo-1-methyl-1H-pyrazol-5-yl)-1,4-oxazepane

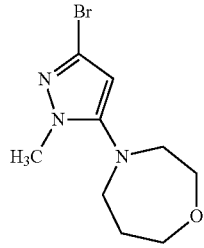

A) ethyl 3-bromo-1-methyl-5-(1,4-oxazepan-4-yl)-1H-pyrazole-4-carboxylate

A mixture of ethyl 3,5-dibromo-1-methyl-1H-pyrazole-4-carboxylate (1.0 g) obtained in Reference Example 2, and 1,4-oxazepane (1.0 g) was stirred at 160° C. for 2 hr. After cooling, water was added to the reaction mixture, and the mixture was stirred at 0° C. for 30 min. The resulting solid was collected by filtration, washed with water, and dried to give the title compound (0.79 g).

MS (ESI+): [M+H]⁺ 331.9.

B) 4-(3-bromo-1-methyl-1H-pyrazol-5-yl)-1,4-oxazepane

A mixture of ethyl 3-bromo-1-methyl-5-(1,4-oxazepan-4-yl)-1H-pyrazole-4-carboxylate (780 mg) obtained in Reference Example 17, Step A, 2 M aqueous sodium hydroxide solution (4.70 mL) and ethanol (9 mL) was stirred at 60° C. for 2 hr. The reaction mixture was allowed to cool, concentrated sulfuric acid (1.00 mL) was added, and the mixture was stirred at 60° C. for 1 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure to give the title compound (570 mg).

MS (ESI+): [M+H]⁺ 259.8.

Reference Example 18

1-(3-bromo-1-methyl-1H-pyrazol-5-yl)-4-methoxypiperidine

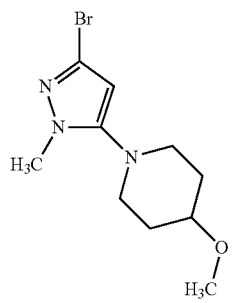

A) ethyl 3-bromo-5-(4-methoxypiperidin-1-yl)-1-methyl-1H-pyrazole-4-carboxylate

A mixture of ethyl 3,5-dibromo-1-methyl-1H-pyrazole-4-carboxylate (2.00 g) obtained in Reference Example 2 and 4-methoxypiperidine (2.95 g) was stirred at 160° C. for 1 hr. After cooling, water was added to the reaction mixture, and the mixture was extracted twice with ethyl acetate. The extracts were combined, washed with saturated brine, and dried over anhydrous magnesium sulfate. The solvent was evaporated under reduced pressure and the residue was purified by silica gel column chromatography (ethyl acetate/hexane) to give the title compound (2.1 g).

MS (ESI+): [M+H]⁺ 346.2.

B) 1-(3-bromo-1-methyl-1H-pyrazol-5-yl)-4-methoxypiperidine

A mixture of ethyl 3-bromo-5-(4-methoxypiperidin-1-yl)-1-methyl-1H-pyrazole-4-carboxylate (2.1 g) obtained in Reference Example 18, Step A, 2 M aqueous sodium hydroxide solution (12.1 mL) and ethanol (12 mL) was stirred at 60° C. for 2 hr. The reaction mixture was cooled, concentrated sulfuric acid (2.59 mL) was added, and the mixture was stirred at 60° C. for 30 min. The reaction mixture was alkalified by adding 8 M aqueous sodium hydroxide solution, and extracted twice with ethyl acetate. The extracts were combined, washed with saturated brine, and dried over anhydrous magnesium sulfate. The solvent was evaporated under reduced pressure to give the title compound (1.59 g).

MS (ESI+): [M+H]⁺ 273.8.

Reference Example 19

2-(1-(3-bromo-1-methyl-1H-pyrazol-5-yl)piperidin-4-yl)propan-2-ol

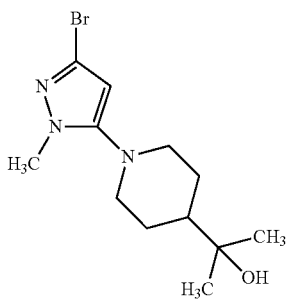 [SMILES: Cn1nc(Br)cc1N1CCC(C(C)(C)O)CC1]

A) ethyl 3-bromo-5-(4-(2-hydroxypropan-2-yl)piperidin-1-yl)-1-methyl-1H-pyrazole-4-carboxylate A mixture of ethyl 3,5-dibromo-1-methyl-1H-pyrazole-4-carboxylate (1.00 g) obtained in Reference Example 2, 2-(piperidin-4-yl)propan-2-ol (1.38 g), and N-methyl-pyrrolidone (10 mL) was heated under microwave irradiation at 160° C. for 5 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (ethyl acetate/hexane) to give the title compound (1.17 g).
MS (ESI+): [M+H]$^+$ 374.0.

B) 2-(1-(3-bromo-1-methyl-1H-pyrazol-5-yl)piperidin-4-yl)propan-2-ol

A mixture of ethyl 3-bromo-5-(4-(2-hydroxypropan-2-yl)piperidin-1-yl)-1-methyl-1H-pyrazole-4-carboxylate (1.07 g) obtained in Reference Example 19, Step A, 2 M aqueous sodium hydroxide solution (7.15 mL) and ethanol (30 mL) was stirred at 70° C. for 2.5 hr. To the reaction mixture was added 2 M aqueous sodium hydroxide solution (2.5 mL) and the mixture was stirred at 70° C. for 0.5 hr. To the reaction mixture was added concentrated sulfuric acid (2.29 mL), and the mixture was stirred at 60° C. for 1 hr. The reaction mixture was alkalified by adding 8 M aqueous sodium hydroxide solution, and extracted twice with ethyl acetate. The extracts were combined, washed with saturated brine, and dried over anhydrous magnesium sulfate. The solvent was evaporated under reduced pressure to give the title compound (0.836 g).
MS (ESI+): [M+H]$^+$ 301.9.

Reference Example 20

1-(3-bromo-1-methyl-1H-pyrazol-5-yl)-4,4-difluoropiperidine

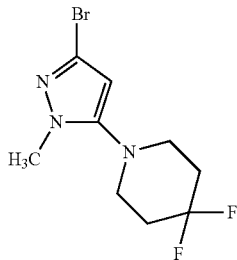

A) ethyl 3-bromo-5-(4,4-difluoropiperidin-1-yl)-1-methyl-1H-pyrazole-4-carboxylate A mixture of ethyl 3,5-dibromo-1-methyl-1H-pyrazole-4-carboxylate (8.25 g) obtained in Reference Example 2, 4,4-difluoropiperidine hydrochloride (5.00 g), N-ethyldiisopropylamine (17.09 g), and N-methyl-pyrrolidone (10 mL) was heated at 160° C. for 5 hr. After cooling, saturated aqueous sodium hydrogen carbonate solution was added to the reaction mixture, and the mixture was extracted 3 times with ethyl acetate. The extracts were combined, washed with water and saturated brine, and dried over anhydrous magnesium sulfate. The solvent was evaporated under reduced pressure and the residue was purified by silica gel column chromatography (basic silica gel, ethyl acetate/hexane) to give the title compound (2.58 g).
MS (ESI+): [M+H]$^+$ 351.8.

B) 1-(3-bromo-1-methyl-1H-pyrazol-5-yl)-4,4-difluoropiperidine

A mixture of ethyl 3-bromo-5-(4,4-difluoropiperidin-1-yl)-1-methyl-1H-pyrazole-4-carboxylate (0.83 g) obtained in Reference Example 20, Step A, 2 M aqueous sodium hydroxide solution (5.89 mL) and ethanol (20 mL) was stirred at 70° C. for 3 hr. To the reaction mixture was added concentrated sulfuric acid (1.51 mL) at 0° C., and the mixture was stirred at 60° C. for 2 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure to give the title compound (0.503 g).
MS (ESI+): [M+H]$^+$ 279.8.

Reference Example 21

1-(4-(3-bromo-1-methyl-1H-pyrazol-5-yl)piperazin-1-yl)-2-methoxyethanone

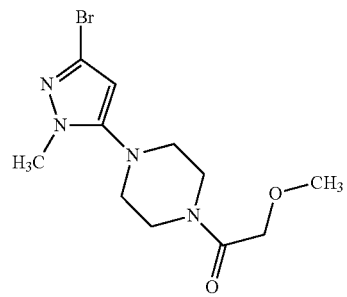

To a solution of 1-(3-bromo-1-methyl-1H-pyrazol-5-yl)piperazine (300 mg) obtained in Reference Example 15, Step B, and triethylamine (248 mg) in tetrahydrofuran (20 mL) was added 2-methoxyacetyl chloride (146 mg) at room temperature. The reaction mixture was stirred at room temperature for 3 hr and the solvent was concentrated under reduced pressure. The reaction mixture was added to water, and the mixture was extracted with ethyl acetate. The extract was separated, washed with saturated brine, and dried over anhydrous magnesium sulfate. The solvent was evaporated under reduced pressure and the residue was purified by silica gel column chromatography (ethyl acetate/hexane) to give the title compound (355 mg).
MS (ESI+): [M+H]$^+$ 316.9.

Reference Example 22

((2S)-1-(3-bromo-1-methyl-1H-pyrazol-5-yl)pyrrolidin-2-yl)methanol

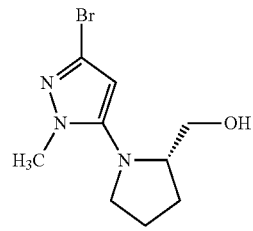

A mixture of ethyl 3,5-dibromo-1-methyl-1H-pyrazole-4-carboxylate (2.00 g) obtained in Reference Example 2, (S)-pyrrolidin-2-ylmethanol (778 mg), potassium carbonate (886 mg), and N-methyl-pyrrolidone (12 mL) was heated under microwave irradiation at 160° C. for 4 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (ethyl acetate/hexane) to give a colorless solid (900 mg). A mixture of the obtained colorless solid (900 mg), 2 M aqueous sodium hydroxide solution (7.5 mL) and ethanol (10 mL) was stirred at 70° C. for 2 hr. The reaction mixture was cooled to room temperature, concentrated sulfuric acid (2.40 mL) was added, and the mixture was stirred at 70° C. for 3 hr. The reaction mixture was cooled to room temperature, alkalified by adding 8 M aqueous sodium hydroxide solution, and extracted twice with ethyl acetate. The extracts were combined, washed with saturated brine, and dried over anhydrous magnesium sulfate. The solvent was evaporated under reduced pressure to give the title compound (723 mg).

MS (ESI+): [M+H]$^+$ 259.8.

Reference Example 23

(3R)-1-(3-bromo-1-methyl-1H-pyrazol-5-yl)pyrrolidin-3-ol

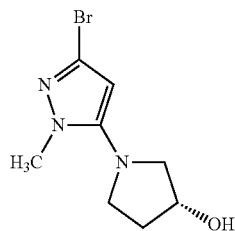

A) (R)-ethyl 3-bromo-5-(3-hydroxypyrrolidin-1-yl)-1-methyl-1H-pyrazole-4-carboxylate A mixture of ethyl 3,5-dibromo-1-methyl-1H-pyrazole-4-carboxylate (1.6 g) obtained in Reference Example 2, (R)-pyrrolidin-3-ol (536 mg), potassium carbonate (0.851 g), and N-methyl-pyrrolidone (12 mL) was heated under microwave irradiation at 160° C. for 4 hr. After cooling, water was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (ethyl acetate/hexane) to give the title compound (1.14 g).

MS (ESI+): [M+H]$^+$ 317.9.

B) (3R)-1-(3-bromo-1-methyl-1H-pyrazol-5-yl) pyrrolidin-3-ol

A mixture of (R)-ethyl 3-bromo-5-(3-hydroxypyrrolidin-1-yl)-1-methyl-1H-pyrazole-4-carboxylate (480 mg) obtained in Reference Example 23, Step A, 2 M aqueous sodium hydroxide solution (3.77 mL) and ethanol (5 mL) was stirred at 70° C. for 2 hr. To the reaction mixture was added concentrated sulfuric acid (0.965 mL) at 0° C., and the mixture was stirred at 70° C. for 2 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure and the residue was crystallized (diethyl ether/hexane) to give the title compound (273 mg).

MS (ESI+): [M+H]$^+$ 245.8.

Reference Example 24

((2R)-1-(3-bromo-1-methyl-1H-pyrazol-5-yl)pyrrolidin-2-yl)methanol

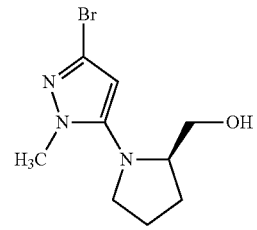

A mixture of ethyl 3,5-dibromo-1-methyl-1H-pyrazole-4-carboxylate (2.00 g) obtained in Reference Example 2, (R)-pyrrolidin-2-ylmethanol (778 mg), potassium carbonate (886 mg), and N-methyl-pyrrolidone (12 mL) was heated under microwave irradiation at 160° C. for 4 hr. After cooling, water was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (ethyl acetate/hexane) to give a colorless solid (2.04 g). A mixture of the obtained colorless solid, 2 M aqueous sodium hydroxide solution (17.91 mL) and ethanol (15 mL) was stirred at 70° C. for 2 hr. To the reaction mixture was added concentrated sulfuric acid (4.58 mL), and the mixture was stirred at 60° C. for 30 min. The reaction mixture was alkalified by adding 8 M aqueous sodium hydroxide solution, added to water at 0° C., and extracted with ethyl acetate. The extract was washed with saturated brine, and dried over anhydrous magnesium sulfate. The solvent was evaporated under reduced pressure and the residue was crystallized (diisopropyl ether/hexane) to give the title compound (464 mg).

MS (ESI+): [M+H]$^+$ 260.2.

Reference Example 25

(3S)-1-(3-bromo-1-methyl-1H-pyrazol-5-yl)pyrrolidin-3-ol

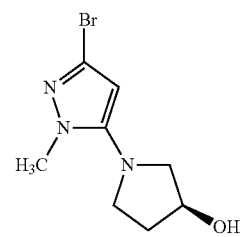

A) (S)-ethyl 3-bromo-5-(3-hydroxypyrrolidin-1-yl)-1-methyl-1H-pyrazole-4-carboxylate A mixture of ethyl 3,5-dibromo-1-methyl-1H-pyrazole-4-carboxylate (1.6 g) obtained in Reference Example 2, (S)-pyrrolidin-3-ol (536 mg), potassium carbonate (0.851 g), and N-methyl-pyrrolidone (12 mL) was heated under microwave irradiation at 160° C. for 4 hr. After cooling, water was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (ethyl acetate/hexane) to give the title compound (1.61 g).
MS (ESI+): [M+H]$^+$ 318.2.

B) (3S)-1-(3-bromo-1-methyl-1H-pyrazol-5-yl)pyrrolidin-3-ol

A mixture of (S)-ethyl 3-bromo-5-(3-hydroxypyrrolidin-1-yl)-1-methyl-1H-pyrazole-4-carboxylate (800 mg) obtained in Reference Example 25, Step A, 2 M aqueous sodium hydroxide solution (6.29 mL) and ethanol (5 mL) was stirred at 70° C. for 2 hr. To the reaction mixture was added concentrated sulfuric acid (1.61 mL), and the mixture was stirred at 70° C. for 2 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure and the residue was crystallized (diethyl ether/hexane) to give the title compound (398 mg).
MS (ESI+): [M+H]$^+$ 246.2.

Reference Example 26

3-bromo-5-((3R)-3-methoxypyrrolidin-1-yl)-1-methyl-1H-pyrazole

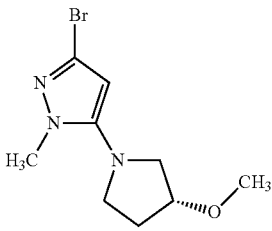

A) (R)-ethyl 3-bromo-5-(3-methoxypyrrolidin-1-yl)-1-methyl-1H-pyrazole-4-carboxylate To a mixture of (R)-ethyl 3-bromo-5-(3-hydroxypyrrolidin-1-yl)-1-methyl-1H-pyrazole-4-carboxylate (600 mg) obtained in Reference Example 23, Step A and N,N-dimethylformamide (5 mL) was added sodium hydride (60% in mineral oil, 113 mg) at 0° C., and the mixture was stirred at the same temperature for 30 min. Under an ice bath, to the reaction mixture was added methyl iodide (0.176 mL), and the mixture was stirred at room temperature for 16 hr. Water was added to the reaction mixture, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (306 mg).
MS (ESI+): [M+H]$^+$ 331.9.

B) 3-bromo-5-((3R)-3-methoxypyrrolidin-1-yl)-1-methyl-1H-pyrazole

A mixture of (R)-ethyl 3-bromo-5-(3-methoxypyrrolidin-1-yl)-1-methyl-1H-pyrazole-4-carboxylate (306 mg) obtained in Reference Example 26, Step A, 2 M aqueous sodium hydroxide solution (2.30 mL) and ethanol (4 mL) was stirred at 70° C. for 2 hr. To the reaction mixture was added concentrated sulfuric acid (0.589 mL) at 0° C., and the mixture was stirred at 70° C. for 2 hr. The reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure and the residue was crystallized (diethyl ether/hexane) to give the title compound (216 mg).
MS (ESI+): [M+H]$^+$ 259.8.

Reference Example 27

3-bromo-5-((3S)-3-methoxypyrrolidin-1-yl)-1-methyl-1H-pyrazole

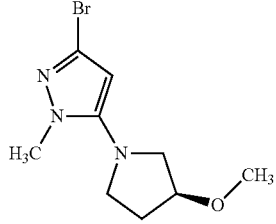

A) (S)-ethyl 3-bromo-5-(3-methoxypyrrolidin-1-yl)-1-methyl-1H-pyrazole-4-carboxylate To a mixture of (S)-ethyl 3-bromo-5-(3-hydroxypyrrolidin-1-yl)-1-methyl-1H-pyrazole-4-carboxylate (800 mg) obtained in Reference Example 25, Step A and N,N-dimethylformamide (5 mL) was added sodium hydride (60% in mineral oil, 151 mg) at 0° C., and the mixture was stirred at the same temperature for 30 min. Under an ice bath, to the reaction mixture was added methyl iodide (0.235 mL), and the mixture was stirred at room temperature for 16 hr. Water was added to the reaction mixture, and the mixture was extracted with ethyl acetate. The obtained organic layer was washed with saturated brine, and dried over anhydrous magnesium sulfate. The solvent was evaporated under reduced pressure and the residue was purified by silica gel column chromatography (hexane/ethyl acetate) to give the title compound (487 mg).
MS (ESI+): [M+H]$^+$ 332.2.

B) 3-bromo-5-((3S)-3-methoxypyrrolidin-1-yl)-1-methyl-1H-pyrazole

A mixture of (S)-ethyl 3-bromo-5-(3-methoxypyrrolidin-1-yl)-1-methyl-1H-pyrazole-4-carboxylate (487 mg)

obtained in Reference Example 27, Step A, 2 M aqueous sodium hydroxide solution (3.67 mL) and ethanol (5 mL) was stirred at 70° C. for 2 hr. To the reaction mixture was added concentrated sulfuric acid (0.938 mL), and the mixture was stirred at 70° C. for 2 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure to give the title compound (380 mg).

MS (ESI+): [M+H]$^+$ 260.2.

Reference Example 29

3-bromo-1-methyl-5-(pyrrolidin-1-yl)-1H-pyrazole

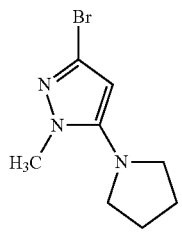

A) ethyl 3-bromo-1-methyl-5-(pyrrolidin-1-yl)-1H-pyrazole-4-carboxylate

A mixture of ethyl 3,5-dibromo-1-methyl-1H-pyrazole-4-carboxylate (1.00 g) obtained in Reference Example 2 and pyrrolidine (963 mg) was stirred at 150° C. for 1 hr. After cooling, water was added to the reaction mixture, and the mixture was stirred at room temperature over the weekend. The solid was collected by filtration, washed with water, and dried to give the title compound (0.95 g).

MS (ESI+): [M+H]$^+$ 301.8.

B) 3-bromo-1-methyl-5-(pyrrolidin-1-yl)-1H-pyrazole

A mixture of ethyl 3-bromo-1-methyl-5-(pyrrolidin-1-yl)-1H-pyrazole-4-carboxylate (940 mg) obtained in Reference Example 29, Step A, 2 M aqueous sodium hydroxide solution (6.22 mL) and ethanol (5 mL) was stirred at 60° C. for 2.5 hr. To the reaction mixture was added concentrated sulfuric acid (1.66 mL) at 0° C., and the mixture was stirred at 60° C. for 30 min. The reaction mixture was alkalified by adding 8 M aqueous sodium hydroxide solution at 0° C., and extracted twice with ethyl acetate. The extracts were combined, washed with saturated brine, and dried over anhydrous magnesium sulfate. The solvent was evaporated under reduced pressure to give the title compound (710 mg).

MS (ESI+): [M+H]$^+$ 229.7.

Reference Example 33

4-(3-bromo-1-methyl-1H-pyrazol-5-yl)-2-methylmorpholine

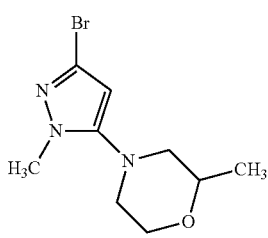

A) ethyl 3-bromo-1-methyl-5-(2-methylmorpholino)-1H-pyrazole-4-carboxylate

A mixture of ethyl 3,5-dibromo-1-methyl-1H-pyrazole-4-carboxylate (1.19 g) obtained in Reference Example 2, 2-methylmorpholine (1.01 g), and N-methyl-pyrrolidone (10 mL) was heated under microwave irradiation at 160° C. for 5 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified twice by silica gel column chromatography (ethyl acetate/hexane) to give the title compound (727 mg).

MS (ESI+): [M+H]$^+$ 331.9.

B) 4-(3-bromo-1-methyl-1H-pyrazol-5-yl)-2-methylmorpholine

A mixture of ethyl 3-bromo-1-methyl-5-(2-methylmorpholino)-1H-pyrazole-4-carboxylate (700 mg) obtained in Reference Example 33, Step A, 2 M aqueous sodium hydroxide solution (5.27 mL) and ethanol (20 mL) was stirred at 70° C. for 3 hr. To the reaction mixture was added concentrated sulfuric acid (1.69 mL), and the mixture was stirred at 70° C. for 2 hr. The reaction mixture was alkalified by adding 8 M aqueous sodium hydroxide solution, and extracted twice with ethyl acetate. The extracts were combined, washed with saturated brine, and dried over anhydrous magnesium sulfate. The solvent was evaporated under reduced pressure to give the title compound (526 mg).

MS (ESI+): [M+H]$^+$ 259.8.

Reference Example 34

2-(3-bromo-1-methyl-1H-pyrazol-5-yl)octahydropyrrolo[1,2-a]pyrazine

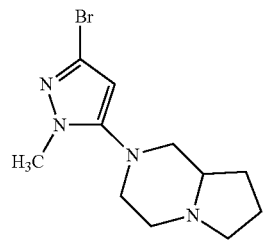 [SMILES: Cn1nc(Br)cc1N1CCN2CCCC2C1]

A) ethyl 3-bromo-5-(hexahydropyrrolo[1,2-a]pyrazin-2(1H)-yl)-1-methyl-1H-pyrazole-4-carboxylate A mixture of ethyl 3,5-dibromo-1-methyl-1H-pyrazole-4-carboxylate (650 m g) obtained in Reference Example 2, octahydropyrrolo[1,2-a]pyrazine (789 mg), and N-methyl-pyrrolidone (10 mL) was heated under microwave irradiation at 160° C. for 5 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate. The solvent was evaporated under reduced pressure and the residue was purified by silica gel column chromatography (basic silica gel, ethyl acetate/hexane) to give the title compound (740 mg).
MS (ESI+): [M+H]$^+$ 356.9.

B) 2-(3-bromo-1-methyl-1H-pyrazol-5-yl)octahydropyrrolo[1,2-a]pyrazine

A mixture of ethyl 3-bromo-5-(hexahydropyrrolo[1,2-a]pyrazin-2(1H)-yl)-1-methyl-1H-pyrazole-4-carboxylate (710 mg) obtained in Reference Example 34, Step A, 2 M aqueous sodium hydroxide solution (4.97 mL) and ethanol (10 mL) was stirred at 70° C. for 3 hr. To the reaction mixture was added concentrated sulfuric acid (1.27 mL), and the mixture was stirred at 60° C. for 3 hr and at 70° C. for 8 hr. The reaction mixture was alkalified by adding 8 M aqueous sodium hydroxide solution, and extracted 3 times with ethyl acetate. The extracts were combined, washed with saturated brine, and dried over anhydrous magnesium sulfate. The solvent was evaporated under reduced pressure to give the title compound (505 mg).
MS (ESI+): [M+H]$^+$ 284.9.

Reference Example 35

1-(3-bromo-1-methyl-1H-pyrazol-5-yl)-3-methylpyrrolidin-3-ol

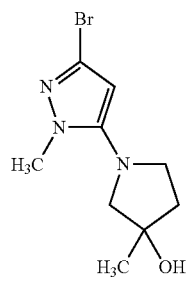

A) ethyl 3-bromo-5-(3-hydroxy-3-methylpyrrolidin-1-yl)-1-methyl-1H-pyrazole-4-carboxylate A mixture of ethyl 3,5-dibromo-1-methyl-1H-pyrazole-4-carboxylate (3.39 g) obtained in Reference Example 2,3-methylpyrrolidin-3-ol (1.1 g), potassium carbonate (1.50 g), and N-methyl-pyrrolidone (14 mL) was heated under microwave irradiation at 160° C. for 4 hr. After cooling, water was added to the reaction mixture, and the mixture was extracted twice with ethyl acetate. The extracts were combined, washed with saturated brine, and dried over anhydrous magnesium sulfate. The solvent was evaporated under reduced pressure and the residue was purified by silica gel column chromatography (ethyl acetate/hexane) to give the title compound (2.77 g).
MS (ESI+): [M+H]$^+$ 331.8.

B) 1-(3-bromo-1-methyl-1H-pyrazol-5-yl)-3-methylpyrrolidin-3-ol

A mixture of ethyl 3-bromo-5-(3-hydroxy-3-methylpyrrolidin-1-yl)-1-methyl-1H-pyrazole-4-carboxylate (2.70 g) obtained in Reference Example 35, Step A, 2 M aqueous sodium hydroxide solution (20.3 mL) and ethanol (30 mL) was stirred at 70° C. for 2 hr. To the reaction mixture was added concentrated sulfuric acid (5.20 mL) at 0° C., and the mixture was stirred at 60° C. for 30 min. After allowing to cool, the reaction mixture was alkalified by adding 8 M aqueous sodium hydroxide solution at 0° C., and extracted 3 times with ethyl acetate. The extracts were combined, washed with saturated brine, and dried over anhydrous magnesium sulfate. The solvent was evaporated under reduced pressure to give the title compound (1.88 g).
MS (ESI+): [M+H]$^+$ 259.8.

Reference Examples 28 and 30-32

The compounds of Reference Examples 28 and 30-32 were obtained by a method similar to Reference Examples 2 and 12, or a method analogous thereto, and using ethyl 3,5-dibromo-1H-pyrazole-4-carboxylate obtained in Reference Example 1, or ethyl 3,5-dibromo-1-methyl-1H-pyrazole-4-carboxylate obtained in Reference Example 2, and reagents corresponding to the compounds of Reference Examples 28 and 30-32. MS in the Tables shows measured values.

TABLE 8

| Ref. Ex. No. | IUPAC name | structure | MS |
|---|---|---|---|
| 14 | 1-(3-bromo-1-methyl-1H-pyrazol-5-yl)-4-methylpiperazine | 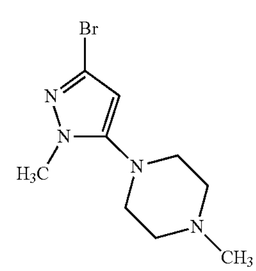 | 258.8 |

TABLE 8-continued

| Ref. Ex. No. | IUPAC name | structure | MS |
|---|---|---|---|
| 15 | 1-(4-(3-bromo-1-methyl-1H-pyrazol-5-yl)piperazin-1-yl)ethanone | 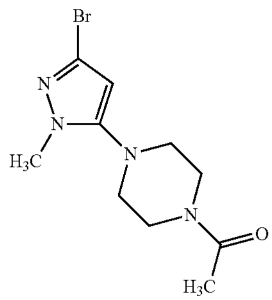 [SMILES: CC(=O)N1CCN(c2cc(Br)nn2C)CC1] | 286.8 |
| 16 | 4-(3-bromo-1-methyl-1H-pyrazol-5-yl)thiomorpholine 1,1-dioxide | 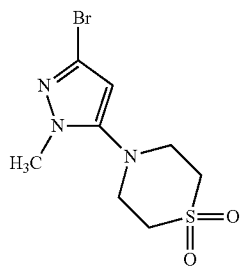 | 293.8 |
| 17 | 4-(3-bromo-1-methyl-1H-pyrazol-5-yl)-1,4-oxazepane | 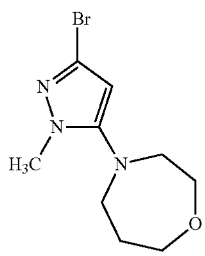 | 259.8 |
| 18 | 1-(3-bromo-1-methyl-1H-pyrazol-5-yl)-4-methoxypiperidine | 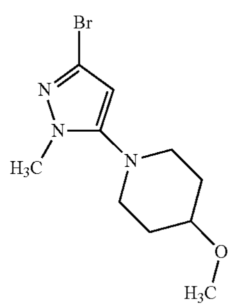 | 273.8 |
| 19 | 2-(1-(3-bromo-1-methyl-1H-pyrazol-5-yl)piperidin-4-yl)propan-2-ol | 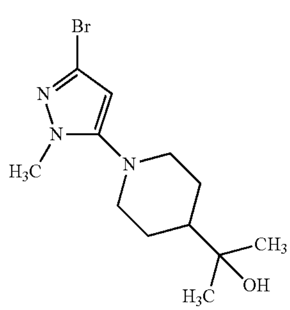 [SMILES: Cn1nc(Br)cc1N1CCC(C(C)(C)O)CC1] | 301.9 |

TABLE 8-continued

| Ref. Ex. No. | IUPAC name | structure | MS |
|---|---|---|---|
| 20 | 1-(3-bromo-1-methyl-1H-pyrazol-5-yl)-4,4-difluoropiperidine | 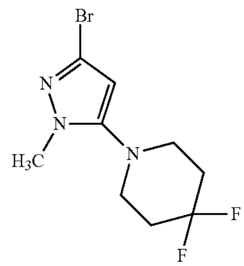 | 279.8 |
| 21 | 1-(4-(3-bromo-1-methyl-1H-pyrazol-5-yl)piperazin-1-yl)-2-methoxyethanone | 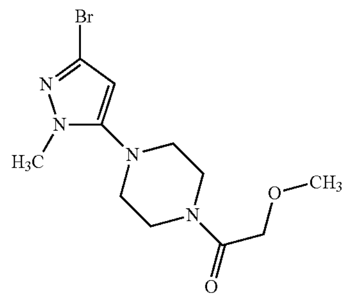 | 316.9 |
| 22 | ((2S)-1-(3-bromo-1-methyl-1H-pyrazol-5-yl)pyrrolidin-2-yl)methanol | 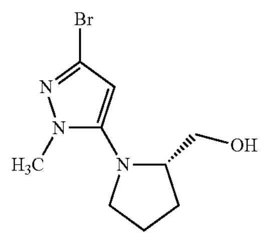 | 259.8 |
| 23 | (3R)-1-(3-bromo-1-methyl-1H-pyrazol-5-yl)pyrrolidin-3-ol | 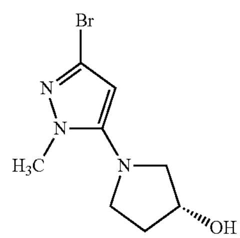 | 245.8 |
| 24 | ((2R)-1-(3-bromo-1-methyl-1H-pyrazol-5-yl)pyrrolidin-2-yl)methanol | 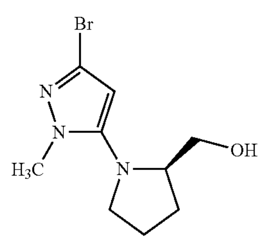 | 260.2 |
| 25 | (3S)-1-(3-bromo-1-methyl-1H-pyrazol-5-yl)pyrrolidin-3-ol | 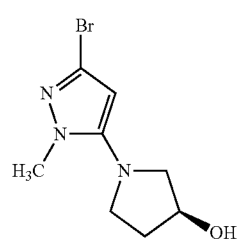 | 246.2 |

TABLE 8-continued

| Ref. Ex. No. | IUPAC name | structure | MS |
|---|---|---|---|
| 26 | 3-bromo-5-((3R)-3-methoxypyrrolidin-1-yl)-1-methyl-1H-pyrazole | 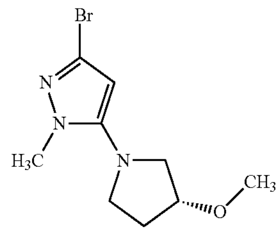 | 259.8 |
| 27 | 3-bromo-5-((3S)-3-methoxypyrrolidin-1-yl)-1-methyl-1H-pyrazole | 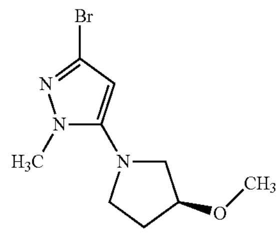 | 260.2 |
| 28 | 3-bromo-5-((2S)-2-(methoxymethyl)pyrrolidin-1-yl)-1-methyl-1H-pyrazole | 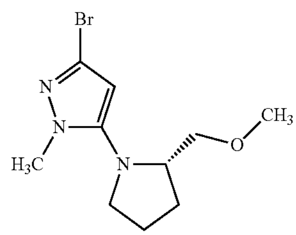 | 273.8 |
| 29 | 3-bromo-1-methyl-5-(pyrrolidin-1-yl)-1H-pyrazole | 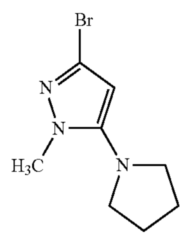 | 229.7 |
| 30 | 4-(3-bromo-1-ethyl-1H-pyrazol-5-yl)thiomorpholine 1,1-dioxide | 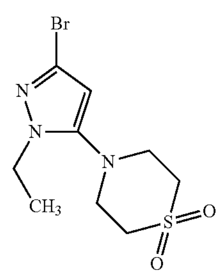 [SMILES: CCn1nc(Br)cc1N1CCS(=O)(=O)CC1] | 307.8 |
| 31 | 4-(3-bromo-1-(2,2,2-trifluoroethyl)-1H-pyrazol-5-yl)thiomorpholine 1,1-dioxide | 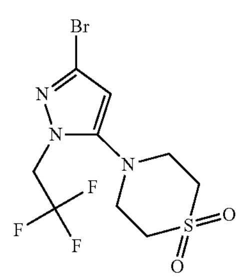 [SMILES: O=S1(=O)CCN(c2cc(Br)nn2CC(F)(F)F)CC1] | 361.8 |

TABLE 8-continued

| Ref. Ex. No. | IUPAC name | structure | MS |
|---|---|---|---|
| 32 | 4-(3-bromo-1-methyl-1H-pyrazol-5-yl)-2,2-dimethylmorpholine | 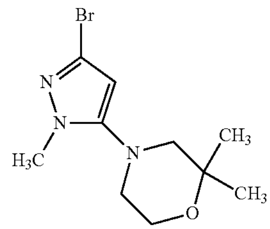 | 273.8 |
| 33 | 4-(3-bromo-1-methyl-1H-pyrazol-5-yl)-2-methylmorpholine | 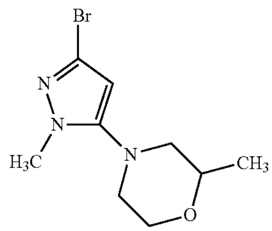 | 259.8 |
| 34 | 2-(3-bromo-1-methyl-1H-pyrazol-5-yl)octahydropyrrolo[1,2-a]pyrazine | 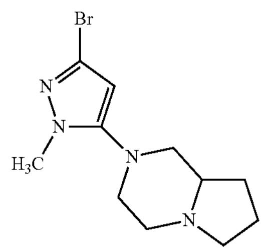 [SMILES: Cn1nc(Br)cc1N1CCN2CCCC2C1] | 284.9 |
| 35 | 1-(3-bromo-1-methyl-1H-pyrazol-5-yl)-3-methylpyrrolidin-3-ol | 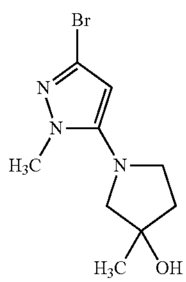 | 259.8 |

Reference Example 36 methyl 3-(methoxymethoxy)-1-methyl-1H-pyrazole-5-carboxylate

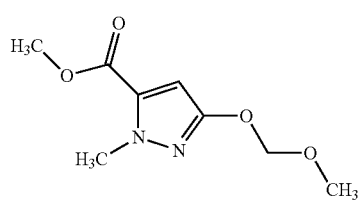

A mixture of methyl 3-(methoxymethoxy)-1H-pyrazole-5-carboxylate (4.98 g) synthesized according to WO 2007/018314, methyl iodide (2.00 mL), potassium carbonate (4.44 g) and N,N-dimethylformamide (50 mL) was stirred at room temperature for 20 hr. Water was added to the reaction mixture, and the mixture was extracted with ethyl acetate. The extract was washed successively with water and saturated brine, and dried over anhydrous sodium sulfate, and the solvent was evaporated under reduced pressure. The residue was purified by column chromatography (ethyl acetate/hexane) to give the title compound (3.36 g).

$^1$H NMR (300 MHz, CDCl$_3$) δ 3.51 (3H, s), 3.87 (3H, s), 4.05 (3H, s), 5.20 (2H, s), 6.32 (1H, s).

Reference Example 37

3-(methoxymethoxy)-1-methyl-1H-pyrazole-5-carboxylic acid

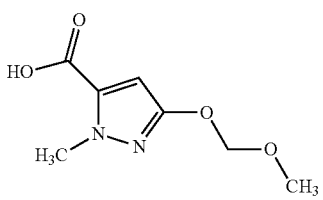

To a solution of methyl 3-(methoxymethoxy)-1-methyl-1H-pyrazole-5-carboxylate (2.36 g) obtained in Reference Example 36 in methanol (30 mL) was added 2 M aqueous sodium hydroxide solution (8.84 mL) at room temperature, and the reaction mixture was stirred at room temperature for 3 days. To the reaction mixture was added 1 M hydrochloric acid (5.0 mL), methanol was evaporated under reduced pressure, and the mixture was extracted with ethyl acetate. The extract was washed with saturated brine, and dried over sodium sulfate, and the solvent was evaporated under reduced pressure to give the title compound (2.19 g).

MS (ESI+): [M+H]187.1.

Reference Example 38

(3-(methoxymethoxy)-1-methyl-1H-pyrazol-5-yl)(morpholin-4-yl)methanone

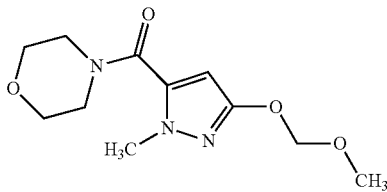 [SMILES: COCOc1cc(C(=O)N2CCOCC2)n(C)n1]

A mixture of 3-(methoxymethoxy)-1-methyl-1H-pyrazole-5-carboxylic acid (728 mg) obtained in Reference Example 37, morpholine (0.682 mL), 1-(3-dimethylaminopropyl)-3-ethylcarbodiimide hydrochloride (900 mg), 1-hydroxybenzotriazole (634 mg), triethylamine (2.73 mL) and N,N-dimethylformamide (10 mL) was stirred at room temperature overnight. Water was added to the reaction mixture, and the mixture was extracted with ethyl acetate/2-propanol mixture (4:1). The extract was washed with saturated brine, and dried over anhydrous sodium sulfate, and the solvent was evaporated under reduced pressure. The residue was purified by silica gel column chromatography (ethyl acetate/hexane) to give the title compound (466 mg).

MS (ESI+): [M+H]$^+$ 256.1.

Reference Example 39

(3-hydroxy-1-methyl-1H-pyrazol-5-yl) (morpholin-4-yl)methanone

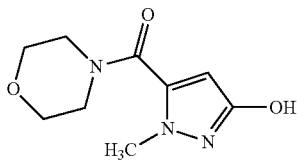

To a solution of (3-(methoxymethoxy)-1-methyl-1H-pyrazol-5-yl) (morpholin-4-yl)methanone (466 mg) obtained in Reference Example 38 in ethanol (10 mL) was added concentrated hydrochloric acid (0.1 mL) at room temperature. The reaction mixture was stirred overnight at 50° C. The solvent was evaporated under reduced pressure and the residue was purified by silica gel column chromatography (methanol/ethyl acetate) to give the title compound (322.8 mg).

MS (ESI+): [M+H]$^+$ 212.2.

Reference Example 40

1-methyl-5-(morpholin-4-ylcarbonyl)-1H-pyrazol-3-yl trifluoromethanesulfonate

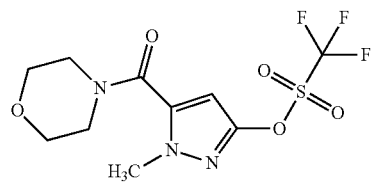 [SMILES: Cn1nc(OS(=O)(=O)C(F)(F)F)cc1C(=O)N1CCOCC1]

To a solution of (3-hydroxy-1-methyl-1H-pyrazol-5-yl)(morpholin-4-yl)methanone (322 mg) obtained in Reference Example 39 in tetrahydrofuran (10 mL) was added sodium hydride (60% in mineral oil, 91 mg) at 0° C. Under a nitrogen atmosphere, the reaction mixture was stirred at 0° C. for 30 min, and N-phenylbis(trifluoromethanesulfonimide) (654 mg) was added. The reaction mixture was stirred at room temperature for 20 hr, water was added, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane and basic silica gel, ethyl acetate/hexane) to give the title compound (448.3 mg).

$^1$H NMR (300 MHz, CDCl$_3$) δ 3.61-3.82 (8H, m), 3.94 (3H, s), 6.16 (1H, s).

Reference Example 41

1-methyl-5-(methylcarbamoyl)-1H-pyrazol-3-yl trifluoromethanesulfonate

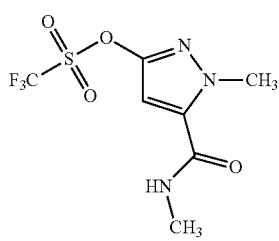 [SMILES: CNC(=O)c1cc(OS(=O)(=O)C(F)(F)F)nn1C]

The title compound was obtained by a method similar to Reference Examples 38, 39 and 40 and using 3-(methoxymethoxy)-1-methyl-1H-pyrazole-5-carboxylic acid obtained in Reference Example 37.

MS (ESI+): [M−H]$^+$286.0.

Reference Example 42

3-(benzyloxy)-1-methyl-1H-pyrazole-5-carboxylic acid

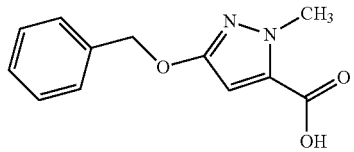 [SMILES: Cn1nc(OCc2ccccc2)cc1C(=O)O]

To a solution of methyl 3-(benzyloxy)-1-methyl-1H-pyrazole-5-carboxylate (6.34 g) synthesized according to WO 2003/099793 in methanol (65 mL) was added 1 M aqueous sodium hydroxide solution (38.6 mL) at room temperature, and the mixture was stirred at room temperature overnight. The reaction mixture was adjusted to about pH 3 by adding 1 M hydrochloric acid at 0° C., and the mixture was extracted with ethyl acetate. The extract was washed successively with water and saturated brine, and dried over sodium sulfate. The solvent was evaporated under reduced pressure to give the title compound (5.85 g).
$^1$H NMR (300 MHz, CDCl$_3$) δ 4.06 (3H, s), 5.20 (2H, s), 6.33 (1H, s), 7.30-7.47 (5H, m).

Reference Example 43 tert-butyl(3-(benzyloxy)-1-methyl-1H-pyrazol-5-yl)carbamate

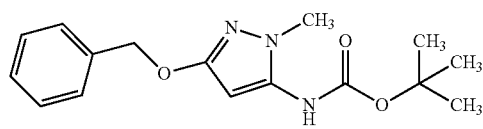 [SMILES: Cn1nc(OCc2ccccc2)cc1NC(=O)OC(C)(C)C]

To a solution of 3-(benzyloxy)-1-methyl-1H-pyrazole-5-carboxylic acid (5.0 g) obtained in Reference Example 42 and triethylamine (9.00 mL) in tert-butyl alcohol (55 mL) was further added diphenylphosphoryl azide (6.96 mL) at 0° C. The reaction mixture was heated under reflux under a nitrogen atmosphere for 3 hr, and cooled to room temperature. To the reaction mixture was added water at room temperature, and the mixture was extracted with ethyl acetate. The extract was washed with saturated brine, and dried over anhydrous magnesium sulfate. The solvent was evaporated under reduced pressure. To the residue was added toluene, and the precipitate was removed by filtration, and the filtrate was purified by silica gel column chromatography (ethyl acetate/hexane) to give the title compound (6.1 g).
MS (ESI+): [M+H]$^+$ 304.2.

Reference Example 44

3-(benzyloxy)-1-methyl-1H-pyrazol-5-amine

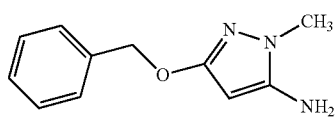

To a solution of tert-butyl(3-(benzyloxy)-1-methyl-1H-pyrazol-5-yl)carbamate (6.0 g) obtained in Reference Example 43 in methanol (20 mL) and ethyl acetate (80 mL) was added a solution (49 mL) of 4 M hydrogen chloride in ethyl acetate at 0° C., and the mixture was stirred under a nitrogen atmosphere at room temperature overnight. To the reaction mixture was added 2 M aqueous sodium hydroxide solution (99 mL) at 0° C., and the mixture was extracted with ethyl acetate. The extract was washed with saturated brine, and dried over anhydrous magnesium sulfate. The solvent was evaporated under reduced pressure to give the title compound (3.90 g).
MS (ESI+): [M+H]$^+$ 204.2.

Reference Example 45

4-(3-(benzyloxy)-1-methyl-1H-pyrazol-5-yl)morpholine

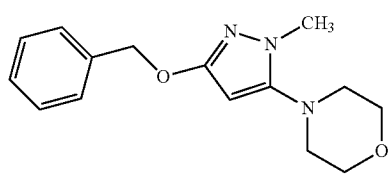 [SMILES: Cn1nc(OCc2ccccc2)cc1N1CCOCC1]

To a solution of 3-(benzyloxy)-1-methyl-1H-pyrazol-5-amine (4.50 g) obtained in Reference Example 44, 1-chloro-2-(2-chloroethoxy)ethane (3.11 mL) and triethylamine (7.41 mL) in N,N-dimethylformamide (55 mL) was further added sodium iodide (0.332 g) at room temperature. Under an argon atmosphere, the reaction mixture was stirred overnight at 150° C. To the reaction mixture was added saturated sodium hydrogen carbonate and water (1:1) at room temperature, and the mixture was extracted with ethyl acetate. The extract was washed with saturated brine, and dried over anhydrous magnesium sulfate. The solvent was evaporated under reduced pressure and the residue was purified by silica gel column chromatography (basic silica gel, ethyl acetate/hexane) to give the title compound (800 mg).
MS (ESI+): [M+H]$^+$ 274.2.

Reference Example 46

1-methyl-5-(morpholin-4-yl)-1H-pyrazol-3-ol

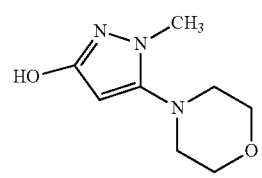

A mixture of 4-(3-(benzyloxy)-1-methyl-1H-pyrazol-5-yl)morpholine (800 mg) obtained in Reference Example 45, 10% palladium-carbon (80 mg) and ethanol (10 mL) was stirred under a hydrogen atmosphere at room temperature for 4 hr. The catalyst was removed by filtration, and the filtrate was concentrated under reduced pressure to give the title compound (499 mg).
MS (ESI+): [M+H]$^+$ 184.2.

Reference Example 47

1-methyl-5-(morpholin-4-yl)-1H-pyrazol-3-yl trifluoromethanesulfonate

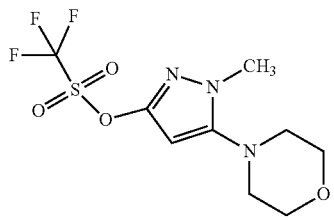 [SMILES: Cn1nc(OS(=O)(=O)C(F)(F)F)cc1N1CCOCC1]

To a solution of 1-methyl-5-(morpholin-4-yl)-1H-pyrazol-3-ol (500 mg) obtained in Reference Example 46 and triethylamine (0.571 mL) in acetonitrile (9.0 mL) was further added trifluoromethanesulfonic anhydride (0.689 mL) at 0° C. The reaction mixture was stirred under a nitrogen atmosphere at 0° C. for 1 hr, saturated aqueous sodium hydrogen carbonate solution was added at 0° C., and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (501 mg).

MS (ESI+): [M+H]$^+$ 316.2.

Reference Example 49

5-(cyclopentyl(methyl)carbamoyl)-1-methyl-1H-pyrazol-3-yl trifluoromethanesulfonate

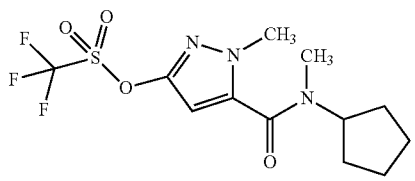 [SMILES: CN(C(=O)c1cc(OS(=O)(=O)C(F)(F)F)nn1C)C1CCCC1]

A) 3-(benzyloxy)-N-cyclopentyl-N,1-dimethyl-1H-pyrazole-5-carboxamide

To a mixture of 3-(benzyloxy)-1-methyl-1H-pyrazole-5-carboxylic acid (700 mg) obtained in Reference Example 42, N-methylcyclopentanamine hydrochloride (491 mg), N-ethyldiisopropylamine (1.84 mL), and N,N-dimethylformamide (5 mL) was added O-(7-azabenzotriazol-1-yl)-N,N,N',N'-tetramethyluronium hexafluorophosphate (1.38 g), and the mixture was stirred at room temperature overnight. To the reaction mixture was added saturated aqueous sodium hydrogen carbonate solution, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (860 mg).

MS (ESI+): [M+H]$^+$ 314.0.

B) N-cyclopentyl-3-hydroxy-N,1-dimethyl-TH-pyrazole-5-carboxamide

A mixture of 3-(benzyloxy)-N-cyclopentyl-N,1-dimethyl-1H-pyrazole-5-carboxamide (860 mg) obtained in Reference Example 49, Step A, 10% palladium-carbon (90 mg) and a mixed solvent of tetrahydrofuran (15 mL)/methanol (15 mL) was stirred under a hydrogen atmosphere at room temperature for 1 hr. The catalyst was removed by filtration, and the filtrate was concentrated under reduced pressure to give the title compound (610 mg).

MS (ESI+): [M+H]$^+$ 223.9.

C) 5-(cyclopentyl(methyl)carbamoyl)-1-methyl-1H-pyrazol-3-yl trifluoromethanesulfonate To a solution of N-cyclopentyl-3-hydroxy-N,1-dimethyl-1H-pyrazole-5-carboxamide (610 mg) obtained in Reference Example 49, Step B, in tetrahydrofuran (5 mL) was added sodium hydride (60% in mineral oil, 109 mg) at 0° C. The reaction mixture was stirred at 0° C. for 30 min, and N-phenylbis(trifluoromethanesulfonimide) (1.17 g) was added. The reaction mixture was stirred at room temperature under a nitrogen atmosphere, saturated aqueous sodium hydrogen carbonate solution was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (970 mg).

MS (ESI+): [M+H]$^+$ 355.9.

Reference Examples 48, 50 and 51

The compounds of Reference Examples 48, 50 and 51 were obtained by a method similar to Reference Examples 38, 39, 40 and 47, or a method analogous thereto, and using 3-(benzyloxy)-1-methyl-1H-pyrazole-5-carboxylic acid obtained in Reference Example 42, and reagents corresponding to the compounds of Reference Examples 48, 50 and 51. MS in the Tables shows measured values.

TABLE 9

| Ref. Ex. No. | IUPAC name | structure | MS |
|---|---|---|---|
| 48 | 5-((2-methoxyethyl)-(methyl)carbamoyl)-1-methyl-1H-pyrazol-3-yl trifluoromethanesulfonate | 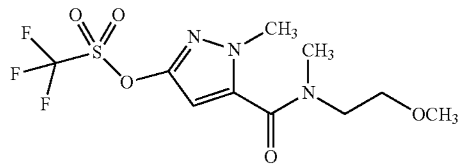 [SMILES: COCCN(C)C(=O)c1cc(OS(=O)(=O)C(F)(F)F)nn1C] | 345.9 |
| 49 | 5-(cyclopentyl(methyl)-carbamoyl)-1-methyl-1H-pyrazol-3-yl trifluoromethanesulfonate | 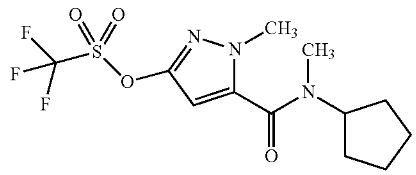 [SMILES: CN(C(=O)c1cc(OS(=O)(=O)C(F)(F)F)nn1C)C1CCCC1] | 355.9 |
| 50 | 1-methyl-5-(methyl(tetrahydro-2H-pyran-4-yl)carbamoyl)-1H-pyrazol-3-yl trifluoromethanesulfonate | 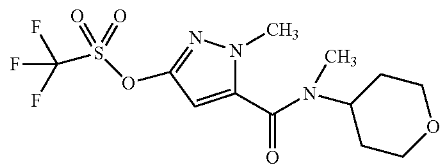 [SMILES: CN(C(=O)c1cc(OS(=O)(=O)C(F)(F)F)nn1C)C1CCOCC1] | 371.9 |
| 51 | 5-(1,1-dioxidothiomorpholine-4-carbonyl)-1-methyl-1H-pyrazol-3-yl trifluoromethanesulfonate | 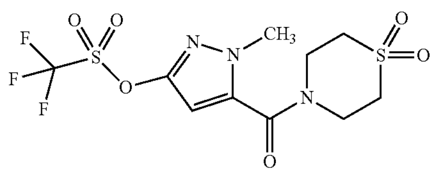 [SMILES: Cn1nc(OS(=O)(=O)C(F)(F)F)cc1C(=O)N1CCS(=O)(=O)CC1] | 392.1 |

Reference Example 52

1-methyl-5-(2-oxopiperidin-1-yl)-1H-pyrazol-3-yl trifluoromethanesulfonate

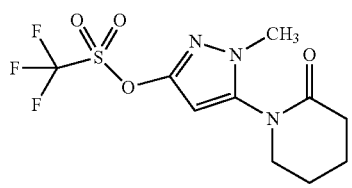 [SMILES: Cn1nc(OS(=O)(=O)C(F)(F)F)cc1N1CCCCC1=O]

A) 1-(3-(benzyloxy)-1-methyl-1H-pyrazol-5-yl)piperidin-2-one

To a mixture of 3-(benzyloxy)-1-methyl-1H-pyrazol-5-amine (700 mg) obtained in Reference Example 44, triethylamine (0.96 mL) and tetrahydrofuran (10 mL) was added 5-chloropentanoyl chloride (587 mg) at 0° C., and the mixture was stirred at room temperature overnight. The reaction mixture was added to water at room temperature, and the mixture was extracted with ethyl acetate. The extract was washed with saturated brine, and dried over anhydrous magnesium sulfate. The solvent was evaporated under reduced pressure. To a mixture of the residue and N,N-dimethylformamide (5 mL) was added sodium hydride (60% in mineral oil, 193 mg) at 0° C. After stirring at room temperature for 2 hr, water was added, and the mixture was extracted twice with ethyl acetate. The extracts were combined, washed with saturated brine, and dried over anhydrous magnesium sulfate. The solvent was evaporated under reduced pressure and the residue was purified by silica gel column chromatography (ethyl acetate/hexane) to give the title compound (630 mg).
MS (ESI+): [M+H]$^+$ 285.9.

B) 1-(3-hydroxy-1-methyl-1H-pyrazol-5-yl)piperidin-2-one

A mixture of 1-(3-(benzyloxy)-1-methyl-1H-pyrazol-5-yl)piperidin-2-one (630 mg) obtained in Reference Example 52, Step A, 10% palladium-carbon (60 mg) and a mixed solvent of tetrahydrofuran (15 mL)/methanol (15 mL) was stirred under a hydrogen atmosphere at room temperature for 3 hr. The catalyst was removed by filtration, and the filtrate was concentrated under reduced pressure to give the title compound (410 mg).
$^1$H NMR (400 MHz, DMSO-d$_6$) δ1.83 (4H, m), 2.39 (2H, t, J=5.9 Hz), 3.32 (3H, s), 3.47 (2H, t, J=5.1 Hz), 5.35 (1H, s), 9.59 (1H, brs).

C) 1-methyl-5-(2-oxopiperidin-1-yl)-1H-pyrazol-3-yl trifluoromethanesulfonate

To a mixed solution of 1-(3-hydroxy-1-methyl-1H-pyrazol-5-yl)piperidin-2-one (410 mg) obtained in Reference Example 52, Step B, in tetrahydrofuran (5 mL)/N,N-dimethylformamide (2 mL) was added sodium hydride (60% in mineral oil, 84 mg) at 0° C. The reaction mixture was stirred at 0° C. for 30 min, and N-phenylbis(trifluoromethanesulfonimide) (900 mg) was added. The reaction mixture was stirred at room temperature under a nitrogen atmosphere overnight, saturated aqueous sodium hydrogen carbonate solution was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (660 mg).

MS (ESI+): [M+H]$^+$ 327.8.

Reference Example 53

1-methyl-5-(3-oxomorpholino)-1H-pyrazol-3-yl trifluoromethanesulfonate

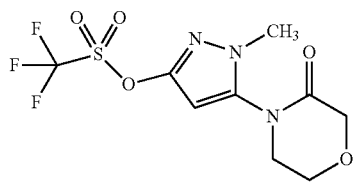 [SMILES: Cn1nc(OS(=O)(=O)C(F)(F)F)cc1N1CCOCC1=O]

A) 4-(3-(benzyloxy)-1-methyl-1H-pyrazol-5-yl)morpholin-3-one

To a mixture of 3-(benzyloxy)-1-methyl-1H-pyrazol-5-amine (760 mg) obtained in Reference Example 44, triethylamine (1.04 mL) and tetrahydrofuran (10 mL) was added 2-(2-chloroethoxy)acetyl chloride (646 mg) at 0° C., and the mixture was stirred at room temperature overnight under a nitrogen atmosphere. The reaction mixture was added to water at room temperature, and the mixture was extracted with ethyl acetate. The extract was washed with saturated brine, and dried over anhydrous magnesium sulfate. The solvent was evaporated under reduced pressure. To a mixture of the residue and N,N-dimethylformamide (5 mL) was added sodium hydride (60% in mineral oil, 209 mg) at 0° C., and the reaction mixture was stirred at 0° C. under a nitrogen atmosphere for 2 hr. Water was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (630 mg).

MS (ESI+): [M+H]$^+$ 287.9.

B) 4-(3-hydroxy-1-methyl-1H-pyrazol-5-yl)morpholin-3-one

A mixture of 4-(3-(benzyloxy)-1-methyl-1H-pyrazol-5-yl)morpholin-3-one (620 mg) obtained in Reference Example 53, Step A, 10% palladium-carbon (60 mg) and a mixed solvent of tetrahydrofuran (15 mL)/methanol (15 mL) was stirred under a hydrogen atmosphere at room temperature for 2 hr. The catalyst was removed by filtration, and the filtrate was concentrated under reduced pressure to give the title compound (250 mg).

$^1$H NMR (400 MHz, DMSO-d$_6$) δ3.38 (3H, s), 3.61 (2H, t, J=5.1 Hz), 3.89-4.00 (2H, m), 4.22 (2H, s), 5.47 (1H, s), 9.67 (1H, s).

C) 1-methyl-5-(3-oxomorpholino)-1H-pyrazol-3-yl trifluoromethanesulfonate

To a mixed solution of 4-(3-hydroxy-1-methyl-1H-pyrazol-5-yl)morpholin-3-one (250 mg) obtained in Reference Example 53, Step B and tetrahydrofuran (5 mL)/N,N-dimethylformamide (2 mL) was added sodium hydride (60% in mineral oil, 51 mg) at 0° C. The reaction mixture was stirred at 0° C. for 30 min, and N-phenylbis(trifluoromethanesulfonimide) (544 mg) was added. The reaction mixture was stirred at room temperature under a nitrogen atmosphere for 3 hr, saturated aqueous sodium hydrogen carbonate solution was added, and the mixture was extracted twice with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (340 mg).

MS (ESI+): [M+H]$^+$ 329.8.

Reference Example 54

1-methyl-5-(2-oxooxazolidin-3-yl)-1H-pyrazol-3-yl trifluoromethanesulfonate

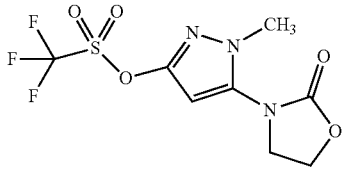 [SMILES: Cn1nc(OS(=O)(=O)C(F)(F)F)cc1N1CCOC1=O]

A) 3-(3-(benzyloxy)-1-methyl-1H-pyrazol-5-yl)oxazolidin-2-one

To a mixture of 3-(benzyloxy)-1-methyl-1H-pyrazol-5-amine (2.00 g) obtained in Reference Example 44, N-ethyldiisopropylamine (3.44 mL) and tetrahydrofuran (30 mL) was added 2-chloroethyl carbonochloridate (1.55 g) at 0° C., and the mixture was stirred at room temperature overnight. The reaction mixture was added to water at room temperature, and the mixture was extracted twice with ethyl acetate. The extract was washed with saturated brine, and dried over anhydrous magnesium sulfate. The solvent was evaporated under reduced pressure and the residue was purified by silica gel column chromatography (ethyl acetate/hexane) to give a yellow solid (2.50 g). To a mixture of the solid and tetrahydrofuran (30 mL) was added potassium tert-butoxide (1.81 g). The reaction mixture was stirred at room temperature under a nitrogen atmosphere overnight, water was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (760 mg).

MS (ESI+): [M+H]$^+$ 273.9.

B) 3-(3-hydroxy-1-methyl-1H-pyrazol-5-yl)oxazolidin-2-one

A mixture of 3-(3-(benzyloxy)-1-methyl-1H-pyrazol-5-yl)oxazolidin-2-one (700 mg) obtained in Reference Example 54, Step A, 10% palladium-carbon (70 mg) and a mixed solvent of tetrahydrofuran (15 mL)/methanol (15 mL) was stirred under a hydrogen atmosphere at room temperature for 1 hr. The catalyst was removed by filtration, and the filtrate was concentrated under reduced pressure to give the title compound (160 mg).
MS (ESI+): [M+H]$^+$ 183.8.

C) 1-methyl-5-(2-oxooxazolidin-3-yl)-1H-pyrazol-3-yl trifluoromethanesulfonate

To a mixed solution of 3-(3-hydroxy-1-methyl-1H-pyrazol-5-yl)oxazolidin-2-one (155 mg) obtained in Reference Example 54, Step B, in tetrahydrofuran (4 mL)/N,N-dimethylformamide (2 mL) was added sodium hydride (60% in mineral oil, 34 mg) at 0° C. The reaction mixture was stirred at room temperature for 30 min, and N-phenylbis(trifluoromethanesulfonimide) (363 mg) was added. The reaction mixture was stirred at room temperature under a nitrogen atmosphere overnight, water was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (230 mg).
MS (ESI+): [M+H]$^+$ 315.8.

Reference Example 55

1-methyl-5-(2-oxopyrrolidin-1-yl)-1H-pyrazol-3-yl trifluoromethanesulfonate

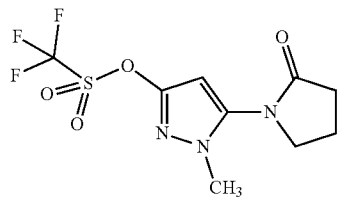 [SMILES: Cn1nc(OS(=O)(=O)C(F)(F)F)cc1N1CCCC1=O]

A) 1-(3-(benzyloxy)-1-methyl-1H-pyrazol-5-yl)pyrrolidin-2-one

To a mixture of 3-(benzyloxy)-1-methyl-1H-pyrazol-5-amine (2.00 g) obtained in Reference Example 44, triethylamine (2.74 mL) and tetrahydrofuran (30 mL) was added 4-chlorobutanoyl chloride (1.53 g) at 0° C., and the mixture was stirred at room temperature over the weekend. The reaction mixture was added to water at room temperature, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give a yellow oil (2.08 g). To a mixture of the oil and tetrahydrofuran (30 mL) was added potassium tert-butoxide (1.77 g) at room temperature. The reaction mixture was stirred at room temperature overnight, saturated brine was added, and the mixture was extracted twice with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (350 mg).
MS (ESI+): [M+H]$^+$ 271.9.

B) 1-(3-hydroxy-1-methyl-1H-pyrazol-5-yl)pyrrolidin-2-one

A mixture of 1-(3-(benzyloxy)-1-methyl-1H-pyrazol-5-yl)pyrrolidin-2-one (350 mg) obtained in Reference Example 55, Step A, 10% palladium-carbon (40 mg) and a mixed solvent of tetrahydrofuran (10 mL)/methanol (10 mL) was stirred under a hydrogen atmosphere at room temperature for 1 hr. The catalyst was removed by filtration, and the filtrate was concentrated under reduced pressure to give the title compound (220 mg).
MS (ESI+): [M+H]$^+$ 181.8.

C) 1-methyl-5-(2-oxopyrrolidin-1-yl)-1H-pyrazol-3-yl trifluoromethanesulfonate

To a mixed solution of 1-(3-hydroxy-1-methyl-1H-pyrazol-5-yl)pyrrolidin-2-one (220 mg) obtained in Reference Example 55, Step B, in tetrahydrofuran (4 mL)/N,N-dimethylformamide (2 mL) was added sodium hydride (60% in mineral oil, 49 mg) at 0° C. The reaction mixture was stirred at room temperature for 30 min, and N-phenylbis(trifluoromethanesulfonimide) (521 mg) was added. The reaction mixture was stirred at room temperature overnight, water was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (260 mg).
MS (ESI+): [M+H]$^+$ 313.8.

TABLE 10

| Ref. Ex. No. | IUPAC name | structure | MS |
|---|---|---|---|
| 53 | 1-methyl-5-(3-oxomorpholino)-1H-pyrazol-3-yl trifluoromethanesulfonate | 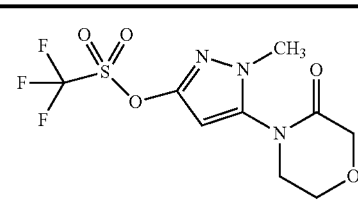 | 329.8 |

TABLE 10-continued

| Ref. Ex. No. | IUPAC name | structure | MS |
|---|---|---|---|
| 54 | 1-methyl-5-(2-oxooxazolidin-3-yl)-1H-pyrazol-3-yl trifluoromethanesulfonate | 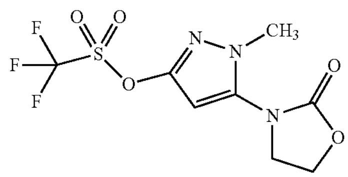 [SMILES: Cn1nc(OS(=O)(=O)C(F)(F)F)cc1N1CCOC1=O] | 315.8 |
| 55 | 1-methyl-5-(2-oxopyrrolidin-1-yl)-1H-pyrazol-3-yl trifluoromethanesulfonate | 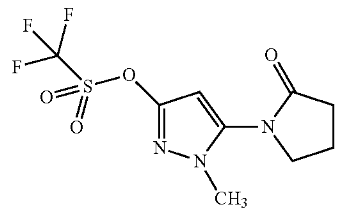 [SMILES: Cn1nc(OS(=O)(=O)C(F)(F)F)cc1N1CCCC1=O] | 313.8 |

Reference Example 56

(3-(benzyloxy)-1-methyl-1H-pyrazol-5-yl)methanol

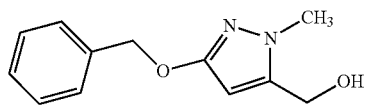 [SMILES: Cn1nc(OCc2ccccc2)cc1CO]

To a mixture of methyl 3-(benzyloxy)-1-methyl-1H-pyrazole-5-carboxylate (2.0 g) synthesized according to WO 2003/099793 and tetrahydrofuran (70 mL) was added lithium aluminum hydride (0.31 g) at 0° C., and the mixture was stirred under a nitrogen atmosphere at 0° C. for 3 hr. To the reaction mixture was added sodium sulfate decahydrate (2.88 g), and the mixture was stirred at room temperature overnight and filtered through celite. The obtained filtrate was concentrated under reduced pressure to give the title compound (1.64 g).

MS (ESI+): [M+H]$^+$ 218.8.

Reference Example 57

3-(benzyloxy)-5-(bromomethyl)-1-methyl-1H-pyrazole

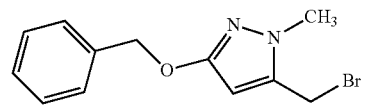 [SMILES: Cn1nc(OCc2ccccc2)cc1CBr]

To a mixture of 3-(benzyloxy)-5-(bromomethyl)-1-methyl-1H-pyrazole (800 mg) obtained in Reference Example 56, carbon tetrabromide (1.34 g) and acetonitrile (15 mL) was added triphenylphosphine (1.06 g) at room temperature, and the mixture was stirred under a nitrogen atmosphere at 0° C. overnight. The reaction mixture was concentrated under reduced pressure, and the residue was purified by silica gel column chromatography (ethyl acetate/hexane) to give the title compound (630 mg).

MS (ESI+): [M+H]$^+$ 280.8.

Reference Example 58

1-methyl-5-((2-oxopyrrolidin-1-yl)methyl)-1H-pyrazol-3-yl trifluoromethanesulfonate

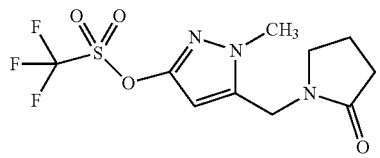 [SMILES: Cn1nc(OS(=O)(=O)C(F)(F)F)cc1CN1CCCC1=O]

A) 1-((3-(benzyloxy)-1-methyl-1H-pyrazol-5-yl)methyl)pyrrolidin-2-one

To a mixture of pyrrolidin-2-one (216 mg) and N,N-dimethylformamide (5 mL) was added sodium hydride (60% in mineral oil, 102 mg) at 0° C. Under a nitrogen atmosphere, the reaction mixture was stirred at 0° C. for 30 min, and a solution of 3-(benzyloxy)-5-(bromomethyl)-1-methyl-1H-pyrazole (650 mg) obtained in Reference Example 57 in N,N-dimethylformamide (0.5 mL) was added. Under a nitrogen atmosphere, the mixture was stirred at room temperature overnight, water was added to the reaction mixture, and the mixture was extracted twice with ethyl acetate. The extracts were combined, washed with saturated brine, and dried over anhydrous magnesium sulfate. The solvent was evaporated under reduced pressure and the residue was purified by silica gel column chromatography (ethyl acetate/hexane) to give the title compound (550 mg).

MS (ESI+): [M+H]$^+$ 285.9.

B) 1-((3-hydroxy-1-methyl-1H-pyrazol-5-yl)methyl)pyrrolidin-2-one

A mixture of 1-((3-(benzyloxy)-1-methyl-1H-pyrazol-5-yl)methyl)pyrrolidin-2-one (540 mg) obtained in Reference Example 58, Step A, 10% palladium-carbon (54 mg) and a mixed solvent of tetrahydrofuran (15 mL)/methanol (15 mL)

was stirred under a hydrogen atmosphere at room temperature for 2 hr. The catalyst was removed by filtration, and the filtrate was concentrated under reduced pressure to give the title compound (320 mg).
MS (ESI+): [M+H]$^+$ 195.8.

C) 1-methyl-5-((2-oxopyrrolidin-1-yl)methyl)-1H-pyrazol-3-yl trifluoromethanesulfonate To a mixed solution of 1-((3-hydroxy-1-methyl-1H-pyrazol-5-yl)methyl)pyrrolidin-2-one (310 mg) obtained in Reference Example 58, Step B, in tetrahydrofuran (6 mL)/N,N-dimethylformamide (3 mL) was added sodium hydride (60% in mineral oil, 64 mg) at 0° C. The reaction mixture was stirred at room temperature for 30 min, and N-phenylbis(trifluoromethanesulfonimide) (681 mg) was added. The reaction mixture was stirred at room temperature under a nitrogen atmosphere overnight, water was added, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (510 mg).
MS (ESI+): [M+H]$^+$ 327.9.

Reference Example 59

1-methyl-5-(pyrrolidin-1-ylmethyl)-1H-pyrazol-3-yl trifluoromethanesulfonate

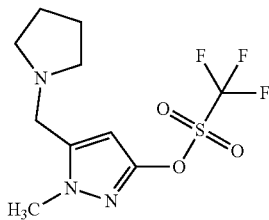

A) 3-(benzyloxy)-1-methyl-1H-pyrazole-5-carbaldehyde

A mixture of (3-(benzyloxy)-1-methyl-1H-pyrazol-5-yl)methanol (2.60 g) obtained in Reference Example 56, manganese dioxide (5.18 g) and tetrahydrofuran (80 mL) was stirred at 60° C. for 20 hr. Insoluble material was removed by filtration, and the filtrate was concentrated under reduced pressure. The residue was purified by silica gel column chromatography (ethyl acetate/hexane) to give the title compound (1.45 g).
MS (ESI+): [M+H]$^+$ 216.8.

B) 3-(benzyloxy)-1-methyl-5-(pyrrolidin-1-ylmethyl)-1H-pyrazole

To a solution of 3-(benzyloxy)-1-methyl-1H-pyrazole-5-carbaldehyde (600 mg) obtained in Reference Example 59, Step A, and pyrrolidine (0.695 mL) in acetonitrile (20 mL) was added sodium triacetoxyborohydride (1176 mg) at room temperature. The mixture was stirred at room temperature for 3 hr, saturated aqueous sodium hydrogen carbonate solution was added to the reaction mixture, and the mixture was extracted with ethyl acetate. The extract was washed with saturated brine, and dried over anhydrous magnesium sulfate. The solvent was evaporated under reduced pressure and the residue was purified by silica gel column chromatography (basic silica gel, ethyl acetate/hexane) to give the title compound (721 mg).
MS (ESI+): [M+H]$^+$ 271.9.

C) 1-methyl-5-(pyrrolidin-1-ylmethyl)-1H-pyrazol-3-yl trifluoromethanesulfonate

The title compound was obtained by a method similar to Reference Examples 46 and 40 and using 3-(benzyloxy)-1-methyl-5-(pyrrolidin-1-ylmethyl)-1H-pyrazole obtained in Reference Example 59, Step B.
MS (ESI+): [M+H]$^+$ 313.9.

Reference Example 60

5-((1,1-dioxidothiomorpholin-4-yl)methyl)-1-methyl-1H-pyrazol-3-yl trifluoromethanesulfonate

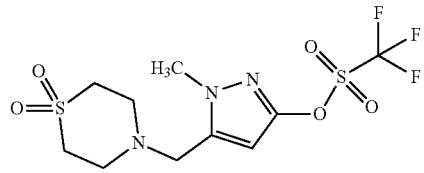 [SMILES: Cn1nc(OS(=O)(=O)C(F)(F)F)cc1CN1CCS(=O)(=O)CC1]

The title compound was obtained by a method similar to Reference Example 59, Step B, and Reference Example 41 and using 3-(benzyloxy)-1-methyl-1H-pyrazole-5-carbaldehyde obtained in Reference Example 59, Step A and thiomorpholine 1,1-dioxide.
MS (ESI+): [M+H]$^+$ 377.9.

Reference Example 61

1-(3-bromo-1-methyl-1H-pyrazol-5-yl)piperidine

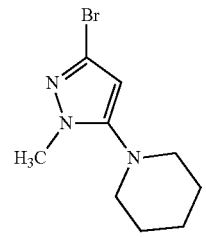

To a mixture of 3,5-dibromo-1-methyl-1H-pyrazole (1057 mg) obtained in Reference Example 3, piperidine (250 mg), sodium tert-butoxide (423 mg) and toluene (30 mL) were added (+)-2,2'-bis(diphenylphosphino)-1,1'-binaphthyl (91 mg) and tris(dibenzylideneacetone)dipalladium(0) (67.2 mg) at room temperature, and the mixture was stirred under an argon atmosphere at 100° C. for 5 hr. After cooling, insoluble material was removed by filtration, and the filtrate was concentrated under reduced pressure. The residue was purified by silica gel column chromatography (ethyl acetate/hexane) to give the title compound (230 mg).
MS (ESI+): [M+H]$^+$ 243.8.

Reference Example 62

7-(3-bromo-1-methyl-1H-pyrazol-5-yl)-2-oxa-7-azaspiro[3.5]nonane

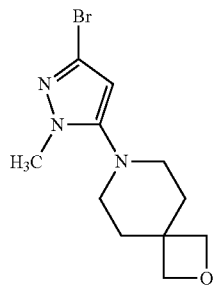 [SMILES: Cn1nc(Br)cc1N1CCC2(CC1)COC2]

To a mixture of 3,5-dibromo-1-methyl-1H-pyrazole (1100 mg) obtained in Reference Example 3,2-oxa-7-azaspiro[3.5]nonane 0.5 oxalate (200 mg), sodium tert-butoxide (335 mg) and toluene (15 mL) were added (±)-2,2'-bis(diphenylphosphino)-1,1'-binaphthyl (36 mg) and tris(dibenzylideneacetone)dipalladium(0) (27 mg) at room temperature, and the mixture was stirred under an argon atmosphere at 80° C. overnight. After cooling, insoluble material was removed by filtration, and the filtrate was concentrated under reduced pressure. The residue was purified by silica gel column chromatography (ethyl acetate/hexane) to give the title compound (150 mg).

MS (ESI+): [M+H]$^+$ 285.8.

Reference Example 66

1-(3-bromo-1-methyl-1H-pyrazol-5-yl)cyclobutanol

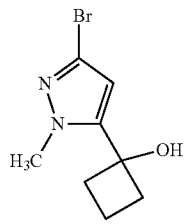

To a solution of 3,5-dibromo-1-methyl-1H-pyrazole (1.0 g) obtained in Reference Example 3 in tetrahydrofuran (40 mL) was added dropwise n-butyllithium (1.6 M hexane solution, 2.84 mL) at −78° C. Under a nitrogen atmosphere, the mixture was stirred at −78° C. for 30 min. To the reaction mixture was added cyclobutanone (380 mg), and the mixture was stirred under a nitrogen atmosphere at room temperature for 10 hr. Water was added to the reaction mixture, and the mixture was extracted with ethyl acetate. The extract was washed with saturated brine, and dried over anhydrous magnesium sulfate. The solvent was evaporated under reduced pressure and the residue was purified by silica gel column chromatography (hexane/ethyl acetate) to give the title compound (557 mg).

MS (ESI+): [M+H]$^+$ 230.8.

Reference Examples 63-65

The compounds of Reference Examples 63-65 were obtained by a method similar to Reference Examples 1-4, or a method analogous thereto, and using ethyl 1H-pyrazole-4-carboxylate and reagents corresponding to Reference Example 63-65. MS in the Table shows measured values.

TABLE 11

| Ref. Ex. No. | IUPAC name | structure | MS |
|---|---|---|---|
| 63 | 4-(3-bromo-1-methyl-1H-pyrazol-5-yl)tetrahydro-2H-pyran-4-ol | 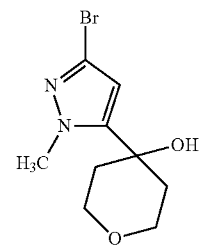 | 261.9 |
| 64 | 2-(3-bromo-1-(2-methoxyethyl)-1H-pyrazol-5-yl)propan-2-ol | 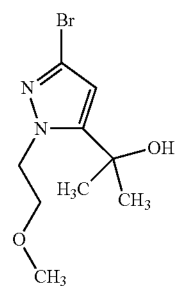 | 263.8 |
| 65 | 1-(3-bromo-1-methyl-1H-pyrazol-5-yl)-4,4-difluorocyclohexanol | 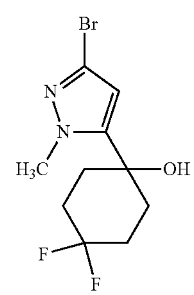 [SMILES: Cn1nc(Br)cc1C1(O)CCC(F)(F)CC1] | 294.8 |
| 66 | 1-(3-bromo-1-methyl-1H-pyrazol-5-yl)cyclobutanol | 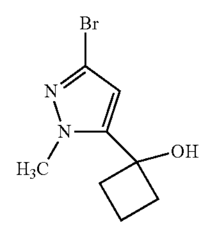 | 230.8 |

Reference Example 67

3-bromo-5-(3,6-dihydro-2H-pyran-4-yl)-1-methyl-1H-pyrazole

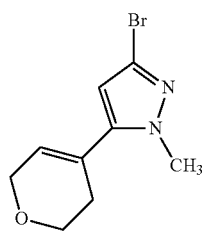

A mixture of 3,5-dibromo-1-methyl-1H-pyrazole (800 mg) obtained in Reference Example 3, 4-(4,4,5,5-tetramethyl-1,3,2-dioxaborolan-2-yl)-3,6-dihydro-2H-pyran (841 mg), tetrakis(triphenylphosphine)palladium(0) (385 mg), aqueous sodium carbonate solution (2 M, 3.33 mL) and 1,2-dimethoxyethane (30 mL) was heated under an argon atmosphere at 80° C. for 4 hr. To the reaction mixture was added tetrakis(triphenylphosphine)palladium(0) (190 mg), and the mixture was heated under an argon atmosphere at 80° C. for 16 hr. Water was added to the reaction mixture, and the mixture was extracted with ethyl acetate. The extract was successively washed with saturated brine, and dried over anhydrous magnesium sulfate, and the solvent was evaporated under reduced pressure. The residue was purified by silica gel column chromatography (ethyl acetate/hexane) to give the title compound (522 mg).

MS (ESI+): [M+H]$^+$ 242.8.

Reference Example 68

4-(3-bromo-1-methyl-1H-pyrazol-5-yl)-N-methylbenzamide

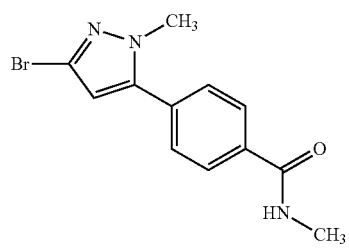 [SMILES: CNC(=O)c1ccc(-c2cc(Br)nn2C)cc1]

The title compound was obtained by a method similar to Reference Example 67 and using 3,5-dibromo-1-methyl-1H-pyrazole obtained in Reference Example 3 and N-methyl-4-(4,4,5,5-tetramethyl-1,3,2-dioxaborolan-2-yl)benzamide.

MS (ESI+): [M+H]$^+$ 293.8.

Reference Example 69

1-methyl-5-(trifluoromethyl)-1H-pyrazol-3-yl trifluoromethanesulfonate

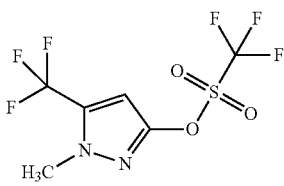

To a solution of 1-methyl-5-(trifluoromethyl)-1H-pyrazol-3-ol (250 mg) and triethylamine (0.315 mL) in acetonitrile (5.0 mL) was further added trifluoromethanesulfonic anhydride (0.38 mL) at 0° C. The reaction mixture was stirred at 0° C. for 1 hr, saturated aqueous sodium hydrogen carbonate solution was added at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (280 mg).

$^1$H NMR (400 MHz, CDCl$_3$) δ3.97 (3H, d, J=0.7 Hz), 6.50 (1H, s)

Reference Example 70

5-cyclopropyl-1-methyl-1H-pyrazol-3-yl trifluoromethanesulfonate

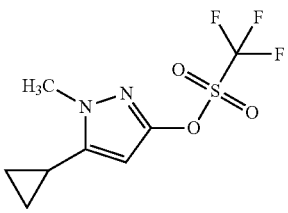 [SMILES: Cn1nc(OS(=O)(=O)C(F)(F)F)cc1C1CC1]

A) 5-cyclopropyl-1-methyl-1H-pyrazol-3-ol

To a solution of methylhydrazine (0.43 mL) in methanol (20 mL)/water (20 mL) was added methyl 3-cyclopropyl-prop-2-ynoate (1.0 g) at 0° C. The reaction mixture was stirred under a nitrogen atmosphere at room temperature overnight. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (620 mg).

MS (ESI+): [M+H]$^+$ 139.2.

B) 5-cyclopropyl-1-methyl-1H-pyrazol-3-yl trifluoromethanesulfonate

To a solution of 5-cyclopropyl-1-methyl-1H-pyrazol-3-ol (250 mg) obtained in Reference Example 70, Step A, and triethylamine (0.378 mL) in acetonitrile (6.0 mL) was further added trifluoromethanesulfonic anhydride (0.46 mL) at 0° C. The reaction mixture was stirred at 0° C. under a nitrogen atmosphere for 1 hr, saturated aqueous sodium hydrogen carbonate solution was added at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (381 mg).

MS (ESI+): [M+H]$^+$ 271.1.

Reference Example 71

N-(2-(3-iodo-1-methyl-1H-pyrazol-5-yl)-2-methylpropyl)acetamide

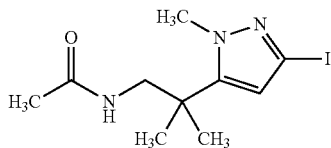

A) 2-(5-(1-hydroxy-2-methylpropan-2-yl)-1-methyl-1H-pyrazol-3-yl)-1H-isoindole-1,3(2H)-dione A mixture of 2-(5-(1-((4-methoxybenzyl)oxy)-2-methylpropan-2-yl)-1-methyl-1H-pyrazol-3-yl)-1H-isoindole-1,3(2H)-dione (4.97 g) obtained in Reference Example 9 and trifluoroacetic acid (18.3 mL) was stirred under a nitrogen atmosphere at 0° C. for 20 min. To the reaction mixture was added saturated aqueous sodium hydrogen carbonate solution at 0° C., and the mixture was extracted with ethyl acetate. The extract was successively washed with water and saturated brine, and dried over anhydrous magnesium sulfate, and the solvent was evaporated under reduced pressure to give the title compound (2.93 g).

MS (ESI+): [M+H]$^+$ 300.1.

B) 2-(3-(1,3-dioxo-1,3-dihydro-2H-isoindol-2-yl)-1-methyl-1H-pyrazol-5-yl)-2-methylpropyl methanesulfonate To a solution of 2-(5-(1-hydroxy-2-methylpropan-2-yl)-1-methyl-1H-pyrazol-3-yl)-1H-isoindole-1,3(2H)-dione (2.93 g) and triethylamine (2.73 mL) in tetrahydrofuran (50 mL) was added methanesulfonyl chloride (0.91 mL) at 0° C. The reaction mixture was stirred under a nitrogen atmosphere at room temperature for 40 min. Water was added to the reaction mixture, and the mixture was extracted with ethyl acetate. The obtained organic layer was washed with saturated brine, and dried over anhydrous magnesium sulfate. The solvent was evaporated under reduced pressure. The residue was purified by silica gel column chromatography (hexane/ethyl acetate) to give the title compound (2.60 g).

MS (ESI+): [M+H]$^+$ 378.2.

C) 2-(5-(1-azido-2-methylpropan-2-yl)-1-methyl-1H-pyrazol-3-yl)-1H-isoindole-1,3(2H)-dione To a solution of 2-(3-(1,3-dioxo-1,3-dihydro-2H-isoindol-2-yl)-1-methyl-1H-pyrazol-5-yl)-2-methylpropyl methanesulfonate (2.6 g) obtained in Reference Example 71, Step B, in N,N'-dimethylpropyleneurea (60 mL) was added sodium azide (2.69 g) at room temperature. The reaction mixture was stirred under an argon atmosphere at 90° C. overnight. Water was added to the reaction mixture, and the mixture was extracted with methyl tert-butyl ether. The obtained organic layer was successively washed with water and saturated brine, and dried over anhydrous magnesium sulfate. The solvent was evaporated under reduced pressure. The residue was purified by silica gel column chromatography (hexane/ethyl acetate) to give the title compound (1.51 g).

MS (ESI+): [M+H]$^+$ 325.3.

D) N-(2-(3-(1,3-dioxo-1,3-dihydro-2H-isoindol-2-yl)-1-methyl-1H-pyrazol-5-yl)-2-methylpropyl)acetamide To a mixture of 2-(5-(1-azido-2-methylpropan-2-yl)-1-methyl-1H-pyrazol-3-yl)-1H-isoindole-1,3(2H)-dione (1.51 g) obtained in Reference Example 71, Step C, acetic anhydride (17.6 mL) and acetic acid (15 mL) was added 10% palladium carbon (0.15 g), and the mixture was stirred under a hydrogen atmosphere at room temperature for 4 hr. The catalyst was removed by filtration, and the filtrate was concentrated under reduced pressure. To the obtained residue was added saturated aqueous sodium hydrogen carbonate solution, and the mixture was extracted with ethyl acetate. The obtained organic layer was successively washed with water and saturated brine, and dried over anhydrous magnesium sulfate. The solvent was evaporated under reduced pressure. The residue was purified by silica gel column chromatography (methanol/ethyl acetate) to give the title compound (0.74 g).

MS (ESI+): [M+H]$^+$ 341.3.

E) N-(2-(3-amino-1-methyl-1H-pyrazol-5-yl)-2-methylpropyl)acetamide

To a solution of N-(2-(3-(1,3-dioxo-1,3-dihydro-2H-isoindol-2-yl)-1-methyl-1H-pyrazol-5-yl)-2-methylpropyl)acetamide (739 mg) obtained in Reference Example 71, Step D, in methanol (15 mL) was added hydrazine monohydrate (0.12 mL) at room temperature. The reaction mixture was stirred under a nitrogen atmosphere at 65° C. for 1 hr. The precipitate was removed by filtration, and washed with ethyl acetate, and the filtrate was concentrated under reduced pressure. The residue was purified by silica gel column chromatography (basic silica gel, ethyl acetate/methanol) to give the title compound (325 mg).

MS (ESI+): [M+H]$^+$ 211.3.

F) N-(2-(3-iodo-1-methyl-1H-pyrazol-5-yl)-2-methylpropyl)acetamide

To a mixture of N-(2-(3-amino-1-methyl-1H-pyrazol-5-yl)-2-methylpropyl)acetamide (0.32 g) obtained in Reference Example 71, Step E, and diiodomethane (6.13 mL) was added isoamyl nitrite (1.15 mL) at room temperature. The reaction mixture was stirred under a nitrogen atmosphere at 130° C. for 2 hr. The mixture was concentrated under reduced pressure, and the residue was purified by silica gel column chromatography (basic silica gel, ethyl acetate/hexane) to give the title compound (375 mg).

MS (ESI+): [M+H]$^+$ 322.1.

Reference Example 72

2-(3-bromo-1-methyl-1H-pyrazol-5-yl)-N,N,2-trimethylpropanamide

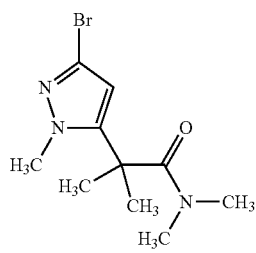

A) diethyl(3-bromo-4-(ethoxycarbonyl)-1-methyl-1H-pyrazol-5-yl)malonate

To a mixture of diethyl malonate (16.43 g) and N,N-dimethylacetamide (90 mL) was added sodium hydride (60% in mineral oil, 4.31 g) at 0° C. After stirring at room temperature for 30 min, to the reaction mixture was added ethyl 3,5-dibromo-1-methyl-1H-pyrazole-4-carboxylate (16.0 g) obtained in Reference Example 2 at room temperature. The reaction mixture was stirred at 120° C. for 9 hr and at 130° C. for 16 hr. The reaction mixture was cooled to room temperature, water was added, and the mixture was extracted with ethyl acetate. The obtained organic layer was washed with water and saturated brine, and dried over anhydrous magnesium sulfate. The solvent was evaporated under reduced pressure. The residue was purified by silica gel column chromatography (hexane/ethyl acetate) to give the title compound (7.75 g).

MS (ESI+): [M+H]$^+$ 390.9.

B) (3-bromo-1-methyl-1H-pyrazol-5-yl)acetic acid

A mixture of diethyl(3-bromo-4-(ethoxycarbonyl)-1-methyl-1H-pyrazol-5-yl)malonate (7.75 g) obtained in Reference Example 72, Step A, 8 M aqueous sodium hydroxide solution (29.7 mL) and ethanol (60 mL)/water (30 mL) was stirred at 60° C. overnight. To the reaction mixture was added concentrated sulfuric acid (31.7 mL) at 0° C., and the mixture was stirred at 120° C. overnight. The reaction mixture was cooled to room temperature and the solvent was evaporated under reduced pressure. Ethyl acetate was added to the residue, the mixture was washed successively with water and saturated brine, and dried over anhydrous magnesium sulfate, and the solvent was evaporated under reduced pressure. To the residue was added 50% aqueous sulfuric acid solution (60 mL, v/v), and the reaction mixture was stirred at 160° C. for 2 hr. The reaction mixture was diluted with ice water at 0° C. and extracted with ethyl acetate. The extract was washed with saturated brine, and dried over anhydrous magnesium sulfate. The solvent was evaporated under reduced pressure to give the title compound (3.94 g).

MS (ESI+): [M+H]$^+$ 218.8.

C) ethyl(3-bromo-1-methyl-1H-pyrazol-5-yl)acetate

To a mixture of (3-bromo-1-methyl-1H-pyrazol-5-yl)acetic acid (3.30 g) obtained in Reference Example 72, Step B, and ethanol (200 mL) was added concentrated sulfuric acid (2 mL) at room temperature. The reaction mixture was stirred at 100° C. for 5 hr. The reaction mixture was cooled to room temperature, and the solvent was evaporated under reduced pressure. Ethyl acetate was added to the residue, and the mixture was washed successively with saturated aqueous sodium hydrogen carbonate solution, water and saturated brine, and dried over anhydrous magnesium sulfate. The solvent was evaporated under reduced pressure to give the title compound (3.34 g).

MS (ESI+): [M+H]$^+$ 246.8.

D) ethyl 2-(3-bromo-1-methyl-1H-pyrazol-5-yl)-2-methylpropanoate

To a solution of ethyl(3-bromo-1-methyl-1H-pyrazol-5-yl)acetate (500 mg) obtained in Reference Example 72, Step C, in N,N-dimethylformamide (10 mL) was added sodium hydride (60% in mineral oil, 202 mg) at 0° C. The reaction mixture was stirred at 0° C. for 30 min, and methyl iodide (0.38 mL) was added at 0° C. The reaction mixture was stirred at room temperature for 1.5 hr. Water was added to the reaction mixture, and the mixture was extracted with ethyl acetate. The obtained organic layer was successively washed with water and saturated brine, and dried over anhydrous magnesium sulfate. The solvent was evaporated under reduced pressure. The residue was purified by silica gel column chromatography (hexane/ethyl acetate) to give the title compound (356 mg).

MS (ESI+): [M+H]$^+$ 274.8.

E) 2-(3-bromo-1-methyl-1H-pyrazol-5-yl)-2-methylpropanoic acid

To a solution of ethyl 2-(3-bromo-1-methyl-1H-pyrazol-5-yl)-2-methylpropanoate obtained in Reference Example 72, Step D, in ethanol (10 mL)/tetrahydrofuran (10 mL) was added 2 M aqueous sodium hydroxide solution (6.02 mL) at room temperature, and the reaction mixture was stirred at room temperature for 2 hr and at 50° C. for 2 hr. The solvent was evaporated under reduced pressure, 2 M hydrochloric acid was added to the reaction mixture, and the mixture was extracted with ethyl acetate. The extract was washed with saturated brine, and dried over magnesium sulfate, and the solvent was evaporated under reduced pressure to give the title compound (1.00 g).

MS (ESI+): [M+H]$^+$ 246.7.

F) 2-(3-bromo-1-methyl-1H-pyrazol-5-yl)-N,N,2-trimethylpropanamide

A mixture of 2-(3-bromo-1-methyl-1H-pyrazol-5-yl)-2-methylpropanoic acid (400 mg) obtained in Reference Example 72, Step E, dimethylamine hydrochloride (198 mg), 1-(3-dimethylaminopropyl)-3-ethylcarbodiimide hydrochloride (466 mg), 1-hydroxybenzotriazole (328 mg), triethylamine (0.677 mL) and N,N-dimethylformamide (5 mL) was stirred at room temperature for 16 hr. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (359 mg).

MS (ESI+): [M+H]$^+$ 273.8.

Reference Example 73

2-(3-bromo-1-methyl-1H-pyrazol-5-yl)-2-methylpropanenitrile

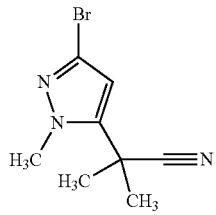

A) 2-(3-bromo-1-methyl-1H-pyrazol-5-yl)-2-methylpropanamide

The title compound was obtained by a method similar to Reference Example 38 and using 2-(3-bromo-1-methyl-1H-pyrazol-5-yl)-2-methylpropanoic acid obtained in Reference Example 72, Step E and 1H-benzotriazol-1-ol ammonium salt.

MS (ESI+): [M+H]$^+$ 245.7.

B) 2-(3-bromo-1-methyl-1H-pyrazol-5-yl)-2-methylpropanenitrile

To a mixture of 2-(3-bromo-1-methyl-1H-pyrazol-5-yl)-2-methylpropanamide (574 mg) obtained in Example 73, Step A, pyridine (0.57 mL) and tetrahydrofuran (10 mL) was added trifluoroacetic anhydride (0.97 mL) at room temperature. The reaction mixture was stirred at room temperature for 3 hr. To the reaction mixture was added saturated aqueous sodium hydrogen carbonate solution, and the mixture was extracted with ethyl acetate. The obtained organic layer was washed successively with 1 M hydrochloric acid and saturated brine, and dried over anhydrous magnesium sulfate. The solvent was evaporated under reduced pressure to give the title compound (530 mg).

MS (ESI+): [M+H]$^+$ 227.7.

Reference Example 74

1,1-difluoro-3-methylbutan-2-ol

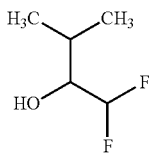

To a solution of ethyl difluoroacetate (14.8 g) in diethyl ether (240 mL) were added dropwise isopropylmagnesium bromide (1 M tetrahydrofuran solution, 239 mL) and diethyl ether (240 mL) over 30 min at 0° C. The reaction mixture was stirred under a nitrogen atmosphere at room temperature overnight. To the reaction mixture was added 1 M hydrochloric acid at 0° C., and the mixture was extracted three times with diethyl ether. The obtained organic layer was washed with saturated brine, and dried over anhydrous magnesium sulfate. The solvent was evaporated under reduced pressure to give tetrahydrofuran solution of the title compound (8.30 g, containing 20% tetrahydrofuran).

$^1$H NMR (400 MHz, CDCl$_3$) δ1.02 (6H, t, J=7.6 Hz), 1.90-1.99 (1H, m), 3.44-3.59 (1H, m), 5.55-5.90 (1H, m).

Reference Example 75

4-(3-bromo-1-methyl-1H-pyrazol-5-yl)-2,2-dimethylthiomorpholine

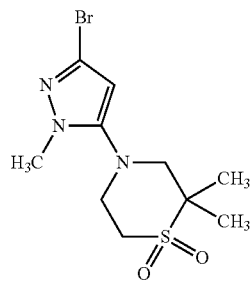

A) ethyl 3-bromo-5-(2,2-dimethylthiomorpholino)-1-methyl-1H-pyrazole-4-carboxylate A mixture of ethyl 3,5-dibromo-1-methyl-1H-pyrazole-4-carboxylate (2.38 g) obtained in Reference Example 2, 2,2-dimethylthiomorpholine (1.00 g), potassium carbonate (1.05 g) and N-methyl-pyrrolidone (12 mL) was heated under microwave irradiation at 180° C. for 4 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane) to give the title compound (0.78 g).

MS (ESI+): [M+H]$^+$ 362.0.

B) 4-(3-bromo-1-methyl-1H-pyrazol-5-yl)-2,2-dimethylthiomorpholine

A mixture of ethyl 3-bromo-5-(2,2-dimethylthiomorpholino)-1-methyl-1H-pyrazole-4-carboxylate (770 mg) obtained in Reference Example 75, Step A, 2 M aqueous sodium hydroxide solution (4.25 mL) and ethanol (10 mL) was stirred at 60° C. for 2.5 hr. To the reaction mixture was added concentrated sulfuric acid (1.36 mL) at 0° C., and the mixture was stirred at 60° C. for 1 hr. The reaction mixture was adjusted to pH 7-8 by adding 8 M aqueous sodium hydroxide solution and sodium hydrogen carbonate at 0° C., and extracted with ethyl acetate. The extract was washed with saturated brine, and dried over anhydrous magnesium sulfate, and the solvent was evaporated under reduced pressure to give the title compound (391 mg).

MS (ESI+): [M+H]$^+$ 289.9.

C) 4-(3-bromo-1-methyl-1H-pyrazol-5-yl)-2,2-dimethylthiomorpholine 1,1-dioxide A mixture of 4-(3-bromo-1-methyl-1H-pyrazol-5-yl)-2,2-dimethylthiomorpholine (381 mg) obtained in Reference Example 75, Step B, m-chloroperbenzoic acid (680 mg) and ethyl acetate (15 mL) was stirred at room temperature for 5 hr. To the reaction mixture was added saturated aqueous sodium hydrogen carbonate solution, and the mixture was extracted with ethyl acetate/tetrahydrofuran. The extract was washed with saturated aqueous sodium hydrogen carbonate solution and saturated brine, and dried over anhydrous magnesium sulfate, and the solvent was evaporated under reduced pressure. The residue was solidified from ethyl acetate/methanol to give the title compound (381 mg).

MS (ESI+): [M+H]$^+$ 321.8.

Reference Example 76

1-(3-(3-bromo-1-methyl-1H-pyrazol-5-yl)-3-methoxyazetidin-1-yl)-2-methylpropan-1-one

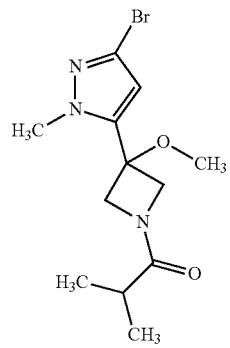

A) tert-butyl 3-(3-bromo-1-methyl-1H-pyrazol-5-yl)-3-hydroxyazetidine-1-carboxylate To a solution of 3,5-dibromo-1-methyl-1H-pyrazole (10.0 g) obtained in Reference Example 3 in tetrahydrofuran (100 mL) was added dropwise n-butyllithium (1.6 M hexane solution, 28.7 mL) under an argon atmosphere at −78° C. After stirring under an argon atmosphere at −78° C. for 30 min, a solution of tert-butyl 3-oxoazetidine-1-carboxylate (9.28 g) in tetrahydrofuran (25 mL) was added to the reaction mixture, and the mixture was stirred under an argon atmosphere at −78° C. for 30 min and at room temperature for 16 hr. Water was added to the reaction mixture, and the mixture was extracted with ethyl acetate. The extract was washed with saturated brine and dried over anhydrous magnesium sulfate. The solvent was evaporated under reduced pressure. The residue was purified by silica gel column chromatography (hexane/ethyl acetate) to give the title compound (7.37 g).

MS (ESI+): [M+H]$^+$ 331.9.

B) tert-butyl 3-(3-bromo-1-methyl-1H-pyrazol-5-yl)-3-methoxyazetidine-1-carboxylate To a solution of tert-butyl 3-(3-bromo-1-methyl-1H-pyrazol-5-yl)-3-hydroxyazetidine-1-carboxylate (6.3 g) obtained in Reference Example 76, Step A, in tetrahydrofuran (100 mL) was added sodium hydride (60% in mineral oil, 910 mg) at 0° C. The reaction mixture was stirred at 0° C. for 30 min, and methyl iodide (2.36 mL) was added. The reaction mixture was stirred at 50° C. for 2 hr. Under ice-cooling, water was added to the reaction mixture, and the mixture was extracted with ethyl acetate. The obtained organic layer was washed with saturated brine, and dried over anhydrous magnesium sulfate. The solvent was evaporated under reduced pressure. The residue was solidified from diisopropyl ether, and washed with diisopropyl ether/hexane to give the title compound (2.3 g). The mother liquor was concentrated to give the title compound (4.2 g).

$^1$H NMR (400 MHz, CDCl$_3$) δ1.44 (9H, s), 3.05 (3H, s), 3.78 (3H, s), 4.10-4.21 (4H, m), 6.30 (1H, s).

C) 3-bromo-5-(3-methoxyazetidin-3-yl)-1-methyl-1H-pyrazole hydrochloride

A mixture of tert-butyl 3-(3-bromo-1-methyl-1H-pyrazol-5-yl)-3-methoxyazetidine-1-carboxylate (6.5 g) obtained in Reference Example 76, Step B, 4N hydrogen chloride in ethyl acetate solution (10 mL) and ethyl acetate (25 mL) was stirred at 50° C. for 1 hr. To the reaction mixture was added methanol (25 mL), and the mixture was stirred at 50° C. for 3 hr. To the reaction mixture was added 4N hydrogen chloride in ethyl acetate solution (5 mL), and the mixture was stirred at 50° C. for 2 hr and at room temperature Overnight. The solvent was evaporated under reduced pressure, and the obtained residue was washed with diethyl ether to give the title compound (4.75 g).

MS, found: 245.8.

D) 1-(3-(3-bromo-1-methyl-1H-pyrazol-5-yl)-3-methoxyazetidin-1-yl)-2-methylpropan-1-one To a mixture of 3-bromo-5-(3-methoxyazetidin-3-yl)-1-methyl-1H-pyrazole hydrochloride (1200 mg) obtained in Reference Example 76, Step C, triethylamine (1.78 mL) and tetrahydrofuran (40 mL) was added isobutyryl chloride (0.672 mL) at 0° C., and the mixture was stirred at room temperature for 2 hr. The reaction mixture was added to saturated aqueous sodium hydrogen carbonate solution under ice-cooling, and the mixture was extracted with ethyl acetate. The extract was washed with saturated aqueous ammonium chloride solution and saturated brine, and dried over anhydrous magnesium sulfate, and the solvent was evaporated under reduced pressure to give the title compound (1.31 g).

MS (ESI+): [M+H]$^+$ 315.8.

Reference Example 77

3-bromo-5-(1-(isopropylsulfonyl)-3-methoxyazetidin-3-yl)-1-methyl-1H-pyrazole

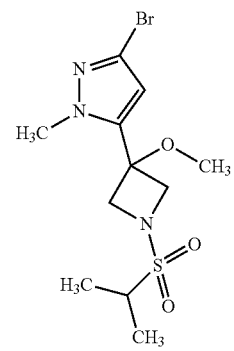

To a mixture of 3-bromo-5-(3-methoxyazetidin-3-yl)-1-methyl-1H-pyrazole hydrochloride (1200 mg) obtained in Reference Example 76, Step C, triethylamine (1.78 mL) and tetrahydrofuran (40 mL) was added propane-2-sulfonyl chloride (0.71 mL) at 0° C., and the mixture was stirred at room temperature for 16 hr. The reaction mixture was added to saturated aqueous sodium hydrogen carbonate solution under ice-cooling, and the mixture was extracted with ethyl acetate. The extract was washed with saturated aqueous ammonium chloride solution and saturated brine, and dried over anhydrous magnesium sulfate, and the solvent was evaporated under reduced pressure to give the title compound (1.50 g).

MS (ESI+): [M+H]$^+$ 351.8.

Reference Example 78

4-(3-bromo-1-methyl-1H-pyrazol-5-yl)-1-isopropylpiperazin-2-one

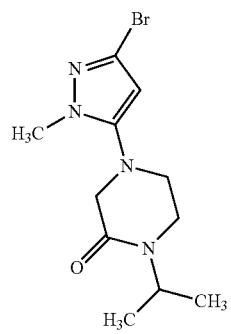 [SMILES: CC(C)N1CCN(c2cc(Br)nn2C)CC1=O]

A) ethyl 3-bromo-5-(4-isopropyl-3-oxopiperazin-1-yl)-1-methyl-1H-pyrazole-4-carboxylate A mixture of ethyl 3,5-dibromo-1-methyl-1H-pyrazole-4-carboxylate (3.05 g) obtained in Reference Example 2,1-isopropylpiperazin-2-one (1.39 g), potassium carbonate (1.35 g) and N-methyl-pyrrolidone (12 mL) was heated under microwave irradiation at 160° C. for 4 hr. After cooling, water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (0.97 g).

MS (ESI+): [M+H]$^+$ 372.9.

B) 4-(3-bromo-1-methyl-1H-pyrazol-5-yl)-1-isopropylpiperazin-2-one

A mixture of ethyl 3-bromo-5-(4-isopropyl-3-oxopiperazin-1-yl)-1-methyl-1H-pyrazole-4-carboxylate (970 mg) obtained in Reference Example 78, Step A, 2 M aqueous sodium hydroxide solution (6.5 mL) and ethanol (8 mL) was stirred at 60° C. for 3 hr. To the reaction mixture was added concentrated sulfuric acid (1.39 mL) at 0° C., and the mixture was stirred at 40° C. overnight. The reaction mixture was alkalified with 8 M aqueous sodium hydroxide solution under ice-cooling, and extracted twice with ethyl acetate. The extracts were combined, washed with saturated brine, dried over anhydrous magnesium sulfate, and the solvent was evaporated under reduced pressure to give the title compound (310 mg).

MS (ESI+): [M+H]$^+$ 300.8.

Reference Example 79

1-(3-bromo-1-methyl-1H-pyrazol-5-yl)-4-(trifluoromethyl)piperidin-4-ol

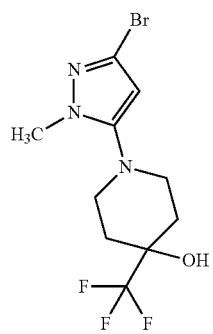 [SMILES: Cn1nc(Br)cc1N1CCC(O)(C(F)(F)F)CC1]

A) ethyl 3-bromo-5-(4-hydroxy-4-(trifluoromethyl)piperidin-1-yl)-1-methyl-1H-pyrazole-4-carboxylate A mixture of ethyl 3,5-dibromo-1-methyl-1H-pyrazole-4-carboxylate (1.8 g) obtained in Reference Example 2, 4-(trifluoromethyl)piperidin-4-ol hydrochloride (1.42 g), potassium carbonate (1.91 g), and N-methyl-pyrrolidone (10 mL) was heated under microwave irradiation at 160° C. for 4 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane) to give the title compound (1.12 g).

MS (ESI+): [M+H]$^+$ 399.9.

B) 1-(3-bromo-1-methyl-1H-pyrazol-5-yl)-4-(trifluoromethyl)piperidin-4-ol

A mixture of ethyl 3-bromo-5-(4-hydroxy-4-(trifluoromethyl)piperidin-1-yl)-1-methyl-1H-pyrazole-4-carboxylate (1.12 g) obtained in Reference Example 79, Step A, 2 M aqueous sodium hydroxide solution (7.00 mL) and ethanol (10 mL) was stirred at 70° C. for 2 hr. To the reaction mixture was added concentrated sulfuric acid (5.97 mL), and the mixture was stirred at 70° C. for 2 hr. The reaction mixture was alkalified by adding 8 M aqueous sodium hydroxide solution, and extracted three times with ethyl acetate. The extracts were combined, washed with saturated brine, and dried over anhydrous magnesium sulfate, and the solvent was evaporated under reduced pressure to give the title compound (769 mg).

MS (ESI+): [M+H]327.8.

Reference Example 80

3-bromo-N-isopropyl-N,1-dimethyl-1H-pyrazol-5-amine

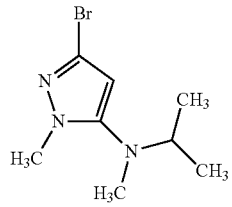

A) ethyl 3-bromo-5-(isopropyl(methyl)amino)-1-methyl-1H-pyrazole-4-carboxylate A mixture of ethyl 3,5-dibromo-1-methyl-1H-pyrazole-4-carboxylate (2.00 g) obtained in Reference Example 2, N-methylpropan-2-amine (1.41 g), potassium carbonate (0.975 g), and N-methyl-pyrrolidone (12 mL) was heated under microwave irradiation at 180° C. for 4 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane) to give the title compound (0.72 g).

MS (ESI+): [M+H]$^+$ 303.9.

B) 3-bromo-N-isopropyl-N,1-dimethyl-1H-pyrazol-5-amine

A mixture of ethyl 3-bromo-5-(isopropyl(methyl)amino)-1-methyl-1H-pyrazole-4-carboxylate (830 mg) obtained in Reference Example 80, Step A, 2 M aqueous sodium hydroxide solution (5.46 mL) and ethanol (10 mL) was stirred at 60° C. for 2.5 hr. To the reaction mixture was added concentrated sulfuric acid (1.75 mL) under ice-cooling, and the mixture was stirred at 60° C. for 30 min. The reaction mixture was adjusted to pH 7-8 with 8 M aqueous sodium hydroxide solution and sodium hydrogen carbonate under ice-cooling, and extracted with ethyl acetate. The extract was washed with saturated brine, and dried over anhydrous magnesium sulfate, and the solvent was evaporated under reduced pressure to give the title compound (620 mg).

MS (ESI+): [M+H]$^+$ 231.9.

Reference Example 81

1-(3-bromo-1-methyl-1H-pyrazol-5-yl)-4-(isopropylsulfonyl)piperazine

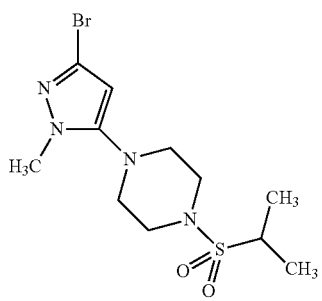 [SMILES: CC(C)S(=O)(=O)N1CCN(c2cc(Br)nn2C)CC1]

To a solution of 1-(3-bromo-1-methyl-1H-pyrazol-5-yl)piperazine (465 mg) obtained in Reference Example 15, Step B and triethylamine (288 mg) in tetrahydrofuran (15 mL) was added isopropylsulfonyl chloride (325 mg) at 0° C. The reaction mixture was stirred at room temperature overnight. To the reaction mixture was added saturated aqueous sodium hydrogen carbonate solution, and the mixture was extracted with ethyl acetate. The extract was washed with saturated brine and dried over anhydrous magnesium sulfate. The solvent was evaporated under reduced pressure. The residue was purified by silica gel column chromatography (ethyl acetate/hexane) to give the title compound (510 mg).

MS (ESI+): [M+H]350.9.

Reference Example 82

1-(1-(3-bromo-1-methyl-1H-pyrazol-5-yl)pyrrolidin-2-yl)-N,N-dimethylmethanamine

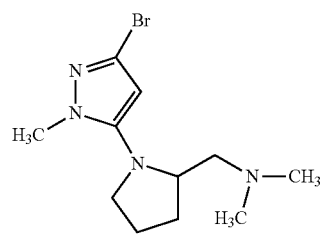

A) ethyl 3-bromo-5-(2-((dimethylamino)methyl)pyrrolidin-1-yl)-1-methyl-1H-pyrazole-4-carboxylate A mixture of ethyl 3,5-dibromo-1-methyl-1H-pyrazole-4-carboxylate (760 m g) obtained in Reference Example 2, N,N-dimethyl-1-(pyrrolidin-2-yl)methanamine dihydrochloride (588 mg), N-ethyldiisopropylamine (1.70 mL) and N-methyl-pyrrolidone (12 mL) was heated under microwave irradiation at 200° C. for 4 hr.

A mixture of ethyl 3,5-dibromo-1-methyl-1H-pyrazole-4-carboxylate (750 m g) obtained in Reference Example 2, N,N-dimethyl-1-(pyrrolidin-2-yl)methanamine dihydrochloride (580 mg), N-ethyldiisopropylamine (1.68 mL) and N-methyl-pyrrolidone (12 mL) was heated under microwave irradiation at 200° C. for 4 hr.

After cooling, the above-mentioned two reaction mixtures were combined, saturated aqueous sodium hydrogen carbonate solution was added, and the mixture was extracted with ethyl acetate. The extract was washed with 1 M aqueous hydrochloric acid solution. The aqueous layer was alkalified with 8 M aqueous sodium hydroxide solution, and extracted with ethyl acetate. The organic layer was washed with saturated brine, and dried over anhydrous magnesium sulfate, and the solvent was evaporated under reduced pressure. The residue was purified by silica gel column chromatography (basic silica gel, ethyl acetate/hexane) to give the title compound (235 mg).

MS (ESI+): [M+H]$^+$ 359.2.

B) 1-(1-(3-bromo-1-methyl-1H-pyrazol-5-yl)pyrrolidin-2-yl)-N,N-dimethylmethanamine A mixture of ethyl 3-bromo-5-(2-((dimethylamino)methyl)pyrrolidin-1-yl)-1-methyl-1H-pyrazole-4-carboxylate (330 mg) obtained in Reference Example 82, Step A, 2 M aqueous sodium hydroxide solution (2.30 mL) and ethanol (5 mL) was stirred at 70° C. for 4 hr. To the reaction mixture was added concentrated sulfuric acid (0.588 mL), and the mixture was stirred at 70° C. for 2 hr. The reaction mixture was alkalified with 8 M aqueous sodium hydroxide solution, and extracted three times with ethyl acetate. The extracts were combined, washed with saturated brine, and dried over anhydrous magnesium sulfate, and the solvent was evaporated under reduced pressure to give the title compound (290 mg).

MS (ESI+): [M+H]$^+$ 286.8.

Reference Example 83

6-(3-bromo-1-methyl-1H-pyrazol-5-yl)-2-oxa-6-azaspiro[3.3]heptane

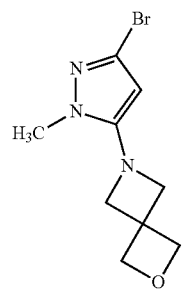

To a mixture of 3,5-dibromo-1-methyl-1H-pyrazole (1248 mg) obtained in Reference Example 3, 2-oxa-6-azaspiro[3.3]heptane 0.5 oxalate (500 mg), sodium tert-butoxide (1000 mg) and toluene (30 mL) were added (±)-2,2'-bis(diphenylphosphino)-1,1'-binaphthyl (108 mg) and tris(dibenzylideneacetone)dipalladium(0) (79 mg) at room temperature, and the mixture was stirred under an argon atmosphere at 80° C. overnight. After cooling, the insoluble material was removed by filtration, and the filtrate was concentrated under reduced pressure. The residue was purified by silica gel column chromatography (basic silica gel, ethyl acetate/hexane) to give the title compound (159 mg).

MS (ESI+): [M+H]$^+$ 257.8.

Reference Example 84

3-bromo-5-(3,3-difluoropyrrolidin-1-yl)-1-methyl-1H-pyrazole

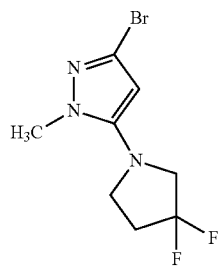

A) ethyl 3-bromo-5-(3,3-difluoropyrrolidin-1-yl)-1-methyl-1H-pyrazole-4-carboxylate A mixture of ethyl 3,5-dibromo-1-methyl-1H-pyrazole-4-carboxylate (1.81 g) obtained in Reference Example 2, 3,3-difluoropyrrolidine hydrochloride (1.00 g), potassium carbonate (1.93 g) and N-methyl-pyrrolidone (12 mL) was heated under microwave irradiation at 160° C. for 4 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane), further fractionated by HPLC (C18, mobile phase: water/acetonitrile (containing 10 mM NH$_4$HCO$_3$)), and the obtained fraction was concentrated under reduced pressure to give the title compound (426 mg).

MS (ESI+): [M+H]$^+$ 337.9.

B) 3-bromo-5-(3,3-difluoropyrrolidin-1-yl)-1-methyl-1H-pyrazole

A mixture of ethyl 3-bromo-5-(3,3-difluoropyrrolidin-1-yl)-1-methyl-1H-pyrazole-4-carboxylate (426 mg) obtained in Reference Example 84, Step A, 2 M aqueous sodium hydroxide solution (3.15 mL) and ethanol (5 mL) was stirred at 70° C. for 2 hr. To the reaction mixture was added concentrated sulfuric acid (0.806 mL), and the mixture was stirred at 70° C. for 2 hr. The reaction mixture was alkalified with 8 M aqueous sodium hydroxide solution, and extracted three times with ethyl acetate. The extracts were combined, washed with saturated brine, and dried over anhydrous magnesium sulfate, and the solvent was evaporated under reduced pressure to give the title compound (335 mg).

MS (ESI+): [M+H]$^+$ 266.2.

Reference Example 85

1-(3-bromo-1-methyl-1H-pyrazol-5-yl)-4-(cyclopropylsulfonyl)piperazine

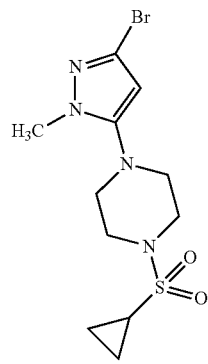 [SMILES: Cn1nc(Br)cc1N1CCN(S(=O)(=O)C2CC2)CC1]

To a solution of 1-(3-bromo-1-methyl-1H-pyrazol-5-yl)piperazine (300 mg) obtained in Reference Example 15, Step B, and triethylamine (0.256 mL) in tetrahydrofuran (10 mL) was added cyclopropanesulfonyl chloride (206 mg) at 0° C. The reaction mixture was stirred at room temperature overnight. To the reaction mixture was added saturated aqueous sodium hydrogen carbonate solution, and the mixture was extracted with ethyl acetate. The extract was washed with saturated brine and dried over anhydrous magnesium sulfate. The solvent was evaporated under reduced pressure. The residue was purified by silica gel column chromatography (ethyl acetate/hexane) to give the title compound (300 mg).

MS (ESI+): [M+H]$^+$ 348.8.

Reference Example 86

1-(3-bromo-1-methyl-1H-pyrazol-5-yl)-4-(methylsulfonyl)piperazine

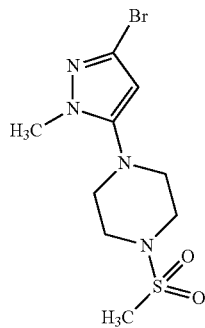

To a solution of 1-(3-bromo-1-methyl-1H-pyrazol-5-yl)piperazine (465 mg) obtained in Reference Example 15, Step B, and triethylamine (0.397 mL) in tetrahydrofuran (15 mL) was added methanesulfonyl chloride (261 mg) at 0° C. The reaction mixture was stirred at room temperature for 2 hr. To the reaction mixture was added saturated aqueous sodium hydrogen carbonate solution, and the mixture was extracted with ethyl acetate. The extract was washed with saturated brine and dried over anhydrous magnesium sulfate. The solvent was evaporated under reduced pressure. The residue was purified by silica gel column chromatography (ethyl acetate/hexane) to give the title compound (570 mg).

MS (ESI+): [M+H]$^+$ 322.9.

Reference Example 87

3-bromo-5-(2-methoxypropan-2-yl)-1-methyl-1H-pyrazole

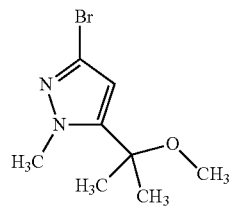

To a solution of 2-(3-bromo-1-methyl-1H-pyrazol-5-yl)propan-2-ol (500 mg) obtained in Reference Example 4 in tetrahydrofuran (20 mL) was added sodium hydride (60% in mineral oil, 100 mg) at 0° C. The reaction mixture was stirred under a nitrogen atmosphere at 0° C. for 30 min, and methyl iodide (389 mg) was added. The reaction mixture was stirred under a nitrogen atmosphere at room temperature for 10 hr. Water was added to the reaction mixture, and the mixture was extracted with ethyl acetate. The obtained organic layer was washed with saturated brine, and dried over anhydrous magnesium sulfate. The solvent was evaporated under reduced pressure. The residue was purified by silica gel column chromatography (ethyl acetate/hexane) to give the title compound (382 mg).

MS (ESI+): [M+H]$^+$ 232.8.

Reference Example 88

3-bromo-5-(4-methoxy-1,1-dioxidotetrahydro-2H-thiopyran-4-yl)-1-methyl-1H-pyrazole

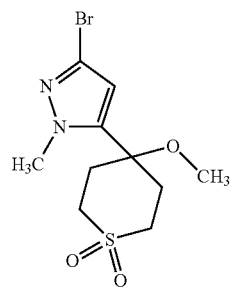

A) 4-(3-bromo-1-methyl-1H-pyrazol-5-yl)-4-hydroxytetrahydro-2H-thiopyran 1,1-dioxide To a solution of 3,5-dibromo-1-methyl-1H-pyrazole (1.0 g) obtained in Reference Example 3 in tetrahydrofuran (40 mL) was added dropwise n-butyllithium (1.6 M hexane solution, 2.87 mL) at −78° C. After stirring under a nitrogen atmosphere at −78° C. for 30 min, dihydro-2H-thiopyran-4(3H)-one 1,1-dioxide (803 mg) was added to the reaction mixture, and the mixture was stirred under a nitrogen atmosphere at room temperature for 10 hr. Water was added to the reaction mixture, and the mixture was extracted with ethyl acetate. The extract was washed with saturated brine, and dried over anhydrous magnesium sulfate. The solvent was evaporated under reduced pressure. The residue was purified by silica gel column chromatography (hexane/ethyl acetate) to give the title compound (338 mg).

MS (ESI+): [M+H]$^+$ 308.8.

B) 3-bromo-5-(4-methoxy-1,1-dioxidotetrahydro-2H-thiopyran-4-yl)-1-methyl-1H-pyrazole To a solution of 4-(3-bromo-1-methyl-1H-pyrazol-5-yl)-4-hydroxytetrahydro-2H-thiopyran 1,1-dioxide (300 mg) obtained in Reference Example 88, Step A, in tetrahydrofuran (20 mL) was added sodium hydride (60% in mineral oil, 43 mg) at 0° C. The reaction mixture was stirred under a nitrogen atmosphere at 0° C. for 30 min, and methyl iodide (165 mg) was added. The reaction mixture was stirred under a nitrogen atmosphere at room temperature for 10 hr and at 80° C. for 4 hr. Water was added to the reaction mixture, and the mixture was extracted with ethyl acetate. The obtained organic layer was washed with saturated brine and dried over anhydrous magnesium sulfate. The solvent was evaporated under reduced pressure. The residue was purified by silica gel column chromatography (hexane/ethyl acetate) to give the title compound (275 mg).

MS (ESI+): [M+H]$^+$ 322.8.

Reference Example 89

3-bromo-N-cyclopentyl-N,1-dimethyl-1H-pyrazol-5-amine

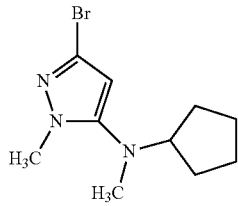

A) ethyl 3-bromo-5-(cyclopentyl(methyl)amino)-1-methyl-1H-pyrazole-4-carboxylate A mixture of ethyl 3,5-dibromo-1-methyl-1H-pyrazole-4-carboxylate (4.0 g) obtained in Reference Example 2, N-methylcyclopentanamine (2.54 g), potassium carbonate (1.77 g) and N-methyl-pyrrolidone (12 mL) was heated under microwave irradiation at 200° C. for 4 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane) to give the title compound (1.94 g).

MS (ESI+): [M+H]$^+$ 330.0.

B) 3-bromo-N-cyclopentyl-N,1-dimethyl-1H-pyrazol-5-amine

A mixture of ethyl 3-bromo-5-(cyclopentyl(methyl)amino)-1-methyl-1H-pyrazole-4-carboxylate (1.9 g) obtained in Reference Example 89, Step A, 2 M aqueous sodium hydroxide solution (11.5 mL) and ethanol (20 mL) was stirred at 60° C. for 2.5 hr. To the reaction mixture was added concentrated sulfuric acid (3.68 mL), and the mixture was stirred at 60° C. for 30 min. The reaction mixture was adjusted to pH 7-8 with 8 M aqueous sodium hydroxide solution and sodium hydrogen carbonate, and the mixture was extracted with ethyl acetate. The extract was washed with saturated brine, and dried over anhydrous magnesium sulfate, and the solvent was evaporated under reduced pressure to give the title compound (1.38 g).

MS (ESI+): [M+H]$^+$ 257.9.

Reference Example 90 cis-3-(3-bromo-1-methyl-1H-pyrazol-5-yl)-3-methoxy-N,N-dimethyl cyclobutanecarboxamide

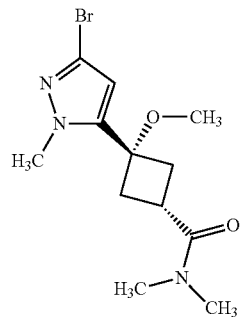 [SMILES: CO[C@]1(c2cc(Br)nn2C)C[C@H](C(=O)N(C)C)C1]

A) cis-3-(3-bromo-1-methyl-1H-pyrazol-5-yl)-3-hydroxy-N,N-dimethylcyclobutanecarboxamide To a solution of 3,5-dibromo-1-methyl-1H-pyrazole (900 mg) obtained in Reference Example 3 in tetrahydrofuran (10 mL) was added dropwise n-butyllithium (1.6 M hexane solution, 2.81 mL) under an argon atmosphere at −78° C. After stirring under an argon atmosphere at −78° C. for 30 min, a solution of N,N-dimethyl-3-oxocyclobutanecarboxamide (583 mg) in tetrahydrofuran (5 mL) was added to the reaction mixture, and the mixture was stirred under an argon atmosphere at −78° C. for 30 min and at room temperature for 16 hr. Water was added to the reaction mixture, and the mixture was extracted with ethyl acetate. The extract was washed with saturated brine, and dried over anhydrous magnesium sulfate. The solvent was evaporated under reduced pressure. The residue was purified by silica gel column chromatography (hexane/ethyl acetate) to give the title compound (511 mg).

$^1$H NMR (400 MHz, CDCl$_3$) δ2.58-2.68 (2H, m), 2.73-2.86 (2H, m), 2.99-3.02 (6H, m), 3.10-3.21 (1H, m), 3.89 (3H, s), 4.98 (1H, s), 6.17 (1H, s).

B) cis-3-(3-bromo-1-methyl-1H-pyrazol-5-yl)-3-methoxy-N,N-dimethylcyclobutanecarboxamide To a solution of cis-3-(3-bromo-1-methyl-1H-pyrazol-5-yl)-3-hydroxy-N,N-dimethylcyclobutanecarboxamide (500 mg) obtained in Reference Example 90, Step A, in tetrahydrofuran (10 mL) was added sodium hydride (60% in mineral oil, 79 mg) at 0° C. The reaction mixture was stirred at 0° C. for 30 min, and methyl iodide (0.206 mL) was added. The reaction mixture was stirred at 50° C. for 2 hr. To the reaction mixture was added methyl iodide (0.1 mL), and the reaction mixture was stirred at 50° C. for 1 hr. Under ice-cooling, water was added to the reaction mixture, and the mixture was extracted with ethyl acetate. The obtained organic layer was washed with saturated brine, and dried over anhydrous magnesium sulfate. The solvent was evaporated under reduced pressure to give the title compound (436 mg).

MS (ESI+): [M+H]$^+$ 316.0.

Reference Example 91

(3R)-1-(3-bromo-1-methyl-1H-pyrazol-5-yl)-N,N-dimethylpyrrolidin-3-amine

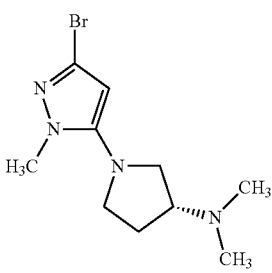

A) (R)-ethyl 3-bromo-5-(3-(dimethylamino)pyrrolidin-1-yl)-1-methyl-1H-pyrazole-4-carboxylate A mixture of ethyl 3,5-dibromo-1-methyl-1H-pyrazole-4-carboxylate (2.7 g) obtained in Reference Example 2, (R)—N,N-dimethylpyrrolidin-3-amine (0.99 g), potassium carbonate (3.59 g) and N-methyl-pyrrolidone (10 mL) was heated under a nitrogen atmosphere at 160° C. for 6 hr. Water was added to the reaction mixture, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (2.39 g).

MS (ESI+): [M+H]$^+$ 344.9.

B) (3R)-1-(3-bromo-1-methyl-1H-pyrazol-5-yl)-N,N-dimethylpyrrolidin-3-amine

A mixture of (R)-ethyl 3-bromo-5-(3-(dimethylamino)pyrrolidin-1-yl)-1-methyl-1H-pyrazole-4-carboxylate (2.39 g) obtained in Reference Example 91, Step A, 2 M aqueous sodium hydroxide solution (17.3 mL) and ethanol (20 mL) was stirred at 70° C. for 1.5 hr. To the reaction mixture was added concentrated sulfuric acid (5.54 mL) under ice-cooling, and the mixture was stirred at 70° C. for 2 hr. The solvent was concentrated under reduced pressure to half. The reaction mixture was alkalified with 8 M aqueous sodium hydroxide solution, and extracted twice with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (1.42 g).

MS (ESI+): [M+H]$^+$ 273.0.

Reference Example 92

1-((2R)-1-(3-bromo-1-methyl-1H-pyrazol-5-yl)pyrrolidin-2-yl)-N,N-dimethylmethanamine

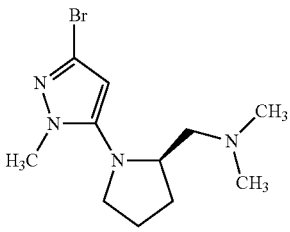

To a mixture of ((2R)-1-(3-bromo-1-methyl-1H-pyrazol-5-yl)pyrrolidin-2-yl)methanol (1400 mg) obtained in Reference Example 24 and toluene (30 mL) was added thionyl chloride (0.589 mL) at 0° C. The reaction mixture was stirred under a nitrogen atmosphere at 80° C. for 4 hr. To the reaction mixture was added saturated aqueous sodium hydrogen carbonate solution at 0° C., and the mixture was extracted with ethyl acetate. The extract was washed with water and saturated brine, and dried over anhydrous magnesium sulfate, and the solvent was evaporated under reduced pressure. To the obtained residue were added N,N-dimethylacetamide (30 mL), sodium carbonate (856 mg), sodium iodide (1210 mg) and dimethylamine (2 M, methanol solution, 8.07 mL), and the mixture was stirred at 100° C. for 5 hr. To the reaction mixture were added sodium carbonate (856 mg), sodium iodide (1210 mg) and dimethylamine (2 M, methanol solution, 35 mL), and the mixture was stirred under a nitrogen atmosphere at 100° C. for 11 hr. The reaction mixture was cooled to room temperature, and partitioned between 1 M aqueous hydrochloric acid solution and ethyl acetate. To the aqueous layer was added 8 M aqueous sodium hydroxide solution under ice-cooling, and the mixture was extracted with ethyl acetate. The extract was washed with water and saturated brine, dried over anhydrous magnesium sulfate, and the solvent was evaporated under reduced pressure. The residue was purified by silica gel column chromatography (basic silica gel, ethyl acetate/hexane) to give the title compound (141 mg).

MS (ESI+): [M+H]$^+$ 286.8.

Reference Example 93

1-(3-bromo-1-methyl-1H-pyrazol-5-yl)-4-methylpiperidine-4-carbonitrile

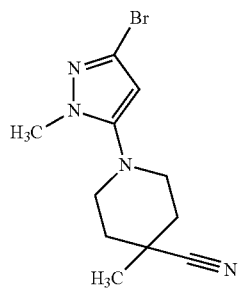 [SMILES: Cn1nc(Br)cc1N1CCC(C)(C#N)CC1]

A) ethyl 3-bromo-5-(4-cyano-4-methylpiperidin-1-yl)-1-methyl-1H-pyrazole-4-carboxylate A mixture of ethyl 3,5-dibromo-1-methyl-1H-pyrazole-4-carboxylate (2.12 g) obtained in Reference Example 2, 4-methylpiperidine-4-carbonitrile hydrochloride (1.31 g), potassium carbonate (2.82 g) and N-methyl-pyrrolidone (10 mL) was heated under a nitrogen atmosphere at 160° C. for 8 hr. After cooling, water was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (ethyl acetate/hexane) to give the title compound (1.46 g).
MS (ESI+): [M+H]354.9.

B) 1-(3-bromo-1-methyl-1H-pyrazol-5-yl)-4-methyl-piperidine-4-carbonitrile

A mixture of ethyl 3-bromo-5-(4-cyano-4-methylpiperidin-1-yl)-1-methyl-1H-pyrazole-4-carboxylate (1.46 g) obtained in Reference Example 93, Step A, 2 M aqueous sodium hydroxide solution (10.28 mL) and ethanol (15 mL) was stirred at 70° C. for 2 hr. To the reaction mixture was added concentrated sulfuric acid (8.76 mL), and the mixture was stirred at 70° C. for 2 hr. The reaction mixture was alkalified with 8 M aqueous sodium hydroxide solution, and extracted three times with ethyl acetate. The extracts were combined, washed with saturated brine, and dried over anhydrous magnesium sulfate, and the solvent was evaporated under reduced pressure to give the title compound (903 mg).
MS (ESI+): [M+H]$^+$ 282.8.

Reference Example 94

3-bromo-5-((2R)-2-(methoxymethyl)pyrrolidin-1-yl)-1-methyl-1H-pyrazole

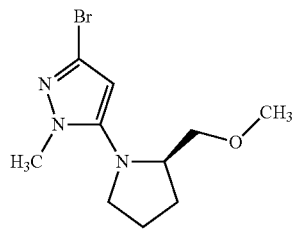

To a mixture of ((2R)-1-(3-bromo-1-methyl-1H-pyrazol-5-yl)pyrrolidin-2-yl)methanol (700 mg) obtained in Reference Example 24 and N,N-dimethylformamide (8 mL) was added sodium hydride (60% in mineral oil, 161 mg) at 0° C., and the mixture was stirred at the same temperature for 30 min. Under an ice bath, methyl iodide (0.251 mL) was added to the reaction mixture, and the mixture was stirred at room temperature for 5 hr. Methyl iodide (0.200 mL) was added to the reaction mixture, and the mixture was stirred at room temperature for 16 hr. Water was added to the reaction mixture, and the mixture was extracted with ethyl acetate. The obtained organic layer was washed with saturated brine, and dried over anhydrous magnesium sulfate. The solvent was evaporated under reduced pressure. The residue was purified by silica gel column chromatography (hexane/ethyl acetate) to give the title compound (617 mg).
MS (ESI+): [M+H]$^+$ 273.8.

Reference Example 95

1-(3-(3-bromo-1-methyl-1H-pyrazol-5-yl)-3-methoxyazetidin-1-yl)ethanone

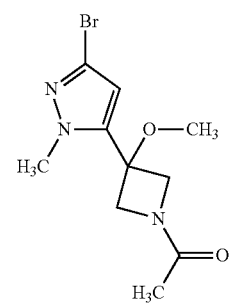

To a mixture of 3-bromo-5-(3-methoxyazetidin-3-yl)-1-methyl-1H-pyrazole hydrochloride (400 mg) obtained in Reference Example 76, Step C, triethylamine (0.592 mL) and tetrahydrofuran (10 mL) was added acetyl chloride (0.15 mL) at 0° C., and the mixture was stirred at room temperature for 2 hr. Saturated aqueous sodium hydrogen carbonate solution was added to the reaction mixture at room temperature, and the mixture was extracted with ethyl acetate. The extract was washed with saturated aqueous ammonium chloride solution and saturated brine, and dried over anhydrous magnesium sulfate, and the solvent was evaporated under reduced pressure to give the title compound (376 mg).
MS (ESI+): [M+H]$^+$ 287.8.

Reference Example 96

3-bromo-5-(3-methoxy-1-(methylsulfonyl)azetidin-3-yl)-1-methyl-1H-pyrazole

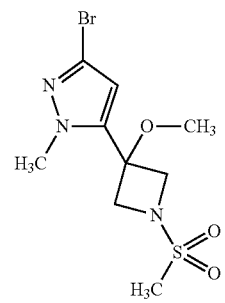 [SMILES: COC1(c2cc(Br)nn2C)CN(S(C)(=O)=O)C1]

To a mixture of 3-bromo-5-(3-methoxyazetidin-3-yl)-1-methyl-1H-pyrazole hydrochloride (400 mg) obtained in Reference Example 76, Step C, triethylamine (0.592 mL) and tetrahydrofuran (10 mL) was added methanesulfonyl chloride (0.165 mL) at 0° C., and the mixture was stirred at room temperature for 2 hr. Saturated aqueous sodium hydrogen carbonate solution was added to the reaction mixture at room temperature, and the mixture was extracted with ethyl acetate. The extract was washed with saturated aqueous ammonium chloride solution and saturated brine, and dried over anhydrous magnesium sulfate, and the solvent was evaporated under reduced pressure to give the title compound (426 mg).

MS (ESI+): [M+H]$^+$ 323.8.

Reference Example 97

3-bromo-5-(4,4-difluoro-1-methoxycyclohexyl)-1-methyl-1H-pyrazole

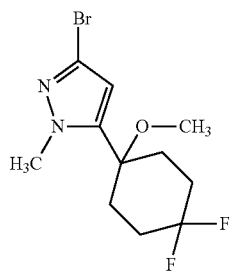 [SMILES: COC1(c2cc(Br)nn2C)CCC(F)(F)CC1]

The title compound was obtained by a method similar to Reference Example 88 and using 3,5-dibromo-1-methyl-1H-pyrazole obtained in Reference Example 3 and 4,4-difluorocyclohexanone.

MS (ESI+): [M+H]$^+$ 308.8.

Reference Example 98

(S)-1-(3-bromo-1-methyl-1H-pyrazol-5-yl)-N,N-dimethylpyrrolidin-3-amine

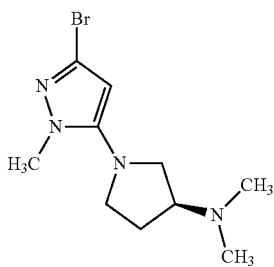

A) (S)-ethyl 3-bromo-5-(3-(dimethylamino)pyrrolidin-1-yl)-1-methyl-1H-pyrazole-4-carboxylate A mixture of ethyl 3,5-dibromo-1-methyl-1H-pyrazole-4-carboxylate (2.70 g) obtained in Reference Example 2, (S)—N,N-dimethylpyrrolidin-3-amine (988 mg), potassium carbonate (3.59 g) and N-methyl-pyrrolidone (10 mL) was heated under a nitrogen atmosphere at 160° C. for 4 hr. After cooling, water was added to the reaction mixture, and the mixture was extracted twice with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (3.06 g).

MS (ESI+): [M+H]$^+$ 344.9.

B) (S)-1-(3-bromo-1-methyl-1H-pyrazol-5-yl)-N,N-dimethylpyrrolidin-3-amine

A mixture of (S)-ethyl 3-bromo-5-(3-(dimethylamino)pyrrolidin-1-yl)-1-methyl-1H-pyrazole-4-carboxylate (3.06 g) obtained in Reference Example 98, Step A, 2 M aqueous sodium hydroxide solution (22.2 mL) and ethanol (20 mL) was stirred at 70° C. for 2.5 hr. To the reaction mixture was added concentrated sulfuric acid (7.09 mL) at 0° C., and the mixture was stirred at 70° C. for 2 hr. The solvent was concentrated under reduced pressure to half. The reaction mixture was alkalified with 8 M aqueous sodium hydroxide solution, and extracted twice with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (1.46 g).

MS (ESI+): [M+H]$^+$ 272.8.

Reference Example 99

1-(3-bromo-1-methyl-1H-pyrazol-5-yl)piperidine-4-carbonitrile

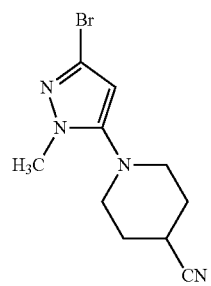

The title compound was obtained by a method similar to Reference Example 75 and using ethyl 3,5-dibromo-1-methyl-1H-pyrazole-4-carboxylate obtained in Reference Example 2 and piperidine-4-carbonitrile.

MS (ESI+): [M+H]$^+$ 268.8.

Reference Example 100

3-bromo-5-(cyclohex-1-en-1-yl)-1-methyl-1H-pyrazole

A mixture of 3,5-dibromo-1-methyl-1H-pyrazole (500 mg) obtained in Reference Example 3, 2-(cyclohex-1-en-1-yl)-4,4,5,5-tetramethyl-1,3,2-dioxaborolane (520 mg), tetrakis(triphenylphosphine)palladium(0) (241 mg), aqueous sodium carbonate solution (2 M, 2.08 mL) and 1,2-dimethoxyethane (10 mL) was heated under an argon atmosphere at 80° C. for 20 hr. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (345 mg).

MS (ESI+): [M+H]$^+$ 240.8.

Reference Example 101

1-(3-bromo-1-methyl-1H-pyrazol-5-yl)-4-methyl-1,4-diazepane

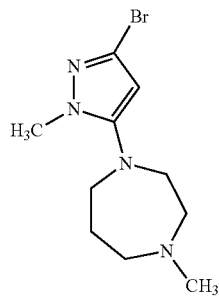

A) ethyl 3-bromo-1-methyl-5-(4-methyl-1,4-diazepan-1-yl)-1H-pyrazole-4-carboxylate A mixture of ethyl 3,5-dibromo-1-methyl-1H-pyrazole-4-carboxylate (1.00 g) obtained in Reference Example 2, methyl homopiperazine (549 mg), potassium carbonate (532 mg) and N-methyl-pyrrolidone (6 mL) was heated under microwave irradiation at 160° C. for 4 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (basic silica gel, ethyl acetate/hexane) to give the title compound (931 mg).

MS (ESI+): [M+H]$^+$ 345.0.

B) 1-(3-bromo-1-methyl-1H-pyrazol-5-yl)-4-methyl-1,4-diazepane

A mixture of ethyl 3-bromo-1-methyl-5-(4-methyl-1,4-diazepan-1-yl)-1H-pyrazole-4-carboxylate (931 mg) obtained in Reference Example 101, Step A, 2 M aqueous sodium hydroxide solution (6.74 mL) and ethanol (10 mL) was stirred at 70° C. for 2 hr. Concentrated sulfuric acid (1.73 mL) was added to the reaction mixture at 0° C., and the mixture was stirred at 70° C. for 2 hr. The reaction mixture was alkalified with 8 M aqueous sodium hydroxide solution at 0° C., and extracted three times with ethyl acetate. The extracts were combined, washed with saturated brine, and dried over anhydrous magnesium sulfate, and the solvent was evaporated under reduced pressure. The residue was purified by silica gel column chromatography (basic silica gel, ethyl acetate/hexane) to give the title compound (673 mg).

MS (ESI+): [M+H]$^+$ 272.8.

Reference Example 102

8-(3-bromo-1-methyl-1H-pyrazol-5-yl)-3-oxa-8-azabicyclo[3.2.1]octane

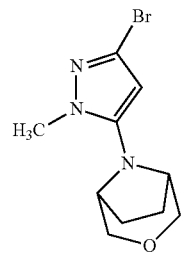

A) ethyl 5-(3-oxa-8-azabicyclo[3.2.1]octan-8-yl)-3-bromo-1-methyl-1H-pyrazole-4-carboxylate A mixture of ethyl 3,5-dibromo-1-methyl-1H-pyrazole-4-carboxylate (1.00 g) obtained in Reference Example 2,3-oxa-8-azabicyclo[3.2.1]octane hydrochloride (576 mg), potassium carbonate (1063 mg) and N-methyl-pyrrolidone (6 mL) was heated under microwave irradiation at 160° C. for 4 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (basic silica gel, ethyl acetate/hexane) to give the title compound (278 mg).

MS (ESI+): [M+H]$^+$ 343.9.

B) 8-(3-bromo-1-methyl-1H-pyrazol-5-yl)-3-oxa-8-azabicyclo[3.2.1]octane

A mixture of ethyl 5-(3-oxa-8-azabicyclo[3.2.1]octan-8-yl)-3-bromo-1-methyl-1H-pyrazole-4-carboxylate (278 mg) obtained in Reference Example 102, Step A, 2 M aqueous sodium hydroxide solution (2.02 mL) and ethanol (10 mL) was stirred at 70° C. for 2 hr. Concentrated sulfuric acid (0.517 mL) was added to the reaction mixture at 0° C., and the mixture was stirred at 70° C. for 2 hr. The reaction mixture was alkalified with 8 M-aqueous sodium hydroxide solution at 0° C., and extracted three times with ethyl acetate. The extracts were combined, washed with saturated brine, and dried over anhydrous magnesium sulfate, and the solvent was evaporated under reduced pressure to give the title compound (220 mg).

MS (ESI+): [M+H]$^+$ 272.0.

Reference Example 103

(R)-3-bromo-1-methyl-5-(2-(pyrrolidin-1-ylmethyl)pyrrolidin-1-yl)-1H-pyrazole

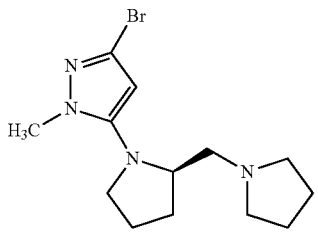 [SMILES: Cn1nc(Br)cc1N1CCC[C@@H]1CN1CCCC1]

To a mixture of ((2R)-1-(3-bromo-1-methyl-1H-pyrazol-5-yl)pyrrolidin-2-yl)methanol (300 mg) obtained in Reference Example 24, triethylamine (0.209 mL) and tetrahydrofuran (4 mL) was added methanesulfonyl chloride (0.107 mL) at 0° C., and the mixture was stirred at room temperature for 2 hr. The resulting salt was removed by filtration, and the filtrate was concentrated under reduced pressure. To a mixture of the obtained residue, 1,8-diazabicyclo[5.4.0]undec-7-ene (0.017 mL) and toluene (4 mL) was added pyrrolidine (0.385 mL) at room temperature. The reaction mixture was stirred at 100° C. for 3 hr. The reaction mixture was concentrated under reduced pressure, and the residue was purified by silica gel column chromatography (basic silica gel, ethyl acetate/hexane) to give the title compound (360 mg).

MS (ESI+): [M+H]$^+$ 313.1.

Reference Example 104

(S)-2-(3-bromo-1-methyl-1H-pyrazol-5-yl)octahydropyrrolo[1,2-a]pyrazine

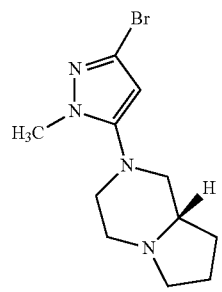 [SMILES: Cn1nc(Br)cc1N1CCN2CCC[C@H]2C1]

A) (S)-ethyl 3-bromo-5-(hexahydropyrrolo[1,2-a]pyrazin-2(1H)-yl)-1-methyl-1H-pyrazole-4-carboxylate A mixture of ethyl 3,5-dibromo-1-methyl-1H-pyrazole-4-carboxylate (1.00 g) obtained in Reference Example 2, (S)-1,4-diazabicyclo[4.3.0]nonane (485 mg), potassium carbonate (576 mg) and N-methyl-pyrrolidone (6 mL) was heated under microwave irradiation at 160° C. for 4 hr. After cooling, saturated aqueous sodium hydrogen carbonate solution was added to the reaction mixture, and the mixture was extracted twice with ethyl acetate. The extracts were combined, washed with water and saturated brine, and dried over anhydrous magnesium sulfate, and the solvent was evaporated under reduced pressure. The residue was purified by silica gel column chromatography (basic silica gel, ethyl acetate/hexane) to give the title compound (1.06 g).

MS (ESI+): [M+H]$^+$ 357.0.

B) (S)-2-(3-bromo-1-methyl-1H-pyrazol-5-yl) octahydropyrrolo[1,2-a]pyrazine

A mixture of (S)-ethyl 3-bromo-5-(hexahydropyrrolo[1,2-a]pyrazin-2(1H)-yl)-1-methyl-1H-pyrazole-4-carboxylate (1.06 g) obtained in Reference Example 104, Step A, 2 M aqueous sodium hydroxide solution (7.42 mL) and ethanol (10 mL) was stirred at 70° C. for 2 hr. Concentrated sulfuric acid (1.90 mL) was added to the reaction mixture at 0° C., and the mixture was stirred at 70° C. for 2 hr. The reaction mixture was alkalified with 8 M aqueous sodium hydroxide solution at 0° C., and extracted three times with ethyl acetate. The extracts were combined, washed with saturated brine, and dried over anhydrous magnesium sulfate, and the solvent was evaporated under reduced pressure. The residue was crystallized from hexane to give the title compound (167 mg).

MS (ESI+): [M+H]$^+$ 285.0.

Reference Example 105

(R)-2-(3-bromo-1-methyl-1H-pyrazol-5-yl)octahydropyrrolo[1,2-a]pyrazine

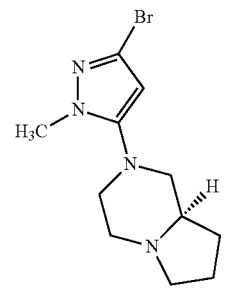 [SMILES: Cn1nc(Br)cc1N1CCN2CCC[C@@H]2C1]

A) (R)-ethyl 3-bromo-5-(hexahydropyrrolo[1,2-a]pyrazin-2(1H)-yl)-1-methyl-1H-pyrazole-4-carboxylate A mixture of ethyl 3,5-dibromo-1-methyl-1H-pyrazole-4-carboxylate (1.00 g) obtained in Reference Example 2, (R)-octahydropyrrolo[1,2-a]pyrazine (485 mg), potassium carbonate (576 mg) and N-methyl-pyrrolidone (6 mL) was heated under microwave irradiation at 160° C. for 4 hr. After cooling, saturated aqueous sodium hydrogen carbonate solution was added to the reaction mixture, and the mixture was extracted twice with ethyl acetate. The extracts were combined, washed with water and saturated brine, dried over anhydrous magnesium sulfate, and the solvent was evaporated under reduced pressure. The residue was purified by silica gel column chromatography (basic silica gel, ethyl acetate/hexane) to give a crude purification product of the title compound (1.48 g).

MS (ESI+): [M+H]$^+$ 357.0.

B) (R)-2-(3-bromo-1-methyl-1H-pyrazol-5-yl) octahydropyrrolo[1,2-a]pyrazine

A mixture of (R)-ethyl 3-bromo-5-(hexahydropyrrolo[1,2-a]pyrazin-2(1H)-yl)-1-methyl-1H-pyrazole-4-carboxylate (1.48 g) obtained in Reference Example 105, Step A, 2 M aqueous sodium hydroxide solution (10.36 mL) and ethanol (10 mL) was stirred at 70° C. for 2 hr. Concentrated sulfuric acid (2.65 mL) was added to the reaction mixture at 0° C., and the mixture was stirred at 70° C. for 2 hr. The reaction mixture was alkalified with 8 M aqueous sodium hydroxide solution at 0° C., and extracted three times with ethyl acetate. The extracts were combined, washed with saturated brine, and dried over anhydrous magnesium sulfate, and the solvent was evaporated under reduced pressure. The residue was crystallized from hexane to give the title compound (387 mg).
MS (ESI+): [M+H]+ 285.0.

Reference Example 106

(R)-1-(1-(3-bromo-1-methyl-1H-pyrazol-5-yl)pyrrolidin-2-yl)-N-methylmethanamine

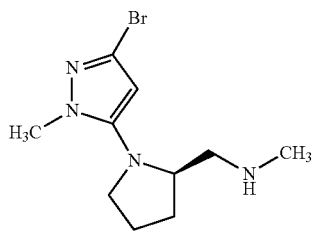

To a mixture of ((2R)-1-(3-bromo-1-methyl-1H-pyrazol-5-yl)pyrrolidin-2-yl)methanol (300 mg) obtained in Reference Example 24, triethylamine (0.209 mL), and tetrahydrofuran (4 mL) was added methanesulfonyl chloride (0.107 mL) at 0° C., and the mixture was stirred at room temperature for 2 hr. The resulting salt was removed by filtration, and the filtrate was concentrated under reduced pressure. A mixture of the obtained residue, 40% methylamine (methanol solution) (4 mL) and tetrahydrofuran (4 mL) was stirred at 60° C. overnight. The reaction mixture was concentrated under reduced pressure, and the residue was purified by silica gel column chromatography (basic silica gel, ethyl acetate/hexane) to give the title compound (311 mg).
MS (ESI+): [M+H]273.0.

Reference Example 107

(R)-tert-butyl((1-(3-bromo-1-methyl-1H-pyrazol-5-yl)pyrrolidin-2-yl)methyl)(methyl)carbamate

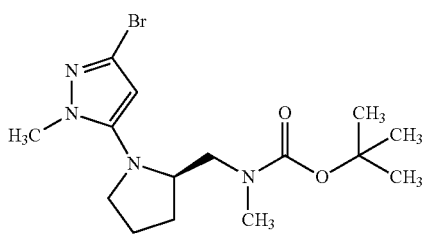 [SMILES: CN(C[C@H]1CCCN1c1cc(Br)nn1C)C(=O)OC(C)(C)C]

To a mixture of (R)-1-(1-(3-bromo-1-methyl-1H-pyrazol-5-yl)pyrrolidin-2-yl)-N-methylmethanamine (311 mg) obtained in Reference Example 106, triethylamine (0.206 mL) and tetrahydrofuran (4 mL) was added di-tert-butyl dicarbonate (0.317 mL) at 0° C., and the mixture was stirred at room temperature for 2 hr. The resulting salt was removed by filtration, and the filtrate was concentrated under reduced pressure. The residue was purified by silica gel column chromatography (ethyl acetate/hexane) to give the title compound (306 mg).
MS (ESI+): [M+H]+ 373.0.

Reference Example 108

(R)—N-((1-(3-bromo-1-methyl-1H-pyrazol-5-yl)pyrrolidin-2-yl)methyl)-N-methylacetamide

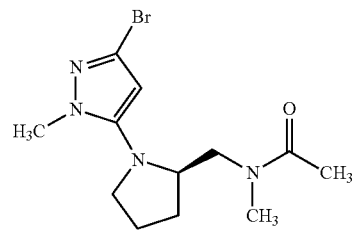 [SMILES: CC(=O)N(C)C[C@H]1CCCN1c1cc(Br)nn1C]

To a mixture of (R)-1-(1-(3-bromo-1-methyl-1H-pyrazol-5-yl)pyrrolidin-2-yl)-N-methylmethanamine (230 mg) obtained in Reference Example 106, triethylamine (0.153 mL), and tetrahydrofuran (4 mL) was added acetyl chloride (0.072 mL) at 0° C., and the mixture was stirred at room temperature for 2 hr. The resulting salt was removed by filtration, and the filtrate was concentrated under reduced pressure. The residue was purified by silica gel column chromatography (basic silica gel, ethyl acetate/hexane) to give the title compound (175 mg).
MS (ESI+): [M+H]+ 314.9.

Reference Example 109

(R)—N-((1-(3-bromo-1-methyl-1H-pyrazol-5-yl)pyrrolidin-2-yl)methyl)-N-methylmethanesulfonamide

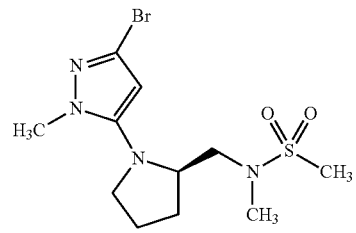

To a mixture of (R)-1-(1-(3-bromo-1-methyl-1H-pyrazol-5-yl)pyrrolidin-2-yl)-N-methylmethanamine (230 mg) obtained in Reference Example 106, triethylamine (0.153 mL) and tetrahydrofuran (4 mL) was added methanesulfonyl chloride (0.078 mL) at 0° C., and the mixture was stirred at room temperature for 2 hr. The resulting salt was removed by filtration, and the filtrate was concentrated under reduced pressure. The residue was purified by silica gel column chromatography (basic silica gel, ethyl acetate/hexane) to give the title compound (226 mg).

MS (ESI+): [M+H]$^+$ 350.9.

Formulation Example 1 (Production of Capsule)

| 1) compound of Example 1 | 30 mg |
|---|---|
| 2) fine powdered cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablet)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The entire amounts of 1), 2) and 3) and 30 g of 4) are kneaded with water, vacuum-dried and sieved. The sieved powder is mixed with 14 g of 4) and 1 g of 5), and the mixture is tableted by a tableting machine, whereby 1000 tablets containing 30 mg of the compound of Example 1 per tablet are obtained.

Experimental Example 1

JAK1 Enzyme Inhibition Test

JAK1 enzyme inhibitory activity of test compounds was measured by the LANCE method (PerkinElmer). First, a test compound diluted with assay buffer (50 mM HEPES (pH 7.5), 10 mM MgCl$_2$, 1 mM EGTA, 2 mM DTT, 0.01% Tween20, 0.01% BSA) was added to a 384-well plate by 2 µL each. Then, a JAK1 (Invitrogen) solution and a fluorescence-labeled peptide substrate (ULight-JAK1, PerkinElmer) solution diluted with assay buffer to 187.5 ng/mL and 300 nM, respectively, were added by 2 µL each. Then, an enzyme reaction was started by adding 2 µL each of ATP solution prepared with assay buffer to 150 µM. After the reaction at room temperature for 1 hr, Detection Buffer (PerkinElmer) prepared to contain 20 mM EDTA, 4 nM europium-labeled anti-phosphotyrosine antibody (PerkinElmer) was added by 6 µL each. After standing at room temperature for 1 hr, fluorescence intensity (excitation wavelength 340 nm, fluorescence wavelength 665 nm, delay time 100 microseconds) was measured by a plate reader, Envision (PerkinElmer). The inhibitory activity of each compound was calculated as a relative activity value to the fluorescence intensity of a well free of enzyme as 100% inhibition. The results are shown in Table 12.

Experimental Example 2

JAK2 Enzyme Inhibition Test

JAK2 enzyme inhibitory activity of test compounds was measured by the LANCE method (PerkinElmer). First, a test compound diluted with assay buffer (50 mM HEPES (pH 7.5), 10 mM MgCl$_2$, 1 mM EGTA, 2 mM DTT, 0.01% Tween20, 0.01% BSA) was added to a 384-well plate by 2 µL each. Then, a JAK2 (Invitrogen) solution and a fluorescence-labeled peptide substrate (ULight-JAK1, PerkinElmer) solution diluted with assay buffer to 6 ng/mL and 300 nM, respectively, were added by 2 µL each. Then, an enzyme reaction was started by adding 2 µL each of ATP solution prepared with assay buffer to 45 µM. After the reaction at room temperature for 1 hr, Detection Buffer (PerkinElmer) prepared to contain 20 mM EDTA, 4 nM europium-labeled anti-phosphotyrosine antibody (PerkinElmer) was added by 6 µL each. After standing at room temperature for 1 hr, fluorescence intensity (excitation wavelength 340 nm, fluorescence wavelength 665 nm, delay time 100 microseconds) was measured by a plate reader, Envision (PerkinElmer). The inhibitory activity of each compound was calculated as a relative activity value to the fluorescence intensity of a well free of enzyme as 100% inhibition. The results are shown in Table 12.

Experimental Example 3

JAK3 Enzyme Inhibition Test

JAK3 enzyme inhibitory activity of test compounds was measured by the LANCE method (PerkinElmer). First, a test compound diluted with assay buffer (50 mM HEPES (pH 7.5), 10 mM MgCl$_2$, 1 mM EGTA, 2 mM DTT, 0.01% Tween20, 0.01% BSA) was added to a 384-well plate by 2 µL each. Then, a JAK3 (Invitrogen) solution and a fluorescence-labeled peptide substrate (ULight-JAK1, PerkinElmer) solution diluted with assay buffer to 12 ng/mL and 300 nM, respectively, were added by 2 µL each. Then, an enzyme reaction was started by adding 2 µL each of ATP solution prepared with assay buffer to 15 µM. After the reaction at room temperature for 1 hr, Detection Buffer (PerkinElmer) prepared to contain 20 mM EDTA, 4 nM europium-labeled anti-phosphotyrosine antibody (PerkinElmer) was added by 6 µL each. After standing at room temperature for 1 hr, fluorescence intensity (excitation wavelength 340 nm, fluorescence wavelength 665 nm, delay time 100 microseconds) was measured by a plate reader, Envision (PerkinElmer). The inhibitory activity of each compound was calculated as a relative activity value to the fluorescence intensity of a well free of enzyme as 100% inhibition. The results are shown in Table 12.

Experimental Example 4

TYK2 Enzyme Inhibition Test

TYK2 enzyme inhibitory activity of test compounds was measured by the LANCE method (PerkinElmer). First, a test compound diluted with assay buffer (50 mM HEPES (pH 7.5), 10 mM MgCl$_2$, 1 mM EGTA, 2 mM DTT, 0.01% Tween20, 0.01% BSA) was added to a 384-well plate by 2 µL each. Then, a TYK2 (Invitrogen) solution and a fluorescence-labeled peptide substrate (ULight-JAK1, PerkinElmer) solution diluted with assay buffer to 375 ng/mL and 300 nM, respectively, were added by 2 µL each. Then, an enzyme reaction was started by adding 2 µL each of ATP solution prepared with assay buffer to 30 µM. After the reaction at room temperature for 1 hr, Detection Buffer (PerkinElmer) prepared to contain 20 mM EDTA, 4 nM europium-labeled anti-phosphotyrosine antibody (PerkinElmer) was added by 6 µL each. After standing at room temperature for 1 hr, fluorescence intensity (excitation wavelength 340 nm, fluorescence wavelength 665 nm, delay time 100 microseconds) was measured by a plate reader, Envision (PerkinElmer). The inhibitory activity of each compound was calculated as a relative activity value to the fluorescence intensity of a well free of enzyme as 100% inhibition. The results are shown in Table 12.

TABLE 12

| Ex. No. | JAK1 enzyme inhibitory activity (%, 1 μM) | JAK2 enzyme inhibitory activity (%, 1 μM) | JAK3 enzyme inhibitory activity (%, 1 μM) | TYK2 enzyme inhibitory activity (%, 1 μM) |
|---|---|---|---|---|
| 1 | 97% | 98% | 100% | 99% |
| 2 | 97% | 98% | 99% | 99% |
| 3 | 98% | 99% | 100% | 100% |
| 4 | 99% | 99% | 100% | 99% |
| 5 | 99% | 100% | 100% | 100% |
| 6 | 96% | 93% | 98% | 100% |
| 7 | 100% | 100% | 100% | 99% |
| 8 | 99% | 99% | 100% | 99% |
| 9 | 98% | 99% | 100% | 99% |
| 10 | 96% | 98% | 99% | 99% |
| 11 | 98% | 99% | 99% | 100% |
| 12 | 93% | 99% | 99% | 100% |
| 13 | 97% | 99% | 99% | 100% |
| 14 | 97% | 99% | 99% | 99% |
| 15 | 97% | 99% | 100% | 100% |
| 16 | 97% | 99% | 100% | 100% |
| 17 | 97% | 99% | 99% | 100% |
| 18 | 96% | 98% | 99% | 99% |
| 19 | 98% | 98% | 99% | 99% |
| 20 | 95% | 98% | 100% | 99% |
| 21 | 97% | 98% | 99% | 99% |
| 22 | 96% | 98% | 99% | 99% |
| 23 | 97% | 98% | 99% | 99% |
| 24 | 96% | 98% | 99% | 100% |
| 25 | 98% | 98% | 99% | 100% |
| 26 | 88% | 96% | 98% | 98% |
| 27 | 98% | 98% | 100% | 100% |
| 28 | 78% | 90% | 95% | 98% |
| 29 | 47% | 49% | 67% | 93% |
| 30 | 97% | 99% | 99% | 99% |
| 31 | 97% | 98% | 99% | 99% |
| 32 | 96% | 98% | 99% | 99% |
| 33 | 96% | 98% | 99% | 99% |
| 34 | 97% | 99% | 100% | 100% |
| 35 | 97% | 99% | 100% | 99% |
| 36 | 55% | 80% | 85% | 91% |
| 37 | 98% | 99% | 100% | 99% |
| 38 | 99% | 99% | 100% | 100% |
| 39 | 99% | 99% | 100% | 100% |
| 40 | 99% | 98% | 99% | 100% |
| 41 | 97% | 99% | 100% | 101% |
| 42 | 96% | 96% | 99% | 98% |
| 43 | 97% | 97% | 99% | 100% |
| 44 | 90% | 96% | 99% | 101% |
| 45 | 98% | 99% | 99% | 100% |
| 46 | 95% | 98% | 99% | 99% |
| 47 | 93% | 98% | 100% | 99% |
| 48 | 94% | 97% | 100% | 99% |
| 49 | 96% | 97% | 100% | 99% |
| 50 | 96% | 99% | 100% | 99% |
| 51 | 97% | 97% | 97% | 99% |
| 52 | 96% | 99% | 99% | 100% |
| 53 | 95% | 96% | 99% | 98% |
| 54 | 98% | 98% | 99% | 98% |
| 55 | 98% | 98% | 99% | 99% |
| 56 | 70% | 94% | 94% | 98% |
| 57 | 99% | 99% | 99% | 99% |
| 58 | 97% | 99% | 100% | 100% |
| 59 | 97% | 98% | 99% | 100% |
| 60 | 96% | 98% | 99% | 99% |
| 61 | 97% | 99% | 100% | 99% |
| 62 | 97% | 99% | 99% | 99% |
| 63 | 96% | 99% | 100% | 99% |
| 64 | 97% | 99% | 99% | 100% |
| 65 | 99% | 98% | 100% | 100% |
| 66 | 99% | 99% | 100% | 100% |
| 67 | 98% | 97% | 99% | 100% |
| 68 | 99% | 97% | 99% | 99% |
| 69 | 97% | 96% | 98% | 99% |
| 70 | 97% | 96% | 99% | 100% |
| 71 | 98% | 97% | 98% | 99% |
| 72 | 99% | 100% | 100% | 100% |
| 73 | 99% | 99% | 100% | 100% |
| 74 | 98% | 100% | 99% | 99% |
| 75 | 66% | 87% | 93% | 92% |
| 76 | 99% | 99% | 100% | 100% |
| 77 | 79% | 84% | 90% | 96% |
| 78 | 98% | 99% | 100% | 99% |
| 79 | 99% | 99% | 100% | 99% |
| 80 | 89% | 91% | 98% | 99% |
| 81 | 99% | 100% | 100% | 99% |
| 82 | 89% | 87% | 97% | 99% |
| 83 | 99% | 100% | 100% | 100% |
| 84 | 84% | 87% | 97% | 83% |
| 85 | 68% | 86% | 89% | 89% |
| 86 | 98% | 98% | 99% | 100% |
| 88 | 99% | 100% | 99% | 99% |
| 89 | 97% | 99% | 99% | 100% |
| 90 | 96% | 99% | 99% | 100% |
| 91 | 96% | 88% | 97% | 99% |
| 92 | 100% | 100% | 99% | 99% |
| 94 | 100% | 100% | 100% | 99% |
| 95 | 100% | 100% | 100% | 99% |
| 96 | 99% | 100% | 100% | 100% |
| 97 | 97% | 99% | 99% | 100% |
| 98 | 97% | 100% | 100% | 100% |
| 99 | 83% | 85% | 97% | 99% |
| 100 | 82% | 65% | 86% | 96% |
| 101 | 96% | 97% | 99% | 100% |
| 102 | 97% | 98% | 99% | 100% |
| 103 | 51% | 93% | 97% | 96% |
| 104 | 72% | 96% | 98% | 100% |
| 105 | 97% | 99% | 99% | 99% |
| 106 | 97% | 99% | 99% | 100% |
| 107 | 97% | 98% | 99% | 100% |
| 108 | 98% | 98% | 99% | 100% |
| 109 | 98% | 99% | 99% | 99% |
| 110 | 89% | 99% | 99% | 100% |
| 111 | 83% | 97% | 98% | 100% |
| 112 | 98% | 98% | 99% | 100% |
| 113 | 97% | 98% | 99% | 99% |
| 114 | 68% | 74% | 84% | 95% |
| 115 | 93% | 91% | 99% | 100% |
| 116 | 101% | 100% | 101% | 102% |
| 117 | 85% | 85% | 97% | 99% |
| 118 | 98% | 97% | 99% | 100% |
| 119 | 99% | 98% | 100% | 100% |
| 120 | 100% | 100% | 100% | 101% |
| 121 | 98% | 98% | 97% | 100% |
| 122 | 97% | 93% | 97% | 101% |
| 123 | 97% | 94% | 95% | 100% |
| 124 | 99% | 99% | 100% | 101% |
| 125 | 98% | 98% | 99% | 99% |
| 126 | 92% | 98% | 99% | 98% |
| 127 | 99% | 99% | 100% | 100% |
| 128 | 98% | 98% | 99% | 100% |
| 129 | 97% | 99% | 99% | 100% |
| 130 | 96% | 98% | 99% | 101% |
| 131 | 95% | 98% | 99% | 100% |
| 132 | 94% | 98% | 99% | 100% |
| 133 | 91% | 87% | 96% | 99% |
| 134 | 97% | 98% | 99% | 99% |
| 135 | 96% | 98% | 99% | 100% |
| 136 | 80% | 98% | 98% | 100% |
| 137 | 92% | 99% | 98% | 99% |
| 138 | 96% | 99% | 99% | 99% |
| 139 | 32% | 80% | 66% | 93% |
| 140 | 98% | 99% | 100% | 99% |
| 141 | 98% | 99% | 100% | 100% |
| 142 | 98% | 98% | 99% | 98% |

TABLE 12-continued

| Ex. No. | JAK1 enzyme inhibitory activity (%, 1 μM) | JAK2 enzyme inhibitory activity (%, 1 μM) | JAK3 enzyme inhibitory activity (%, 1 μM) | TYK2 enzyme inhibitory activity (%, 1 μM) |
|---|---|---|---|---|
| 143 | 99% | 98% | 99% | 100% |
| 144 | 92% | 98% | 99% | 100% |
| 145 | 89% | 98% | 99% | 100% |
| 146 | 99% | 99% | 100% | 100% |
| 147 | 101% | 101% | 103% | 110% |
| 148 | 101% | 101% | 104% | 110% |
| 149 | 100% | 99% | 101% | 106% |
| 150 | 98% | 100% | 101% | 102% |
| 151 | 99% | 100% | 101% | 102% |
| 152 | 100% | 101% | 101% | 102% |
| 153 | 99% | 98% | 101% | 103% |
| 154 | 97% | 98% | 100% | 102% |
| 155 | 76% | 81% | 98% | 101% |
| 156 | 100% | 99% | 100% | 100% |
| 157 | 99% | 99% | 100% | 101% |
| 158 | 92% | 99% | 100% | 101% |
| 159 | 99% | 99% | 100% | 100% |
| 160 | 99% | 100% | 100% | 100% |
| 161 | 100% | 99% | 100% | 100% |
| 162 | 99% | 100% | 100% | 101% |
| 163 | 100% | 100% | 100% | 101% |
| 164 | 99% | 99% | 100% | 101% |
| 165 | 100% | 98% | 100% | 100% |
| 166 | 100% | 99% | 100% | 101% |
| 167 | 100% | 99% | 100% | 101% |
| 168 | 98% | 94% | 100% | 101% |
| 169 | 98% | 98% | 99% | 98% |
| 170 | 99% | 99% | 99% | 98% |
| 171 | 93% | 94% | 98% | 98% |
| 172 | 93% | 98% | 98% | 98% |
| 173 | 98% | 96% | 99% | 98% |
| 174 | 99% | 98% | 99% | 98% |
| 175 | 96% | 97% | 98% | 98% |
| 176 | 97% | 98% | 99% | 98% |

INDUSTRIAL APPLICABILITY

The compound of the present invention has an excellent JAK inhibitory action, and is useful as a prophylactic or therapeutic agent for autoimmune diseases (rheumatoid arthritis, psoriasis, inflammatory bowel disease, Sjogren's syndrome, Behcet's syndrome, multiple sclerosis, systemic lupus erythematosus, etc.), cancer (leukemia, uterine leiomyosarcoma, prostate cancer, multiple myeloma, cachexia, myelofibrosis, etc.) and the like.

This application is based on patent application No. 2013-70477 filed in Japan, the entire contents of which are incorporated by reference herein.

The invention claimed is:

1. A compound of formula (I):

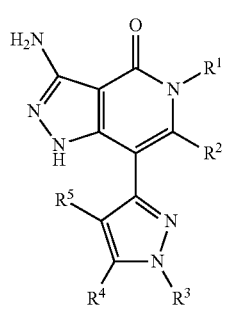

(I)

wherein
R$^1$ is an optionally substituted C$_{1-6}$ alkyl group, or an optionally substituted cyclic group;
R$^2$ is a hydrogen atom or a cyano group;
R$^3$ is an optionally substituted C$_{1-3}$ alkyl group;
R$^4$ is a halogen atom, a cyano group, an optionally substituted hydroxyl group, an optionally substituted amino group, an acyl group, an optionally substituted hydrocarbon group, or an optionally substituted heterocyclic group; and
R$^5$ is a hydrogen atom, a halogen atom, a cyano group, an optionally substituted C$_{1-6}$ alkyl group, an optionally substituted C$_{1-6}$ alkoxy group, or an acyl group,
or a salt thereof.

2. The compound according to claim 1, wherein
R$^1$ is
(1) a C$_{1-6}$ alkyl group optionally substituted by 1 to 5 substituents selected from the group consisting of:
 (a) a halogen atom,
 (b) a C$_{3-8}$ cycloalkyl group optionally substituted by 1 to 3 C$_{1-6}$ alkyl groups,
 (c) a C$_{1-6}$ alkoxy-carbonyl group, and
 (d) a carbamoyl group,
(2) a C$_{3-10}$ cycloalkyl group optionally substituted by 1 to 3 C$_{1-6}$ alkyl groups, or
(3) a C$_{6-14}$ aryl group optionally substituted by 1 to 3 substituents selected from the group consisting of:
 (a) a halogen atom,
 (b) a C$_{1-6}$ alkyl group optionally substituted by 1 to 3 halogen atoms, and
 (c) a cyano group;
R$^2$ is a hydrogen atom or a cyano group;
R$^3$ is a C$_{1-3}$ alkyl group optionally substituted by 1 to 3 substituents selected from the group consisting of a halogen atom and a C$_{1-6}$ alkoxy group;
R$^4$ is
(1) a C$_{1-6}$ alkyl group optionally substituted by 1 to 3 substituents selected from the group consisting of:
 (a) a halogen atom,
 (b) a cyano group,
 (c) a hydroxy group,
 (d) an amino group optionally mono- or di-substituted by C$_{1-6}$ alkyl-carbonyl group(s), and
 (e) a carbamoyl group optionally mono- or di-substituted by C$_{1-6}$ alkyl group(s),
(2) a C$_{3-10}$ cycloalkyl group,
(3) a C$_{6-14}$ aryl group optionally substituted by 1 to 3 carbamoyl groups optionally mono-or di-substituted by C$_{1-6}$ alkyl group(s),
(4) a 5-or 6-membered non-aromatic heterocyclic group having one oxygen atom, or
(5) a group represented by the formula:

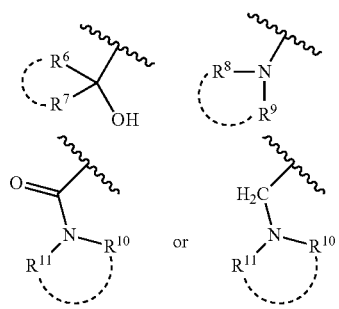

wherein $R^6$ and $R^7$ are each independently a $C_{1-6}$ alkyl group; or $R^6$ and $R^7$ form, together with the adjacent carbon atom, cyclobutane, cyclohexane, tetrahydropyran or tetrahydrothiopyran, each of which is optionally substituted by 1 to 3 substituents selected from the group consisting of a halogen atom and an oxo group;

$R^8$ and $R^9$ are each independently (i) a hydrogen atom, (ii) a $C_{1-6}$ alkyl group optionally substituted by 1 to 3 substituents selected from the group consisting of a halogen atom, a $C_{3-8}$ cycloalkyl group and a $C_{1-6}$ alkoxy group, (iii) a $C_{3-10}$ cycloalkyl group optionally substituted by 1 to 3 halogen atoms, (iv) a $C_{6-14}$ aryl group optionally substituted by 1 to 3 halogen atoms, (v) a $C_{1-6}$ alkoxy group optionally substituted by 1 to 3 halogen atoms, (vi) a $C_{6-14}$ aryloxy group optionally substituted by 1 to 3 halogen atoms, (vii) a $C_{1-6}$ alkyl-carbonyl group optionally substituted by 1 to 3 halogen atoms, (viii) a $C_{1-6}$ alkoxy-carbonyl group optionally substituted by 1 to 3 halogen atoms, (ix) a $C_{1-6}$ alkylsulfonyl group optionally substituted by 1 to 3 halogen atoms, (x) a carbamoyl group optionally mono- or di-substituted by $C_{1-6}$ alkyl group(s) optionally substituted by 1 to 3 halogen atoms, (xi) an aromatic heterocyclic group, or (xii) a 5- or 6-membered non-aromatic heterocyclic group having one oxygen atom; or $R^8$ and $R^9$ form, together with the adjacent nitrogen atom, (i) an aromatic nitrogen-containing heterocycle optionally substituted by 1 to 3 substituents selected from the group consisting of:

(a) a $C_{1-6}$ alkyl group optionally substituted by 1 to 3 halogen atoms, (b) a hydroxy group, (c) a $C_{1-6}$ alkoxy group optionally substituted by 1 to 3 halogen atoms, and (d) a halogen atom, or (ii) a non-aromatic nitrogen-containing heterocycle optionally forming a fused ring or a spiro ring, and optionally substituted by 1 to 3 substituents selected from the group consisting of:

(a) a $C_{1-6}$ alkyl group optionally substituted by 1 to 3 substituents selected from the group consisting of a halogen atom, a hydroxyl group and a $C_{1-6}$ alkoxy group, (b) a hydroxy group, (c) a $C_{1-6}$ alkoxy group optionally substituted by 1 to 3 halogen atoms, (d) a halogen atom, (e) a $C_{1-6}$ alkyl-carbonyl group, (f) a $C_{1-6}$ alkoxy-$C_{1-6}$ alkyl-carbonyl group, and (g) an oxo group $R^{10}$ and $R^{11}$ are each independently (i) a hydrogen atom, (ii) a $C_{1-6}$ alkyl group optionally substituted by 1 to 3 substituents selected from the group consisting of a halogen atom, a $C_{3-8}$ cycloalkyl group and a $C_{1-6}$ alkoxy group, (iii) a $C_{3-10}$ cycloalkyl group optionally substituted by 1 to 3 halogen atoms, (iv) a $C_{6-14}$ aryl group optionally substituted by 1 to 3 halogen atoms, (v) a $C_{1-6}$ alkoxy group optionally substituted by 1 to 3 halogen atoms, (vi) a $C_{6-14}$ aryloxy group optionally substituted by 1 to 3 halogen atoms, (vii) a $C_{1-6}$ alkyl-carbonyl group optionally substituted by 1 to 3 halogen atoms, (viii) a $C_{1-6}$ alkoxy-carbonyl group optionally substituted by 1 to 3 halogen atoms, (ix) a $C_{1-6}$ alkylsulfonyl group optionally substituted by 1 to 3 halogen atoms, (x) a carbamoyl group optionally mono- or di-substituted by $C_{1-6}$ alkyl group(s) optionally substituted by 1 to 3 halogen atoms, (xi) an aromatic heterocyclic group, or (xii) a 5- or 6-membered non-aromatic heterocyclic group having one oxygen atom; or $R^{10}$ and $R^{11}$ form, together with the adjacent nitrogen atom, (i) an aromatic nitrogen-containing heterocycle optionally substituted by 1 to 3 substituents selected from the group consisting of:

(a) a $C_{1-6}$ alkyl group optionally substituted by 1 to 3 halogen atoms, (b) a hydroxy group, (c) a $C_{1-6}$ alkoxy group optionally substituted by 1 to 3 halogen atoms, and (d) a halogen atom, or (ii) a non-aromatic nitrogen-containing heterocycle optionally forming a fused ring or a spiro ring, which is optionally substituted by 1 to 3 substituents selected from the group consisting of:

(a) a $C_{1-6}$ alkyl group optionally substituted by 1 to 3 substituents selected from the group consisting of a halogen atom, a hydroxy group and a $C_{1-6}$ alkoxy group, (b) a hydroxy group, (c) a $C_{1-6}$ alkoxy group optionally substituted by 1 to 3 halogen atoms, (d) a halogen atom, (e) a $C_{1-6}$ alkyl-carbonyl group, (f) a $C_{1-6}$ alkoxy-$C_{1-6}$ alkyl-carbonyl group, and (g) an oxo group; and $R^5$ is a hydrogen atom, or a salt thereof.

3. 3-Amino-7-(5-(2-hydroxypropan-2-yl)-1-methyl-1H-pyrazol-3-yl)-5-((2S)-3-methylbutan-2-yl)-1,5-dihydro-4H-pyrazolo[4,3-c]pyridin-4-one or a salt thereof.

4. 3-Amino-5-(dicyclopropylmethyl)-7-(1-methyl-5-(morpholin-4-yl)-1H-pyrazol-3-yl)-1,5-dihydro-4H-pyrazolo[4,3-c]pyridin-4-one or a salt thereof.

5. A pharmaceutical composition comprising the compound or salt according to claim 1, and a pharmaceutically acceptable carrier.

6. The pharmaceutical composition according to claim 5, which is a Janus kinase inhibitor.

* * * * *